US009181591B2

(12) United States Patent
Robins et al.

(10) Patent No.: US 9,181,591 B2
(45) **Date of Patent: *Nov. 10, 2015**

(54) QUANTIFICATION OF ADAPTIVE IMMUNE CELL GENOMES IN A COMPLEX MIXTURE OF CELLS

(71) Applicant: Adaptive Biotechnologies Corporation, Seattle, WA (US)

(72) Inventors: Harlan S. Robins, Seattle, WA (US); Robert J. Livingston, Seattle, WA (US)

(73) Assignee: ADAPTIVE BIOTECHNOLOGIES CORPORATION, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/471,821

(22) Filed: Aug. 28, 2014

(65) Prior Publication Data

US 2015/0051089 A1 Feb. 19, 2015

Related U.S. Application Data

(63) Continuation of application No. 14/199,167, filed on Mar. 6, 2014, which is a continuation of application No. 13/656,265, filed on Oct. 19, 2012.

(60) Provisional application No. 61/550,311, filed on Oct. 21, 2011.

(51) Int. Cl.
*C12Q 1/68* (2006.01)

(52) U.S. Cl.
CPC ............ *C12Q 1/6888* (2013.01); *C12Q 1/6881* (2013.01); *C12Q 1/686* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS 5,189,147 A 2/1993 Saito et al.
5,506,126 A 4/1996 Seed et al.
5,627,052 A 5/1997 Schrader
6,143,496 A 11/2000 Brown et al.
6,440,706 B1 8/2002 Vogelstein et al.
6,919,434 B1 7/2005 Goto et al.
7,148,040 B2 12/2006 Meagher et al.
7,741,463 B2 6/2010 Gormley et al.
7,785,783 B2 8/2010 Morley et al.
7,915,015 B2 3/2011 Vogelstein et al.
8,236,503 B2 8/2012 Faham et al.
8,507,205 B2 8/2013 Faham
8,628,927 B2 1/2014 Faham
8,691,510 B2 4/2014 Faham
8,748,103 B2 6/2014 Faham
8,795,970 B2 8/2014 Faham
2002/0110807 A1 8/2002 Pilarski et al.
2003/0120061 A1 6/2003 Zhang
2005/0255482 A1 11/2005 Morley et al.
2006/0228350 A1 10/2006 Wu et al.
2006/0233812 A1 10/2006 Burnie et al.
2006/0234234 A1 10/2006 Van Dongen et al.
2007/0020670 A1 1/2007 Loken et al.
2007/0117134 A1 5/2007 Kou
2007/0243564 A1 10/2007 Lawson et al.
2008/0069770 A1 3/2008 Hercend et al.
2008/0166704 A1 7/2008 Marche et al.
2009/0208955 A1* 8/2009 Robins et al. ..................... 435/6
2010/0021896 A1* 1/2010 Han ................................ 435/6
2010/0027896 A1 2/2010 Geva et al.
2010/0151471 A1* 6/2010 Faham et al. ..................... 435/6
2010/0159456 A1 6/2010 Albitar
2010/0167353 A1 7/2010 Walder et al.
2010/0330571 A1 12/2010 Robins et al.
2011/0003291 A1 1/2011 Pasqual et al.
2011/0014659 A1* 1/2011 Balazs et al. ................ 435/91.2
2011/0129830 A1 6/2011 Ladner et al.
2011/0207134 A1* 8/2011 Faham et al. ................ 435/6.11
2011/0207135 A1* 8/2011 Faham et al. ................ 435/6.11
2012/0058902 A1* 3/2012 Livingston et al. ............... 506/7
2012/0135409 A1 5/2012 Faham
2012/0220466 A1* 8/2012 Fire et al. .......................... 506/2
2013/0005584 A1 1/2013 Faham
2013/0065768 A1 3/2013 Zheng
2013/0150252 A1 6/2013 Faham (Continued)

FOREIGN PATENT DOCUMENTS

EP 2062982 A1 5/2009
EP 2088432 A1 8/2009

(Continued)

OTHER PUBLICATIONS

Robins et al. (Comprehensive assessment of T-cell receptor β-chain diversity in αβ T cells, Blood, vol. 114, No. 19, Nov. 5, 2009).*

Boyd et al. (Measurement and Clinical Monitoring of Human Lymphocyte Clonality by Massively Parallel V-D-J Pyrosequencing, Sci Transl Med. Dec. 23, 2009;1(12):12ra23).*

Boyd et al. (Individual Variation in the Germline Ig Gene Repertoire Inferred from Variable Region Gene Rearrangements, J Immunol. Jun. 15, 2010;184(12):6986-92).*

(Continued)

*Primary Examiner* — Stephanie K Mummert
*Assistant Examiner* — Aaron Priest
(74) *Attorney, Agent, or Firm* — Cooley LLP

(57) ABSTRACT

Compositions and methods are described for highly sensitive quantification of the relative representation of DNA from adaptive immune cells (e.g., T and/or B lymphocytes) in DNA extracted from complex mixtures of cells that include cells which are not adaptive immune cells. Included are methods for determining the relative presence in a tumor of tumor infiltrating lymphocytes (TIL), the relative presence of lymphocytes infiltrating a somatic tissue that is the target of an autoimmune disease, and the relative presence of lymphocytes infiltrating a transplanted organ.

23 Claims, 10 Drawing Sheets

(56) References Cited

U.S. PATENT DOCUMENTS

| | | | |
|---|---|---|---|
| 2013/0196328 | A1 | 8/2013 | Pepin |
| 2013/0202718 | A1 | 8/2013 | Pepin |
| 2013/0236895 | A1 | 9/2013 | Faham |
| 2013/0253842 | A1 | 9/2013 | Sherwood et al. |
| 2013/0267427 | A1 | 10/2013 | Faham |
| 2013/0288237 | A1 | 10/2013 | Robins et al. |
| 2013/0302801 | A1 | 11/2013 | Asbury |
| 2013/0344066 | A1 | 12/2013 | Faham |
| 2014/0057799 | A1 | 2/2014 | Johnson et al. |
| 2014/0155277 | A1 | 6/2014 | Wiley |
| 2014/0186848 | A1 | 7/2014 | Robins et al. |
| 2014/0194295 | A1 | 7/2014 | Robins et al. |
| 2014/0206548 | A1 | 7/2014 | Robins et al. |
| 2014/0206549 | A1 | 7/2014 | Robins et al. |
| 2014/0213463 | A1 | 7/2014 | Robins et al. |
| 2014/0221220 | A1 | 8/2014 | Robins et al. |
| 2014/0234835 | A1 | 8/2014 | Pepin |
| 2014/0235454 | A1 | 8/2014 | Faham |
| 2014/0255929 | A1 | 9/2014 | Zheng |
| 2014/0255944 | A1 | 9/2014 | Carlton |
| 2014/0256567 | A1 | 9/2014 | Robins et al. |
| 2014/0256592 | A1 | 9/2014 | Faham |
| 2014/0322716 | A1 | 10/2014 | Robins et al. |
| 2015/0017652 | A1 | 1/2015 | Robins et al. |
| 2015/0031555 | A1 | 1/2015 | Johnson et al. |

FOREIGN PATENT DOCUMENTS

| | | | |
|---|---|---|---|
| JP | 2006-501842 | A | 1/2006 |
| JP | 2007-515955 | A | 6/2007 |
| WO | WO 97/13877 | A1 | 4/1997 |
| WO | WO 2006/110855 | A2 | 10/2006 |
| WO | WO 2006/138284 | A2 | 12/2006 |
| WO | WO 2009/095567 | A2 | 8/2009 |
| WO | WO 2010/053857 | A2 | 5/2010 |
| WO | WO 2010/151416 | A1 | 12/2010 |
| WO | WO 2011106738 | A2 * | 9/2011 |
| WO | WO 2011/139371 | A1 | 11/2011 |
| WO | WO 2012/027503 | A2 | 3/2012 |
| WO | WO 2012/083069 | A2 | 6/2012 |
| WO | WO 2012/083225 | A2 | 6/2012 |
| WO | WO 2013/134302 | A1 | 9/2012 |
| WO | WO 2013/059725 | A1 | 4/2013 |
| WO | WO 2013/086450 | A1 | 6/2013 |
| WO | WO 2013/134162 | A2 | 9/2013 |
| WO | WO 2013/155119 | A1 | 10/2013 |
| WO | WO 2013/158936 | A1 | 10/2013 |
| WO | WO 2013/181428 | A2 | 12/2013 |
| WO | WO 2013/188471 | A2 | 12/2013 |
| WO | WO 2014/018460 | A1 | 1/2014 |
| WO | WO 2014/026031 | A1 | 2/2014 |
| WO | WO 2014/062945 | A1 | 4/2014 |
| WO | WO 2014/062959 | A1 | 4/2014 |
| WO | WO 2014/066184 | A1 | 5/2014 |
| WO | WO 2014/130685 | A1 | 8/2014 |

OTHER PUBLICATIONS

Faham et al. (Deep-sequencing approach for minimal residual disease detection in acute lymphoblastic leukemia, Blood. Dec. 20, 2012; 120(26): 5173-5180).*

Logan et al. (High-throughput VDJ sequencing for quantification of minimal residual disease in chronic lymphocytic leukemia and immune reconstitution assessment, Proc Natl Acad Sci U S A. Dec. 27, 2011;108(52):21194-9).*

Wu et al. (High-throughput immunoglobulin repertoire analysis distinguishes between human IgM memory and switched memory B-cell populations, Blood, Aug. 19, 2010, vol. 116, No. 7).*

Sherwood et al (Deep Sequencing of the Human TCRg and TCRb Repertoires Suggests that TCRb Rearranges After ab and gd T Cell Commitment, Sci Transl Med. Jul. 6, 2011;3(90):90ra61).*

Robins et al. (Overlap and Effective Size of the Human CD8+ T Cell Receptor Repertoire, Sci Transl Med. Sep. 1, 2010;2(47):47ra64).*

Robins (Detecting and monitoring lymphoma with high-throughput sequencing, Oncotarget 2011; 2: 287-288).*

Klarenbeek et al. (Human T-cell memory consists mainly of unexpanded clones, Immunology Letters 133 (2010) 42-48).*

Freeman et al. (Profiling the T-cell receptor beta-chain repertoire by massively parallel sequencing, Genome Res. Oct. 2009;19(10):1817-24).*

Robins (The Computational Detection of Functional Nucleotide Sequence Motifs in the Coding Regions of Organisms, Exp Biol Med (Maywood). Jun. 2008;233(6):665-73).*

Akatsuka Y. et al., "Rapid screening of T-cell receptor (TCR) variable gene usage by multiplex PCR: Application for assessment of clonal composition", *Tissue Antigens*, 53:122-134 (1999).

Al-Lazikani, B. et al., "Standard Conformations for the Canonical Structures of Immunoglobulins," *J. Mol. Biol.*, 273:927-948 (1997).

Alexandre, D. et al. "H. sapiens rearranged T-cell receptor gamma chain gene, V2-JP1", GenBank accession No: X57737, NCBI, Nov. 14, 2006, 8 pages [online] [retrieved on Jun. 26, 2013] Retrieved from the Internet <URL:http://www.ncbi.nlm.nih.gov/nuccore/x57737>.

Alexandre, D. et al. "H. sapiens rearranged T-cell receptor gamma chain gene, V3RS-J1 (hybrid joint)", GenBank accession No: X57740, NCBI, Feb. 11, 1997, 8 pages [online] [retrieved on Jun. 26, 2013] Retrieved from the internal <URL:http://www.ncbi.nlm.nih.gov/nuccore/x57740>.

Arstila, T.P., et al., "A direct estimate of the human αβ T cell receptor diversity," *Science*, 286(5441):958-961 (1999).

Bahloul, M. et al., "Clinical impact of molecular diagnostics in low-grade lymphoma," *Best Practice & Research Clinical Haematology*, 18(1):97-111 (2005).

Benichou, J. et al., "Rep-Seq: uncovering the immunological repertoire through next-generation sequencing", *Immunology*, 135(3):183-191 (2012).

Bernardin, F. et al., "Estimate of the total number of CD8+ clonal expansions in healthy adults using a new DNA heteroduplex-tracking assay for CDR3 repertoire analysis", *Journal of Immunological Methods*, 274(1-2):159-175 (2003).

Berquam-Vrieze, K. et al., "Cell of origin strongly influences genetic selection in a mouse model of T-ALL", *Blood*, 118:4646-4656 (2011).

Blow, N., "PCR's next frontier," *Nature Methods*, 4(10):869-875 (2007).

Bolotin, D.A, et al., "Next generation sequencing for TCR repertoire profiling: Platform-specific features and correction algorithms", *Eur. J. Immunol.*, 42:3073-3083 (2012).

Bonarius, H.P.J. et al., "Monitoring the T-Cell Receptor Repertoire at Single-Clone Resolution", *PLOS One*, 1(e55):1-10 (2006).

Bradfield, S.M. et al., "Graft-versus-leukemia effect in acute lymphoblastic leukemia: the importance of tumor burden and early detection," *Leukemia*,18:1156-1158 (2004).

Brenan, C. et al., "High throughput, nanoliter quantitative PCR," *Drug Discovery Today: Technologies*, 2(3):247-253 (2005).

Buck, G.A. et al., "Design Strategies and Performance of Custom DNA Sequencing Primers", *Biotechnigues*, 27(3):528-536 (1999).

Butkus, B., "Hutch Team Uses ddPCR to Quantify T-Cell Response in Tumors; Adaptive Biotech Eyes Market", *PCR Insider*, Dec. 12, 2013, 3 pages http://www.genomeweb.com/print/1323296.

Campana, D., "Progress of Minimal Residual Disease Studies in Childhood Acute Leukemia," *Curr Hematol Malig Rep*, 5:169-176 (2010).

Caporaso, J.G. et al., "Global patterns of 16S rRNA diversity at a depth of millions, of sequences per sample", *PNAS*, 108(Suppl. 1):4516-4522 (2010).

Carlson, C.S. et al., "Using synthetic templates to design an unbiased multiplex PCR assay", *Nature Communications*, 4:2680, pp. 1-9 (2013).

Cavé, H. et al., "Clinical Significance of minimal residual disease in childhood acute lymphoblastic leukemia," *The New England Journal of Medicine*, 339:591-598 (1998).

Chen, Y. et al., "T-cell receptor gene expression in tumour-infiltrating lymphocytes and peripheral blood lymphocytes of patients with nasopharyngeal carcinoma", *British Journal of Cancer*, 72(1):117-22 (1995).

Chothia, C. et al., "Canonical structures for the hypervariable regions of immunoglobulins," *J. Mol. Biol.*, 196:901-917, Abstract only (1987).

(56) References Cited

OTHER PUBLICATIONS

Chothia, C. et al., "Conformations of immunoglobulin hypervariable regions," *Nature*, 342:877-883 (1989).

Ciudad, J. et al., "Detection of abnormalities in B-cell differentiation pattern is a useful tool to predict relapse in precursor-B-ALL," *British Journal of Haematology*, 104:695-705 (1999).

Coustan-Smith, E. et al., "Clinical importance of minimal residual disease in childhood acute lymphoblastic leukemia," *Blood*, 96(8):2691-2696 (2000).

Coustan-Smith, E. et al., "Early T-cell precursor leukaemia: a subtype of very high-risk acute lymphoblastic leukaemia," *Lancet Oncology*, 10:147-156 (2009).

Coustan-Smith, E. et al., "Prognostic importance of measuring early clearance of leukemic cells by flow cytometry in childhood acute lymphoblastic leukemia", Blood, 100(1):52-58 (2002).

Curran-Everett, D., "Multiple comparisons: philosophies and illustrations", *Am J Physiol Regulatory Integrative Comp Physiol.*, 279:R1-R8 (2000).

Dash, P. et al., "Paired analysis of TCR[alpha] and TCR[beta] chains at the single-cell level in mice", *Journal of Clinical Investigation*, 121(1):288-295 (2011).

De Jonge, H.J.M., et al., "Evidence Based Selection of Housekeeping Genes," *PLoS One*, 9(e989):1-5.(2007).

DeNucci, C.C. et al., "Integrin function in T-cell homing to lymphoid and nonlymphoid sites: getting there and staying there," *Critical Reviews in Immunology*, 29(2):87-109 (2009).

Dheda, K., et al., "Validation of housekeeping genes for normalizing RNA expression in real-time PCR," *Bio Techniques*, 37:112-119 (2004).

Dik, W., et al. "New insights on human T cell development by quantitative T cell receptor gene rearrangement studies and gene expression profiling," *JEM*, 201(11):1715-1723 (2005).

Dobosy, J. et al., "RNase H-dependent PCR (rhPCR): improved specificity and single nucleotide polymorphism detection using blocked cleavable primers," *BMC Biotechnology*, 11(80):1-18 (2011).

Droese, J., et al., "Validation of BIOMED-2 multiplex PCR tubes for detection of TCRB gene rearrangements in T-cell malignancies," *Leukemia*, 18:1531-1538 (2004).

Duby, A.U. et al., "Human T-cell receptor aberrantly rearranged beta-chain J1.5-Dx-J2.1 gene," PNAS, GenBank accession No. M13574.1, bases 1 to 100, 4 pages (1986).

Edwards and Gibbs, "Multiplex PCR: advantages, development, and applications," *Genome Research*, 3:S65-S75 (1994).

Elnifro, E.M., et al., "Multiplex PCR: Optimization and Application in Diagnostic Virology", *Clinical Microbiology Reviews*, 13(4):559-570 (2000).

Emerson, R.O. et al., "High-throughput sequencing of T-cell receptors reveals a homogeneous repertoire of tumour-infiltrating lymphocytes in ovarian cancer", *Journal of Pathology*, 231:433-440 (2013).

Flohr, T., et al., "Minimal residual disease-directed risk stratification using real-time quantitative PCT analysis of immunoglobulin and T-cell receptor gene rearrangements in the international multicenter trial AIEOP-BFM ALL 2000 for childhood acute lymphoblastic leukemia", *Leukemia*, 22:771-782 (2008).

Gerlinger, M. et al., "Ultra deep T cell receptor sequencing reveals the complexity and intratumour heterogeneity of T cell clones in renal cell carcinomas", *Journal of Pathology*, 231:424-432 (2013).

Gonzalez, S.F. et al., "Trafficking of B Cell Antigen in Lymph Nodes," *Ann. Rev. Immunol.*, 29:215-233 (2011).

Henegariu, O. et al., "Multiplex PCR: Critical Parameters and Step-By-Step Protocol," *Biotechniques*, Informa HealthCare, 23(3):504-511 (1997).

Hodges, E. et al., "Diagnostic role of tests for T cell receptor (TCR) genes", *J Clin Pathol.*, 56(1):1-11 2003).

Hwang, H.Y. et al., "Identification of a Commonly used CDR3 Region of Infiltrating T Cells Expressing Vβ13 and Vβ15 Derived from Psoriasis Patients", *The Journal of Investigative Dermatology*, 120(3):359-384 (2003).

Jochems and Schlom, "Tumor-infiltrating immune cells and prognosis: the potential link between conventional cancer therapy and immunity," *Experimental Biology and Medicine*, 236:567-579 (2011).

Kalinina, O. et al., "Nanoliter scale PCT with TaqMan detection," *Nucleic Acids Research*, 25(10):1999-2004 (1997).

Kalos, M. et al., "T Cells with Chimeric Antigen Receptors Have Potent Antitiumor Effects and Can Establish Memory in Patients with Advanced Leukemia", *Science Translational Medicine*, 3(95ra73):1-11 (2011).

Kaplinski and Remm, "MultiPLX Automatic Grouping and Evaluation of PCR Primers", *Methods in Molecular Biology*, 402(PCR Primer Design):287-303 (2004).

Katz, S.C. et al., "T Cell Infiltrate Predicts Long-Term Survival Following Resection of Colorectal Cancer Liver Metastases," *Ann. Surg. Oncol.*, 16:2524-2530 (2009).

Kehrl, J.H. et al., "Chemoattractant Receptor Signaling and Its Role in Lymphocyte Motility and Trafficking," *Current Topics in Microbiology and Immunology*, 334:107-127 (2009).

Kiianitsa, et al., "Development of Tools for T-Cell Repertoire Analysis (TCRB Spectratyping) for the Canine Model of Hematopoietic Cell Transplantation", *Blood*, ASH—Annual Meeting Abstracts, 110:Abstract 4873, 2 pages (2007).

Kneba, M., et al., "Analysis of Rearranged T-cell Receptor β-Chain Genes by Polymerase Chain Reaction (PCR) DNA Sequencing and Automated High Resolution PCR Fragment Analysis", *Blood*, 86:3930-3937 (1995).

Ladányi, A., et al., "Prognostic impact of β-cell density in cutaneous melanoma", *Cancer Immunol. Immunother*, 60(12):1729-1738 (2011).

Larimore, K., et al., "Shaping of Human Germline IgH Repertoires Revealed by Deep Sequencing," *The Journal of Immunology*, 189(6):3221-3230 (2012).

Ladetto, M. et al., "Real-Time Polymerase Chain Reaction of Immunoglobulin Rearrangements for Quantitative Evaluation of Minimal Residual Disease in Multiple Myeloma", *American Society for Blood and Marrow Transplantation*, 6(3):241-253 (2000).

Ladetto, M. et al., "Real-time polymerase chain reaction in multiple myeloma: Quantitative analysis of tumor contamination of stem cell harvests", *Experimental Hematology*, 30:529-536 (2002).

Lowe, T., et al., "A computer program for selection of oligonucleotide primers for polymerase chain reactions," *Nucleic Acids Research*, 18(7):1757-1761 (1990).

Lúcio, P. et al., "Flow cytometric analysis of normal B cell differentiation: a frame of reference for the detection of minimal residual disease in precursor-B-ALL", *Leukemia*, 13:419-427 (1999).

Mahmoud, S.M.A. et al., "Tumor-Infiltrating CDs+ Lymphocytes Predict Clinical Outcome in Breast Cancer", *Journal of Clinical Oncology*, 29(15):1949-1955 (2011).

Marelli-Berg, F.M., et al., "Memory T-cell trafficking: new directions for busy commuters," Immunology, 130:158-165 (2010).

Mariani, S. et al., "Comprehensive assessment of the TCRBV repertoire in small T-cell samples by means of an improved and convenient multiplex PCR method," *Experimental Hematology*, 37(6):728-738 (2009).

Markoulatos, P. et al., "Multiplex Polymerase Chain Reaction: A Practical Approach", *Journal of Clinical Laboratory Analysis*, 16:47-51 (2002).

Maryanski, J.L. et al., "A quantitative, single-cell PCR analysis of an antigen-specific TCR repertoire 8 selected during an in vivo CD8 response: direct evidence for a wide range of clone sizes with uniform tissue distribution", *Molecular Immunology*, 36:745-753 (1999).

Maślanka, K. et al., "Molecular Analysis of T-Cell Repertoires: Spectratypes Generated by Multiplex Polymerase Chain Reaction and Evaluated by Radioactivity or Fluorescence", *Human Technology*, 44(1):28-34 (1995).

Merriam-Webster, 4 pages (definition of "substantial," accessed Apr. 25, 2014).

Merriam-Webster, 2 pages (definition of "e.g.," accessed Apr. 25, 2014).

Miqueu, P. et al., "Statistical analysis of CDR3 length distributions for the assessment of T and B cell repertoire biases," *Molecular Immunology*, 44:1057-1064 (2007).

(56) References Cited

OTHER PUBLICATIONS

Monod, M.Y. et al., "IMGT/JunctionAnalysis: the first tool for the analysis of the immunoglobulin and T cell receptor complex V-J and V-D-J JUNCTIONs", *Bioinformatics*, 20(Suppl 1):i379-385 (2004).

Slightom, J.L. et al., "Homo sapiens germline beta T-cell receptor locus," NCBI Accession No. L36092 NCBI, 254 pages (2009) Retrieved from the Internet: <URL:http://www.ncbi.nlm.nih.gov/nuccore/L36092>.

Nicot, N. et al., "Housekeeping gene selection for real-time RT-PCR normalization in potato during biotic and abiotic stress," *Journal of Experimental Botany*, 56(421):2907-2914 (2005).

Nolan, T. et al., "Quantification of mRNA using real-time RT-PCR," Nature Protocols, 1(3):1559-1582 (2006).

PCT International Search Report and Written Opinion, PCT/US2010/021264, mailed Apr. 14, 2010, 7 pages.

PCT International Preliminary Report on Patentability, PCT/US2010/021264, mailed Jul. 19, 2011, 5 pages.

PCT International Search Report and Written Opinion, PCT/US2013/040221, mailed Sep. 23, 2013, 15 Pages.

PCT International Preliminary Report on Patentability, PCT/US2013/040221, dated Apr. 24, 2014, 41 pages.

PCT International Search Report and Written Opinion, PCT/US2010/037477, mailed Sep. 24, 2010, 10 pages.

PCT International Preliminary Report on Patentability, PCT/US2010/037477, dated Jan. 4, 2012, 7 pages.

PCT International Search Report and Written Opinion, PCT/US2012/061193, mailed Mar. 28, 2013, 13 pages.

PCT International Preliminary Report on Patentability, PCT/US2012/061193, mailed Apr. 22, 2014, 8 pages.

PCT International Search Report and Written Opinion, PCT/US2012/068617, mailed Mar. 28, 2013, 10 pages.

PCT International Preliminary Report on Patentability, PCT/US2012/068617, mailed Jun. 10, 2014, 6 pages.

PCT International Search Report and Written Opinion, PCT/US2013/062925, mailed Nov. 25, 2013, 12 pages.

PCT Second Written Opinion for PCT/US2013/062925 mailed Jan. 23, 2015, 7 pages.

PCT International Search Report and Written Opinion, PCT/US2011/049012, mailed Apr. 10, 2012, 9 pages.

PCT International Preliminary Report on Patentability, PCT/US2011/049012, dated Feb. 26, 2013, 5 pages.

PCT International Search Report and Written Opinion, PCT/US2013/045994, mailed Oct. 25, 2013, 15 pages.

PCT International Preliminary Report on Patentability, PCT/US2013/045994, dated Dec. 16, 2014, 10 pages.

PCT International Search Report and Written Opinion, PCT/US2011/026373, mailed Oct. 20, 2011, 17 pages.

PCT International Preliminary Report on Patentability, PCT/US2011/026373, dated Aug. 28, 2012, 11 pages.

PCT International Search Report and Written Opinion, PCT/US2014/030859, mailed Jul. 18, 2014, 7 pages.

Pekin, D. et al., "Quantitative and sensitive detection of rare mutations using droplet-based microfluidics", *Lab Chip*, 11(3):2156 (2011).

Perkel, J., "Overcoming the Challenges of Multiplex PCR," Biocompare Editorial Article, Oct. 23, 2012, 6 Pages, can be retrieved at URL:http://www.biocompare.com/Editorial-Articles/117895-Multiplex-PCR/>.

Pohl, G. and Shih, "Principle and applications of digital PCR," *Expert Rev. Mol. Diagn.*, 4(1):41-47 (2004).

Puisieux, I. et al., "Oligoclonality of Tumor-Infiltrating Lymphocytes from Human Melanomas," *The Journal of Immunology*, 153:2807-2818 (1994).

Rasmussen, T. et al., Quantitation of minimal residual disease in multiple myeloma using an allele-specific real-time PCR assay, *Experimental Hematology*, 28:1039-1045 (2000).

Reischl and Kochanowski, at al., "Quantitative PCR a Survey of the Present Technology," *Molecular Biotechnology*, 3:55-71 (1995).

Robins, H.S. et al., "Digital Genomic Quantification of Tumor Infiltrating Lymphocytes", *Science Translational Medicine*, 5:214ra169, 19 pages, Supplementary Materials (2013).

Robins, H., et al., "Ultra-sensitive detection of rare T cell clones", *Journal of Immunological Methods*, 375:14-19 (2012).

Rock, E.P. et al., "CDR3 Length in Antigen-specific Immune Receptors", *J. Exp. Med.*, 179:323-328 (1994).

Rosenberg, S.A. et al., "New Approach to the Adoptive Immunotherapy of Cancer with Tumor-Infiltrating Lymphocytes", *Science*, 233(4770):1318-1321 (1986).

Roshal, M. et al., "Immaturity Associated Antigens Are Lost During Induction for T Cell Lymphoblastic Leukemia: Implications for Minimal Residual Disease Detection", *Cytometry Part B (Clinical Cytometry)*, 78:139-146 (2010).

Rozen, S., et al., "Primer3 on the WWW for General Users and for Biologist Programmers," *Methods in Molecular Biology*, Bioinformatics Methods and Protocols, 132:365-386 (2000).

Saada, R. et al., "Models for antigen receptor gene rearrangement: CDR3 length", *Immunology and Cell Biology*, 85:323-332 (2007).

Santalucia, Jr., J., "Physical Principles and Visual-OMP Software for Optimal PCR Design," *Methods in Molecular Biology*, 402(PCR Primer Design):3-33, 40 pages (2007).

Santamaria, P. et al., "Beta-Cell-Cytotoxic CDS T Cells from Nonobese Diabetic Mice Use Highly Homologous T Cell Receptor a-Chain CDR3 Sequences", *The Journal of Immunology*, 154(5):2494-2503 (1995).

Schlissel, M.S. et al., "Leukemia and lymphoma: a cost of doing business for adaptive immunity", *Genes Dev.*, 20(12):1539-1544 (2006).

Schrappe, M. et al., "Late MRd response determines relapse risk overall and in subsets of childhood T-cell ALL: results of the AIEOP-BFM-ALL 2000 study",*Blood*, 118(8):2077-2084 (2011).

Silver, N. et al., "Selection of housekeeping genes for gene expression studies in human reticulocytes using real-time PCR", *BMC Molecular Biology*, 7(33):1-9 (2006).

Sint, D., et al., "Advances in multiplex PCR: balancing primer efficiencies and improving detection success," *Methods in Ecology and Evolution*, 3(5):898-905 (2012).

Standard Sequencing Primers, Max Planck Genome Center Cologne, Jan. 15, 2011, downloaded from https://genomecentre.mpipz.mpg.de/SeqOrderDB/export/sequencing-primers.html.

Stein and Nombela-Arrieta, "Chemokine control of lymphocyte trafficking: a general overview," *Immunology*, 116(10):1-12 (2005).

Steinmetz, O.M. et al., "Chemokines and B cells in renal inflammation and allograft rejection," Frontiers in Bioscience (Schol. Ed.), 1:13-22 (2009).

Straten, Per thor et al., "T-cell clonotypes in cancer", *Journal of Translational Medicine*, 2(1):11 (2004).

Supplementary European Search Report for European Application No. 10732172.1, dated May 29, 2012, 5 pages.

Szczepanski, T. at al., "Minimal residual disease in leukemia patients", *Lancet Oncology*, 2:409-417 (2001).

Tewhey, R. et al., "Corrigendum: Microdroplet-based PCR enrichment for large-scale targeted sequencing", *Nature Biotechnology*, 28(2):178, 1 page (2010).

Tewhey, R. et al., "Microdroplet-based PCR enrichment for large-scale targeted sequencing," *Nature Biotechnology*, 27(11):1025-1031 (2009).

Triebel, F. et al., "A Unique V-J-C-Rearranged Gene Encodes A y Protein Expressed on the Majority of CD3+ T Cell Receptor -a/fr Circulating Lymphocytes", *J. Exp. Med.*, 167:694-699 (1988).

Van Der Velden, V.H.J et al., "Analysis of minimal residual disease by Ig/TCR gene rearrangements: guidelines for interpretation of real-time quantitative PCR data," *Leukemia*, 21:604-611 (2007).

Van Der Velden, V.H.J et al., "Optimization of PCR-based minimal residual disease diagnostics for childhood acute lymphoblastic leukemia in a multi-center setting," *Leukemia*, 21:706-713 (2007).

Van Der Velden, V.H.J., et al., "Detection of minimal residual disease in hematologic malignancies by realtime quantitative PCR: principles, approaches, and laboratory aspects," *Leukemia*, 17:1013-1034 (2003).

Van Der Velden, V.H.J., et al., "Real-time quantitative PCR for detection of minimal residual disease before allogeneic stem cell trans-

(56) References Cited

OTHER PUBLICATIONS plantation predicts outcome in children with acute lymphoblastic leukemia", *Leukemia*, 15:1485-1487 (2001).
Van Dongen, J.J.M. et al., "Design and standardization of PCR primers and protocols for detection of clonal immunoglobulin and I-cell receptor gene recombinations in suspect lymphoproliferations: Report of the BIOMED-2 Concerted Action BMHC-CT98-3936", *Leukemia*, 17:2257-2317 (2003).
Van Dongen, J.J.M. et al., "Prognostic value of minimal residual disease in acute lymphoblastic leukaemia in childhood," *The Lancet*, 352:1731-1738 (1998).
Venturi, V. et al., "The molecular basis for public T-cell responses?" *Nature Reviews*, 8:231-238 (2008).
Venturi, V. et al., "TCR β-Chain Sharing in Human CD8+ T Cell Responses to Cytomegalovirus and EBV[1]", *The Journal of Immunology*, 181:7853-7862 (2008).
Verhagen, O.J.H.M., et al., "Application of germline IGH probes in real-time quantitative PCR for the detection of minimal residual disease in acute lymphoblastic leukemia," *Leukemia*, 14:1426-1435 (2000).
Volgelstein and Kinzler, "Digital PCR," *Genetics*, PNAS, 96:9236-9241 (1999).
Wang, X. et al., "Quantitative Measurement of Pathogen Specific Human Memory T Cell Repertoire Diversity using a CDR3 B-Specific Microarray", *BMC Genomics*, 8(329): 1-13 (2007).
Ward and Marelli-Berg, "Mechanisms of chemokine and antigen-dependent T-lymphocyte navigation," *Biochem. J.*, 418:13-27 (2009).
Weinstein, J.A. et al., "High-Throughput Sequencing of the Zebrafish Antibody Repertoire", *Science*, 324:807-810 (2009).
Wood, B., "9-Color and 10-Color Flow Cytometry in the Clinical Laboratory," *Arch Pathol Lab Med*, 130:680-690 (2006).
Wu, H.D. et al., "The Lymphocytic Infiltration in Calcific Aortic Stenosis Predominantly Consists of Clonally Expanded T Cells", *The Journal of Immunology*, 178(8):5329-5339 (2007).
Xu, W. et al., "A Novel Universal Primer-Multiplex-PCR Method with Sequencing Gel Electrophoresis Analysis," *PLoS One*, 7(1):e22900, pp. 1-10 (2012).
Yassai, M.B. et al., "A clonotype nomenclature for T cell receptors", *Immunogenetics*, 61:493-502 (2009).
Zhong, Q. et al., "Multiplex digital PCR: breaking the one target per color barrier of quantitative PCR", *Lab Chip*, 11:2167-2174 (2011).
US 8,642,750, 02/2014, Faham et al. (withdrawn)

* cited by examiner

QUANTIFICATION OF ADAPTIVE IMMUNE CELL GENOMES IN A COMPLEX MIXTURE OF CELLS

CROSS REFERENCE TO RELATED APPLICATIONS

This application is a continuation of U.S. patent application Ser. No. 14/199,167, filed Mar. 6, 2014, titled, "Quantification of Adaptive Immune Cell Genomes in a Complex Mixture of Cells", which is a continuation of U.S. patent application Ser. No. 13/656,265, filed Oct. 19, 2012, titled, "Quantification of Adaptive Immune Cell Genomes in a Complex Mixture of Cells", which claims the benefit of U.S. Provisional Patent Application Ser. No. 61/550,311, filed Oct. 21, 2011, titled, "Quantification of Adaptive Immune Cell Genomes in a Complex Mixture of Cells", all of which are incorporated herein by reference, in their entirety, for all purposes.

SEQUENCE LISTING

The Sequence Listing associated with this application is provided in text format in lieu of a paper copy, and is hereby incorporated by reference into the specification. The name of the text file containing the Sequence Listing is 22442US_CRF_sequencelisting.txt. This text file was created on Feb. 20, 2014, is about 359,060 bytes in size, and is being submitted electronically via EFS-Web.

BACKGROUND

1. Technical Field

The present disclosure relates generally to the highly sensitive quantification of the relative representation of adaptive immune cells in complex mixtures of cells using multiplex digital polymerase chain reaction (dPCR) or multiplex quantitative polymerase chain reaction (qPCR). In particular, the present disclosure relates to methods for quantitative determination of lymphocyte presence in complex tissues including solid tissues, such as quantification of tumor-infiltrating lymphocyte (TIL) genomes as a relative proportion of all cellular genomes that are represented in a tumor DNA sample, or quantification of the genomes of lymphocytes that have infiltrated somatic tissue in the pathogenesis of inflammation, allergy or autoimmune disease or in transplanted organs as a relative proportion of all cellular genomes that are represented in a tissue DNA sample.

2. Description of the Related Art

The adaptive immune system protects higher organisms against infections and other pathological events that may be attributable to foreign substances, using adaptive immune receptors, the antigen-specific recognition proteins that are expressed by hematopoietic cells of the lymphoid lineage and that are capable of distinguishing self from non-self molecules in the host. These lymphocytes may be found in the circulation and tissues of a host, and their recirculation between blood and the lymphatics has been described, including their extravasation via lymph node high endothelial venules, as well as at sites of infection, inflammation, tissue injury and other clinical insults. (See, e.g., Stein et al., 2005 *Immunol.* 116:1-12; DeNucci et al., 2009 *Crit. Rev. Immunol.* 29:87-109; Marelli-Berg et al., 2010 *Immunol.* 130:158; Ward et al., 2009 *Biochem. J.* 418:13; Gonzalez et al., 2011 *Ann. Rev. Immunol.* 29:215; Kehrl et al., 2009 *Curr. Top. Microb. Immunol.* 334:107; Steinmetz et al., 2009 *Front. Biosci.* (*Schol. Ed.*) 1:13.)

Accordingly, the dynamic nature of movement by lymphocytes throughout a host organism is reflected in changes in the qualitative (e.g., antigen-specificity of the clonally expressed adaptive immune receptor (immunoglobulin or T cell receptor), T cell versus B cell, T helper ($T_h$) cell versus T regulatory ($T_{reg}$) cell, effector T cell versus memory T cell, etc.) and quantitative distribution of lymphocytes among tissues, as a function of changes in host immune status.

For example, numerous studies have found an association between (i) the presence of tumor infiltrating lymphocytes (TIL) in a variety of solid tumors and (ii) patient prognosis and overall survival rates. In some studies, tumor infiltrating T cells having a specific phenotype (e.g., $CD8^+$ and $CD4^+$ T cells or regulatory T cells) are positive or negative predictors of survival (e.g., Jochems et al., 2011 *Experimental Biol. Med.* 236:567-579). In certain cases, however, TIL count alone is a predictor of long-term survival (e.g., Katz et al., 2009 *Ann. Surg. Oncol.* 16:2524-2530). Thus, quantitative determination of TIL counts has high prognostic value in a variety of cancers including colorectal, hepatocellular, gallbladder, pancreatic, esophageal, ovarian endometrial, cervical, bladder and urothelial cancers. While more is known about the association of tumor-infiltrating T cells, B cells are also known to infiltrate tumors and studies have shown an association of tumor-infiltrating B cells with survival advantage (e.g., Ladányi, et al., *Cancer Immunol. Immunother.* 60(12):1729-38, Jul. 21, 2011 (epub ahead of print).

The quantitative determination of the presence of adaptive immune cells (e.g., T and B lymphocytes) in diseased tissues may therefore provide useful information for diagnostic, prognostic and other purposes, such as in cancer, infection, inflammation, tissue injury and other conditions.

The adaptive immune system employs several strategies to generate a repertoire of T- and B-cell antigen receptors with sufficient diversity to recognize the universe of potential pathogens. B lymphocytes mature to express antibodies (immunoglobulins, Igs) that occur as heterodimers of a heavy (H) a light (L) chain polypeptide, while T lymphocytes express heterodimeric T cell receptors (TCR). The ability of T cells to recognize the universe of antigens associated with various cancers or infectious organisms is conferred by its T cell antigen receptor (TCR), which is made up of both an a (alpha) chain and a β (beta) chain or a γ (gamma) and a δ (delta) chain. The proteins which make up these chains are encoded by DNA, which employs a unique mechanism for generating the tremendous diversity of the TCR. This multi-subunit immune recognition receptor associates with the CD3 complex and binds to peptides presented by the major histocompatibility complex (MHC) class I and II proteins on the surface of antigen-presenting cells (APCs). Binding of TCR to the antigenic peptide on the APC is the central event in T cell activation, which occurs at an immunological synapse at the point of contact between the T cell and the APC.

Each TCR peptide contains variable complementarity determining regions (CDRs), as well as framework regions (FRs) and a constant region. The sequence diversity of αβ T cells is largely determined by the amino acid sequence of the third complementarity-determining region (CDR3) loops of the α and β chain variable domains, which diversity is a result of recombination between variable ($V_\beta$), diversity ($D_\beta$), and joining ($J_\beta$) gene segments in the β chain locus, and between analogous $V_\alpha$ and $J_\alpha$ gene segments in the α chain locus, respectively. The existence of multiple such gene segments in the TCR α and β chain loci allows for a large number of distinct CDR3 sequences to be encoded. CDR3 sequence diversity is further increased by independent addition and deletion of nucleotides at the $V_\beta$-$D_\beta$, $D_\beta$-$J_\beta$, and $V_\alpha$-$J_\alpha$ junctions during the process of TCR gene rearrangement. In this respect, immunocompetence is reflected in the diversity of TCRs.

The γδ TCR is distinctive from the αβ TCR in that it encodes a receptor that interacts closely with the innate immune system. TCRγδ, is expressed early in development, has specialized anatomical distribution, has unique pathogen and small-molecule specificities, and has a broad spectrum of innate and adaptive cellular interactions. A biased pattern of TCRγ V and J segment expression is established early in ontogeny as the restricted subsets of TCRγδ cells populate the mouth, skin, gut, vagina, and lungs prenatally. Consequently, the diverse TCRγ repertoire in adult tissues is the result of extensive peripheral expansion following stimulation by environmental exposure to pathogens and toxic molecules.

Igs expressed by B cells are proteins consisting of four polypeptide chains, two heavy chains (H chains) and two light chains (L chains), forming an $H_2L_2$ structure. Each pair of H and L chains contains a hypervariable domain, consisting of a $V_L$ and a $V_H$ region, and a constant domain. The H chains of Igs are of several types, μ, δ, γ, α, and β. The diversity of Igs within an individual is mainly determined by the hypervariable domain. Similar to the TCR, the V domain of H chains is created by the combinatorial joining of the $V_H$, $D_H$, and $J_H$ gene segments. Hypervariable domain sequence diversity is further increased by independent addition and deletion of nucleotides at the $V_H$-$D_H$, $D_H$-$J_H$, and $V_H$-$J_H$ junctions during the process of Ig gene rearrangement. In this respect, immunocompetence is reflected in the diversity of Igs.

Quantitative characterization of adaptive immune cells based on the presence in such cells of functionally rearranged Ig and TCR encoding genes that direct productive expression of adaptive immune receptors has been achieved using biological samples from which adaptive immune cells can be readily isolated in significant numbers, such as blood, lymph or other biological fluids. In these samples, adaptive immune cells occur as particles in fluid suspension. See, e.g., US 2010/0330571; see also, e.g., Murphy, *Janeway's Immunobiology* ($8^{th}$ Ed.), 2011 Garland Science, NY, Appendix I, pp. 717-762.

Current approaches to the detection and quantification of adaptive immune cells in tissues or organs from which adaptive immune cells cannot be readily isolated, however, are far more limited. For example, in solid tissues and solid tumors, adaptive immune cell detection typically requires histological detection in a small, non-representative sample such as a fixed or frozen section of a biopsy specimen, using laborious and at most semi-quantitative techniques such as immunohistochemistry or in situ hybridization (e.g., Bancroft and Gamble, *Theory and Practice of Histological Techniques*, Churchill Livingstone, 2007; Carson and Hladik, *Histotechnology: A Self-Instructional Text,* 2009 Am. Soc. Clin. Pathol.). In conventional practice, the excised tissue may be cut into a plurality of serial histological sections along substantially parallel planes, for analysis by any of a number of known histological, histochemical, immunohistological, histopathologic, microscopic (including morphometric analysis and/or three-dimensional reconstruction), cytological, biochemical, pharmacological, molecular biological, immunochemical, imaging or other analytical techniques, which techniques are known to persons skilled in the relevant art. See, e.g., Bancroft and Gamble, *Theory and Practice of Histological Techniques* ($6^{th}$ Ed.), 2007 Churchill Livingstone, Oxford, UK; Kiernan, *Histological and Histochemical Methods: Theory and Practice,* 2001 Cold Spring Harbor Laboratory Press, Cold Spring Harbor, N.Y.; M. A. Hayat (Ed.), *Cancer Imaging*—Vols. 1 and 2, 2007 Academic Press, NY.

Efforts to obtain meaningful quantitative data from such approaches are severely limited with regard to the number of adaptive immune cells that may have infiltrated a tissue, for instance, where high statistical significance cannot be achieved when sample collection depends on the number of events that can be detected by observation of a finite number of small fields on microscope slides. Alternatively, a tissue sample must be mechanically and/or enzymatically dissociated to produce a single-cell suspension that is amenable to flow immunocytofluorimetric analysis (e.g., Murphy, 2011, pp. 740-742), although such time-consuming and labor-intensive steps are likely to result in incomplete recovery of lymphocytes from the sample due to loss or destruction of a portion of the sample in the course of handling. These and related limitations of the current approaches compromise the quality of quantitative data that may be obtained.

Clearly there is a need for an improved method for quantifying adaptive immune cells in a complex biological sample containing a mixture of cells that are not all adaptive immune cells, without requiring the isolation of adaptive immune cells from the sample, e.g., without having to separate the adaptive immune cells from the non-adaptive immune cells. The presently described embodiments address this need and offer other related advantages.

BRIEF SUMMARY

In one aspect the present invention provides a method for quantifying the relative representation of adaptive immune cells in a test biological sample that comprises a mixture of cells, the mixture comprising adaptive immune cells and cells that are not adaptive immune cells, the method comprising (a) distributing test sample template DNA extracted from the test biological sample to form a set of assay samples, (b) amplifying said test sample template DNA in the set of assay samples in a multiplex digital polymerase chain reaction (dPCR) that comprises: (1) (i) a plurality of V-segment oligonucleotide primers that are each independently capable of specifically hybridizing to at least one polynucleotide encoding a T cell receptor (TCR) V-region polypeptide or an immunoglobulin (Ig) V-region polypeptide, wherein each V-segment primer comprises a nucleotide sequence of at least 15 contiguous nucleotides that is complementary to at least one functional TCR or Ig V-encoding gene segment and wherein the plurality of V-segment primers specifically hybridize to substantially all functional TCR or Ig V-encoding gene segments that are present in the test sample, and (ii) a plurality of J-segment oligonucleotide primers that are each independently capable of specifically hybridizing to at least one polynucleotide encoding a T cell receptor (TCR) J-region polypeptide or an immunoglobulin (Ig) J-region polypeptide, wherein each J-segment primer comprises a nucleotide sequence of at least 15 contiguous nucleotides that is complementary to at least one functional TCR or Ig J-encoding gene segment and wherein the plurality of J-segment primers specifically hybridize to substantially all functional TCR or Ig J-encoding gene segments that are present in the test sample, wherein the V-segment and J-segment primers are capable of amplifying in said multiplex dPCR substantially all rearranged TCR or Ig CDR3-encoding regions in the test sample to produce a multiplicity of amplified rearranged DNA molecules from the adaptive immune cells in the test sample; and (2) a set of control primers to produce an internal control gene amplification product, wherein the set of control primers amplifies an internal control gene segment that is not specific to adaptive immune cells; and (c) comparing a first number of assay samples that detectably contain said multiplicity of amplified rearranged DNA molecules of (b)(1) with a second number of assay samples that detectably contain said internal control gene amplification product of (b)(2), and therefrom quantifying the relative representation of adaptive immune cells in said test biological sample.

In certain embodiments the plurality of V-segment oligonucleotide primers and the plurality of J-segment oligonucleotide primers comprise the sequences set forth in SEQ ID NOS:1-65, 644-708 and 843-883. In certain embodiments either or both of (i) the V-segment oligonucleotide primers comprise one or a plurality of oligonucleotides that exhibit at least 90% sequence identity to one or more of the nucleotide sequences set forth in SEQ ID NOS:1-52, 644-685, and 880-883, and (ii) the J-segment primers comprise one or a plurality of oligonucleotides that exhibit at least 90% sequence identity to one or more of the nucleotide sequences set forth in SEQ ID NOS:53-65, 696-708, and 880-883. In certain embodiments each amplified rearranged DNA molecule in the multiplicity of amplified rearranged DNA molecules is less than 600 nucleotides in length. In certain embodiments each functional TCR or Ig V-encoding gene segment comprises a V gene recombination signal sequence (RSS) and each functional TCR or Ig J-encoding gene segment comprises a J gene RSS, and wherein each amplified rearranged DNA molecule comprises (i) at least 10, 20, 30 or 40 contiguous nucleotides of a sense strand of the TCR or Ig V-encoding gene segment, said at least 10, 20, 30 or 40 contiguous nucleotides being situated 5' to the V gene RSS and (ii) at least 10, 20 or 30 contiguous nucleotides of a sense strand of the TCR or Ig J-encoding gene segment, said at least 10, 20 or 30 contiguous nucleotides being situated 3' to the J gene RSS.

In certain embodiments the above described method is capable of detecting a presence of at least ten adaptive immune cells per 10,000 cells in the mixture of cells. In certain embodiments the adaptive immune cells are T cells and in certain other embodiments the adaptive immune cells are B cells. In certain embodiments the biological sample is fresh tissue, frozen tissue, or fixed tissue. In certain embodiments the rearranged TCR or Ig CDR3-encoding regions are selected from rearranged TCR$\alpha$ CDR3-encoding regions, TCR$\beta$ CDR3-encoding regions, TCR$\gamma$ CDR3-encoding regions, TCR$\delta$ CDR3-encoding regions, IgH CDR3-encoding regions, Ig$\kappa$ CDR3-encoding regions, and Ig$\lambda$ CDR3-encoding regions. In certain embodiments the test biological sample comprises human cells, mouse cells, or rat cells. In certain embodiments either or both of the first and second numbers of assay samples are determined by detecting fluorescence of a non-specific DNA-intercalating dye in the assay samples. In certain embodiments the first number of assay samples is determined by detecting fluorescence of a labeled probe or of multiple labeled probes that specifically hybridize to the multiplicity of amplified rearranged DNA molecules, and the second number of assay samples is determined by detecting fluorescence of a labeled probe that specifically hybridizes to the internal control gene amplification products. In certain further embodiments the labeled probe that specifically hybridizes to the multiplicity of amplified rearranged DNA molecules comprises a sequence selected from SEQ ID NOS:66 and 709-839, or one or more of the multiple labeled probes that specifically hybridize to the multiplicity of amplified rearranged DNA molecules comprise one or more sequence selected from SEQ ID NOS:66 and 709-839.

In certain embodiments the test biological sample comprises somatic tissue, which in certain further embodiments is from a subject having an autoimmune disease and the tissue is targeted by an autoimmune reaction. In certain still further embodiments the autoimmune disease is selected from type 1 diabetes, rheumatoid arthritis, multiple sclerosis, Crohn's disease, Graves' disease, Addison's disease, celiac disease, Sjögren's, psoriasis, Guillian-Barre syndrome, and myasthenia gravis. In certain embodiments the somatic tissue comprises neoplastic tissue, which in certain further embodiments is obtained or derived from a solid tumor. In certain embodiments the somatic tissue is from a transplanted organ, which in certain further embodiments is selected from liver, lung, kidney, heart, spleen, pancreas, skin, intestine, and thymus. In certain further embodiments of the above described methods, the plurality of V-segment oligonucleotide primers and the plurality of J-segment oligonucleotide primers are RN2 modified.

Turning to another aspect of the present invention there is provided a method for assessing an effect of a therapeutic treatment on relative representation of adaptive immune cells in at least one tissue of a subject, the tissue comprising adaptive immune cells and cells that are not adaptive immune cells, the method comprising (I) obtaining one or a plurality of test biological samples from a first tissue of the subject at one or a plurality of time points prior to administering the therapeutic treatment, wherein the test biological sample contains DNA from a mixture of cells, the mixture comprising adaptive immune cells and cells that are not adaptive immune cells; (II) obtaining one or a plurality of test biological samples from a second tissue of the subject at one or a plurality of time points after administering the therapeutic treatment, wherein the test biological sample contains DNA from a mixture of cells, the mixture comprising adaptive immune cells and cells that are not adaptive immune cells; (III) for each of said test biological samples from (I) and (II): (a) distributing test sample template DNA extracted from the test biological sample to form a set of assay samples, (b) amplifying said test sample template DNA in the set of assay samples in a multiplex digital polymerase chain reaction (dPCR) that comprises: (1) (i) a plurality of V-segment oligonucleotide primers that are each independently capable of specifically hybridizing to at least one polynucleotide encoding a T cell receptor (TCR) V-region polypeptide or an immunoglobulin (Ig) V-region polypeptide, wherein each V-segment primer comprises a nucleotide sequence of at least 15 contiguous nucleotides that is complementary to at least one functional TCR or Ig V-encoding gene segment and wherein the plurality of V-segment primers specifically hybridize to substantially all functional TCR or Ig V-encoding gene segments that are present in the test sample, and (ii) a plurality of J-segment oligonucleotide primers that are each independently capable of specifically hybridizing to at least one polynucleotide encoding a T cell receptor (TCR) J-region polypeptide or an immunoglobulin (Ig) J-region polypeptide, wherein each J-segment primer comprises a nucleotide sequence of at least 15 contiguous nucleotides that is complementary to at least one functional TCR or Ig J-encoding gene segment and wherein the plurality of J-segment primers specifically hybridize to substantially all functional TCR or Ig J-encoding gene segments that are present in the test sample, wherein the V-segment and J-segment primers are capable of amplifying in said multiplex dPCR of substantially all rearranged TCR or Ig CDR3-encoding regions in the test sample to produce a multiplicity of amplified rearranged DNA molecules from the adaptive immune cells in the test sample; and (2) a set of control primers to produce an internal control gene amplification product, wherein the set of control primers amplifies an internal control gene DNA segment that is not specific to adaptive immune cells; and (c) comparing a first number of assay samples that detectably contain said multiplicity of amplified rearranged DNA molecules of (b)(1) with a second number of assay samples that detectably contain said internal control gene amplification product of (b)(2), and therefrom quantifying the relative representation of adaptive immune cells in said test biological sample; and (IV) comparing the relative representation of adaptive immune cells in at least one test biological sample obtained at a time point prior to administering the therapeutic treatment to the relative representation of adaptive immune cells in at least one test biological sample obtained at a time point after administering the therapeutic treatment, and thereby assessing an effect of the therapeutic treatment on relative representation of adaptive immune cells in at least one tissue of a subject.

In certain further embodiments the first and second tissues are the same tissue, and in certain other further embodiments the first and second tissues are different tissues. In certain embodiments the method assesses a dose-related effect of the therapeutic treatment, wherein a plurality of test biological samples are obtained from the second tissue of the subject at a plurality of time points after administering the therapeutic treatment, and wherein the therapeutic treatment is administered at a plurality of different dosages. In certain embodiments the method assesses a prognosis for the subject receiving the therapeutic treatment, wherein an altered relative representation of adaptive immune cells in at least one test biological sample obtained at a time point after administering the therapeutic treatment, compared to the relative representation of adaptive immune cells in at least one test biological sample obtained at a time point prior to administering the therapeutic treatment, indicates an effect of the therapeutic treatment on relative representation of adaptive immune cells in at least one tissue of a subject. In certain embodiments the method is selected from: (i) the method in which the subject has cancer and an increased relative representation of adaptive immune cells in at least one test biological sample obtained at a time point after administering the therapeutic treatment compared to the relative representation of adaptive immune cells in at least one test biological sample obtained at a time point prior to administering the therapeutic treatment, indicates a beneficial effect of the therapeutic treatment; (ii) the method in which the subject has an autoimmune disease and a decreased relative representation of adaptive immune cells in at least one test biological sample obtained at a time point after administering the therapeutic treatment compared to the relative representation of adaptive immune cells in at least one test biological sample obtained at a time point prior to administering the therapeutic treatment, indicates a beneficial effect of the therapeutic treatment; and (iii) the method in which the subject has a transplanted organ and a decreased relative representation of adaptive immune cells in at least one test biological sample from the transplanted organ obtained at a time point after administering the therapeutic treatment compared to the relative representation of adaptive immune cells in at least one test biological sample from the transplanted organ obtained at a time point prior to administering the therapeutic treatment, indicates a beneficial effect of the therapeutic treatment.

In certain embodiments of the above described methods, the method further comprises determining a polynucleotide sequence for each amplified rearranged DNA molecule from the population of adaptive immune cells in the test sample. In certain embodiments the plurality of V-segment oligonucleotide primers and the plurality of J-segment oligonucleotide primers comprise at least one of (1) the sequences set forth in SEQ ID NOS:1-65, (2) the sequences set forth in SEQ ID NOS:66-214, (3) the sequences set forth in SEQ ID NOS: 215-238, (4) the sequences set forth in SEQ ID NOs:239-545, (5) the sequences set forth in SEQ ID NOS:546-549 and 634-637, (6) the sequences set forth in SEQ ID NOS:550-633 and 638-643, (7) the sequences set forth in SEQ ID NOS:644-708, (8) the sequences set forth in SEQ ID NOS:644-773, (9) the sequences set forth in SEQ ID NOS:843-879, (10) the sequences set forth in SEQ ID NOS:880-883, and (11) portions of sequences (1) to (10) that are at least 15 nucleotides in length. In certain embodiments either or both of: (i) the V-segment oligonucleotide primers comprise one or a plurality of oligonucleotides that exhibit at least 90% sequence identity to one or more of: (1) the nucleotide sequences set forth in SEQ ID NOS:1-52, (2) the nucleotide sequences set forth in SEQ ID NOS:67-201, (3) the nucleotide sequences set forth in SEQ ID NOS:221-238, (4) the nucleotide sequences set forth in SEQ ID NOS:255-545, (5) the nucleotide sequences set forth in SEQ ID NOS:546-549, (6) the nucleotide sequences set forth in SEQ ID NOS:550-633, (7) the nucleotide sequences set forth in SEQ ID NOS:644-695, (8) the nucleotide sequences set forth in SEQ ID NOS:843-879, and (9) portions of sequences (1) to (8) that are at least 15 nucleotides in length; and (ii) the J-segment primers comprise one or a plurality of oligonucleotides that exhibit at least 90% sequence identity to one or more of: (1) the nucleotide sequences set forth in SEQ ID NOS:53-65, (2) the nucleotide sequences set forth in SEQ ID NOS:202-214, (3) the nucleotide sequences set forth in SEQ ID NOS:215-220, (4) the nucleotide sequences set forth in SEQ ID NOS:239-254, (5) the nucleotide sequences set forth in SEQ ID NOS:634-637, (6) the nucleotide sequences set forth in SEQ ID NOS:638-643, (7) the nucleotide sequences set forth in SEQ ID NOS: 696-708, (8) the nucleotide sequences set forth in SEQ ID NOS:880-883, and (9) portions of sequences (1) to (8) that are at least 15 nucleotides in length.

Turning to another embodiment of the presently disclosed invention, there is provided a method for quantifying the relative representation of adaptive immune cell DNA in a test biological sample that contains DNA from a mixture of cells, the mixture comprising adaptive immune cells and cells that are not adaptive immune cells, the method comprising: (a) amplifying test sample template DNA extracted from the test biological sample in a multiplex quantitative polymerase chain reaction (qPCR) that comprises: (i) a plurality of V-segment oligonucleotide primers that are each independently capable of specifically hybridizing to at least one polynucleotide encoding a T cell receptor (TCR) V-region polypeptide or an immunoglobulin (Ig) V-region polypeptide, wherein each V-segment primer comprises a nucleotide sequence of at least 15 contiguous nucleotides that is complementary to at least one functional TCR or Ig V-encoding gene segment and wherein the plurality of V-segment primers specifically hybridize to substantially all functional TCR or Ig V-encoding gene segments that are present in the test sample, and (ii) a plurality of J-segment oligonucleotide primers that are each independently capable of specifically hybridizing to at least one polynucleotide encoding a T cell receptor (TCR) J-region polypeptide or an immunoglobulin (Ig) J-region polypeptide, wherein each J-segment primer comprises a nucleotide sequence of at least 15 contiguous nucleotides that is complementary to at least one functional TCR or Ig J-encoding gene segment and wherein the plurality of J-segment primers specifically hybridize to substantially all functional TCR or Ig J-encoding gene segments that are present in the test sample, wherein the V-segment and J-segment primers are capable of promoting amplification in said multiplex polymerase chain reaction (PCR) of substantially all rearranged TCR or Ig CDR3-encoding regions in the test sample to produce a multiplicity of amplified rearranged DNA molecules from a population of adaptive immune cells in the test sample; and (b) concurrently with said step of amplifying, measuring at one or a plurality of time points a first DNA signal level that is detectable in said multiplicity of amplified rearranged DNA molecules of (a); (c) comparing at said one or plurality of time points the first DNA signal level measured in (b) to a second DNA signal level that is detectable in amplification products of a known amount of control adaptive immune cell template DNA extracted from a control adaptive immune cell sample that has been amplified by the plurality of V-segment oligonucleotide primers and the plurality of J-segment oligonucleotide primers, and therefrom quantifying a relative amount of adaptive immune cell DNA in the test sample template DNA extracted from the test biological sample; and (d) determining, from the relative amount of adaptive immune cell DNA quantified in (c), the relative representation of adaptive immune cell DNA in the test biological sample.

In certain embodiments the plurality of V-segment oligonucleotide primers and the plurality of J-segment oligonucleotide primers comprise the sequences set forth in SEQ ID NOS:1-65, 644-708, and 843-883. In certain embodiments either or both of: (i) the V-segment oligonucleotide primers comprise one or a plurality of oligonucleotides that exhibit at least 90% sequence identity to one or more of the nucleotide sequences set forth in SEQ ID NOS:1-52, 644-695, and 843-879; and (ii) the J-segment primers comprise one or a plurality of oligonucleotides that exhibit at least 90% sequence identity to one or more of the nucleotide sequences set forth in SEQ ID NOS:53-65, 696-708, and 880-883. In certain embodiments each amplified rearranged DNA molecule in the multiplicity of amplified rearranged DNA molecules is less than 600 nucleotides in length. In certain embodiments each functional TCR or Ig V-encoding gene segment comprises a V gene recombination signal sequence (RSS) and each functional TCR or Ig J-encoding gene segment comprises a J gene RSS, and wherein each amplified rearranged DNA molecule comprises (i) at least 10, 20, 30 or 40 contiguous nucleotides of a sense strand of the TCR or Ig V-encoding gene segment, said at least 10, 20, 30 or 40 contiguous nucleotides being situated 5' to the V gene RSS and (ii) at least 10, 20 or 30 contiguous nucleotides of a sense strand of the TCR or Ig J-encoding gene segment, said at least 10, 20 or 30 contiguous nucleotides being situated 3' to the J gene RSS. In certain embodiments the above described method is capable of detecting a presence of at least ten adaptive immune cells per 10,000 cells in the mixture of cells. In certain embodiments the adaptive immune cells are T cells. In certain embodiments the adaptive immune cells are B cells. In certain embodiments the biological sample is fresh tissue, frozen tissue, or fixed tissue. In certain embodiments the rearranged TCR or Ig CDR3-encoding regions are selected from rearranged TCRα CDR3-encoding regions, TCRβ CDR3-encoding regions, TCRγ CDR3-encoding regions, TCRδ, CDR3-encoding regions, IgH CDR3-encoding regions, Igκ CDR3-encoding regions, and Igλ CDR3-encoding regions.

In certain further embodiments of the above described methods, the test biological sample and the control adaptive immune cell sample comprise cells that are selected from human cells, mouse cells and rat cells. In certain embodiments either or both of the first and second DNA signal levels are measured by detecting fluorescence of a non-specific DNA-intercalating dye. In certain embodiments the first DNA signal level is measured by detecting fluorescence of a labeled probe or of multiple labeled probes that specifically hybridize to the multiplicity of amplified rearranged DNA molecules and the second DNA signal level is measured by detecting fluorescence of a labeled probe or of multiple labeled probes that specifically hybridize to the amplification products of the control adaptive immune cell template DNA. In certain further embodiments the labeled probe that specifically hybridizes to the multiplicity of amplified rearranged DNA molecules comprises a sequence selected from SEQ ID NOS:66 and 709-839, or one or more of the multiple labeled probes that specifically hybridize to the multiplicity of amplified rearranged DNA molecules comprise a sequence selected from SEQ ID NOS:66 and 709-839.

In certain further embodiments of the above described methods, the method comprises quantifying a relative amount of DNA in the mixture of cells that comprises adaptive immune cells and cells that are not adaptive immune cells, the method comprising: (e) amplifying test sample template DNA extracted from the test biological sample with a set of control primers to produce internal control gene amplification products, wherein the set of control primers amplifies an internal control gene DNA segment that is not specific to adaptive immune cells; (f) concurrently with step (e), measuring at one or a plurality of time points a third DNA signal level that is detectable in the amplification products of (e); (g) comparing, at said one or plurality of time points, the third DNA signal level in (f) to a fourth DNA signal level that is detectable in amplification products of a known amount of internal control gene DNA that has been amplified by the control primers, and therefrom quantifying a relative amount of internal control gene DNA in the test sample template DNA extracted from the test biological sample; and (h) determining, from the relative amount of internal control gene DNA quantified in (g), the relative amount of DNA in the mixture of cells.

In certain further embodiments the control primers are present in the qPCR reaction of (a). In certain embodiments, in step (e) the control primers are present in a qPCR reaction that is separate from the qPCR reaction of (a). In certain embodiments the test biological sample comprises somatic tissue, which in certain further embodiments is from a subject having an autoimmune disease and the tissue is targeted by an autoimmune reaction. In certain still further embodiments the autoimmune disease is selected from type 1 diabetes, rheumatoid arthritis, multiple sclerosis, Crohn's disease, Graves' disease, Addison's disease, celiac disease, Sjögren's, psoriasis, Guillian-Barre syndrome, and myasthenia gravis. In certain embodiments the somatic tissue comprises neoplastic tissue, which in certain further embodiments is obtained or derived from a solid tumor. In certain other embodiments the somatic tissue is from a transplanted organ, which in certain further embodiments is selected from liver, lung, kidney, heart, spleen, pancreas, skin, intestine, and thymus. In certain embodiments the plurality of V-segment oligonucleotide primers and the plurality of J-segment oligonucleotide primers are RN2 modified.

Turning to another embodiment, there is provided herein a method for assessing an effect of a therapeutic treatment on relative representation of adaptive immune cells in at least one tissue of a subject, the tissue comprising adaptive immune cells and cells that are not adaptive immune cells, the method comprising: (I) obtaining one or a plurality of test biological samples from a first tissue of the subject at one or a plurality of time points prior to administering the therapeutic treatment, wherein the test biological sample contains DNA from a mixture of cells, the mixture comprising adaptive immune cells and cells that are not adaptive immune cells; (II) obtaining one or a plurality of test biological samples from a second tissue of the subject at one or a plurality of time points after administering the therapeutic treatment, wherein the test biological sample contains DNA from a mixture of cells, the mixture comprising adaptive immune cells and cells that are not adaptive immune cells; (III) for each of said test biological samples from (I) and (II): (a) amplifying test sample template DNA extracted from the test biological sample in a multiplex quantitative polymerase chain reaction (qPCR) that comprises: (i) a plurality of V-segment oligonucleotide primers that are each independently capable of specifically hybridizing to at least one polynucleotide encoding a T cell receptor (TCR) V-region polypeptide or an immunoglobulin (Ig) V-region polypeptide, wherein each V-segment primer comprises a nucleotide sequence of at least 15 contiguous nucleotides that is complementary to at least one functional TCR or Ig V-encoding gene segment and wherein the plurality of V-segment primers specifically hybridize to substantially all functional TCR or Ig V-encoding gene segments that are present in the test sample, and (ii) a plurality of J-segment oligonucleotide primers that are each independently capable of specifically hybridizing to at least one polynucleotide encoding a T cell receptor (TCR) J-region polypeptide or an immunoglobulin (Ig) J-region polypeptide, wherein each J-segment primer comprises a nucleotide sequence of at least 15 contiguous nucleotides that is complementary to at least one functional TCR or Ig J-encoding gene segment and wherein the plurality of J-segment primers specifically hybridize to substantially all functional TCR or Ig J-encoding gene segments that are present in the test sample, wherein the V-segment and J-segment primers are capable of promoting amplification in said multiplex polymerase chain reaction (PCR) of substantially all rearranged TCR or Ig CDR3-encoding regions in the test sample to produce a multiplicity of amplified rearranged DNA molecules from a population of adaptive immune cells in the test sample; and (b) concurrently with said step of amplifying, measuring at one or a plurality of time points a first DNA signal level that is detectable in said multiplicity of amplified rearranged DNA molecules of (a); (c) comparing at said one or plurality of time points the first DNA signal level measured in (b) to a second DNA signal level that is detectable in amplification products of a known amount of control adaptive immune cell template DNA extracted from a control adaptive immune cell sample that has been amplified by the plurality of V-segment oligonucleotide primers and the plurality of J-segment oligonucleotide primers, and therefrom quantifying a relative amount of adaptive immune cell DNA in the test sample template DNA extracted from the test biological sample; and (d) determining, from the relative amount of adaptive immune cell DNA quantified in (c), the relative representation of adaptive immune cell DNA in the test biological sample; and (IV) comparing the relative representation of adaptive immune cell DNA in at least one test biological sample obtained at a time point prior to administering the therapeutic treatment to the relative representation of adaptive immune cell DNA in at least one test biological sample obtained at a time point after administering the therapeutic treatment, and thereby assessing an effect of the therapeutic treatment on relative representation of adaptive immune cells in at least one tissue of a subject.

In certain further embodiments the first and second tissues are the same tissue, and in certain other further embodiments the first and second tissues are different tissues. In certain embodiments of the above described method, step (III) further comprises, for each test biological sample, quantifying a relative amount of DNA in the mixture of cells that comprises adaptive immune cells and cells that are not adaptive immune cells, the method comprising: (e)amplifying test sample template DNA extracted from the test biological sample with a set of control primers to produce internal control gene amplification products, wherein the set of control primers amplifies an internal control gene DNA segment that is not specific to adaptive immune cells; (f) concurrently with step (e), measuring at one or a plurality of time points a third DNA signal level that is detectable in the amplification products of (e); (g) comparing, at said one or plurality of time points, the third DNA signal level in (f) to a fourth DNA signal level that is detectable in amplification products of a known amount of internal control gene DNA that has been amplified by the control primers, and therefrom quantifying a relative amount of internal control gene DNA in the test sample template DNA extracted from the test biological sample; and (h) determining, from the relative amount of internal control gene DNA quantified in (g), the relative amount of DNA in the mixture of cells. In certain embodiments the method assesses a dose-related effect of the therapeutic treatment, wherein a plurality of test biological samples are obtained from the second tissue of the subject at a plurality of time points after administering the therapeutic treatment, and wherein the therapeutic treatment is administered at a plurality of different dosages. In certain embodiments the method assesses a prognosis for the subject receiving the therapeutic treatment, wherein an altered relative representation of adaptive immune cell DNA in at least one test biological sample obtained at a time point after administering the therapeutic treatment compared to the relative representation of adaptive immune cell DNA in at least one test biological sample obtained at a time point prior to administering the therapeutic treatment, indicates an effect of the therapeutic treatment on relative representation of adaptive immune cells in at least one tissue of a subject.

In certain further embodiments the method is selected from: (i) the method in which the subject has cancer and an increased relative representation of adaptive immune cell DNA in at least one test biological sample obtained at a time point after administering the therapeutic treatment compared to the relative representation of adaptive immune cell DNA in at least one test biological sample obtained at a time point prior to administering the therapeutic treatment, indicates a beneficial effect of the therapeutic treatment; (ii) the method in which the subject has an autoimmune disease and a decreased relative representation of adaptive immune cell DNA in at least one test biological sample obtained at a time point after administering the therapeutic treatment compared to the relative representation of adaptive immune cell DNA in at least one test biological sample obtained at a time point prior to administering the therapeutic treatment, indicates a beneficial effect of the therapeutic treatment; and (iii) the method in which the subject has a transplanted organ and a decreased relative representation of adaptive immune cell DNA in at least one test biological sample from the transplanted organ obtained at a time point after administering the therapeutic treatment compared to the relative representation of adaptive immune cell DNA in at least one test biological sample from the transplanted organ obtained at a time point prior to administering the therapeutic treatment, indicates beneficial effect of the therapeutic treatment. In certain embodiments the method further comprises determining a polynucleotide sequence for each amplified rearranged DNA molecule from the population of adaptive immune cells in the test sample.

In certain other further embodiments the plurality of V-segment oligonucleotide primers and the plurality of J-segment oligonucleotide primers comprise at least one of (1) the sequences set forth in SEQ ID NOS:1-65, (2) the sequences set forth in SEQ ID NOS:67-214, (3) the sequences set forth in SEQ ID NOS:215-238, (4) the sequences set forth in SEQ ID NOS:239-545, (5) the sequences set forth in SEQ ID NOS:546-549 and 634-637, (6) the sequences set forth in SEQ ID NOS:550-633 and 638-643, (7) the sequences set forth in SEQ ID NOs:644-708, (8) the sequences set forth in SEQ ID NOS:644-773, (9) the sequences set forth in SEQ ID NOS:843-879, (10) the sequences set forth in SEQ ID NOS: 880-883, and (11) portions of sequences (1) to (10) that are at least 15 nucleotides in length.

In certain other further embodiments either or both of: (i) the V-segment oligonucleotide primers comprise one or a plurality of oligonucleotides that exhibit at least 90% sequence identity to one or more of: (1) the nucleotide sequences set forth in SEQ ID NOS:1-52, (2) the nucleotide sequences set forth in SEQ ID NOS:67-201, (3) the nucleotide sequences set forth in SEQ ID NOS:221-238, (4) the nucleotide sequences set forth in SEQ ID NOS:255-545, (5) the nucleotide sequences set forth in SEQ ID NOS:546-549, (6) the nucleotide sequences set forth in SEQ ID NOS:550-633, (7) the nucleotide sequences set forth in SEQ ID NOS: 644-695, (8) the nucleotide sequences set forth in SEQ ID NOS:843-879, and (9) portions of sequences (1) to (8) that are at least 15 nucleotides in length; and (ii) the J-segment primers comprise one or a plurality of oligonucleotides that exhibit at least 90% sequence identity to one or more of: (1) the nucleotide sequences set forth in SEQ ID NOS:53-65, (2) the nucleotide sequences set forth in SEQ ID NOS:202-214, (3) the nucleotide sequences set forth in SEQ ID NOS:215-220, (4) the nucleotide sequences set forth in SEQ ID NOS:239-254, (5) the nucleotide sequences set forth in SEQ ID NOS: 634-637, (6) the nucleotide sequences set forth in SEQ ID NOS:638-643, (7) the nucleotide sequences set forth in SEQ ID NOS:696-708, (8) the nucleotide sequences set forth in SEQ ID NO:880-883, and (9) portions of sequences (1) to (8) that are at least 15 nucleotides in length.

These and other aspects of the herein described invention embodiments will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the invention can be modified, if necessary, to employ concepts of the various patents, applications and publications to provide yet further embodiments.

BRIEF DESCRIPTION OF THE SEVERAL VIEWS OF THE DRAWINGS

FIG. 1A shows an amplification profile; FIG. 1B shows a standard curve generated from known amounts of peripheral blood T cell DNA, as used to extrapolate T cell concentrations in complex cell mixtures of peripheral blood and tissue DNA.

FIG. 5A shows dPCR T cell quantification using subgroups A-H by detection of rearranged TCR genes in template DNA from peripheral blood lymphocytes from a healthy donor. FIG. 5B shows dPCR T cell quantification by detecting TCR rearrangements when template DNA was obtained from a bone marrow sample obtained from a T-ALL patient (79.7% for the subgroup A segment, which was a pattern characteristic of the disease state of the patient). FIG. 5C shows dPCR T cell quantification results when template DNA was obtained from a patient with ETP T-ALL, characterized by a primary T cell clone that has not undergone TCR encoding DNA rearrangement.

DETAILED DESCRIPTION

Figure 1A:
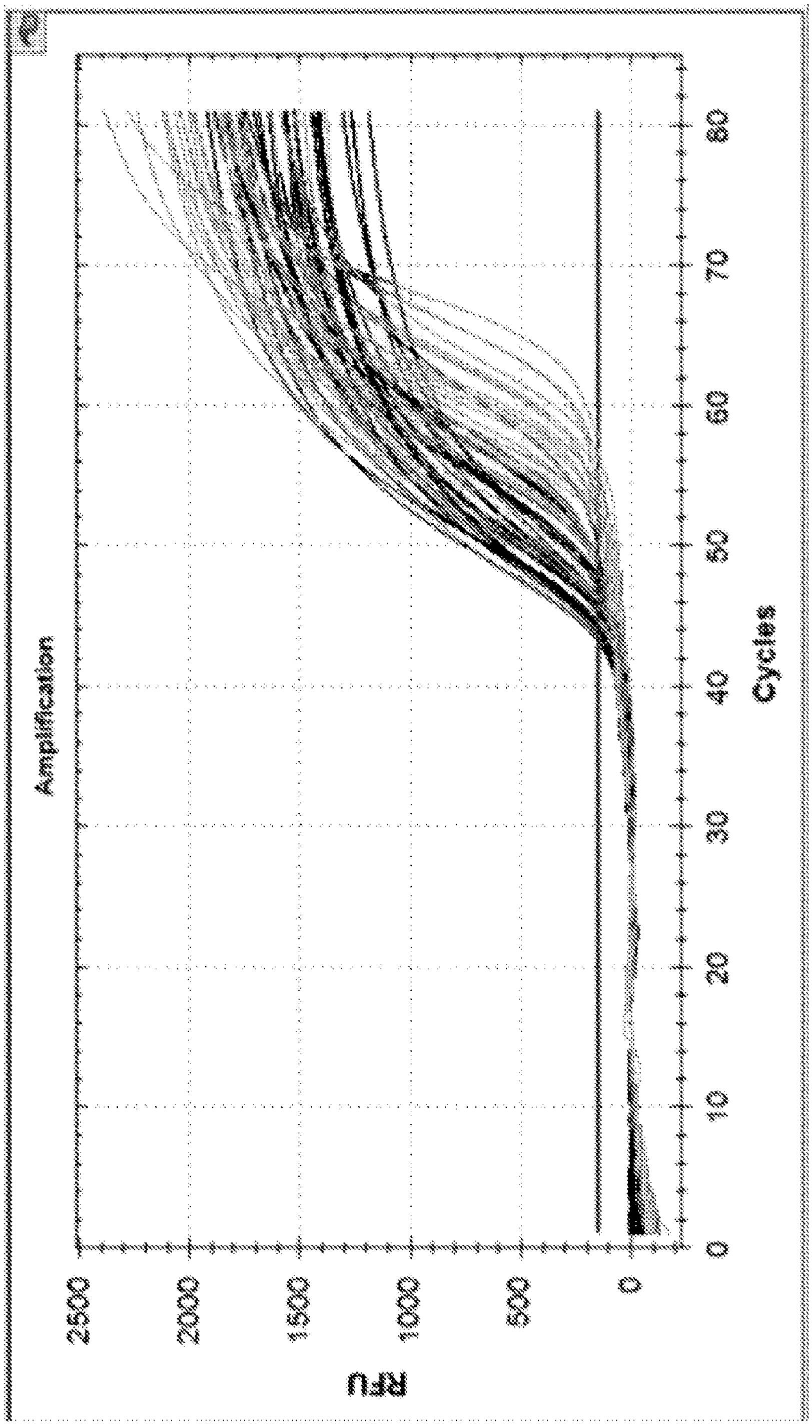
FIGS. 1A and 1B show quantitative PCR determination of the relative representation of T cell DNA in total DNA extracted from a tumor sample containing tumor infiltrating lymphocytes (TIL).

According to certain embodiments as described herein there is provided a highly sensitive and accurate method for determining the relative representation of adaptive immune cells in a biological sample that contains a mixture of cells, where the mixture comprises adaptive immune cells as provided herein, and also comprises cells that are not adaptive immune cells.

Based on the present disclosure, the relative representation of DNA from adaptive immune cells (e.g., T and/or B lymphocytes having rearranged adaptive immune receptor genes, including T- and B-lineage cells of different maturational stages such as precursors, blast cells, progeny or the like) in DNA from a sample of mixed cell types may be quantified. For instance, certain embodiments permit determination, in DNA extracted from a biological sample, of the relative representation of DNA from tumor infiltrating lymphocytes (TIL) in the DNA from the biological sample, where the sample comprises all or a portion of a tumor that contains adaptive immune cells and cells that are not adaptive immune cells (including tumor cells). Certain other embodiments, for example, permit determination, in DNA extracted from a biological sample, of the relative representation of DNA from infiltrating lymphocytes in the DNA from the biological sample, where the sample comprises all or a portion of a somatic tissue that contains adaptive immune cells and cells that are not adaptive immune cells, such as cells of a solid tissue.

In certain embodiments, as described herein and according to non-limiting theory, rearranged adaptive immune cell DNA is amplified in real time quantitative PCR using rearranged adaptive immune receptor-specific oligonucleotide primer sets to quantify an adaptive immune cell-specific DNA signal that may be used as a marker for the relative contribution of adaptive immune cells to the total DNA that is extracted from a sample of mixed cell types. The present embodiments therefore provide quantitative determination of the relative representation of adaptive immune cell DNA in a DNA sample extracted from a mixture of cells. The cells in the mixture of cells may not all be adaptive immune cells, and certain unforeseen advantages of the herein described embodiments are obtained where the cells in the mixture of cells need not all be adaptive immune cells. As described herein, compositions and methods are provided for quantifying the proportion of cellular genomes in a DNA sample that are contributed by adaptive immune cells relative to the total number of cellular genomes in the sample, starting from a DNA sample that has been extracted from a mixture of cell types, such as a solid tumor or a solid tissue.

Further according to non-limiting theory, the present embodiments exploit the capability, in a real time quantitative polymerase chain reaction (qPCR), that is afforded by oligonucleotide primer sets that specifically amplify substantially all rearranged adaptive immune receptor genes (e.g., CDR3 encoding polynucleotide-containing portions of rearranged T cell receptor and/or immunoglobulin genes) that may be present in a DNA sample, to generate a first detectable DNA signal that quantitatively reflects the production of a multiplicity of amplified rearranged adaptive immune receptor encoding DNA molecules. A second detectable DNA signal is generated, using the same oligonucleotide primer sets, in qPCR from a known amount of adaptive immune cell template DNA (e.g., sourced from a known number of adaptive immune cells or a known number of adaptive immune cell genomes), to produce a calibration curve, from which the relative amount of adaptive immune cell DNA reflected in the first detectable DNA signal can be determined.

Certain related embodiments may further include qPCR amplification and detection of a third detectable DNA signal that quantitatively reflects the production of a multiplicity of amplified DNA molecules, using template DNA extracted from the mixture of cells with oligonucleotide primers that amplify an internal control gene that is present in adaptive immune cells and in cells that are not adaptive immune cells, and generation of a fourth detectable DNA signal using such primers in qPCR amplification of a known amount of template internal control gene DNA, to produce a calibration curve from which the relative amount of DNA in the cell mixture and hence the number of cellular genomes (e.g., cell number) can be determined.

In another embodiment, the present disclosure provides a method for quantifying the relative representation of adaptive immune cells in a test biological sample using digital polymerase chain reaction (dPCR). Substantially all rearranged adaptive immune cell DNA is amplified in dPCR using rearranged adaptive immune receptor-specific oligonucleotide primer sets. The number of assay samples that detectably contain rearranged DNA amplified using diluted DNA from the test biological sample of interest as templates is compared to the number of assay samples that detectably contain an internal control gene amplified using the same diluted DNA as templates. Because the copy number of the internal control gene is known (e.g., 2), the relative representation of adaptive immune cells in the test biological sample (e.g., percentage of the total cells in the test biological sample that are adaptive immune cells) may be determined from the above comparison.

The present invention is thus directed in certain embodiments as described herein to quantification of DNA from adaptive immune cells that are present in solid tissues, and in particular embodiments, to solid tumors, such that the relative presence of adaptive immune cells as a proportion of all cell types that may be present in the tissue (e.g., tumor) can be determined. These and related embodiments are in part a result of certain surprising and heretofore unrecognized advantages disclosed in greater detail below that derive from exquisite sensitivity that is afforded, for the detection of adaptive immune cells, by the design of multiplexed qPCR or multiplexed dPCR using the herein described oligonucleotide primer sets. These primer sets permit production of amplified rearranged DNA molecules that encode portions of adaptive immune receptors. These and related embodiments feature the selection of a plurality of oligonucleotide primers that specifically hybridize to adaptive immune receptor (e.g., T cell receptor, TCR; or immunoglobulin, Ig) V-region polypeptide encoding polynucleotide sequences and J-region polypeptide encoding polynucleotide sequences. The primers promote qPCR amplification of DNA molecules that include substantially all rearranged TCR CDR3-encoding or Ig CDR3-encoding gene regions that may be present in a test biological sample, where the sample contains a mixture of cells which comprises adaptive immune cells (e.g., T- and B-lymphocyte lineage cells) and cells that are not adaptive immune cells. For example, a cell mixture may be obtained from a solid tumor that comprises tumor cells and TIL.

In certain embodiments, qPCR amplification may be monitored at one or a plurality of time points during the course of the qPCR reaction, i.e., in “real time”. Real-time monitoring permits determination of the quantity of DNA that is being generated by comparing a so-measured adaptive immune receptor-encoding DNA-quantifying signal to an appropriate control DNA-quantifying signal, which may be used as a calibration standard.

In certain other embodiments, rearranged adaptive immune cell DNA is quantified by dPCR. The DNA isolated from a test biological sample is distributed to form a set of assay samples, and the reaction is carried out in each assay sample individually. After the amplification, each assay sample produces either a negative result (i.e., no rearranged adaptive immune cell DNA is amplified) or a positive result (i.e., rearranged adaptive immune cell DNA is amplified). The amount of rearranged adaptive immune cell DNA may be quantified by counting the number of assay samples that produce positive results. For dPCR, the amplification process does not need to be monitored (as opposed to real time qPCR), which eliminates the reliance on uncertain exponential data to quantify target nucleic acid as in real time qPCR. In addition, dPCR does not require a calibration curve produced by amplifying a known amount of adaptive immune cell template DNA. Instead, dPCR amplifies an internal control (e.g., “housekeeping”) gene that is present in adaptive immune cells and in cells that are not adaptive immune cells, which allows the determination of the total numbers of cells from which the template DNA is extracted.

In certain embodiments, a test biological sample of interest comprises somatic tissue. The somatic tissue may comprise a solid tissue that is a site for autoimmune disease pathology, such as a tissue that is inappropriately targeted by a host’s immune system for an “anti-self” immune response. In certain other embodiments, the somatic tissue may comprise a solid tissue that is a site of an infection, such as a bacterial, yeast, viral or other microbial infection, for example, a Herpes Simplex Virus (HSV) infection. In yet other embodiments, the somatic tissue is from a transplanted organ (e.g., a transplanted liver, lung, kidney, heart, spleen, pancreas, skin, intestine and thymus). These and related embodiments, as described in greater detail below, will find uses in diagnostic, prognostic, disease monitoring, therapeutic efficacy monitoring and other contexts, thereby providing important information, such as quantification of adaptive immune cell representation in complex tissues that comprise a mixture of cell types. Adaptive immune cell quantification (e.g., quantification of the relative representation of adaptive immune cells in samples) or adaptive immune cell DNA quantification (e.g., quantification of the relative representation of adaptive immune cell DNA in samples that contain DNA from a mixture of cells) in tissues before and after, and/or during the course of treatment of a subject, will usefully provide information of relevance to the diagnosis and prognosis in patients having cancer, inflammation and/or autoimmune disease, or any of a number of other conditions that may be characterized by alterations (e.g., statistically significant increases or decreases) in adaptive immune cell presence in one or more tissues.

As provided herein, the relative representation of adaptive immune cells or their DNA may be quantified in adaptive immune cells or their DNA obtained from a test biological sample that contains a mixture of cells, including adaptive immune cells and cells that are not adaptive immune cells, where the test sample is obtained from a solid tissue in a subject such as a solid tumor, prior to, during and/or following administration of a therapeutic regimen to the subject. A test biological sample may be obtained, for example, by excision of tissue from a pre- or post-treatment subject.

Adaptive immune cell quantification or adaptive immune cell DNA quantification as an indicator of the relative presence of adaptive immune cells in a mixed cell population as described herein may, in certain embodiments, optionally be accompanied by evaluation or analysis of the tissue according to other art-accepted criteria. Indicators of status (e.g., evidence of presence or absence of pathology, or of efficacy of a previously or contemporaneously administered therapeutic treatment) may be, for example, detectable indicator compounds, nanoparticles, nanostructures or other compositions that comprise a reporter molecule which provides a detectable signal indicating the physiological status of a cell or tissue, such as a vital dye (e.g., Trypan blue), a colorimetric pH indicator, a fluorescent compound that may exhibit distinct fluorescence as a function of any of a number of cellular physiological parameters (e.g., pH, intracellular $Ca^{2+}$ or other physiologically relevant ion concentration, mitochondrial membrane potential, plasma membrane potential, etc., see Haugland, *The Handbook: A Guide to Fluorescent Probes and Labeling Technologies* ($10^{th}$ Ed.) 2005, Invitrogen Corp., Carlsbad, Calif.), an enzyme substrate, a specific oligonucleotide probe, a reporter gene, or the like.

Certain embodiments contemplate comparison of relative adaptive immune cell DNA quantities in view of total cell DNA (e.g., from adaptive immune cells plus non-adaptive immune cells in the cell mixture) and optionally other relevant parameters before, during or after administration to a control subject of control compositions that may be, for example, negative controls that have been previously demonstrated to have undergone no statistically significant alteration of physiological state, such as sham injection, saline, DMSO or other vehicle or buffer control, inactive enantiomers, scrambled peptides or nucleotides, etc.; and/or before, during or after administration of positive controls that have been previously demonstrated to cause a statistically significant alteration of physiological state, such as an FDA-approved therapeutic compound.

The subject or biological source, from which a test biological sample may be obtained, may be a human or non-human animal, or a transgenic or cloned or tissue-engineered (including through the use of stem cells) organism. In certain preferred embodiments of the invention, the subject or biological source may be known to have, or may be suspected of having or being at risk for having, a solid tumor or other malignant condition, or an autoimmune disease, or an inflammatory condition, and in certain preferred embodiments of the invention the subject or biological source may be known to be free of a risk or presence of such disease.

Certain preferred embodiments contemplate a subject or biological source that is a human subject such as a patient that has been diagnosed as having or being at risk for developing or acquiring cancer according to art-accepted clinical diagnostic criteria, such as those of the U.S. National Cancer Institute (Bethesda, Md., USA) or as described in *DeVita, Hellman, and Rosenberg's Cancer: Principles and Practice of Oncology* (2008, Lippincott, Williams and Wilkins, Philadelphia/Ovid, New York); Pizzo and Poplack, *Principles and Practice of Pediatric Oncology* (Fourth edition, 2001, Lippincott, Williams and Wilkins, Philadelphia/Ovid, New York); and Vogelstein and Kinzler, *The Genetic Basis of Human Cancer* (Second edition, 2002, McGraw Hill Professional, New York); certain embodiments contemplate a human subject that is known to be free of a risk for having, developing or acquiring cancer by such criteria.

Certain other embodiments contemplate a non-human subject or biological source, for example a non-human primate such as a macaque, chimpanzee, gorilla, vervet, orangutan, baboon or other non-human primate, including such non-human subjects that may be known to the art as preclinical models, including preclinical models for solid tumors and/or other cancers. Certain other embodiments contemplate a non-human subject that is a mammal, for example, a mouse, rat, rabbit, pig, sheep, horse, bovine, goat, gerbil, hamster, guinea pig or other mammal; many such mammals may be subjects that are known to the art as preclinical models for certain diseases or disorders, including solid tumors and/or other cancers (e.g., Talmadge et al., 2007 *Am. J. Pathol.* 170:793; Kerbel, 2003 *Canc. Biol. Therap.* 2(4 Suppl 1):S134; Man et al., 2007 *Canc. Met. Rev.* 26:737; Cespedes et al., 2006 *Clin. Transl. Oncol.* 8:318). The range of embodiments is not intended to be so limited, however, such that there are also contemplated other embodiments in which the subject or biological source may be a non-mammalian vertebrate, for example, another higher vertebrate, or an avian, amphibian or reptilian species, or another subject or biological source.

Biological samples may be provided by obtaining a blood sample, biopsy specimen, tissue explant, organ culture, biological fluid or any other tissue or cell preparation from a subject or a biological source. In certain preferred embodiments a test biological sample may be obtained from a solid tissue (e.g., a solid tumor), for example by surgical resection, needle biopsy or other means for obtaining a test biological sample that contains a mixture of cells.

Solid tissues are well known to the medical arts and may include any cohesive, spatially discrete non-fluid defined anatomic compartment that is substantially the product of multicellular, intercellular, tissue and/or organ architecture, such as a three-dimensionally defined compartment that may comprise or derive its structural integrity from associated connective tissue and may be separated from other body areas by a thin membrane (e.g., meningeal membrane, pericardial membrane, pleural membrane, mucosal membrane, basement membrane, omentum, organ-encapsulating membrane, or the like). Non-limiting exemplary solid tissues may include brain, liver, lung, kidney, prostate, ovary, spleen, lymph node (including tonsil), skin, thyroid, pancreas, heart, skeletal muscle, intestine, larynx, esophagus and stomach. Anatomical locations, morphological properties, histological characterization, and invasive and/or non-invasive access to these and other solid tissues are all well known to those familiar with the relevant arts.

Solid tumors of any type are contemplated as being suitable for characterization of TIL using the compositions and methods described herein. In certain preferred embodiments, the solid tumor may be a benign tumor or a malignant tumor, which may further be a primary tumor, an invasive tumor or a metastatic tumor. Certain embodiments contemplate a solid tumor that comprises one of a prostate cancer cell, a breast cancer cell, a colorectal cancer cell, a lung cancer cell, a brain cancer cell, a renal cancer cell, a skin cancer cell (such as squamous cell carcinoma, basal cell carcinoma, or melanoma) and an ovarian cancer cell, but the invention is not intended to be so limited and other solid tumor types and cancer cell types may be used. For example, the tumor may comprise a cancer selected from adenoma, adenocarcinoma, squamous cell carcinoma, basal cell carcinoma, melanoma (e.g., malignant melanoma), small cell carcinoma, large cell undifferentiated carcinoma, chondrosarcoma and fibrosarcoma, or the like. As also noted elsewhere herein, art-accepted clinical diagnostic criteria have been established for these and other cancer types, such as those promulgated by the U.S. National Cancer Institute (Bethesda, Md., USA) or as described in *DeVita, Hellman, and Rosenberg's Cancer: Principles and Practice of Oncology* (2008, Lippincott, Williams and Wilkins, Philadelphia/Ovid, New York); Pizzo and Poplack, *Principles and Practice of Pediatric Oncology* (Fourth edition, 2001, Lippincott, Williams and Wilkins, Philadelphia/Ovid, New York); and Vogelstein and Kinzler, *The Genetic Basis of Human Cancer* (Second edition, 2002, McGraw Hill Professional, New York). Other non-limiting examples of typing and characterization of particular cancers are described, e.g., in Ignatiadis et al. (2008 *Pathobiol.* 75:104); Kunz (2008 *Curr. Drug Discov. Technol.* 5:9); and Auman et al. (2008 *Drug Metab. Rev.* 40:303).

Accordingly, described herein are methods for measuring the number of adaptive immune cells, particularly T cells, in a complex mixture of cells. The present methods have particular utility in quantifying tumor-infiltrating lymphocytes or lymphocytes infiltrating somatic tissue that is the target of an autoimmune response. Existing methods for T and B cell quantification rely upon the physical separation of such cells from the mixture. However, in many cases, T and B cells cannot be separated from the initial sample, such as formalin-fixed or frozen tissue samples. Furthermore, prior methods for adaptive immune cell quantification (e.g., flow immunocytofluorimetry, fluorescence activated cell sorting (FACS), immunohistochemistry (IHC)) rely on the expression of T cell- or B cell-specific proteins, such as cell surface receptors. Since immune cells express varying amounts of these lineage specific receptors, quantifying the number of cells from such a highly variable measure requires costly standardization, specialized equipment and highly trained staff. The presently disclosed methods are, by contrast, platform-independent and can be performed on any real-time PCR instrument or dPCR instrument, and the reagents can be synthesized and provided in kit form. The presently disclosed methods are also highly sensitive and can be applied in high throughput settings not previously attainable. As described herein, quantification of adaptive immune cells may be achieved by a simple preparation of DNA from a complex mixture of cells, in concert with quantification of the relative proportion of adaptive immune cells present by amplification of the uniquely rearranged adaptive immune cell CDR3-encoding genes.

According to certain embodiments, a method for quantification of the relative contribution to total DNA in a sample that is made by DNA from adaptive immune cells in a test biological sample that contains a mixture of cells (only some of which are adaptive immune cells) by qPCR analysis of amplified (using the herein described V- and J-specific primer sets) rearranged V-segments and J-segments from the adaptive immune cell contribution to the DNA extracted from the test sample, may also comprise qPCR analysis of amplified rearranged V- and J-segments amplified (using the same V- and J-primer sets) from DNA extracted from a control adaptive immune cell sample that comprises a known number of adaptive immune cells. The control adaptive immune cell sample comprises a population of pure or substantially pure (e.g., greater than at least 70%, 75%, 80%, 85%, 90%, 95%, 97%, 98% or 99%) adaptive immune cells that may be obtained from a subject or biological source as provided herein. Amplification from a known amount of such control adaptive immune cell DNA that is used as a starting template, and measurement in qPCR of rearranged V-J-encoding amplification products, will permit the generation of a calibration curve from which to determine the quantity of amplified rearranged DNA molecules that are produced in the qPCR from a known number of adaptive immune cells. From such a calibration curve, the quantity of amplified rearranged DNA that is produced from the test biological sample may be compared, and from that quantity the number of adaptive immune cells in the test biological sample may be determined.

B cells and T cells can thus be obtained, for use as a control adaptive immune cell sample, from a biological sample, such as from a variety of tissue and biological fluid samples including bone marrow, thymus, lymph glands, lymph nodes, peripheral tissues and blood, but peripheral blood is most easily accessed. Any peripheral tissue can be sampled for the presence of B and T cells and is therefore contemplated for use in the methods described herein. Tissues and biological fluids from which adaptive immune cells, for use in a control adaptive immune cell sample, may be obtained include, but are not limited to skin, epithelial tissues, colon, spleen, a mucosal secretion, oral mucosa, intestinal mucosa, vaginal mucosa or a vaginal secretion, cervical tissue, ganglia, saliva, cerebrospinal fluid (CSF), bone marrow, cord blood, serum, serosal fluid, plasma, lymph, urine, ascites fluid, pleural fluid, pericardial fluid, peritoneal fluid, abdominal fluid, culture medium, conditioned culture medium or lavage fluid. In certain embodiments, adaptive immune cells may be isolated from an apheresis sample. Peripheral blood samples may be obtained by phlebotomy from subjects. Peripheral blood mononuclear cells (PBMC) are isolated by techniques known to those of skill in the art, e.g., by Ficoll-Hypaque® density gradient separation. In certain embodiments, whole PBMCs are used for analysis.

In certain related embodiments, preparations that comprise predominantly lymphocytes (e.g., T and B cells) or that comprise predominantly T cells or predominantly B cells, may be prepared for use as a control adaptive immune cell sample as provided herein, according to established, art-accepted methodologies. In other related embodiments, specific subpopulations of T or B cells may be isolated prior to analysis using the methods described herein. Various methods and commercially available kits for isolating different subpopulations of T and B cells are known in the art and include, but are not limited to, subset selection immunomagnetic bead separation or flow immunocytometric cell sorting using antibodies specific for one or more of any of a variety of known T and B cell surface markers. Illustrative markers include, but are not limited to, one or a combination of CD2, CD3, CD4, CD8, CD14, CD19, CD20, CD25, CD28, CD45RO, CD45RA, CD54, CD62, CD62L, CDw137 (41BB), CD154, GITR, FoxP3, CD54, and CD28. For example, and as is known to the skilled person, cell surface markers, such as CD2, CD3, CD4, CD8, CD14, CD19, CD20, CD45RA, and CD45RO may be used to determine T, B, and monocyte lineages and subpopulations in flow cytometry. Similarly, forward light-scatter, side-scatter, and/or cell surface markers such as CD25, CD62L, CD54, CD137, CD154 may be used to determine activation state and functional properties of cells.

Illustrative combinations useful in certain of the methods described herein may include $CD8^+CD45RO^{30}$ (memory cylotoxic T cells), $CD4^+CD45RO^+$ (memory T helper), $CD8^+CD45RO^-$ ($CD8^+CD62L^{+CD}45RA^+$ (naive-like cytotoxic T cells); $CD4^+CD25^+CD62L^{hi}GITR^{+FoxP}3+$ (regulatory T cells), Illustrative antibodies for use in immunomagnetic cell separations or flow immunocytometric cell sorting include fluorescently labeled anti-human antibodies, e.g., CD4 FITC (clone M-T446, Miltenyi Biotec), CD8 PE (clone RPA-T8, BD Biosciences), CD45RO ECD (clone. UCHL-1, Beckman Coulter), and CD45 RO APC (clone UCHL-1, Biosciences). Staining of total PBMC's may be done with the appropriate combination of antibodies, followed by washing cells before analysis. Lymphocyte subsets can he isolated by fluorescence activated cell sorting(FACS), e.g., by a BD FACSARIA™ cell-sorting system (BD Biosciences) and by analyzing results with FLOWJO™ software (Treestar Inc,), and also by conceptually similar methods involving specific antibodies immobilized to surfaces or beads.

For nucleic acid extraction, total genomic DNA may be extracted from cells using methods known in the art and/or commercially available kits, e.g., by using the QIAAMP® DNA blood Mini Kit (OIAGEN®). The approximate mass of a single haploid genome is 3 pg. Preferably, at least 100,000 to 200,000 cells are used for analysis, i.e., about 0.6 to 1.2 μg DNA from diploid T or B cells. Using PBMCs as a source, the number of T cells can be estimated to be about 30% of total cells. The number of B cells can also be estimated to be about 30% of total cells in a PBMC preparation.

Adaptive Immune Cell Receptors

The native TCR is a heterodimeric cell surface protein of the immunoglobulin superfamily which is associated with invariant proteins of the CD3 complex involved in mediating signal transduction. TCRs exist in αβ and γδ forms, which are structurally similar but have quite distinct anatomical locations and probably functions. The MHC class I and class II ligands, which bind to the TCR, are also immunoglobulin superfamily proteins but are specialized for antigen presentation, with a highly polymorphic peptide binding site which enables them to present a diverse array of short peptide fragments at the APC cell surface.

The extracellular portions of native heterodimeric αβ and γδ TCRs consist of two polypeptides each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. CDR3 of αβ TCRs interact with the peptide presented by MHC, and CDRs 1 and 2 of αβ TCRs interact with the peptide and the MHC. The diversity of TCR sequences is generated via somatic rearrangement of linked variable (V), diversity (D), joining (J), and constant genes.

The Ig and TCR gene loci contain many different variable (V), diversity (D), and joining (J) gene segments, which are subjected to rearrangement processes during early lymphoid differentiation. Ig and TCR V, D and J gene segment sequences are known in the art and are available in public databases such as GENBANK. TCRB V region gene segment sequences are set forth in the sequence listing at SEQ ID NOS:1-52, 66-201, 644-695, 709-839, and 843-879, and the TCRB J region segment sequences are set forth in SEQ ID NOS:53-65, 202-214, 696-708, and 880-883. TCRG J region gene segment sequences are set forth in SEQ ID NOs:215-220 and 634-637. TCRG V region gene segment sequences are set forth in SEQ ID NOs:221-238 and 546-549. IgH J region gene segment sequences are set forth in SEQ ID NOs: 239-254 and 638-643; IgH V region gene segment sequences are set forth in SEQ ID NOs:255-545 and 550-633.

The V-D-J rearrangements are mediated via a recombinase enzyme complex in which the RAG1 and RAG2 proteins play a key role by recognizing and cutting the DNA at the recombination signal sequences (RSS), which are located downstream of the V gene segments, at both sides of the D gene segments, and upstream of the J gene segments. Inappropriate RSS reduce or even completely prevent rearrangement. The recombination signal sequence (RSS) consists of two conserved sequences (heptamer, 5'-CACAGTG-3', and nonamer, 5'-ACAAAAACC-3'), separated by a spacer of either 12+/−1 bp ("12-signal") or 23+/−1 bp ("23-signal"). A number of nucleotide positions have been identified as important for recombination including the CA dinucleotide at position one and two of the heptamer, and a C at heptamer position three has also been shown to be strongly preferred as well as an A nucleotide at positions 5, 6, 7 of the nonamer. (Ramsden et al. 1994 *Nucl. Ac. Res.* 22:1785; Akamatsu et al. 1994 *J. Immunol.* 153:4520; Hesse et al. 1989 *Genes Dev.* 3:1053). Mutations of other nucleotides have minimal or inconsistent effects. The spacer, although more variable, also has an impact on recombination, and single-nucleotide replacements have been shown to significantly impact recombination efficiency (Fanning et al. 1996 *Cell. Immunol. Immumnopath.* 79:1, Larijani et al. 1999 *Nucl. Ac. Res.* 27:2304; Nadel et al. 1998 *J. Immunol.* 161:6068; Nadel et al. 1998 *J. Exp. Med.* 187:1495). Criteria have been described for identifying RSS polynucleotide sequences having significantly different recombination efficiencies (Ramsden et al. 1994 *Nucl. Ac. Res.* 22:1785; Akamatsu et al. 1994 *J. Immunol.* 153:4520; Hesse et al. 1989 *Genes Dev.* 3:1053, and Lee et al., 2003 *PLoS* 1(1):E1).

The rearrangement process generally starts with a D to J rearrangement followed by a V to D-J rearrangement in the case of Ig heavy chain (IgH), TCR beta (TCRB), and TCR delta (TCRD) genes or concerns direct V to J rearrangements in case of Ig kappa (IgK), Ig lambda (IgL), TCR alpha (TCRA), and TCR gamma (TCRG) genes. The sequences between rearranging gene segments are generally deleted in the form of a circular excision product, also called TCR excision circle (TREC) or B cell receptor excision circle (BREC).

The many different combinations of V, D, and J gene segments represent the so-called combinatorial repertoire, which is estimated to be ~2×10$^6$ for Ig molecules, ~3×10$^6$ for TCRαβ and ~5×10$^3$ for TCRγδ molecules. At the junction sites of the V, D, and J gene segments, deletion and random insertion of nucleotides occurs during the rearrangement process, resulting in highly diverse junctional regions, which significantly contribute to the total repertoire of Ig and TCR molecules, estimated to be $>10^{12}$.

Mature B-lymphocytes further extend their Ig repertoire upon antigen recognition in follicle centers via somatic hypermutation, a process, leading to affinity maturation of the Ig molecules. The somatic hypermutation process focuses on the V- (D-) J exon of IgH and Ig light chain genes and concerns single nucleotide mutations and sometimes also insertions or deletions of nucleotides. Somatically-mutated Ig genes are also found in mature B-cell malignancies of follicular or post-follicular origin.

In certain preferred embodiments described herein, V-segment and J-segment primers may be employed in a qPCR reaction or a dPCR reaction to amplify rearranged TCR or Ig CDR3-encoding DNA regions in a test biological sample, wherein each functional TCR or Ig V-encoding gene segment comprises a V gene recombination signal sequence (RSS) and each functional TCR or Ig J-encoding gene segment comprises a J gene RSS. In these and related embodiments, each amplified rearranged DNA molecule may comprise (i) at least about 10, 20, 30 or 40 contiguous nucleotides of a sense strand of the TCR or Ig V-encoding gene segment, with the at least about 10, 20, 30 or 40 contiguous nucleotides being situated 5' to the V gene RSS and/or each amplified rearranged DNA molecule may comprise (ii) at least about 10, 20 or 30 contiguous nucleotides of a sense strand of the TCR or Ig J-encoding gene segment, with the at least about 10, 20 or 30 contiguous nucleotides being situated 3' to the J gene RSS.

Multiplex Quantitative PCR

As described herein there is provided a method for quantifying the relative representation of adaptive immune cell DNA in DNA from a test biological sample of mixed cell types, and thus for estimating the relative number of T or B cells in a complex mixture of cells. According to certain embodiments, the method involves a multiplex PCR method using a set of forward primers that specifically hybridize to the V segments and a set of reverse primers that specifically hybridize to the J segments where the multiplex PCR reaction allows amplification of all the possible VJ (and VDJ) combinations within a given population of T or B cells. Because the multiplex PCR reaction amplifies substantially all possible combinations of V and J segments, it is possible to determine, using real-time quantitative PCR, the relative number of T cell or B cell genomes in a sample comprising a mixed population of cells. In particular, in order to measure the relative number of TCR or BCR genomes, it is assumed that there is 3 pg DNA per genome, or 6 pg per diploid cell. Once the amount of starting DNA is calculated using real-time qPCR with appropriate standards/controls as described further herein, from this number it is possible to calculate the number of TCR or BCR genomes. A standard DNA dilution panel of TCR genomes is used as a control to determine the amount of DNA in pg or μg in a given sample.

DNA or RNA may be extracted from a mixed population of cells from a sample, such as any neoplastic tissue sample or a sample of somatic tissue that is the target of an autoimmune reaction, blood sample, or cerebrospinal fluid, using standard methods or commercially available kits known in the art. Illustrative samples for use in the present methods include any type of solid tumor, in particular, from colorectal, hepatocellular, gallbladder, pancreatic, esophageal, lung, breast, prostate, head and neck, renal cell carcinoma, ovarian, endometrial, cervical, bladder and urothelial cancers. Any solid tumor in which tumor-infiltrating lymphocytes are to be assessed is contemplated for use in the present methods. Somatic tissues that are the target of an autoimmune reaction that are contemplated for analysis using the methods herein include, but are not limited to, joint tissues, skin, intestinal tissue, all layers of the uvea, iris, vitreous tissue, heart, brain, lungs, blood vessels, liver, kidney, nerve tissue, muscle, spinal cord, pancreas, adrenal gland, tendon, mucus membrane, lymph node, thyroid, endometrium, connective tissue, and bone marrow. In certain embodiments, DNA or RNA may be extracted from a transplanted organ, such as a transplanted liver, lung, kidney, heart, spleen, pancreas, skin, intestine, and thymus.

In certain embodiments, two or more samples may be obtained from a single tissue (e.g., a single neoplastic tissue) and the relative representations of adaptive immune cells in the two or more samples are quantified to consider variations in different sections of a test tissue. In certain other embodiments, the determination of the relative representation of adaptive immune cells in one sample from a test tissue is sufficient due to mimimum variations among different sections of the test tissue (see, e.g., Example 8).

A multiplex PCR system may be used to amplify rearranged adaptive immune cell receptor loci from genomic DNA, preferably from a CDR3 region. In certain embodiments, the CDR3 region is amplified from a TCRα, TCRβ, TCRγ or TCRδ CDR3 region or similarly from an IgH or IgL (lambda or kappa) locus.

Compositions are provided that comprise a plurality of V-segment and J-segment primers that are capable of promoting amplification in a multiplex polymerase chain reaction (PCR) of substantially all productively rearranged adaptive immune receptor CDR3-encoding regions in the sample for a given class of such receptors (e.g., TCRγ, TCRβ, IgH, etc.), to produce a multiplicity of amplified rearranged DNA molecules from a population of T cells (for TCR) or B cells (for Ig) in the sample.

Figure 2:
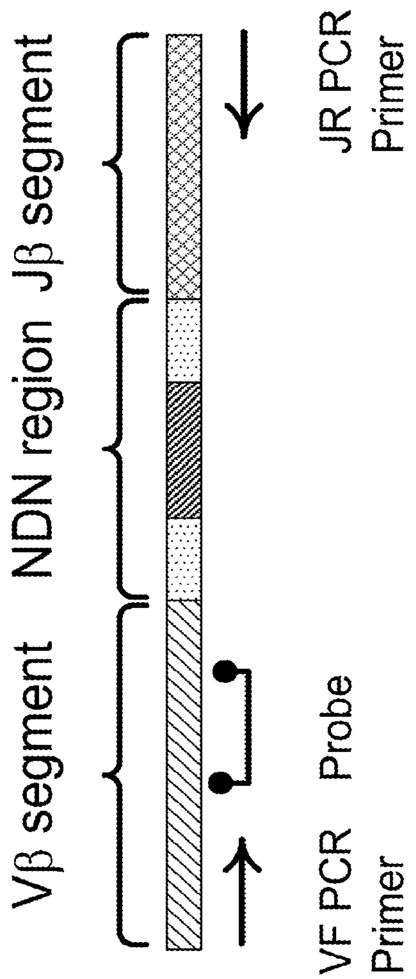
FIG. 2 is a schematic presentation of a PCR assay (e.g., a qPCR assay or a dPCR assay).

Preferably and in certain embodiments, primers are designed so that each amplified rearranged DNA molecule in the multiplicity of amplified rearranged DNA molecules is less than 600 nucleotides in length, thereby excluding amplification products from non-rearranged adaptive immune receptor loci. An exemplary schematic presentation of a qPCR assay (which may also serve as a schematic presentation of a dPCR assay) is shown in FIG. 2. The PCR assay uses forward primers and TaqMan® probes in each V segment and reverse primers in each J segment to selectively amplify the rearranged VDJ from each cell. While these primers can anneal to both rearranged and germline V and J gene segments, PCR amplification is limited to rearranged gene segments, due to size bias (e.g., 250 bp PCR product using rearranged gene segments as templates vs >10Kb PCR product using germline gene segments as templates).

In the human genome there are currently believed to be about 70 TCR Vα and about 61 Jα gene segments, about 52 TCR Vβ, about 2 Dβ and about 13 Jβ gene segments, about 9 TCR Vγ and about 5 Jγ gene segments, and about 46 immunoglobulin heavy chain (IGH) $V_H$, about 23 $D_H$ and about 6 $J_H$ gene segments. Accordingly, where genomic sequences for these loci are known such that specific molecular probes for each of them can be readily produced, it is believed according to non-limiting theory that the present compositions and methods relate to substantially all (e.g., greater than 90%, 91%, 92%, 93%, 94%, 95%, 96%, 97%, 98% or 99%) of these known and readily detectable adaptive immune receptor V-, D- and J-region encoding gene segments.

Primer selection and primer set design may be performed according to certain embodiments in a manner that preferably detects productive V and J gene segments, for example, by excluding TCR or IG pseudogenes. Pseudogenes may include V segments that contain an in-frame stop codon within the V-segment coding sequence, a frameshift between the start codon and the CDR3 encoding sequence, one or more repeat-element insertions, and deletions of critical regions, such as the first exon or the RSS. In the human IGH locus, for instance, the ImmunoGeneTics (IMGT) database (M.-P. LeFranc, Université Montpellier, Montpellier, France; www.imgt.org) annotates 165 V segment genes, of which 26 are orphons on other chromosomes and 139 are in the IGH locus at chromosome 14. Among the 139 V segments within the IGH locus, 51 have at least one functional allele, while 6 are ORFs (open-reading frames) which are missing at least one highly conserved amino-acid residue, and 81 are pseudogenes.

To detect functional TCR or IG rearrangements in a sample while avoiding potentially extraneous amplification signals that may be attributable to non-productive V and/or J gene segments such as pseudogenes and/or orphons, it is therefore contemplated according to certain embodiments to use a subset of oligonucleotide primers which is designed to include only those V segments that participate in a functional rearrangement to encode a TCR or IG, without having to include amplification primers specific to the pseudogene and/or orphon sequences or the like. Advantageous efficiencies with respect, inter alia, to time and expense are thus obtained.

The TCR and Ig genes can generate millions of distinct proteins via somatic mutation. Because of this diversity-generating mechanism, the hypervariable complementarity determining regions of these genes can encode sequences that can interact with millions of ligands, and these regions are linked to a constant region that can transmit a signal to the cell indicating binding of the protein's cognate ligand. The adaptive immune system employs several strategies to generate a repertoire of T- and B-cell antigen receptors with sufficient diversity to recognize the universe of potential pathogens. In αβ and γδ T cells, which primarily recognize peptide antigens presented by MHC molecules, most of this receptor diversity is contained within the third complementarity-determining region (CDR3) of the T cell receptor (TCR) α and β chains (or γ and δ chains).

The assay technology uses two pools of primers to provide for a highly multiplexed PCR reaction. The first, "forward" pool (e.g., by way of illustration and not limitation, V-segment oligonucleotide primers described herein may in certain preferred embodiments be used as "forward" primers when J-segment oligonucleotide primers are used as "reverse" primers according to commonly used PCR terminology, but the skilled person will appreciate that in certain other embodiments J-segment primers may be regarded as "forward" primers when used with V-segment "reverse" primers) includes an oligonucleotide primer that is specific to (e.g., having a nucleotide sequence complementary to a unique sequence region of) each V-region encoding segment ("V segment) in the respective TCR or Ig gene locus. In certain embodiments, primers targeting a highly conserved region are used, to simultaneously capture many V segments, thereby reducing the number of primers required in the multiplex PCR. Similarly, in certain embodiments, the "reverse" pool primers anneal to a conserved sequence in the joining ("J") segment.

Each primer may be designed so that a respective amplified DNA segment is obtained that includes a sequence portion of sufficient length to identify each J segment unambiguously based on sequence differences amongst known J-region encoding gene segments in the human genome database, and also to include a sequence portion to which a J-segment-specific primer may anneal for resequencing. This design of V- and J-segment-specific primers enables direct observation of a large fraction of the somatic rearrangements present in the adaptive immune receptor gene repertoire within an individual. This feature in turn enables rapid comparison of the TCR and/or Ig repertoires (i) in individuals having a particular disease, disorder, condition or other indication of interest (e.g., cancer, an autoimmune disease, an inflammatory disorder or other condition) with (ii) the TCR and/or Ig repertoires of control subjects who are free of such diseases, disorders conditions or indications.

The term "gene" means the segment of DNA involved in producing a polypeptide chain such as all or a portion of a TCR or Ig polypeptide (e.g., a CDR3-containing polypeptide); it includes regions preceding and following the coding region "leader and trailer" as well as intervening sequences (introns) between individual coding segments (exons), and may also include regulatory elements (e.g., promoters, enhancers, repressor binding sites and the like), and may also include recombination signal sequences (RSSs) as described herein.

The nucleic acids of the present embodiments, also referred to herein as polynucleotides, and including oligonucleotides, may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A coding sequence which encodes a TCR or an immunoglobulin or a region thereof (e.g., a V region, a D segment, a J region, a C region, etc.) for use according to the present embodiments may be identical to the coding sequence known in the art for any given TCR or immunoglobulin gene regions or polypeptide domains (e.g., V-region domains, CDR3 domains, etc.), or may be a different coding sequence, which, as a result of the redundancy or degeneracy of the genetic code, encodes the same TCR or immunoglobulin region or polypeptide.

In one embodiment, the present disclosure provides a plurality of V segment primers and a plurality of J segment primers, wherein the plurality of V segment primers and the plurality of J segment primers amplify substantially all combinations of the V and J segments of a rearranged immune receptor locus. By substantially all combinations is meant at least 90%, 91%, 92%, 93%, 94%, 95%, 96%, 97%, 98%, 99% or more of all the combinations of the V and J segments of a rearranged immune receptor locus. In certain embodiments, the plurality of V segment primers and the plurality of J segment primers amplify all of the combinations of the V and J segments of a rearranged immune receptor locus.

In general, a multiplex PCR system may use at least 14, 15, 16, 17, 18, 19, 20, 21, 22, 23, 24, or 25, and in certain embodiments, at least 26, 27, 28, 29, 30, 31, 32, 33, 34, 35, 36, 37, 38, or 39, and in other embodiments 40, 41, 42, 43, 44, 45, 46, 47, 48, 49, 50, 51, 52, 53, 54, 55, 56, 57, 58, 59, 60, 65, 70, 75, 80, 85, or more forward primers, in which each forward primer specifically hybridizes to or is complementary to a sequence corresponding to one or more V region segments. Illustrative V region primers for amplification of the TCRβ are shown in SEQ ID NOs:1-52 (see also Table 1). Illustrative TCRγ V region primers are provided in SEQ ID NOs:546-549. Illustrative IgH V region primers are provided in SEQ ID NOs:550-633. V region gene segment sequences may thus be used to design V region primers. Exemplary TCRB V region gene segment sequences are set forth in the sequence listing at SEQ ID NOS:1-52, 66-201, 644-695, 709-839, and 843-879. Exemplary TCRG V region gene segment sequences are set forth in SEQ ID NOs:221-238 and 546-549. Exemplary IgH V region gene segment sequences are set forth in SEQ ID NOs:255-545 and 550-633.

TABLE 1

Table 1A. TCRB oligonucleotide sequences targeting the 52 TCRBV and 13 TCRBJ gene segments.

| Primer Name | SEQ ID NO: | Sequence (5' to 3') |
|---|---|---|
| TRBV25-1 | 644 | GGAGATCTTTCCTCTGAGTCAACAGTCTCCAGAATA |
| TRBV12-1 | 645 | GGATTGATTCTCAGCACAGATGCCTGATGT |
| TRBV12-5 | 646 | GATTCTCAGCAGAGATGCCTGATGCAACTTTA |
| TRBV2 | 647 | AAGTCTGAAATATTCGATGATCAATTCTCAGTTGAAAGGCC |
| TRBV16 | 648 | AGCTAAGTGCCTCCCAAATTCACCCT |
| TRBV5-1 | 649 | CGATTCTCAGGGCGCCAGTTCTCTA |
| TRBV14 | 650 | TCTTAGCTGAAAGGACTGGAGGGACGTAT |
| TRBV12-4 | 651 | GAGGATCGATTCTCAGCTAAGATGCCTAATGC |
| TRBV28 | 652 | TCCTGAGGGGTACAGTGTCTCTAGAGAGA |
| TRBV27 | 653 | GATGTTCCTGAAGGGTACAAAGTCTCTCGAAAAG |
| TRBV5-4 | 654 | CTCCTAGATTCTCAGGTCTCCAGTTCCCTA |
| TRBV7-1 | 655 | CGTGATCGGTTCTCTGCACAGAGGT |
| TRBV19 | 656 | GCTGAAGGGTACAGCGTCTCTCGGG |
| TRBV5-3 | 657 | CGATTCTCAGGGCGCCAGTTCCATG |
| TRBV9 | 658 | CAACAGTTCCCTGACTTGCACTCTGAACTAAAC |
| TRBV6-7 | 659 | AGAAGTTCCCAATGGCTACAATGTCTCCAGATC |
| TRBV6-4 | 660 | AAGTCCCTGATGGTTATAGTGTCTCCAGAGC |
| TRBV6-1 | 661 | GTCCCCAATGGCTACAATGTCTCCAGATT |
| TRBV7-9 | 662 | TTCTCTGCAGAGAGGCCTAAGGGATCT |
| TRBV7-3 | 663 | GCCCAACGATCGGTTCTTTGCAGT |
| TRBV7-4 | 664 | CCAGTGGTCGGTTCTCTGCAGAG |
| TRBV5-6 | 665 | GCAACTTCCCTGATCGATTCTCAGGTCA |
| TRBV5-8 | 666 | CAGAGGAAACTTCCCTCCTAGATTTTCAGGTCG |
| TRBV7-8 | 667 | GCCCAGTGATCGCTTCTTTGCAGAAA |
| TRBV12-2 | 668 | CGATTCTCAGCTGAGAGGCCTGATGG |
| TRBV15 | 669 | AGGCCGAACACTTCTTTCTGCTTTCTTGAC |
| TRBV6-2 | 670 | CAAAGGAGAGGTCCCTGATGGCTACAA |
| TRBV23-1 | 671 | GATTCTCATCTCAATGCCCCAAGAACGC |
| TRBV10-2 | 672 | CAGATAAAGGAGAAGTCCCCGATGGCTATGT |
| TRBV30 | 673 | CAGGACCGGCAGTTCATCCTGAGT |
| TRBV10-3 | 674 | AGATACTGACAAAGGAGAAGTCTCAGATGGCTATAG |
| TRBV6-6 | 675 | GACAAAGGAGAAGTCCCGAATGGCTACAAC |
| TRBV13 | 676 | CCCTGATCGATTCTCAGCTCAACAGTTCAGT |
| TRBV4-1 | 677 | CCTGAATGCCCCAACAGCTCTCTCTTAAAC |

TABLE 1-continued

Table 1A. TCRB oligonucleotide sequences targeting the 52 TCRBV and 13 TCRBJ gene segments.

| Primer Name | SEQ ID NO: | Sequence (5' to 3') |
|---|---|---|
| TRBV4-3 | 678 | CCTGAATGCCCCAACAGCTCTCACTTATTC |
| TRBV26 | 679 | GGAGATGTCTCTGAGAGGTATCATGTTTCTTGAAATA |
| TRBV6-8 | 680 | TACAATGTCTCTAGATTAAACACAGAGGATTTCCCAC |
| TRBV3-2 | 681 | TTCTCACCTGACTCTCCAGACAAAGCTCAT |
| TRBV11-2 | 682 | CCTAAGGATCGATTTTCTGCAGAGAGGCTC |
| TRBV2 | 683 | CCTGAATGCCCTGACAGCTCTCGCTTATA |
| TRBV3-1 | 684 | GCTTCTCACCTAAATCTCCAGACAAAGCTCACTTAAA |
| TRBV29-1 | 685 | CATCAGCCGCCCAAACCTAACATTCTCAA |
| TRBV18 | 686 | ATTTTCTGCTGAATTTCCCAAAGAGGGCC |
| TRBV17 | 687 | ATTCACAGCTGAAAGACCTAACGGAACGT |
| TRBV20-1 | 688 | CAAGCCTGACCTTGTCCACTCTGACA |
| TRBV7-6 | 689 | GGTTCTCTGCAGAGAGGCCTGAGG |
| TRBV24-1 | 690 | GAGAGATCTCTGATGGATACAGTGTCTCTCGACA |
| TRBV7-2 | 691 | GATCGCTTCTCTGCAGAGAGGACTGG |
| TRBV6-9 | 692 | AAGGAGAAGTCCCCGATGGCTACAATGTA |
| TRBV6-5 | 693 | AAGGAGAAGTCCCCAATGGCTACAATGTC |
| TRBV5-5 | 694 | AAGAGGAAACTTCCCTGATCGATTCTCAGC |
| TRBV10-1 | 695 | GACACTAACAAAGGAGAAGTCTCAGATGGCTACAG |
| TRBJ1-1 | 696 | TTACCTACAACTGTGAGTCTGGTGCCTTGTCCAAA |
| TRBJ1-2 | 697 | TACAACGGTTAACCTGGTCCCCGAACCGAA |
| TRBJ1-3 | 698 | ACCTACAACAGTGAGCCAACTTCCCTCTCCAAAA |
| TRBJ1-4 | 699 | CAAGACAGAGAGCTGGGTTCCACTGCCAAAA |
| TRBJ1-5 | 700 | ACCTAGGATGGAGAGTCGAGTCCCATCACCAAA |
| TRBJ1-6 | 701 | TCACAGTGAGCCTGGTCCCGTTCCCAAA |
| TRBJ2-1 | 702 | CGGTGAGCCGTGTCCCTGGCCCGAA |
| TRBJ2-2 | 703 | CCAGTACGGTCAGCCTAGAGCCTTCTCCAAA |
| TRBJ2-3 | 704 | ACTGTCAGCCGGGTGCCTGGGCCAAA |
| TRBJ2-4 | 705 | AGAGCCGGGTCCCGGCGCCGAA |
| TRBJ2-5 | 706 | GGAGCCGCGTGCCTGGCCCGAA |
| TRBJ2-6 | 707 | GTCAGCCTGCTGCCGGCCCCGAA |
| TRBJ2-7 | 708 | GTGAGCCTGGTGCCCGGCCCGAA |

TABLE 1B

List of TCRB RN2 oligonucleotide sequences targeting the 52 TCRBV and 13 TCRBJ gene segments.

| Primer Name | SEQ ID NO: | Sequence |
|---|---|---|
| TRBV25-1_RN2v3 | 1 | GGAGATCTTTCCTCTGAGTCAACAGTCTCCAGAATArAGGAC/3SpC3/ |
| TRBV12-1_RN2v3 | 2 | GGATTGATTCTCAGCACAGATGCCTGATGTrATCAT/3SpC3/ |
| TRBV12-5_RN2v3 | 3 | GATTCTCAGCAGAGATGCCTGATGCAACTTTArGCCAC/3SpC3/ |
| TRBV2_RN2v3 | 4 | AAGTCTGAAATATTCGATGATCAATTCTCAGTTGAAAGGCCrUGATG/3SpC3/ |
| TRBV16_RN2v3 | 5 | AGCTAAGTGCCTCCCAAATTCACCCTrGTAGC/3SpC3/ |
| TRBV5-1_RN2v3 | 6 | CGATTCTCAGGGCGCCAGTTCTCTArACTCT/3SpC3/ |
| TRBV14_RN2v3 | 7 | TCTTAGCTGAAAGGACTGGAGGGACGTATrUCTAC/3SpC3/ |
| TRBV12-4_RN2v3 | 8 | GAGGATCGATTCTCAGCTAAGATGCCTAATGCrATCAT/3SpC3/ |
| TRBV28_RN2v3 | 9 | TCCTGAGGGGTACAGTGTCTCTAGAGAGArAGAAG/3SpC3/ |
| TRBV27_RN2v3 | 10 | GATGTTCCTGAAGGGTACAAAGTCTCTCGAAAAGrAGAAG/3SpC3/ |
| TRBV5-4_RN2v3 | 11 | CTCCTAGATTCTCAGGTCTCCAGTTCCCTArATTAT/3SpC3/ |
| TRBV7-1_RN2v3 | 12 | CGTGATCGGTTCTCTGCACAGAGGTrCTGAG/3SpC3/ |
| TRBV19_RN2v3 | 13 | GCTGAAGGGTACAGCGTCTCTCGGGrAGAAG/3SpC3/ |
| TRBV5-3_RN2v3 | 14 | CGATTCTCAGGGCGCCAGTTCCATGrACTGT/3SpC3/ |
| TRBV9_RN2v3 | 15 | CAACAGTTCCCTGACTTGCACTCTGAACTAAACrCTGAG/3SpC3/ |
| TRBV6-7_RN2v3 | 16 | AGAAGTTCCCAATGGCTACAATGTCTCCAGATCrAAACA/3SpC3/ |
| TRBV6-4_RN2v3 | 17 | AAGTCCCTGATGGTTATAGTGTCTCCAGAGCrAAACA/3SpC3/ |
| TRBV6-1_RN2v3 | 18 | GTCCCCAATGGCTACAATGTCTCCAGATTrAAACA/3SpC3/ |
| TRBV7-9_RN2v3 | 19 | TTCTCTGCAGAGAGGCCTAAGGGATCTrCTCTC/3SpC3/ |
| TRBV7-3_RN2v3 | 20 | GCCCAACGATCGGTTCTTTGCAGTrCAGGC/3SpC3/ |
| TRBV7-4_RN2v3 | 21 | CCAGTGGTCGGTTCTCTGCAGAGrAGGCC/3SpC3/ |
| TRBV5-6_RN2v3 | 22 | GCAACTTCCCTGATCGATTCTCAGGTCArCCAGT/3SpC3/ |
| TRBV5-8_RN2v3 | 23 | CAGAGGAAACTTCCCTCCTAGATTTTCAGGTCGrCCAGT/3SpC3/ |
| TRBV7-8_RN2v3 | 24 | GCCCAGTGATCGCTTCTTTGCAGAAArGGCCT/3SpC3/ |
| TRBV12-2_RN2v3 | 25 | CGATTCTCAGCTGAGAGGCCTGATGGrATCAT/3SpC3/ |
| TRBV15_RN2v3 | 26 | AGGCCGAACACTTCTTTCTGCTTTCTTGACrATCCG/3SpC3/ |
| TRBV6-2_RN2v3 | 27 | CAAAGGAGAGGTCCCTGATGGCTACAArUGTCT/3SpC3/ |
| TRBV23-1_RN2v3 | 28 | GATTCTCATCTCAATGCCCCAAGAACGCrACCCT/3SpC3/ |
| TRBV10-2_RN2v3 | 29 | CAGATAAAGGAGAAGTCCCCGATGGCTATGTrUGTCT/3SpC3/ |
| TRBV30_RN2v3 | 30 | CAGGACCGGCAGTTCATCCTGAGTrUCTAA/3SpC3/ |
| TRBV10-3_RN2v3 | 31 | AGATACTGACAAAGGAGAAGTCTCAGATGGCTATAGrUGTCT/3SpC3/ |
| TRBV6-6_RN2v3 | 32 | GACAAAGGAGAAGTCCCGAATGGCTACAACrGTCTC/3SpC3/ |
| TRBV13_RN2v3 | 33 | CCCTGATCGATTCTCAGCTCAACAGTTCAGTrGACTA/3SpC3/ |
| TRBV4-1_RN2v3 | 34 | CCTGAATGCCCCAACAGCTCTCTCTTAAACrCTTCA/3SpC3/ |
| TRBV4-3_RN2v3 | 35 | CCTGAATGCCCCAACAGCTCTCACTTATTCrCTTCA/3SpC3/ |
| TRBV26_RN2v3 | 36 | GGAGATGTCTCTGAGAGGTATCATGTTTCTTGAAATArCTATA/3SpC3/ |
| TRBV6-8_RN2v3 | 37 | TACAATGTCTCTAGATTAAACACAGAGGATTTCCCACrUCAGG/3SpC3/ |

TABLE 1B-continued

List of TCRB RN2 oligonucleotide sequences targeting the 52 TCRBV and 13 TCRBJ gene segments.

| Primer Name | SEQ ID NO: | Sequence |
|---|---|---|
| TRBV3-2_RN2v3 | 38 | TTCTCACCTGACTCTCCAGACAAAGCTCATrUTAAA/3SpC3/ |
| TRBV11-2_RN2v3 | 39 | CCTAAGGATCGATTTTCTGCAGAGAGGCTCrAAAGG/3SpC3/ |
| TRBV2_RN2v3 | 40 | CCTGAATGCCCTGACAGCTCTCGCTTATArCCTTC/3SpC3/ |
| TRBV3-1_RN2v3 | 41 | GCTTCTCACCTAAATCTCCAGACAAAGCTCACTTAAArUCTTC/3SpC3/ |
| TRBV29-1_RN2v3 | 42 | CATCAGCCGCCCAAACCTAACATTCTCAArCTCTG/3SpC3/ |
| TRBV18_RN2v3 | 43 | ATTTTCTGCTGAATTTCCCAAAGAGGGCCrCCAGC/3SpC3/ |
| TRBV17_RN2v3 | 44 | ATTCACAGCTGAAAGACCTAACGGAACGTrCTTCC/3SpC3/ |
| TRBV20-1_RN2v3 | 45 | CAAGCCTGACCTTGTCCACTCTGACArGTGAC/3SpC3/ |
| TRBV7-6_RN2v3 | 46 | GGTTCTCTGCAGAGAGGCCTGAGGrGATCC/3SpC3/ |
| TRBV24-1_RN2v3 | 47 | GAGAGATCTCTGATGGATACAGTGTCTCTCGACArGGCAC/3SpC3/ |
| TRBV7-2_RN2v3 | 48 | GATCGCTTCTCTGCAGAGAGGACTGGrGGGAT/3SpC3/ |
| TRBV6-9_RN2v3 | 49 | AAGGAGAAGTCCCCGATGGCTACAATGTArUCCAG/3SpC3/ |
| TRBV6-5_RN2v3 | 50 | AAGGAGAAGTCCCCAATGGCTACAATGTCrUCCAG/3SpC3/ |
| TRBV5-5_RN2v3 | 51 | AAGAGGAAACTTCCCTGATCGATTCTCAGCrUCGCC/3SpC3/ |
| TRBV10-1_RN2v3 | 52 | GACACTAACAAAGGAGAAGTCTCAGATGGCTACAGrUGTCT/3SpC3/ |
| TRBJ1-1_RN2v3 | 53 | TTACCTACAACTGTGAGTCTGGTGCCTTGTCCAAArGAAAG/3SpC3/ |
| TRBJ1-2_RN2v3 | 54 | TACAACGGTTAACCTGGTCCCCGAACCGAArGGTGT/3SpC3/ |
| TRBJ1-3_RN2v3 | 55 | ACCTACAACAGTGAGCCAACTTCCCTCTCCAAAArUATAT/3SpC3/ |
| TRBJ1-4_RN2v3 | 56 | CAAGACAGAGAGCTGGGTTCCACTGCCAAAArAACAG/3SpC3/ |
| TRBJ1-5_RN2v3 | 57 | ACCTAGGATGGAGAGTCGAGTCCCATCACCAAArATGCT/3SpC3/ |
| TRBJ1-6_RN2v3 | 58 | TCACAGTGAGCCTGGTCCCGTTCCCAAArGTGGA/3SpC3/ |
| TRBJ2-1_RN2v3 | 59 | CGGTGAGCCGTGTCCCTGGCCCGAArGAACT/3SpC3/ |
| TRBJ2-2_RN2v3 | 60 | CCAGTACGGTCAGCCTAGAGCCTTCTCCAAArAAACA/3SpC3/ |
| TRBJ2-3_RN2v3 | 61 | ACTGTCAGCCGGGTGCCTGGGCCAAArATACT/3SpC3/ |
| TRBJ2-4_RN2v3 | 62 | AGAGCCGGGTCCCGGCGCCGAArGTACT/3SpC3/ |
| TRBJ2-5_RN2v3 | 63 | GGAGCCGCGTGCCTGGCCCGAArGTACT/3SpC3/ |
| TRBJ2-6_RN2v3 | 64 | GTCAGCCTGCTGCCGGCCCCGAArAGTCA/3SpC3/ |
| TRBJ2-7_RN2v3 | 65 | GTGAGCCTGGTGCCCGGCCCGAArGTACT/3SpC3/ |

In the RN2 oligonucleotides of Table 1B, "r" represents a ribonucleotide base in the oligonucleotide sequence and "/3SpC3/" represents a 3' three-carbon spacer on the hydroxyl group, preventing polymerase extension and amplification. The DNA repair endonuclease cleaves the oligonucleotide at the ribonucleotide after hybridization to a complementary sequence, creating an unblocked hydroxyl group that can be extended by a polymerase.

The multiplex PCR system also uses at least 3, 4, 5, 6, or 7, and in certain embodiments, 8, 9, 10, 11, 12 or 13 reverse primers, in which each reverse primer specifically hybridizes to or is complementary to a sequence corresponding to one or more J region segments. Illustrative TCRβ J segment primers are provided in SEQ ID NOs:53-65 (see also Table 1). Illustrative TCRγ J segment primers are provided in SEQ ID NOs:634-637. Illustrative IgH J segment primers are provided in SEQ ID NOs:638-643. J region gene segment sequences may thus be used to design J region primers. Exemplary TCRB J region segment sequences are set forth in SEQ ID NOS:53-65, 202-214, 696-708, and 880-883. Exemplary TCRG J region gene segment sequences are set forth in SEQ ID NOs:215-220 and 634-637. Exemplary IgH J region gene segment sequences are set forth in SEQ ID NOs:239-254 and 638-643. In one embodiment, there is a J segment primer for every J segment.

Oligonucleotides or polynucleotides that are capable of specifically hybridizing or annealing to a target nucleic acid sequence by nucleotide base complementarity may do so under moderate to high stringency conditions. For purposes of illustration, suitable moderate to high stringency conditions for specific PCR amplification of a target nucleic acid sequence would be between 25 and 80 PCR cycles, with each cycle consisting of a denaturation step (e.g., about 10-30 seconds (s) at at least about 95° C.), an annealing step (e.g., about 10-30 s at about 60-68° C.), and an extension step (e.g., about 10-60 s at about 60-72° C.), optionally according to certain embodiments with the annealing and extension steps being combined to provide a two-step PCR. As would be recognized by the skilled person, other PCR reagents may be added or changed in the PCR reaction to increase specificity of primer annealing and amplification, such as altering the magnesium concentration, optionally adding DMSO, and/or the use of blocked primers, modified nucleotides, peptide-nucleic acids, and the like.

In certain embodiments, nucleic acid hybridization techniques may be used to assess hybridization specificity of the primers described herein. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the primers are designed not to cross an intron/exon boundary. The forward primers in certain embodiments anneal to the V segments in a region of relatively strong sequence conservation between V segments so as to maximize the conservation of sequence among these primers. Accordingly, this minimizes the potential for differential annealing properties of each primer, and so that the amplified region between V and J primers contains sufficient TCR or Ig V sequence information to identify the specific V gene segment used. In one embodiment, the J segment primers hybridize with a conserved element of the J segment, and have similar annealing strength. In one particular embodiment, the J segment primers anneal to the same conserved framework region motif.

Oligonucleotides (e.g., primers) can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Lett.* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (e.g., a DNA polymerase or reverse transcriptase) in an appropriate buffer and at a suitable temperature.

A primer is preferably a single-stranded DNA. The appropriate length of a primer depends on the intended use of the primer but typically ranges from 6 to 50 nucleotides, or in certain embodiments, from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

As described herein, primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning, detection, or sequencing of the amplified product. The region of the primer which is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences which contain the target primer binding sites.

In particular embodiments, primers for use in the methods described herein comprise or consist of a nucleic acid of at least about 15 nucleotides long that has the same sequence as, or is complementary to, a 15 nucleotide long contiguous sequence of the target V or J segment. Longer primers, e.g., those of about 16, 17, 18, 19, 20, 21, 22, 23, 24, 25, 26, 27, 28, 29, 30, 31, 32, 33, 34, 35, 36, 37, 38, 39, 40, 45, or 50 nucleotides long that have the same sequence as, or sequence complementary to, a contiguous sequence of the target V or J segment that is at least 15, 16, 17, 18, 19, 20, 21, 22, 23, 24, 25, 26, 27, 28, 29, 30, 31, 32, 33, 34, 35, 36, 37, 38, 39, 40, 45, or 50 nucleotides long, will also be of use in certain embodiments. All intermediate lengths of the aforementioned primers are contemplated for use herein. As would be recognized by the skilled person, the primers may have additional sequence added (e.g., nucleotides that may not be the same as or complementary to the target V or J segment), such as restriction enzyme recognition sites, adaptor sequences for sequencing, bar code sequences, and the like (see e.g., primer sequences provided herein and in the sequence listing). Therefore, the length of the primers may be longer, such as 55, 56, 57, 58, 59, 60, 65, 70, 75, nucleotides in length or more, depending on the specific use or need. For example, in one embodiment, the forward and reverse primers are both modified at the 5' end with the universal forward primer sequence compatible with a DNA sequencer.

Also contemplated for use in certain embodiments are adaptive immune receptor V-segment or J-segment oligonucleotide primer variants that may share a high degree of sequence identity to the oligonucleotide primers for which nucleotide sequences are presented herein, including those set forth in the Sequence Listing or portions thereof that are at least 15, 16, 17, 18, 19, 20, 21, 22, 23, 24, 25, 26, 27, 28, 29, 30, 31, 32, 33, 34, 35, 36, 37, 38, 39, 40, 45, or 50 nucleotides long. Thus, in these and related embodiments, adaptive immune receptor V-segment or J-segment oligonucleotide primer variants may have substantial identity to the adaptive immune receptor V-segment or J-segment oligonucleotide primer sequences disclosed herein, for example, such oligonucleotide primer variants may comprise at least 70% sequence identity, preferably at least 75%, 80%, 85%, 90%, 91%, 92%, 93%, 94%, 95%, 96%, 97%, 98%, or 99% or higher sequence identity compared to a reference polynucleotide sequence such as the oligonucleotide primer sequences disclosed herein, using the methods described herein (e.g., BLAST analysis using standard parameters). One skilled in this art will recognize that these values can be appropriately adjusted to determine corresponding ability of an oligonucleotide primer variant to anneal to an adaptive immune receptor segment-encoding polynucleotide by taking into account codon degeneracy, reading frame positioning and the like. Typically, oligonucleotide primer variants will contain one or more substitutions, additions, deletions and/or insertions, preferably such that the annealing ability of the variant oligonucleotide is not substantially diminished relative to that of an adaptive immune receptor V-segment or J-segment oligonucleotide primer sequence that is specifically set forth herein. As also noted elsewhere herein, in preferred embodiments adaptive immune receptor V-segment and J-segment oligonucleotide primers are designed to be capable of amplifying a rearranged TCR or IGH sequence that includes the coding region for CDR3.

According to certain embodiments contemplated herein, the primers for use in the multiplex PCR methods of the present disclosure may be functionally blocked to prevent non-specific priming of non-T or B cell sequences. For example, the primers may be blocked with chemical modifications as described in U.S. patent application publication US2010/0167353. According to certain herein disclosed embodiments, the use of such blocked primers in the present multiplex PCR reactions involves primers that may have an inactive configuration wherein DNA replication (i.e., primer extension) is blocked, and an activated configuration wherein DNA replication proceeds. The inactive configuration of the primer is present when the primer is either single-stranded, or when the primer is specifically hybridized to the target DNA sequence of interest but primer extension remains blocked by a chemical moiety that is linked at or near to the 3' end of the primer.

The activated configuration of the primer is present when the primer is hybridized to the target nucleic acid sequence of interest and is subsequently acted upon by RNase H or another cleaving agent to remove the 3' blocking group, thereby allowing an enzyme (e.g., a DNA polymerase) to catalyze primer extension in an amplification reaction. Without wishing to be bound by theory, it is believed that the kinetics of the hybridization of such primers are akin to a second order reaction, and are therefore a function of the T cell or B cell gene sequence concentration in the mixture. Blocked primers minimize non-specific reactions by requiring hybridization to the target followed by cleavage before primer extension can proceed. If a primer hybridizes incorrectly to a sequence that is related to the desired target sequence but which differs by having one or more non-complementary nucleotides that result in base-pairing mismatches, cleavage of the primer is inhibited, especially when there is a mismatch that lies at or near the cleavage site. This strategy to improve the fidelity of amplification reduces the frequency of false priming at such locations, and thereby increases the specificity of the reaction. As would be recognized by the skilled person, reaction conditions, particularly the concentration of RNase H and the time allowed for hybridization and extension in each cycle, can be optimized to maximize the difference in cleavage efficiencies between highly efficient cleavage of the primer when it is correctly hybridized to its true target sequence, and poor cleavage of the primer when there is a mismatch between the primer and the template sequence to which it may be incompletely annealed.

As described in US2010/0167353, a number of blocking groups are known in the art that can be placed at or near the 3' end of the oligonucleotide (e.g., a primer) to prevent extension. A primer or other oligonucleotide may be modified at the 3'-terminal nucleotide to prevent or inhibit initiation of DNA synthesis by, for example, the addition of a 3' deoxyribonucleotide residue (e.g., cordycepin), a 2',3'-dideoxyribonucleotide residue, non-nucleotide linkages or alkane-diol modifications (U.S. Pat. No. 5,554,516). Alkane diol modifications which can be used to inhibit or block primer extension have also been described by Wilk et al., (1990 *Nucleic Acids Res.* 18 (8):2065), and by Arnold et al. (U.S. Pat. No. 6,031,091). Additional examples of suitable blocking groups include 3' hydroxyl substitutions (e.g., 3'-phosphate, 3'-triphosphate or 3'-phosphate diesters with alcohols such as 3-hydroxypropyl), 2'3'-cyclic phosphate, 2' hydroxyl substitutions of a terminal RNA base (e.g., phosphate or sterically bulky groups such as triisopropyl silyl (TIPS) or tert-butyl dimethyl silyl (TBDMS)). 2'-alkyl silyl groups such as TIPS and TBDMS substituted at the 3'-end of an oligonucleotide are described by Laikhter et al., U.S. patent application Ser. No. 11/686,894, which is incorporated herein by reference. Bulky substituents can also be incorporated on the base of the 3'-terminal residue of the oligonucleotide to block primer extension.

In certain embodiments, the oligonucleotide may comprise a cleavage domain that is located upstream (e.g., 5' to) of the blocking group used to inhibit primer extension. As examples, the cleavage domain may be an RNase H cleavage domain, or the cleavage domain may be an RNase H2 cleavage domain comprising a single RNA residue, or the oligonucleotide may comprise replacement of the RNA base with one or more alternative nucleosides. Additional illustrative cleavage domains are described in US2010/0167353. Oligonucleotide primers that comprise an RNase H2 cleavage domain upstream to a blocking group that inhibits primer extension are referred to as “RN2 modified” primers. Exemplary RN2 modified primers are listed above in Table 1B. Thus, a multiplex PCR system may use 40, 45, 50, 55, 60, 65, 70, 75, 80, 85, or more forward primers, wherein each forward primer is complementary to a single functional TCR or Ig V segment or a small family of functional TCR or Ig V segments, e.g., a TCR Vβ segment, or (see e.g., the TCR primers as shown in Table 1), and, for example, thirteen reverse primers, each specific to a TCR or Ig J segment, such as TCR Jβ segment (see e.g., Table 1). In another embodiment, a multiplex PCR reaction may use four forward primers each specific to one or more functional TCRγ V segment and four reverse primers each specific for one or more TCRγ J segments. In another embodiment, a multiplex PCR reaction may use 84 forward primers each specific to one or more functional V segments and six reverse primers each specific for one or more J segments.

The present methods provide the ability to quantify the relative number of T or B cells in a complex mixture of cells by determining the relative representation of adaptive immune cell DNA in a DNA sample extracted from the cell mixture, by multiplex PCR using real-time quantitative PCR methods. Real-time PCR is a technique that evaluates the level of PCR product accumulation during successive amplification cycles (see e.g., *Gibson et al., Genomic Research* 6:995-1001, 1990; Heid *et al., Genome Research* 6:986-904, 1996, *Real-Time PCR: Current Technology and Applications*, Edited by Julie Logan, Kirstin Edwards and Nick Saunders, 2009, Caister Academic Press, Norfolk, UK). This technique permits quantitative evaluation of DNA (or mRNA/cDNA) levels in multiple samples. Briefly, DNA (or mRNA/cDNA) is extracted from a sample (e.g., tumor and normal tissue) using standard techniques. Real-time PCR is performed using the multiplex PCR primer sets as described herein using, for example, any of a variety of commercially available real-time PCR machines, such as LIGHTCYCLER®480 System (Roche Diagnostics Corporation, Indianapolis, IN), real-time detection systems from Bio-Rad (e.g., CFX384™or other similar systems; Bio-Rad; Hercules, CA), or the ECO™ real-time PCR system (Illumina Inc., San Diego CA).

A number of established qPCR methodologies are described herein and my be employed according to certain preferred embodiments of the present invention, but the invention is not intended to be so limited and also contemplates digital PCR (dPCR, e.g., droplet digital PCR or "ddPCR") and various quantitative PCR techniques and instrumentation, including by way of illustration and not limitation the ABI QUANTSTUDIO™12K Flex System (Life Technologies, Carlsbad, Calif.), the QUANTALIFE™digital PCR system (BioRad, Hercules, Calif.) and the RAINDANCE™microdroplet digital PCR system (RainDance Technologies, Lexington, MA) (e.g., Pekin et al., 2011 *Lab. Chip* 11(13):2156; Zhong et al., 2011 *Lab, Chip* 11(13): 2167; Tewhey et al., 2009 *Nature Biotechnol.* 27:1025;2010 *Nature Biotechnol.* 28:178), any of which may be adapted by the skilled person for use with the herein described compositions and methods.

Quantification of amplified DNA molecules that are the products of qPCR or dPCR or other quantitative PCR techniques ma be achieved b detecting a level of a DNA-quantifying signal that is generated by a detectable indicator of the presence of DNA. In preferred embodiments, the detectable indicator generates a DNA-quantifying signal that is a fluorescent signal, using well known reagents and detection instrumentation. In one exemplary embodiment, amplified PCR product may be detected using a DNA intercalating dye, such as SYBR™ green, a fluorescent dye that only intercalates into double-stranded DNA, i.e., the DNA-quantifying signal is SYBR™ green fluorescence and the detectable indicator is SYBR™green, such that fluorimetric quantification of the fluorescent signal provides measureable DNA-quantifying signal level. Other illustrative dyes that may be used as detectable indicators to generate measureable levels of DNA-quantifying signals include SYTO9, SYTO-82 and SYTO-13 EVAGREEN™(see e.g.,Anal Biochem,340:24-34, 2005; *Nucleic Acid Res.* 35: e127, 2007). These detectable indicators may advantageously permit quantitative determination of PCR products without the use of sequence-specific oligonucleotide probes, such as oligonucleotide probes for use in real-time qPCR that may bear a detectable labeling moiety such as a fluorescent moiety and/or a fluorescence quencher or dequenching moiety, examples of which are described below.

The increase in fluorescence may be monitored at one or a plurality of timepoints during the during the amplification process, including monitoring fluorescence throughout all or substantially all of the amplification process. A threshold for detection of fluorescence above background is determined, where the cycle threshold, $C_t$, is the cycle (i.e., the cycle number in the succession of PCR cycles, where each cycle comprises steps of DNA denaturation, primer annealing, and template-directed DNA synthesis via primer extension) at which the fluorescence crosses the threshold. During the exponential phase, the quantity of DNA theoretically doubles every cycle. Therefore, relative amounts of DNA can be calculated, e.g., a first sample for which the $C_t$ is three cycles earlier than the $C_t$ of a second sample has $2^3=8$ times more template than the second sample.

The amount of DNA or RNA in the test sample is determined by comparing the real-time PCR results to a standard curve. The standard curve is generated for each qPCR run using a standard control DNA containing the gene or genes of interest. In one embodiment of the present disclosure, the standard control is prepared by purifying DNA from adaptive immune cells, such as from T and/or B cells (e.g., from T cells or B cells bead sorted from peripheral blood). The purified DNA is quantified and then serially diluted to concentrations ranging from 60 picograms to 250 nanograms per reaction. The skilled person would understand that other similar standard control templates may also be used, such as plasmid DNA containing the target template(s) of interest.

In addition, in certain embodiments, an additional qPCR standard curve may be generated for amplification products of all or a portion of an internal control gene that, unlike the rearranged TCR or Ig CDR3-encoding gene regions found in adaptive immune cells, is common to all of the cells in the test biological sample, i.e., in the adaptive immune cells and in the cells that are not adaptive immune cells. Non-limiting examples of such internal control genes include those that encode β-actin, RNaseP, glyceraldehyde-3-phosphate dehydrogenase, MHC I (major histocompatibility complex type I antigens, such as HLA-A or HLA-B), cyclophilin, and others as are known in the art, and which may be amplified using appropriate concentrations of target DNA (or cDNA) as template. These and related embodiments permit standardization of the initial DNA or RNA content of a tissue sample, and hence quantification of the total number of cells present in a test sample that comprises a mixture of cells (e.g., adaptive immune cells and other cells), based on the amount of internal control gene (e.g., β-actin and RNaseP) DNA that is detectable in qPCR, for comparison purposes.

Thus, the mean copy number for each test biological sample in which rearranged adaptive immune receptor (TCR or Ig) encoding DNA is quantified as a measure of adaptive immune cells, may be normalized relative to the DNA quantity that is determined for the internal control gene, which is present at constant levels in adaptive immune cells and in cells that are not adaptive immune cells. For instance, determination of the amount of β-actin encoding DNA, or another appropriate internal control gene, permits evaluation of the level of adaptive immune receptor encoding DNA relative to the level of the internal control gene DNA in each test sample.

Accordingly, certain of the herein described methods for quantifying the number of adaptive immune cells in a test sample that comprises a mixture of cells may further comprise quantifying the number of cells in the mixture of cells, by amplifying test sample template DNA extracted from the test biological sample with a set of control primers, wherein the set of control primers amplifies an internal control gene DNA segment that is not specific to adaptive immune cells, to produce internal control gene amplification products. Concurrently with the amplification of the internal control gene segment, at one or a plurality of time points a DNA signal level is measured that is detectable for the internal control gene amplification products. This internal control gene amplification signal is compared, at the one or plurality of time points (e.g., in real time), to a reference DNA signal level that is detectable in amplification products of a known amount of the internal control gene DNA that has been amplified by the control primers, to provide a calibration standard for use as a reference. By this comparison, the amount of internal control gene DNA that is present in the test sample template DNA that was extracted from the test biological sample, can be quantified, from which the number of cells in the mixture of cells in the test sample can be determined. In certain such embodiments, the control primers are present in the same qPCR reaction as the reaction in which rearranged adaptive immune receptor encoding DNA is amplified with V-segment and J-segment primers. In certain other embodiments, the control primers are present in a separate qPCR reaction from the reaction in which amplification occurs using the V-segment and J-segment primers.

In another embodiment, matching primers and fluorescent probes (e.g., Taqman® probes from Roche Molecular Systems, Pleasanton, Calif.; or Molecular Probes® fluorescent dyes from Invitrogen Corp., Carlsbad, Calif.), 3' minor groove binding (MGB) DNA probes (e.g., dihydrocyclopyrroloindole tripeptides described by Kutyavin et al., 2000 *Nucl. Ac. Res.* 28:655-661), or other appropriate molecular beacons (see, e.g., Manganelli et al., 2001 *Meth. Mol. Med.* 54:295; Tyagi et al., 2000 *Nat. Biotech.* 18:1191) may be designed for genes of interest (e.g., TCR or Ig V and J segment genes; internal control genes) as described herein. Optimal concentrations of primers and probes may be initially determined by those of ordinary skill in the art, and control (e.g., β-actin) primers and probes may be obtained commercially from, for example, Perkin Elmer/Applied Biosystems (Foster City, Calif.). Table 2A shows exemplary probes designed to target the human TCRB gene family, using the PCR primers presented in Table 1A, the fluorophore FAM (6-carboxyfluorescein), the (MGB) minor groove-binder modification to increase Tm, and a non-fluorescent quencher (NFQ; e.g., QSY21, Kabelac et al., 2010 *Phys Chem Chem Phys* 12:9677; QSY9, Anderson et al., 2009 *Biochem.* 48:8516; 4-(4'-dimethylaminophenylazo)benzoic acid (DABCYL), Manganelli et al., 2001 *Meth. Mol. Med.* 54:295; BHQ-1, (4-(2-nitro-4-toluyldiazo)-2'-methoxy-5-methyl-azobenzene-4"-(N-ethyl)-N-ethyl-2-cyanoethyl-(N,N-diisopropyl)-phosphoramidite) or other members of the BHQ® series, available from Biosearch Technologies, Inc., Novato, Calif.). Related embodiments contemplate alternative means for generating high Tm probes in which the MGB is replaced, such as using longer probes without MGB, or using locked nucleic acids (LNA, see, e.g., Kaur et al., 2007 *Chem. Rev.* 107:4672). Alternative quenchers may also be employed, including fluorescent quenchers (e.g., Marras, 2006 *Meths. Mol. Biol.* 335:3; Stefflova et al., 2007 *Curr. Med. Chem.* 14:2110). Alternative fluorophores including TET, VIC, ROX, TAMRA, Cy3, Cy5, Hex, Yellow 555 and others may also be substituted for FAM (e.g., Marras, 2006; see also Molecular Probes® fluorescent dyes from Invitrogen Corp., Carlsbad, Calif.). Mixtures of fluorophores may also be used in certain embodiments, for example, to detect multiple V segments in a single reaction.

TABLE 2A

TaqMan ® MGB probes for use with the PCR primers of Table 1A.

| Gene segment | SEQ ID NO: | probe |
|---|---|---|
| TCRBV01p | 709 | FAM-ACTGCAGCAAGAAGACTCAGCT-MGB-NFQ |
| TCRBV02 | 710 | FAM-AAGATCCGGTCCACAAAGCT-MGB-NFQ |
| TCRBV03-1 | 711 | FAM-AATTCCCTGGAGCTTGGTGACT-MGB-NFQ |
| TCRBV03-2p | 712 | FAM-AATTCCCTGGAGCTTGGTGACT-MGB-NFQ |
| TCRBV04-1 | 713 | FAM-CAGAAGACTCAGCCCTGTATCT-MGB-NFQ |
| TCRBV04-2 | 714 | FAM-AGAAGACTCGGCCCTGTATCT-MGB-NFQ |
| TCRBV04-3 | 715 | FAM-AGAAGACTCGGCCCTGTATCT-MGB-NFQ |
| TCRBV05-1 | 716 | FAM-AATGTGAGCACCTTGGAGCT-MGB-NFQ |
| TCRBV05-2p | 717 | FAM-ACTGAGTCAAACACGGAGCT-MGB-NFQ |
| TCRBV05-3 | 718 | FAM-AATGTGAGTGCCTTGGAGCT-MGB-NFQ |
| TCRBV05-4 | 719 | FAM-AATGTGAACGCCTTGGAGCT-MGB-NFQ |
| TCRBV05-5 | 720 | FAM-TGTGAACGCCTTGTTGCT-MGB-NFQ |
| TCRBV05-6 | 721 | FAM-TGTGAACGCCTTGTTGCT-MGB-NFQ |
| TCRBV05-7 | 722 | FAM-TGTGAACGCCTTGTTGCT-MGB-NFQ |
| TCRBV05-8 | 723 | FAM-TGTGAACGCCTTGTTGCT-MGB-NFQ |
| TCRBV06-1 | 724 | FAM-CCTCCCAGACATCTGTGTACTT-MGB-NFQ |
| TCRBV06-2 | 725 | FAM-TCCCTCCCAAACATCTGTGT-MGB-NFQ |
| TCRBV06-3 | 726 | FAM-TCCCTCCCAAACATCTGTGT-MGB-NFQ |
| TCRBV06-4 | 727 | FAM-TGCTGTACCCTCTCAGACATCT-MGB-NFQ |
| TCRBV06-5 | 728 | FAM-CCTCCCAGACATCTGTGTACTT-MGB-NFQ |
| TCRBV06-6 | 729 | FAM-CCTCCCAGACATCTGTGTACTT-MGB-NFQ |
| TCRBV06-7 | 730 | FAM-TGCTCCCTCTCAGACTTCTGTT-MGB-NFQ |
| TCRBV06-8 | 731 | FAM-CCTCCCAGACATCTGTGTACTT-MGB-NFQ |
| TCRBV06-9 | 732 | FAM-TCCCTCCCAGACATCTGTAT-MGB-NFQ |
| TCRBV07-1 | 733 | FAM-AAGTTCCAGCGCACACA-MGB-NFQ |
| TCRBV07-2 | 734 | FAM-ATCCAGCGCACACAGCA-MGB-NFQ |
| TCRBV07-3 | 735 | FAM-AAGATCCAGCGCACAGA-MGB-NFQ |
| TCRBV07-4 | 736 | FAM-AAGATCCAGCGCACAGA-MGB-NFQ |
| TCRBV07-5p | 737 | FAM-ATCCAGCGCACAGAGCAA-MGB-NFQ |
| TCRBV07-6 | 738 | FAM-ATCCAGCGCACAGAGCA-MGB-NFQ |
| TCRBV07-7 | 739 | FAM-ATTCAGCGCACAGAGCA-MGB-NFQ |
| TCRBV07-8 | 740 | FAM-AAGATCCAGCGCACACA-MGB-NFQ |
| TCRBV07-9 | 741 | FAM-ATCCAGCGCACAGAGCA-MGB-NFQ |
| TCRBV08-1p | 742 | FAM-AACCCTGGAGTCTACTAGCA-MGB-NFQ |

TABLE 2A-continued

TaqMan ® MGB probes for use with the PCR primers of Table 1A.

| Gene segment | SEQ ID NO: | probe |
|---|---|---|
| TCRBV08-2p | 743 | FAM-AGCCAGACCTATCTGTACCA-MGB-NFQ |
| TCRBV09 | 744 | FAM-AGCTCTCTGGAGCTGG-MGB-NFQ |
| TCRBV10-1 | 745 | FAM-CCTCCTCCCAGACATCTGTATA-MGB-NFQ |
| TCRBV10-2 | 746 | FAM-CGCTCCCAGACATCTGTGTATT-MGB-NFQ |
| TCRBV10-3 | 747 | FAM-AGCTCCCAGACATCTGTGTACT-MGB-NFQ |
| TCRBV11-1 | 748 | FAM-AAGATCCAGCCTGCAGAGCTT-MGB-NFQ |
| TCRBV11-2 | 749 | FAM-ATCCAGCCTGCAAAGCTTGA-MGB-NFQ |
| TCRBV11-3 | 750 | FAM-AAGATCCAGCCTGCAGAGCTT-MGB-NFQ |
| TCRBV12-1p | 751 | FAM-CCAGGGACTTGGGCCTATATTT-MGB-NFQ |
| TCRBV12-2p | 752 | FAM-AAGATCCAGCCTGCAGAGCA-MGB-NFQ |
| TCRBV12-3 | 753 | FAM-AGGGACTCAGCTGTGTACTT-MGB-NFQ |
| TCRBV12-4 | 754 | FAM-AGGGACTCAGCTGTGTACTT-MGB-NFQ |
| TCRBV12-5 | 755 | FAM-CCAGGGACTCAGCTGTGTATTT-MGB-NFQ |
| TCRBV13 | 756 | FAM-AACATGAGCTCCTTGGAGCT-MGB-NFQ |
| TCRBV14 | 757 | FAM-TGCAGAACTGGAGGATTCTGGA-MGB-NFQ |
| TCRBV15 | 758 | FAM-ACGCAGCCATGTACCT-MGB-NFQ |
| TCRBV16 | 759 | FAM-ATCCAGGCTACGAAGCTTGA-MGB-NFQ |
| TCRBV17p | 760 | FAM-AGGGACTCAGCCGTGTATCT-MGB-NFQ |
| TCRBV18 | 761 | FAM-CGAGGAGATTCGGCAGCTTATT-MGB-NFQ |
| TCRBV19 | 762 | FAM-AGAACCCGACAGCTTTCT-MGB-NFQ |
| TCRBV20-1 | 763 | FAM-TCCTGAAGACAGCAGCTTCT-MGB-NFQ |
| TCRBV21-1p | 764 | FAM-AGATCCAGTCCACGGAGTCA-MGB-NFQ |
| TCRBV22p | 765 | FAM-ACACCAGCCAAACAGCTT-MGB-NFQ |
| TCRBV23-1p | 766 | FAM-GGCAATCCTGTCCTCAGAA-MGB-NFQ |
| TCRBV24-1 | 767 | FAM-CCCAACCAGACAGCTCTTTACT-MGB-NFQ |
| TCRBV25-1 | 768 | FAM-CCTCACATACCTCTCAGTACCT-MGB-NFQ |
| TCRBV26p | 769 | FAM-AGCACCAACCAGACATCTGT-MGB-NFQ |
| TCRBV27-1 | 770 | FAM-CCAACCAGACCTCTCTGTACTT-MGB-NFQ |
| TCRBV28 | 771 | FAM-AGCACCAACCAGACATCT-MGB-NFQ |
| TCRBV29-1 | 772 | FAM-TGAGCAACATGAGCCCTGAA-MGB-NFQ |
| TCRBV30 | 773 | FAM-TCCTTCTCAGTGACTCTGGCTT-MGB-NFQ |

In certain embodiments, oligonucleotide probes useful in the methods disclosed herein may be modified, for example, with the ZEN moiety or to contain "locked nucleic acid" (LNA) where the ribose ring is "locked" by a methylene bridge connecting the 2'-O atom and the 4'-C atom (see, Owczarzy et al. 2011 Biochemistry 50(43):9352-67). Both types of oligonucleotides may be obtained from Integrated DNA Technologies, Inc. (IDT, Coralville, Iowa).

To quantitate the amount of specific DNA or RNA in a sample, a standard curve can be generated using standard control DNA (e.g., a plasmid containing the gene(s) of interest, or, as described elsewhere herein, known quantities of purified T cell or B cell DNA). Standard curves are generated using the $C_t$ values determined in the real-time PCR, which are related to the initial template DNA or cDNA concentration used in the assay. Standard dilutions ranging from 10-$10^6$ copies of the gene of interest are generally sufficient. In addition, a standard curve is generated for the control sequence. This permits standardization of initial DNA or RNA content of a tissue sample to the amount of control for comparison purposes.

The present methods are highly sensitive and are capable of detecting the presence of 10 or even fewer adaptive immune cells per 10,000 cells in the mixture of cells. In one embodiment, the present methods are capable of detecting the presence of 9, 8, 7, 6, 5, 4, 3, 2, or 1 adaptive immune cell per 10,000 cells in the mixture of cells.

In certain embodiments, the present methods are capable of detecting 10 picograms of adaptive immune cell DNA in a DNA sample extracted from a population of mixed cells. In certain embodiments, the present methods are capable of detecting, 9, 8, 7, 6, or 5 picograms of adaptive immune cell DNA from a source of DNA extracted from a mixed population of cells, such as a tumor sample.

Multiplex Digital PCR

Alternatively, in a related aspect also contemplated herein, digital PCR methods can be used to quantitate the number of target genomes in a sample, without the need for a standard curve. In digital PCR, the PCR reaction for a single sample is performed in a multitude of more than 100 microcells or droplets (also referred to herein as "assay samples"), such that each droplet either amplifies (e.g., generation of an amplification product provides evidence of the presence of at least one template molecule in the microcell or droplet) or fails to amplify (evidence that the template was not present in a given microcell or droplet). Hence, the individual readout signals are qualitative or "digital" in nature. By simply counting the number of positive microcells, it is possible directly to count the number of target genomes that are present in an input sample. Digital PCR methods typically use an endpoint readout, rather than a conventional quantitative PCR signal that is measured after each cycle in the thermal cycling reaction (see, e.g., Vogelstein and Kinzler, 1999 *Proc. Natl. Acad. Sci. USA* 96:9236-41; Pohl and Shih, 2004 *Expert Rev. Mol. Diagn.* 4(1); 41-7, 2004; Pekin et al., 2011 *Lab. Chip* 11(13):2156; Zhong et al., 2011 *Lab. Chip* 11(13):2167; Tewhey et al., 2009 *Nature Biotechnol.* 27:1025; 2010 *Nature Biotechnol.* 28:178). Compared with traditional PCR, dPCR has the following advantages: (1) there is no need to rely on references or standards, (2) desired precision may be achieved by increasing the total number of PCR replicates, (3) it is highly tolerant to inhibitors, (4) it is capable of analyzing complex mixtures, and (5) it provides a linear response to the number of copies present in a sample to allow for small change in the copy number to be detected.

Accordingly, in a related aspect, the present disclosure provides a method for quantifying the relative representation of adaptive immune cells in a test biological sample that comprises a mixture of cells (i.e., both adaptive immune cells and cells that are not adaptive immune cells). The method comprises first distributing test sample template DNA extracted from the test biological sample to form a set of assay samples followed by amplifying the test sample template DNA in the set of assay samples in a multiplex dPCR. The multiplex dPCR comprises (i) a plurality of V-segment oligonucleotide primers that are each independently capable of specifically hybridizing to at least one polynucleotide encoding a TCR V-region polypeptide or an Ig V-region polypeptide, wherein each V-segment primer comprises a nucleotide sequence of at least 15 contiguous nucleotides that is complementary to at least one functional TCR or Ig V-encoding gene segment and wherein the plurality of V-segment primers specifically hybridize to substantially all functional TCR or IgV-encoding gene segments that are present in the test sample, and (ii) a plurality of J-segment oligonucleotide primers that are each independently capable of specifically hybridizing to at least one polynucleotide encoding a TCR J-region polypeptide or an Ig J-region polypeptide, wherein each J-segment primer comprises a nucleotide sequence of at least 15 contiguous nucleotides that is complementary to at least one functional TCR or Ig J-encoding gene segment and wherein the plurality of J-segment primers specifically hybridize to substantially all functional TCR or Ig J-encoding gene segments that are present in the test sample. The V-segment and J-segment primers are capable of amplifying in the multiplex dPCR substantially all rearranged TCR or Ig CDR3-encoding regions in the test sample to produce a multiplicity of amplified rearranged DNA molecules from the adaptive immune cells in the test sample. The multiplex dPCR further comprises a set of control primers to produce an internal control gene amplification product, wherein the set of control primers amplifies an internal control gene DNA segment that is not specific to adaptive immune cells. The number of assay samples that detectably contain the amplified rearranged DNA molecules is compared with the number of assay samples that detectably contain the internal control gene amplification product, from which the relative representation of adaptive immune cells in the test biological sample is quantified.

Any of the DNA or RNA extracted from a mixed population of cells from a sample described herein (e.g., samples described in connection with multiplex qPCR), any of the amplified regions described herein (e.g., various CDR3 regions), any of the compositions that comprise multiple of V-segment and J-segment primers provided herein (e.g., those described in connection with multiplex qPCR), any of the methods for detecting amplification products (e.g., using fluorescent probes described in connection with multiplex qPCR), and any of the internal controls common to all of the cells (i.e., in the adaptive immune cells and the in the cells that are not adaptive immune cells) in a test biological sample (e.g., the internal controls described in connection with multiplex qPCR) may be used in multiplex dPCR as provided herein.

Unlike qPCR, a known amount of control adaptive immune cell template DNA extracted from a control adaptive immune cell sample is not needed in dPCR. In addition, because dPCR typically uses an endpoint readout, rather than a conventional qPCR signal that is measured after each cycle in the thermal cycling reaction, no standard curve of amplification of adaptive immune cell template DNA is needed. However, in certain embodiments, although not necessary, it is possible that a known amount of control adaptive immune cell template DNA may be amplified separately from template DNA extracted from a test biological sample by qPCR to be used as a positive control for the template DNA extracted from the test biological sample.

As described herein, an internal control gene segment that is not specific to adaptive immune cells may be amplified in a multiplex dPCR. Because the number of copies of the internal control gene segment per cell is known, the number of assay samples that detectably contain the amplification product of the internal control gene segment allows the quantification of the number of the total cells (including adaptive immune cells and those that are not adaptive immune cells) from which test sample template DNA was extracted. If the number of copies of rearranged TCR or Ig CDR3-encoding regions per cell is known (e.g., about 80% of αβ T cells have only one of their two TCRβ alleles rearranged, while the other 20% have both alleles rearranged, with one of the two productive and the other non-productive), comparing the number of assay samples that detectably contain the amplification products of rearranged TCR or IgCDR3-encoding region with the number of assay samples that detectably contain the amplification product of the internal control gene segment allows quantification of the relative representation of adaptive immune cells (i.e., percentage of the cells in the test biological sample that are adaptive immune cells).

In certain embodiments, a DNA sample (e.g., DNA extracted from a test biological sample described herein) is fractionated by the simple process of dilution so that each fraction contains approximately one copy of DNA template or less. By isolating individual DNA templates, this process effectively enriches DNA molecules that were present at very low levels in the original sample. In certain embodiments, the sample is split into many fractions by dilution so that about 0.1 to about 0.3, about 0.3 to about 0.6, about 0.6 to about 1 copy of DNA per individual reactions.

Any systems known in the art for performing digital PCR methodology my be used in the methods provided herein, for example, the ABI QUANTSTUDIO™12K, Flex System (Life Technologies, Carlsbad, Calif.), the QX100™ DROPLET DIGIAL™ PCR system (BioRad, Hercules, Calif.), the QUANTALIFE™ digital PCR system (BioRad, Hercules, Calif.), or the RAINDANCE™ microdroplet digital PCR system (Raindance Technologies, Lexington, MA).

The present methods using dPCR are highly sensitive and are capable of detecting the presence of 10 or even fewer adaptive immune cells per 10,000 cells in the mixture of cells. In one embodiment, the present methods are capable of detecting the presence of 9, 8, 7, 6, 5, 4, 3, 2, or 1 adaptive immune cell per 10,000 cells in the mixture of cells.

In certain embodiments, the present methods using dPCR are capable of detecting 10 picograms of adaptive immune cell DNA in a DNA sample extracted from a population of mixed cells. In certain embodiments, the present methods are capable of detecting, 9, 8, 7, 6, or 5 picograms of adaptive immune cell DNA from a source of DNA extracted from a mixed population of cells, such as a tumor sample.

Methods of Use

The methods described herein may be used to enumerate the relative presence of tumor-infiltrating lymphocytes, or of lymphocytes infiltrating a somatic tissue that is the target of an autoimmune reaction, based on quantification of the relative representation of DNA from such adaptive immune cells in DNA extracted from a biological sample, comprising a mixture of cell types, that has been obtained from such a tumor or tissue. Such methods are useful for determining cancer or autoimmune disease prognosis and diagnosis, for assessing effects of a therapeutic treatment (e.g., assessing drug efficacy and/or dose-response relationships), and for identifying therapeutic courses for cancer treatment, for treatment of autoimmune diseases, or for treatment of transplant rejection, and may find other related uses.

To assess a therapeutic treatment, for example, certain embodiments contemplate a method in which is assessed an effect of the therapeutic treatment on the relative representation of adaptive immune cells in at least one tissue in a subject to whom the treatment has been administered. By way of illustration and not limitation, according to certain such embodiments a treatment that alters (e.g., increases or decreases in a statistically significant manner) the relative representation of adaptive immune cells in a tissue or tissues may confer certain benefits on the subject. For instance, certain cancer immunotherapies are designed to enhance the number of tumor infiltrating lymphocytes (TIL). It has been shown that the presence of CD3+ TIL in ovarian tumors is stongly correlated with patient outcome (see, e.g., Hwang et al., 2011 *Gynecol. Oncol.,* 124(2):192). Further data clarified that in addition to TIL presence, the characteristics of the TIL populations were also significant: CD8+ TILs and clonal TILs were associated with longer Disease Free Survival (DFS), and infiltrating regulatory T cells were associated with shorter DFS (see, Stumpf et al., 2009 *Br. J. Cancer* 101:1513-21). These studies indicated that TIL may be an independent prognostic factor (see, Clarke et al., 2009 *Mod. Pathol.* 22:393-402). Thus, quantification of the relative representation of adaptive immune cell DNA as described herein, for purposes of detecting possible increases in TIL in tumor tissue samples obtained at one or a plurality of time points before treatment, during the course of treatment and/or following treatment may provide highly useful information with respect to determining efficacy of the treatment, and therefrom developing a prognosis for the subject.

As another example, certain autoimmune disease-directed immunotherapies are designed to reduce the number of tissue infiltrating lymphocytes in one or more afflicted tissues such as tissues or organs that may be targets of clinically inappropriate autoimmune attack, such that quantification of the relative representation of adaptive immune cell DNA as described herein, for purposes of detecting possible decreases in adaptive immune cells in tissue samples obtained at one or a plurality of time points before treatment, during the course of treatment and/or following treatment may provide highly useful information with respect to determining efficacy of the treatment, and therefrom developing a prognosis for the subject.

As a further example, certain transplant rejection-directed immunotherapies are designed to reduce the number of tissue infiltrating lymphocytes in transplanted organs, such that quantification of the relative representation of adaptive immune cell DNA as described herein, for purposes of detecting possible decreases in adaptive immune cells in tissue samples from transplanted organs obtained at one or a plurality of time points before treatment, during the course of treatment and/or following treatment may provide highly useful information with respect to determining efficacy of the treatment, and therefrom developing a prognosis for the subject.

In these and related embodiments, the herein described methods for quantifying the relative representation of adaptive immune cell DNA may be practiced using test biological samples obtained from a subject at one or a plurality of time points prior to administering the therapeutic treatment to the subject, and at one or a plurality of time points after administering the therapeutic treatment to the subject. The samples may be obtained from the same or from different tissues, which may vary as a function of the particular condition of the subject. For example, by way of illustration and not limitation, in the case of an inoperable tumor the test biological samples that are obtained from the subject before and after treatment may be from the same tissue, whereas in the case of a tumor that is partially removed surgically, or that occurs at multiple sites in the subject, the test biological samples may be obtained from different tissues or from different tissue sites before and after the therapeutic treatment is administered.

Also contemplated herein are embodiments in which any of the herein described methods may further comprise determination of the relative structural diversity of adaptive immune receptors (e.g., the sequence diversity among products of productively rearranged TCR and/or immunoglobulin genes) in the adaptive immune cell component of the mixture of cells that is present in the test biological sample. In certain such embodiments, the present qPCR methodologies using the herein described rearranged adaptive immune receptor encoding specific oligonucleotide primer sets permit ready identification of the particular primer combinations that generate the production of amplified rearranged DNA molecules. Accordingly, for example, these embodiments permit determination of the relative degree of clonality of an adaptive immune cell population that is present as part of a mixed cell population in a test biological sample, which may have prognostic value.

For instance, in a solid tumor sample in which TILs are detected by quantifying the relative representation of adaptive immune cell DNA in DNA extracted from the sample as described herein, the present methods contemplate determination of whether only one or a few (e.g., no more than 1, 2, 3, 4, 5, 6, 7, 8, 9 or 10) combinations of a particular V-segment oligonucleotide primer and a particular J-segment oligonucleotide primer are predominantly (e.g., generating at least 80, 85, 90, 95, 97 or 99 percent of amplification products) responsible for the PCR production of amplified rearranged adaptive immune cell DNA molecules. Such an observation of one or a few predominant adaptive immune receptor gene-encoding amplification product would, according to non-limiting theory, indicate a low degree of TIL heterogeneity. Conversely, determination of a high degree of heterogeneity in adaptive immune receptor structural diversity by characterization of TIL DNA would indicate that a predominant TIL clone is not present.

Sequencing

It is thus further contemplated for these and related embodiments of any of the herein described methods that such a method may, optionally, further comprise sequencing the amplified adaptive immune receptor encoding DNA molecules that are produced. In certain embodiments, at least 30, 40, 50, 60, 70, 80, 90, 100, 101-150, 151-200, 201-300, 301-500, and not more than 1000 contiguous nucleotides of the amplified adaptive immune receptor encoding DNA molecules are sequenced. Compositions and methods for the sequencing of rearranged adaptive immune receptor gene sequences and for adaptive immune receptor clonotype determination are described in Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09.001; Sherwood et al. 2011 *Sci. Translat. Med.* 3:90ra61; U.S. application Ser. No. 13/217,126 (US Pub. No. 2012/0058902), U.S. application Ser. No. 12/794,507 (US Pub. No. 2010/0330571), WO/2010/151416, WO/2011/106738 (PCT/US2011/026373), WO2012/027503 (PCT/US2011/049012), U.S. application Ser. No. 61/550,311, and U.S. application Ser. No. 61/569,118, herein incorporated by reference.

Another embodiment is the method further comprising a step of sequencing the amplified DNA molecules. Another embodiment is wherein the sequencing step utilizes a set of sequencing oligonucleotides that hybridize to regions within the amplified DNA molecules.

Sequencing may be performed using any of a variety of available high through-put single molecule sequencing machines and systems. Illustrative sequence systems include sequence-by-synthesis systems such as the Illumina Genome Analyzer and associated instruments (Illumina, Inc., San Diego, Calif.), Helicos Genetic Analysis System (Helicos BioSciences Corp., Cambridge, Mass.), Pacific Biosciences PacBio RS (Pacific Biosciences, Menlo Park, Calif.), or other systems having similar capabilities. Sequencing is achieved using a set of sequencing oligonucleotides that hybridize to a defined region within the amplified DNA molecules. The sequencing oligonucleotides are designed such that the V- and J-encoding gene segments can be uniquely identified by the sequences that are generated, based on the present disclosure and in view of known adaptive immune receptor gene sequences that appear in publicly available databases.

The term "gene" means the segment of DNA involved in producing a polypeptide chain such as all or a portion of a TCR or Ig polypeptide (e.g., a CDR3-containing polypeptide); it includes regions preceding and following the coding region "leader and trailer" as well as intervening sequences (introns) between individual coding segments (exons), and may also include regulatory elements (e.g., promoters, enhancers, repressor binding sites and the like), and may also include recombination signal sequences (RSSs) as described herein.

The nucleic acids of the present embodiments, also referred to herein as polynucleotides, may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A coding sequence which encodes a TCR or an immunoglobulin or a region thereof (e.g., a V region, a D segment, a J region, a C region, etc.) for use according to the present embodiments may be identical to the coding sequence known in the art for any given TCR or immunoglobulin gene regions or polypeptide domains (e.g., V-region domains, CDR3 domains, etc.), or may be a different coding sequence, which, as a result of the redundancy or degeneracy of the genetic code, encodes the same TCR or immunoglobulin region or polypeptide.

In certain embodiments, the amplified J-region encoding gene segments may each have a unique sequence-defined identifier tag of 2, 3, 4, 5, 6, 7, 8, 9, 10 or about 15, 20 or more nucleotides, situated at a defined position relative to a RSS site. For example, a four-base tag may be used, in the Jβ-region encoding segment of amplified TCRβ CDR3-encoding regions, at positions +11 through +14 downstream from the RSS site. However, these and related embodiments need not be so limited and also contemplate other relatively short nucleotide sequence-defined identifier tags that may be detected in J-region encoding gene segments and defined based on their positions relative to an RSS site. These may vary between different adaptive immune receptor encoding loci.

The recombination signal sequence (RSS) consists of two conserved sequences (heptamer, 5'-CACAGTG-3', and nonamer, 5'-ACAAAAACC-3'), separated by a spacer of either 12+/−1 bp ("12-signal") or 23+/−1 bp ("23-signal"). A number of nucleotide positions have been identified as important for recombination including the CA dinucleotide at position one and two of the heptamer, and a C at heptamer position three has also been shown to be strongly preferred as well as an A nucleotide at positions 5, 6, 7 of the nonamer. (Ramsden et. al 1994; Akamatsu et. al. 1994; Hesse et. al. 1989). Mutations of other nucleotides have minimal or inconsistent effects. The spacer, although more variable, also has an impact on recombination, and single-nucleotide replacements have been shown to significantly impact recombination efficiency (Fanning et. al. 1996, Larijani et. al 1999; Nadel et. al. 1998). Criteria have been described for identifying RSS polynucleotide sequences having significantly different recombination efficiencies (Ramsden et. al 1994; Akamatsu et. al. 1994; Hesse et. al. 1989 and Cowell et. al. 1994). Accordingly, the sequencing oligonucleotides may hybridize adjacent to a four base tag within the amplified J-encoding gene segments at positions +11 through +14 downstream of the RSS site. For example, sequencing oligonucleotides for TCRB may be designed to anneal to a consensus nucleotide motif observed just downstream of this "tag", so that the first four bases of a sequence read will uniquely identify the J-encoding gene segment (Table 2B).

TABLE 2B

Sequencing oligonucleotides

| Sequencing oligonucleotide | SEQ ID NO: | Oligonucleotide sequence |
|---|---|---|
| Jseq 1-1 | 884 | ACAACTGTGAGTCTGGTGCCTTGTCCAAAGAAA |
| Jseq 1-2 | 885 | ACAACGGTTAACCTGGTCCCCGAACCGAAGGTG |
| Jseq 1-3 | 886 | ACAACAGTGAGCCAACTTCCCTCTCCAAAATAT |
| Jseq 1-4 | 887 | AAGACAGAGAGCTGGGTTCCACTGCCAAAAAAC |
| Jseq 1-5 | 888 | AGGATGGAGAGTCGAGTCCCATCACCAAAATGC |
| Jseq 1-6 | 889 | GTCACAGTGAGCCTGGTCCCGTTCCCAAAGTGG |
| Jseq 2-1 | 890 | AGCACGGTGAGCCGTGTCCCTGGCCCGAAGAAC |
| Jseq 2-2 | 891 | AGTACGGTCAGCCTAGAGCCTTCTCCAAAAAAC |
| Jseq 2-3 | 892 | AGCACTGTCAGCCGGGTGCCTGGGCCAAAATAC |
| Jseq 2-4 | 893 | AGCACTGAGAGCCGGGTCCCGGCGCCGAAGTAC |
| Jseq 2-5 | 894 | AGCACCAGGAGCCGCGTGCCTGGCCCGAAGTAC |
| Jseq 2-6 | 895 | AGCACGGTCAGCCTGCTGCCGGCCCCGAAAGTC |
| Jseq 2-7 | 896 | GTGACCGTGAGCCTGGTGCCCGGCCCGAAGTAC |

The information used to assign identities to the J- and V-encoding segments of a sequence read is entirely contained within the amplified sequence, and does not rely upon the identity of the PCR primers. In particular, the methods described herein allow for the amplification of all possible V-J combinations at a TCR or Ig locus and sequencing of the individual amplified molecules allows for the identification and quantitation of the uniquely rearranged DNA encoding the CDR3 regions. The diversity of the adaptive immune cells of a given sample can be inferred from the sequences generated using the methods and algorithms described herein. One surprising advantage provided in certain preferred embodiments by the compositions and methods of the present disclosure was the ability to amplify successfully all possible V-J combinations of an adaptive immune cell receptor locus in a single multiplex PCR reaction.

In certain embodiments, the sequencing oligonucleotides described herein may be selected such that promiscuous priming of a sequencing reaction for one J-encoding gene segment by an oligonucleotide specific to another distinct J-encoding gene segment generates sequence data starting at exactly the same nucleotide as sequence data from the correct sequencing oligonucleotide. In this way, promiscuous annealing of the sequencing oligonucleotides does not impact the quality of the sequence data generated.

The average length of the CDR3-encoding region, for the TCR, defined as the nucleotides encoding the TCR polypeptide between the second conserved cysteine of the V segment and the conserved phenylalanine of the J segment, is 35+/−3 nucleotides. Accordingly and in certain embodiments, PCR amplification using V-segment oligonucleotide primers with J-segment oligonucleotide primers that start from the J segment tag of a particular TCR or IgH J region (e.g., TCR Jβ, TCR Jγ or IgH JH as described herein) will nearly always capture the complete V-D-J junction in a 50 base pair read. The average length of the IgH CDR3 region, defined as the nucleotides between the conserved cysteine in the V segment and the conserved phenylalanine in the J segment, is less constrained than at the TCRβ locus, but will typically be between about 10 and about 70 nucleotides. Accordingly and in certain embodiments, PCR amplification using V-segment oligonucleotide primers with J-segment oligonucleotide primers that start from the IgH J segment tag will capture the complete V-D-J junction in a 100 base pair read.

PCR primers that anneal to and support polynucleotide extension on mismatched template sequences are referred to as promiscuous primers. In certain embodiments, the TCR and Ig J-segment reverse PCR primers may be designed to minimize overlap with the sequencing oligonucleotides, in order to minimize promiscuous priming in the context of multiplex PCR. In one embodiment, the TCR and Ig J-segment reverse primers may be anchored at the 3' end by annealing to the consensus splice site motif, with minimal overlap of the sequencing primers. Generally, the TCR and Ig V and J-segment primers may be selected to operate in PCR at consistent annealing temperatures using known sequence/primer design and analysis programs under default parameters.

For the sequencing reaction, the exemplary IGHJ sequencing primers extend three nucleotides across the conserved CAG sequences as shown in Table 2C.

TABLE 2C

| IgH J segment | SEQ ID NO: | Sequence |
|---|---|---|
| >IGHJSEQ4_1 | 897 | TGAGGAGACGGTGACCAGGGTTCCTTGGCCCCAG |
| >IGHJSEQ4_3 | 898 | TGAGGAGACGGTGACCAGGGTCCCTTGGCCCCAG |
| >IGHJSEQ4_2 | 899 | TGAGGAGACGGTGACCAGGGTTCCCTGGCCCCAG |
| >IGHJSEQ3_12 | 900 | CTGAAGAGACGGTGACCATTGTCCCTTGGCCCCAG |
| >IGHJSEQ6_1 | 901 | CTGAGGAGACGGTGACCGTGGTCCCTTGCCCCCAG |
| >IGHJSEQ6_2 | 902 | TGAGGAGACGGTGACCGTGGTCCCTTGGCCCCAG |
| >IGHJSEQ6_34 | 903 | CTGAGGAGACGGTGACCGTGGTCCCTTTGCCCCAG |
| >IGHJSEQ2_1 | 904 | CTGAGGAGACAGTGACCAGGGTGCCACGGCCCCAG |
| >IGHJSEQ5_1 | 905 | CTGAGGAGACGGTGACCAGGGTTCCTTGGCCCCAG |
| >IGHJSEQ5_2 | 906 | CTGAGGAGACGGTGACCAGGGTTCCCTGGCCCCAG |
| >IGHJSEQ1_1 | 907 | CTGAGGAGACGGTGACCAGGGTGCCCTGGCCCCAG |

As presently disclosed there are also provided methods for analyzing the sequences of the diverse pool of uniquely rearranged CDR3-encoding regions that are generated using the compositions and methods that are described herein. In particular, an algorithm is provided to correct for PCR bias, sequencing and PCR errors and for estimating true distribution of specific clonotypes (e.g., a TCR or Ig having a uniquely rearranged CDR3 sequence) in blood or in a sample derived from other peripheral tissue or bodily fluid. A preferred algorithm is described in further detail herein. As would be recognized by the skilled person, the algorithms provided herein may be modified appropriately to accommodate particular experimental or clinical situations.

The use of a PCR step to amplify the TCR or Ig CDR3 regions prior to sequencing could potentially introduce a systematic bias in the inferred relative abundance of the sequences, due to differences in the efficiency of PCR amplification of CDR3 regions utilizing different V and J gene segments. As discussed in more detail in the Examples, each cycle of PCR amplification potentially introduces a bias of average magnitude $1.5^{1/15}=1.027$. Thus, the 25 cycles of PCR introduces a total bias of average magnitude $1.027^{25}=1.95$ in the inferred relative abundance of distinct CDR3 region sequences.

Sequenced reads are filtered for those including CDR3 sequences. Sequencer data processing involves a series of steps to remove errors in the primary sequence of each read, and to compress the data. A complexity filter removes approximately 20% of the sequences that are misreads from the sequencer. Then, sequences were required to have a minimum of a six base match to both one of the TCR or Ig J-regions and one of V-regions. Applying the filter to the control lane containing phage sequence, on average only one sequence in 7-8 million passed these steps. Finally, a nearest neighbor algorithm is used to collapse the data into unique sequences by merging closely related sequences, in order to remove both PCR error and sequencing error.

Analyzing the data, the ratio of sequences in the PCR product are derived working backward from the sequence data before estimating the true distribution of clonotypes (e.g., unique clonal sequences) in the blood. For each sequence observed a given number of times in the data herein, the probability that that sequence was sampled from a particular size PCR pool is estimated. Because the CDR3 regions sequenced are sampled randomly from a massive pool of PCR products, the number of observations for each sequence are drawn from Poisson distributions. The Poisson parameters are quantized according to the number of T cell genomes that provided the template for PCR. A simple Poisson mixture model both estimates these parameters and places a pairwise probability for each sequence being drawn from each distribution. This is an expectation maximization method which reconstructs the abundances of each sequence that was drawn from the blood.

To estimate the total number of unique adaptive immune receptor CDR3 sequences that are present in a sample, a computational approach employing the "unseen species" formula may be employed (Efron and Thisted, 1976 *Biometrika*

63, 435-447). This approach estimates the number of unique species (e.g., unique adaptive immune receptor sequences) in a large, complex population (e.g., a population of adaptive immune cells such as T cells or B cells), based on the number of unique species observed in a random, finite sample from a population (Fisher et al., 1943 *J. Anim. Ecol.* 12:42-58; Ionita-Laza et al., 2009 *Proc. Nat. Acad. Sci. USA* 106:5008). The method employs an expression that predicts the number of "new" species that would be observed if a second random, finite and identically sized sample from the same population were to be analyzed. "Unseen" species refers to the number of new adaptive immune receptor sequences that would be detected if the steps of amplifying adaptive immune receptor-encoding sequences in a sample and determining the frequency of occurrence of each unique sequence in the sample were repeated an infinite number of times. By way of non-limiting theory, it is operationally assumed for purposes of these estimates that adaptive immune cells (e.g., T cells, B cells) circulate freely in the anatomical compartment of the subject that is the source of the sample from which diversity is being estimated (e.g., blood, lymph, etc.).

To apply this formula, unique adaptive immune receptors (e.g., TCRβ, TCRα, TCRγ, TCRδ, IgH) clonotypes takes the place of species. The mathematical solution provides that for S, the total number of adaptive immune receptors having unique sequences (e.g., TCRβ, TCRγ, IgH "species" or clonotypes, which may in certain embodiments be unique CDR3 sequences), a sequencing experiment observes $x_s$ copies of sequence s. For all of the unobserved clonotypes, $x_s$ equals 0, and each TCR or Ig clonotype is "captured" in the course of obtaining a random sample (e.g., a blood draw) according to a Poisson process with parameter $\lambda_s$. The number of T or B cell genomes sequenced in the first measurement is defined as 1, and the number of T or B cell genomes sequenced in the second measurement is defined as t.

Because there are a large number of unique sequences, an integral is used instead of a sum. If G(λ) is the empirical distribution function of the parameters $\lambda_1, \ldots, \lambda_S$, and $n_x$ is the number of clonotypes (e.g., unique TCR or Ig sequences, or unique CDR3 sequences) observed exactly x times, then the total number of clonotypes, i.e., the measurement of diversity E, is given by the following formula (I):

$$E(n_x) = S\int_0^\infty \left(\frac{e^{-\lambda}\lambda^x}{x!}\right) dG(\lambda). \tag{I}$$

Accordingly, formula (I) may be used to estimate the total diversity of species in the entire source from which the identically sized samples are taken. Without wishing to be bound by theory, the principle is that the sampled number of clonotypes in a sample of any given size contains sufficient information to estimate the underlying distribution of clonotypes in the whole source. The value for Δ(t), the number of new clonotypes observed in a second measurement, may be determined, preferably using the following equation (II):

$$\begin{aligned}\Delta(t) &= \sum_x E(n_x)_{msmt1+msmt2} - \sum_x E(n_x)_{msmt1} \\ &= S\int_0^\infty e^{-\lambda}(1-e^{-\lambda t})dG(\lambda)\end{aligned} \tag{II}$$

in which msmt1 and msmt2 are the number of clonotypes from measurements 1 and 2, respectively. Taylor expansion of $1\text{-}e^{-\lambda t}$ and substitution into the expression for Δ(t) yields:

$$\Delta(t)=E(x_1)t-E(x_2)t^2+E(x_3)t^3- \ldots , \tag{iii}$$

which can be approximated by replacing the expectations ($E(n_x)$) with the actual numbers sequences observed exactly x times in the first sample measurement. The expression for Δ(t) oscillates widely as t goes to infinity, so Δ(t) is regularized to produce a lower bound for Δ(∞), for example, using the Euler transformation (Efron et al., 1976 *Biometrika* 63:435).

In certain embodiments, there is provided a method for quantifying the relative representation of adaptive immune cells in a mixture of cells in a biological sample, comprising: (a) amplifying DNA extracted from the mixture of cells with a plurality of V segment primers and a plurality of J segment primers in a quantitative polymerase chain reaction (qPCR), wherein the plurality of V segment primers and the plurality of J segment primers permit amplification of substantially all combinations of the V and J segments of a rearranged immune receptor locus; (b) measuring in real time an amount of DNA amplified in (a) by the plurality of V segment primers and the plurality of J segment primers; (c) comparing the amount of amplified DNA measured in (b) to a known amount of adaptive immune cell DNA that has been amplified by the plurality of V segment primers and the plurality of J segment primers, and therefrom determining an amount of adaptive immune cell DNA extracted from the mixture of cells; and (d) quantifying, from the amount of adaptive immune cell DNA of (c), the relative number of adaptive immune cells in the mixture of cells.

In certain other embodiments, there is provided a method for quantifying the relative representation of adaptive immune cells in a mixture of cells in a biological sample, comprising: (a) amplifying DNA extracted from the mixture of cells with a plurality of V segment primers and a plurality of J segment primers in a dPCR, wherein the plurality of V segment primers and the plurality of J segment primers permit amplification of substantially all combinations of the V and J segments of a rearranged immune receptor locus; and (b) comparing the number of assay samples that detectably contain amplified DNA of (a) to the number of assay samples that detectably contain an amplification product of an internal control gene segment, and therefrom determining the relative representation of adaptive immune cells in the mixture of cells.

According to certain herein expressly disclosed embodiments, there are also presently provided methods in which the degree of clonality of adaptive immune cells that are present in a sample, such as a sample that comprises a mixture of cells only some of which are adaptive immune cells, can be determined advantageously without the need for cell sorting or for DNA sequencing. These and related embodiments overcome the challenges of efficiency, time and cost that, prior to the present disclosure, have hindered the ability to determine whether adaptive immune cell presence in a sample (e.g., TIL) is monoclonal or oligoclonal (e.g., whether all TILs are the progeny of one or a relatively limited number of adaptive immune cells), or whether instead adaptive immune cell presence in the sample is polyclonal (e.g., TILs are the progeny of a relatively large number of adaptive immune cells).

According to non-limiting theory, these embodiments exploit current understanding in the art (also described above) that once an adaptive immune cell (e.g., a T or B lymphocyte) has rearranged its adaptive immune receptor-encoding (e.g., TCR or Ig) genes, its progeny cells possess the same adaptive immune receptor-encoding gene rearrangement, thus giving rise to a clonal population that can be uniquely identified by the presence therein of rearranged CDR3-encoding V- and J-gene segments that may be amplified by a specific pairwise combination of V- and J-specific oligonucleotide primers as herein disclosed.

In such presently disclosed embodiments, qPCR or dPCR may be practiced using specifically selected subsets of the adaptive immune receptor-encoding gene V- and J-segment specific oligonucleotide primers as described herein, to determine a degree of adaptive immune cell clonality in a biological sample. For example, in certain embodiments, separate amplification reactions are set up for a plurality of replicate samples of template DNA that has been extracted from a complex biological sample comprising a heterogeneous mixture of cells (e.g., a solid tumor sample containing tumor cells, mesenchymal cells and TILs). A complete set of TCR J region specific primers is added to every replicate sample, but each replicate sample receives only one TCR V region specific primer. Quantitative PCR amplification is then permitted to proceed, and each replicate sample is quantitatively assessed for the presence or absence of amplification products. The relative representation of amplification products that is generated in each separate reaction, using each particular primer combination, indicates the relative abundance in the sample template DNA of TCR-encoding DNA containing the V-J rearrangement that is capable of being amplified by a specific V-J primer pair that is present in the reaction. The relative abundance of each amplification product reflects the relative representation of T cells of distinct clonal origin in the biological sample.

In certain other embodiments, separate amplification reactions (e.g., qPCR or dPCR) are set up for multiple replicate samples of template DNA extracted from a test biological sample. A complete set of TCR J region specific primers is added to every replicate sample, but each replicate sample receives a subgroup of TCR V region specific primers. Exemplary subgroups of TCR V region specific primers include those provided in Example 5. The relative representation of amplification products generated in each separate reaction, using each particular primer combination, indicates the relative abundance in the sample template DNA of TCR-encoding DNA containing the V-J rearrangements capable of being amplified by specific V-J primer pairs present in the reaction.

In certain embodiments, the methods for quantifying the relative representation of adaptive immune cells in a test biological sample further comprise quantifying the relative representation of CD4+ adaptive immune cells and/or CD8+ adaptive immune cells. Similarly, in certain embodiments, the methods for assessing an effect of a therapeutic treatment on relative representation of adaptive immune cells disclosed herein further comprise assessing an effect of a therapeutic treatment on relative representation of CD4+ adaptive immune cells and/or on relative representation of CD8+ adaptive immune cells.

The human cellular adaptive immune system is mediated by two primary types of T cells, killer T cells and helper T cells. Killer T cells, marked by the surface expression of CD8, recognize short peptides (about 8-10 amino acids) presented on the surface of cells by human leukocyte antigen (HLA Class I molecules. Helper T cells, marked by the surface expression of CD4, recognize longer peptides (about 12-16 amino acids) presented on the surface of cells by HLA Class II molecules. Both of these T cell types derive from a common progenitor cell type.

During the development of T cells in the thymus, the DNA coding for the alpha and beta chains of the Y-like T cell receptors (TCR) rearrange in a pseudo-random process to form an enormous variety of TCRs. TCR sequence diversity is primarily contained in the complementarity determining region 3 (CDR3) loops of the α and β chains, which bind to the peptide antigen, conveying specificity. The nucleotide sequences that encode the CDR3 loops are generated by V(D)J recombination: variable ($V_\beta$), diversity ($D_\beta$) and joining ($J_\beta$) genes in the genome are rearranged to form a β chain, while $V_\alpha$ and $J_\alpha$ genes rearrange to form an a chain.

After the alpha and beta chains rearrange, while still in the thymus, T cells are both positively and negatively selected against self peptides displayed by Class I and Class II HLA molecules. If a TCR binds strongly to a self peptide:HLA complex, the T cell usually dies. Additionally, a T cell is positively selected, requiring some minimal threshold of binding to either a Class I or Class II presented peptide. Prior to selection, T cells express both CD4 and CD8 on their surface, and are referred to as double positive T cells. Upon positive selection the T cell halts expression of one of these two surface proteins, leaving a single positive T cell committed as either a helper or killer T cell. These two T cell types serve very different functional roles.

The present inventors have discovered that the TCR sequences from, respectively, helper and killer T cells, preferentially utilize different Vβ gene segments (see, Example 6). For example, 21 of 48 Vβ segments measured have differential usage between CD4+ and CD8+ samples. Exemplary Vβ segments preferentially used by CD4+ cells and exemplary Vβ segments preferentially used by CD8+ cells include the following:

| Vβ segments more frequent in: | |
|---|---|
| CD4+ T cells | CD8+ T cells |
| TRBV11-1*** | TRBV10-2* |
| TRBV18*** | TRBV13*** |
| TRBV30* | TRBV16* |
| TRBV5-1*** | TRBV19** |
| TRBV5-4*** | TRBV4-1** |
| TRBV5-7*** | TRBV4-2* |
| TRBV7-2*** | TRBV4-3** |
| TRBV7-3* | TRBV6-1*** |
| TRBV7-7* | TRBV6-4*** |
| | TRBV7-6*** |
| | TRBV7-8** |
| | TRBV7-9*** |

*$p < 0.05$
**$p < 0.01$
***$p < 0.001$

Based on knowledge about such preferential use of different Vβ gene segments in a subject, the relative representation in a sample of CD4+ adaptive immune cells and/or CD8+ adaptive immune cells may be quantified. For example, the frequency with which productively rearranged TCR sequences use each Vβ segment may be calculated in one or more CD4+ samples isolated from a subject (e.g., a sorted peripheral blood cell population containing predominantly CD4+ T cells, as may be obtained by fluorescence activated cell sorting (FACS) or with anti-CD4 antibody-coated immunomagnetic beads or by other techniques). Similarly, the frequency with which productively rearranged TCR sequences use each Vβ segment may be calculated in one or more CD8+ samples from the subject. Such frequencies may be used to train a likelihood model (e.g., a computer program), which may in turn be used to estimate the proportion of CD4+ cells in a sample from the subject having an unknown proportion of CD4+ cells (e.g., a sample of mixed cell types that is obtained from a solid tumor or from a solid tissue organ) based on the information (e.g., partial or complete sequences) used to train the model with respect to utilization of particular rearranged DNA molecules in the CD4+ and CD8+ compartments, which information is obtained by amplification according to the methods described herein using qPCR or dPCR.

For example, rearranged TCR Vβ segments amplified by qPCR or dPCR as described herein may be sequenced, and the resulting sequences may be used to estimate the proportion of CD4+ cells or CD8+ cells using a likelihood model developed as described herein. Alternatively, primers specific for TCR Vβ gene segments that are preferentially used in CD4+ adaptive immune cells may be grouped together to form one or more subgroups of primers ("first subgroups"), while primers specific for Vβ gene segments preferentially used in CD8+ adaptive immune cells may form one or more other subgroups ("second subgroups"). Multiple qPCR or dPCR reactions are performed individually, each using primers of only one of the first subgroups or one of the second subgroups. For qPCR, the amounts of amplification products using primers from the first subgroups of primers and from the second subgroups are separately measured. Similarly, for dPCR, the numbers of assay samples that detectably contain amplified rearranged DNA molecules using primers from the first subgroups of primers and from the second subgroups are separately measured. The amounts of amplification products from qPCR reactions and the numbers of assay samples from dPCR reactions may then be used to estimate the proportion of CD4+ cells or CD8+ cells using the likelihood model.

In certain embodiments, the preferential usage of different Vβ gene segments in a subject (e.g., a patient) may be determined by sorting cells from the subject (e.g., blood cells) into CD4+ cells and CD8+ cells followed by measuring the frequency of each rearranged TCR sequence in the CD4+ cells and CD8+ cells. The frequencies of rearranged TCR sequences in the CD4+ cells and CD8+ cells may be used to develop a possibility or probability model. A test biological sample from the same subject may then be used to isolate genomic DNA and is used as a template in amplifying rearranged TCR loci by qPCR or dPCR according to the methods described herein. The information about the amplified rearranged adaptive TCR loci (e.g., their sequences or their types based on specific primers or specific groups of primers used in amplification reactions) may then be used to estimate the proportion of CD4+ cells or CD8+ cells in the test biological sample. Using the frequencies of particular rearranged TCR sequences in known CD4+ cells and CD8+ cells (e.g., FACS-sorted peripheral blood cells) of the same subject from which the test biological sample is also obtained may avoid or reduce the observed variability in CD4+-specific or CD8+-specific preferential use of different Vβ gene segments among different subjects.

It will be appreciated by the skilled person based on the present disclosure that variations and permutations of the assay design may be practiced, such as setting up parallel reactions in which every reaction contains template DNA from the mixed cell-type sample and a complete complement of V region primers but only one J region primer, or reactions that contain different known subsets of V and/or J region primers. As another example, replicate qPCR or dPCR amplification reactions may be set up that each contain template DNA from the mixed cell-type sample and a full complement of V and J region oligonucleotide primers such as those disclosed herein, and each individual reaction also contains a single, different detectably labeled V region probe such as one of the labeled probes presented in Table 2A, or a different subset of the labeled probes presented in Table 2A (e.g., 1, 2, 3, 4, 5, 6, 7, 8, 9 or 10 different detectably labeled V region probes from Table 2A). Detection of the presence of amplification products in one or more particular reactions permits determination of the degree of adaptive immune cell clonality in the sample from which template DNA was obtained.

The degree of adaptive immune cell clonality in a sample may in this manner be readily determined, without requiring isolation and sorting of adaptive immune cells, and without requiring (although not precluding, as provided by certain herein disclosed embodiments) DNA sequencing. In a solid tissue tumor sample containing TILs, for example, these and related embodiments permit determination of whether the TIL population is predominantly monoclonal or oligoclonal and thus represents a relatively small number of clones that have undergone extensive expansion via cellular (clonal) proliferation, or whether instead the TIL population is clonally diverse and thus heterogeneous with respect to adaptive immune receptor utilization. Information from such analyses will usefully provide information concerning the physiological and pathological status of the tissue (and hence of the source subject), and will be particularly useful in situations where samples obtained before, during and/or after therapy are assayed, according to certain embodiments described elsewhere herein. For instance, the degree of TIL clonality in a tumor tissue may provide diagnostic and/or prognostic information, including information regarding the potential efficacy of a therapeutic regimen or regarding the optimal dosing regimen. Similarly, the degree of TIL clonality in a tissue that is a target of autoimmune attack may usefully permit identification and refinement of clinical approaches to autoimmune disease.

Also provided herein according to certain embodiments is a method for determining a course of treatment for a patient in need thereof, comprising quantifying the relative representation of tumor-infiltrating lymphocytes or lymphocytes infiltrating a somatic tissue that is the target of an autoimmune reaction, using the methods described herein. In this regard, the patient in need thereof may be a cancer patient or a patient having an autoimmune disease. In certain embodiments, a patient may have a cancer including, but not limited to, colorectal, hepatocellular, gallbladder, pancreatic, esophageal, lung, breast, prostate, skin (e.g., melanoma), head and neck, renal cell carcinoma, ovarian, endometrial, cervical, bladder and urothelial cancer. In certain other embodiments, a patient may have an organ transplant, such as a liver transplant, a lung transplant, a kidney transplant, a heart transplant, a spleen transplant, a pancreas transplant, a skin transplant/graft, an intestine transplant, and a thymus transplant.

Autoimmune diseases include, but are not limited to, arthritis (including rheumatoid arthritis, reactive arthritis), systemic lupus erythematosus (SLE), psoriasis, inflammatory bowel disease (IBD) (including ulcerative colitis and Crohn's disease), encephalomyelitis, uveitis, myasthenia gravis, multiple sclerosis, insulin dependent diabetes, Addison's disease, celiac disease, chronic fatigue syndrome, autoimmune hepatitis, autoimmune alopecia, ankylosing spondylitis, fibromyalgia, pemphigus vulgaris, Sjogren's syndrome, Kawasaki's Disease, hyperthyroidism/Graves disease, hypothyroidism/Hashimoto's disease, endometriosis, scleroderma, pernicious anemia, Goodpasture syndrome, Guillain-Barré syndrome, Wegener's disease, glomerulonephritis, aplastic anemia (including multiply transfused aplastic anemia patients), paroxysmal nocturnal hemoglobinuria, idiopathic thrombocytopenic purpura, autoimmune hemolytic anemia, Evan's syndrome, Factor VIII inhibitor syndrome, systemic vasculitis, dermatomyositis, polymyositis and rheumatic fever, autoimmune lymphoproliferative syndrome (ALPS), autoimmune bullous pemphigoid, Parkinson's disease, sarcoidosis, vitiligo, primary biliary cirrhosis, and autoimmune myocarditis.

The practice of certain embodiments of the present invention will employ, unless indicated specifically to the contrary, conventional methods in microbiology, molecular biology, biochemistry, molecular genetics, cell biology, virology and immunology techniques that are within the skill of the art, and reference to several of which is made below for the purpose of illustration. Such techniques are explained fully in the literature. See, e.g., Sambrook, et al., *Molecular Cloning: A Laboratory Manual* ($3^{rd}$ Edition, 2001); Sambrook, et al., *Molecular Cloning: A Laboratory Manual* ($2^{nd}$ Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); *Perbal, A Practical Guide to Molecular Cloning* (1984); *Next-Generation Genome Sequencing* (Janitz, 2008 Wiley-VCH); *PCR Protocols* (*Methods in Molecular Biology*) (Park, Ed., $3^{rd}$ Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C C Blackwell, eds., 1986); Riott, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

Unless the context requires otherwise, throughout the present specification and claims, the word "comprise" and variations thereof, such as, "comprises" and "comprising" are to be construed in an open, inclusive sense, that is, as "including, but not limited to". By "consisting of" is meant including, and typically limited to, whatever follows the phrase "consisting of." By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and may or may not be present depending upon whether or not they affect the activity or action of the listed elements.

In this specification and the appended claims, the singular forms "a," "an" and "the" include plural references unless the content clearly dictates otherwise. As used herein, in particular embodiments, the terms "about" or "approximately" when preceding a numerical value indicates the value plus or minus a range of 5%, 6%, 7%, 8% or 9%. In other embodiments, the terms "about" or "approximately" when preceding a numerical value indicates the value plus or minus a range of 10%, 11%, 12%, 13% or 14%. In yet other embodiments, the terms "about" or "approximately" when preceding a numerical value indicates the value plus or minus a range of 15%, 16%, 17%, 18%, 19% or 20%.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

It should also be noted that the term "or" is generally employed in its sense including "and/or" (i.e., to mean either one, both, or any combination thereof of the alternatives) unless the content clearly dictates otherwise. The term, "at least one," for example, when referring to at least one compound or to at least one composition, has the same meaning and understanding as the term, "one or more." In addition, any ranges provided herein include all the values in the ranges.

The following examples are for illustration and are not limiting.

EXAMPLES

Example 1

Quantification of Relative T Lymphocyte DNA Representation from T Cells in Normal Tissues and from Tumor-Infiltrating T Lymphocytes in a Tumor Sample Samples of peripheral blood, fresh adipose biopsies, frozen muscle biopsy, and skin biopsies were processed for DNA extraction using the following procedure:

Samples of $1\times10^4$ to $1\times10^6$ fresh, frozen, or fixed cells were lysed in 200 ul of lysis buffer (50 mM TrisHCl pH7.4, 250 mM NaCl, 0.1% SDS, 0.5% Triton-X100) and 20 ul of proteinase K (10 mg/ml) using the kitted ATL buffer and proteinase K reagents from the Qiagen Blood and Tissue kit (Qiagen #69504, Qiagen Corp., Valencia, Calif.), and incubated at 56° C. for one hour with mixing every 20 minutes. The lysate was diluted with 200 ul of an ethanol/buffer mixture (20 mM Tris, pH 7.5, 2.0 mM EDTA, in 50% v/v ethanol) and mixed briefly. Alternatively, the AL buffer of the Qiagen Blood and Tissue kit was used. SDS precipitates formed on occasion, but were not observed to adversely impact DNA extraction or sequencing efficiency. To the diluted lysate was added 200 ul of ethanol (96-100%).

The lysate/ethanol mixture was carefully applied to a solid support of either silica resin Sigma Celite 454 resin (Sigma #419931, Sigma, St. Louis, Mo.) or to a Qiagen Blood and Tissue kit column. The column was centrifuged at 6000×g for one minute in a micro-centrifuge and the filtrate was discarded. The column was washed with 500 ul of Qiagen AW1 wash buffer, or 6 M guanidine thiocyanate (GuSCN), 20 mM EDTA pH 8.0, 10 mM Tris-HCl pH 6.4, 4% Triton X-100 in 50% ethanol (v/v), and was then centrifuged at 6000×g in a microcentrifuge for one minute. The filtrate was discarded the filtrate and the column was washed with 500 ul of Qiagen AW2 wash buffer or 100 mM Tris, pH 7.5 in 70 ethanol (v/v), after which the column was centrifuged at 14,000×g for three minutes, and the filtrate discarded.

Next, the column was centrifuged at 14,000×g for one minute to dry the column of residual ethanol. 100 ul of either Qiagen AE elution buffer, or 10 mM Tris, pH 7.5, 1 mM EDTA, was applied to the column, which was placed on a clean collection tube, incubated at room temperature for five minutes, and then centrifuged at 6000×g for one minute to collect DNA. An aliquot of 2 ul of the eluate was transferred to a clean tube or 96 well plate to determine yield by spectrophotometry ($A_{260}/A_{280}$) and the DNA concentration was calculated. An aliquot of 5 ul of the DNA-containing eluate was transferred to a 96 well plate and diluted with 20 ul TE for processing by qPCR.

The number of T cells in complex mixtures of tissues was estimated by determining the relative representation of T cell DNA in the samples of peripheral blood (PBMC), and in muscle, skin and adipose tissue biopsies, by quantitative PCR amplification of the rearranged TCR-β (TCRB) genes. The relative representation of T cell genomes in each tissue sample was determined by comparing the tissue sample qPCR signal profile to a calibration standard profile generated using a panel of T cell DNAs of known concentrations, and then comparing the values so obtained to the total DNA concentration of the tissue. The percent T cell composition of the tissues ranged from less than 1% in adipose tissue to greater than 92% in PBMC (Table 3).

TABLE 3

Quantitative PCR Amplification/T Cell Quantification in Tissues by Relative Representation of Adaptive Immune Receptor DNA as a Component of Tissue DNA

| sampleID | qPCR measured T cells (nanograms) | Total DNA concentration (nanograms) | Percent T cells |
|---|---|---|---|
| SKIN_FM_6/24/11 | 8.25 | 15.31 | 53.9 |
| SKIN_FMM_9/2/11 | 2.03 | 13.88 | 14.6 |
| SKIN_MP_block | 0.78 | 3.41 | 22.9 |
| SKIN_RB_8/11/11 | 7.43 | 14.85 | 50.0 |
| SKIN_RB_9/8/11 | 2.46 | 18.46 | 13.3 |
| SKIN_TB_7/13/11 | 1.52 | 19.95 | 7.6 |
| MUSCLE_1995-_2-6 | 0.13 | 3.06 | 4.32 |
| MUSCLE_1995-_8-12 | 0.05 | 2.24 | 2.23 |
| MUSCLE_2062-_2-6 | 4.18 | 6.62 | 63.18 |
| MUSCLE_2062-_8-12 | 2.20 | 8.02 | 27.47 |
| MUSCLE_2417-_2-6 | 0.47 | 4.94 | 9.50 |
| MUSCLE_2417-_8-12 | 0.07 | 4.64 | 1.47 |
| MUSCLE_2426-_2-6 | 0.17 | 4.35 | 4.02 |
| MUSCLE_2426-_8-12 | 0.21 | 6.31 | 3.34 |
| MUSCLE_2444-_2-6 | 0.02 | 3.29 | 0.68 |
| MUSCLE_2444-_8-12 | 0.16 | 13.79 | 1.19 |
| MUSCLE_2450-_2-6 | 2.33 | 4.42 | 52.78 |
| MUSCLE-2450-_8-12 | 1.51 | 5.22 | 28.90 |
| PBMC_9 | 15.52 | 90.55 | 17.14 |
| PBMC_8 | 87.59 | 124.32 | 70.45 |
| PBMC_7 | 10.42 | 42.97 | 24.26 |
| PBMC_6 | 115.52 | 125.33 | 92.17 |
| PBMC_5 | 21.15 | 46.09 | 45.88 |
| PBMC_4 | 36.35 | 130.00 | 27.96 |
| PBMC_3 | 10.81 | 142.16 | 7.60 |
| PBMC_14 | 11.14 | 49.08 | 22.70 |
| PBMC_11 | 94.22 | 223.56 | 42.14 |
| ADIPOSE_8-SQ | 0.50 | 10.55 | 4.70 |
| ADIPOSE_8-OM | 1.90 | 19.34 | 9.84 |
| ADIPOSE_6-SQ | 0.43 | 11.22 | 3.80 |
| ADIPOSE_6-OM | 0.64 | 19.14 | 3.35 |
| ADIPOSE_4-SQ | 0.20 | 8.22 | 2.39 |
| ADIPOSE_4-OM | 3.49 | 34.23 | 10.21 |
| ADIPOSE_2-SQ | 0.83 | 11.62 | 7.14 |
| ADIPOSE_2-OM | 1.00 | 18.39 | 5.44 |
| ADIPOSE_17-SQ | 2.44 | 11.59 | 21.10 |
| ADIPOSE_17-OM | 0.24 | 18.94 | 1.27 |
| ADIPOSE_16-SQ | 0.72 | 6.13 | 11.79 |
| ADIPOSE_16-OM | 0.96 | 33.66 | 2.85 |
| ADIPOSE_14-SQ | 0.23 | 8.97 | 2.56 |
| ADIPOSE_14-OM | 1.60 | 10.57 | 15.13 |
| ADIPOSE_11-SQ | 0.60 | 9.67 | 6.22 |
| ADIPOSE_11-OM | 0.06 | 60.21 | 0.10 |
| ADIPOSE_10-SQ | 2.50 | 11.51 | 21.70 |
| ADIPOSE_10-OM | 0.63 | 105.50 | 0.60 |

Example 2

Quantification of Tumor-Infiltrating T Lymphocytes in a Tumor Sample Using a TCRβ V-Region Specific qPCR Probe Tumor-infiltrating T lymphocytes (TILs) were quantified using a multiplex real-time PCR assay as follows.

Multiplex Primer Sequences:

The multiplex oligonucleotide primer sets that were used had the sequences shown in Table 1. The "r" in Table 1B represents a ribonucleotide base in the oligonucleotide sequence and "/3SpC3/" represents a 3' three carbon spacer on the hydroxyl group preventing polymerase extension and amplification. The DNA repair endonuclease cleaves the oligonucleotide at the ribonucleotide after hybridization to a complementary sequence, creating an unblocked hydroxyl group that can be extended by a polymerase.

Assay Reagents: 20 μl PCR reactions were set up having final concentrations of 1× Taq polymerase buffer, 10 ng/ul analyte DNA, 1 micromolar TCRBV_RN2 oligonucleotide primer mix (Table 1), 1 micromolar TCRBJ_RN2 oligonucleotide primer mix (Table 1), and 0.1 milliunits/ul of RNAse H2 (IDT, Coralville, Iowa). Analytes and standard PCR reactions were set up in quadruplicate.

Thermal Cycling Conditions: Reactions were thermal cycled on a real time PCR platform (ILLUMINA ECO™, Illumina Inc., San Diego, Calif.) with the amplification profile of 95° C. for 5 minutes, followed by 80 cycles of incubations at 95° C. for 15 seconds, 58° C. for 30 seconds. Following thermocycling, a melt curve was collected at 55° C. for 15 seconds.

Standards (See Table 4.) Purified T cell DNA was extracted from TCRαβ-positive bead-sorted peripheral blood cells (Miltenyi 130-091-236), then serially diluted and used in the thermal cycling reaction conditions as described above at concentrations ranging from 60 picograms to 250 nanograms per reaction.

Data Analysis: A standard curve was calculated for each replicate of the DNA standards and evaluated for consistency by calculating the $r^2$. The Ct was determined for each replicate of the analytes, then averaged and evaluated for consistency by calculating the standard deviation. The average T cell concentration of each analyte was determined by extrapolating from the standard curve using the Cq for each replicate. In particular, in order to measure the number of TCR genomes, it was assumed that there was 3 pg DNA/cell. Once the amount of starting DNA was calculated using real-time qPCR with the standards as described in Table 4, it was possible to calculate the number of TCR genomes in the sample.

Figure 1B:
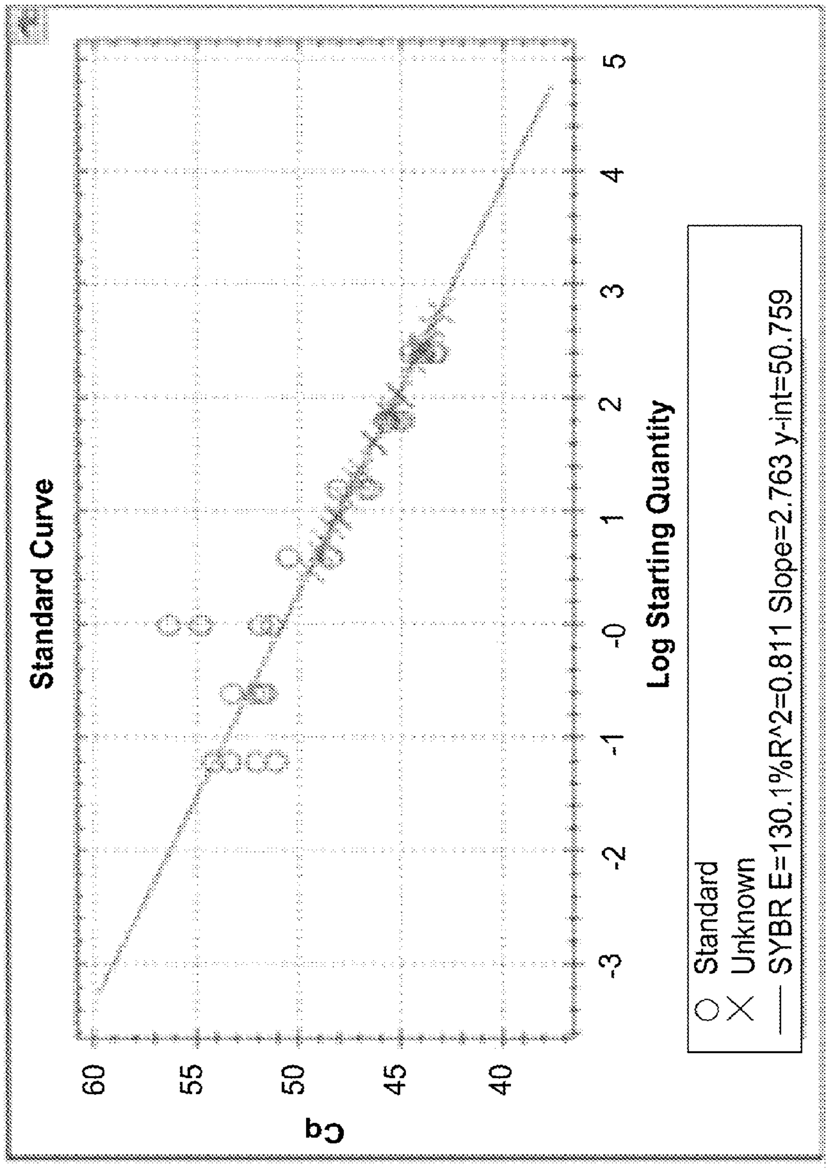

FIG. 1A shows a sample output from a TIL qPCR experiment demonstrating the amplification profile of standard T cell DNA (shown as gray traces in the Amplification plot) and TIL samples (shown as black traces) as measured by the RFU (relative fluorescent units) of SYBR™ green incorporated in the amplification products. T cell sample DNA was obtained from peripheral blood and tissues by purification on a silica matrix (Qiagen 69504). The Ct values of the standards, calculated from the cycle at which the standard DNA amplification profile reached the threshold of exponential amplification (indicated by the horizontal line), were fitted to a standard curve (FIG. 1B) which was used to extrapolate the concentration of T cells in the complex mixtures of peripheral blood DNA. The Cq values were determined for the standards of known DNA concentrations, measured in four replicate amplifications, and are shown as circles in the standard curve plot (FIG. 1B). The T cell DNA concentrations of the peripheral blood and tissue (tumor) samples, indicated by Xs, were determined from the best fit of the log of the standard DNA concentration plotted against standard DNA Cq value.

The DNA concentration of T cell genomes in a complex mixture of solid tumor DNA was thus measured by comparing the Ct value from the sample to the Ct values obtained from known quantities of purified T cell DNA. The Ct values of the standards were obtained from the amplification plot and were then used to prepare the standard curve from which the corresponding T cell concentration was determined for the tumor DNA samples (Table 4).

TABLE 4

TILs Quantified by Relative Representation of Rearranged TCRβ Encoding DNA in Tumor DNA Sample

| SampleID | Replicate | Ct | TCRB starting conc. (ng/ul) | Average estimated T cell DNA concn. (ng/ul) |
|---|---|---|---|---|
| LZ-INF1-tet− | A | 45.19 | 1.13E+02 | 247.06 |
| LZ-INF1-tet− | B | 43.18 | 5.93E+02 | |
| LZ-INF1-tet− | C | 44.46 | 2.08E+02 | |
| LZ-INF1-tet− | D | 45.7 | 7.49E+01 | |
| LZ-INF1-tet+ | A | 48.34 | 8.54E+00 | 6.11 |
| LZ-INF1-tet+ | B | 48.27 | 9.08E+00 | |
| LZ-INF1-tet+ | C | 49.13 | 4.45E+00 | |
| LZ-INF1-tet+ | D | 49.89 | 2.39E+00 | |
| LZ-INF2-D+30 | A | 47.3 | 2.00E+01 | 40.48 |
| LZ-INF2-D+30 | B | 46.4 | 4.21E+01 | |
| LZ-INF2-D+30 | C | 45.53 | 8.62E+01 | |
| LZ-INF2-D+30 | D | 47.77 | 1.36E+01 | |
| LZ-INF2-tet− | A | 45.67 | 7.69E+01 | 269.72 |
| LZ-INF2-tet− | B | 44.06 | 2.87E+02 | |
| LZ-INF2-tet− | C | 44.09 | 2.81E+02 | |
| LZ-INF2-tet− | D | 43.56 | 4.34E+02 | |
| LZ-INF2-tet+ | A | 48.53 | 7.34E+00 | 12.53 |
| LZ-INF2-tet+ | B | 47.09 | 2.39E+01 | |
| LZ-INF2-tet+ | C | 48.88 | 5.50E+00 | |
| LZ-INF2-tet+ | D | 47.79 | 1.34E+01 | |
| GV-INF1-D+508 | A | 46.4 | 4.20E+01 | 178.75 |
| GV-INF1-D+508 | B | 44 | 3.01E+02 | |
| GV-INF1-D+508 | C | 45.22 | 1.11E+02 | |
| GV-INF1-D+508 | D | 44.18 | 2.61E+02 | |

The presently described method provided a quantitative and highly sensitive method for enumerating T or B cell genomes in samples where such analysis was previously not possible, such as formalin fixed or frozen samples. The present methods were sensitive enough to detect as low as picogram quantities of T or B cell genomes (e.g, fewer than 100 T or B cells in a complex mixture of non-T or non-B cells, such as a solid tumor).

TABLE 5

T cell standards

| Standard | Standard conc. (ng/ul) | Amount amplified (ng) | T cell genomes amplified |
|---|---|---|---|
| 1 | 50 | 250 | 83333 |
| 2 | 12.50 | 62.50 | 20833 |
| 3 | 3.13 | 15.63 | 5208 |
| 4 | 0.78 | 3.91 | 1302 |
| 5 | 0.20 | 0.98 | 326 |
| 6 | 0.05 | 0.24 | 81 |
| 7 | 0.01 | 0.06 | 20 |
| 8 | 0 | 0 | 0 |

Example 3

Quantification of Tumor-Infiltrating T Lymphocytes in a Tumor Sample Using a V7-Specific qPCR Probe TCRB V7+ tumor-infiltrating T lymphocytes are quantified using a multiplex real-time PCR assay as follows.

Multiplex Primer Sequences: The multiplex primer sequences are provided in Table 1. The "r" represents a ribonucleotide base in the oligonucleotide sequence and "/3SpC3/" represents a 3' three carbon spacer on the hydroxyl group preventing polymerase extension and amplification. The DNA repair endonuclease cleaves the oligonucleotide at the ribonucleotide after hybridization to a complementary sequence, creating an unblocked hydroxyl group that can be extended by a polymerase.

Assay Reagents (Volumes and Concentrations): The assay consists of a 20 μl PCR reaction at final concentrations of 1× Taq polymerase buffer, 10 ng/ul analyte DNA, 1 micromolar TCRBV_RN2 oligonucleotide primer mix, 1 micromolar TCRBJ_RN2 oligonucleotide primer mix) 100 nanomolar TAQMAN™ probe (SEQ ID NO:66), 0.1 milliunits/ul of RNAse H2 (IDT). Analytes and standard PCR reactions are set up in quadruplicate.

Thermal Cycling Conditions: Reactions are thermal cycled on a real time PCR platform (such as the ILLUMINA ECO™ or Bio Rad CFX384) with the amplification profile of 95° C. for 5 minutes, followed by 80 cycles of incubations at 95° C. for 15 seconds, 58° C. for 30 seconds. Following thermocycling, a melt curve is collected at 55° C. for 15 seconds.

Standards (See Table 5.) Purified T cell DNA is extracted from TCRαβ positive bead-sorted peripheral blood cells (Miltenyi 130-091-236), then serially diluted and used in the thermal cycling reactions as described above at concentrations ranging from 60 picograms to 250 nanograms per reaction.

Data Analysis: A standard curve is calculated for each replicate of the DNA standards and evaluated for consistency by calculating the $r^2$. The cycle threshold, Ct, is determined for each replicate of the analytes, then averaged and evaluated for consistency by calculating the standard deviation. The average T cell concentration of each analyte is determined by extrapolating from the standard curve using the Cq for each replicate. In particular, in order to measure the number of V7+ TCR genomes, it is assumed that there is 3 pg DNA/cell. Once the amount of starting DNA is calculating using real-time qPCR with the standards as described in Table 2A, it is possible to calculate the number of TCR genomes in the sample.

The present Example demonstrates the quantitative and highly sensitive method for enumerating TCRB V7+ T cells in a mixed population of cells.

Example 4

Quantification of TCRB V18+ and TCBV19+ Tumor-Infiltrating T Lymphocytes in a Buffy Coat Sample Using dPCR TCRB V18+ and V19+ tumor-infiltrating T lymphocytes were quantified in a buffy coat sample using a digital PCR (dPCR) assay as described herein, with RNase P as an internal control as follows.

Equipment:

QX100 Droplet Digital PCR System (Bio-rad, Item No. 186-3001)

Heat Sealer (Eppendorf, Item No. 951023078)

Primer and Probe Sequences: The following primers and probes were used for the dPCR assay:

V Region (Forward) Primers

```
V18-specific:
                                    (SEQ ID NO: 686)
ATTTTCTGCTGAATTTCCCAAAGAGGGCC

V19-specific:
                                   (SEQ ID NO: 843,
                         have TATA 5' upstream of TRBV19
                                    SEQ ID NO: 656)
TATAGCTGAAGGGTACAGCGTCTCTCGGG
```

J Region (Reverse) Primers

```
                                        (SEQ ID NO: 696)
J1-1    TTACCTACAACTGTGAGTCTGGTGCCTTGTCCAAA

                                        (SEQ ID NO: 880)
J1-2    ACCTACAACGGTTAACCTGGTCCCCGAACCGAA

                                        (SEQ ID NO: 881)
J1-3    ACCTACAACAGTGAGCCAACTTCCCTCTCCAAA

                                         (SEQ ID NO: 882
J1-4    CCAAGACAGAGAGCTGGGTTCCACTGCCAAA

                                        (SEQ ID NO: 700)
J1-5    ACCTAGGATGGAGAGTCGAGTCCCATCACCAAA

                                        (SEQ ID NO: 883)
J1-6    CTGTCACAGTGAGCCTGGTCCCGTTCCCAAA

                                        (SEQ ID NO: 702)
J2-1    CGGTGAGCCGTGTCCCTGGCCCGAA

                                        (SEQ ID NO: 703)
J2-2    CCAGTACGGTCAGCCTAGAGCCTTCTCCAAA

                                        (SEQ ID NO: 704)
J2-3    ACTGTCAGCCGGGTGCCTGGGCCAAA

                                        (SEQ ID NO: 705)
J2-4    AGAGCCGGGTCCCGGCGCCGAA

                                        (SEQ ID NO: 706)
J2-5    GGAGCCGCGTGCCTGGCCCGAA

                                        (SEQ ID NO: 707)
J2-6    GTCAGCCTGCTGCCGGCCCCGAA

                                        (SEQ ID NO: 708)
J2-7    GTGAGCCTGGTGCCCGGCCCGAA
```

TCRB V Region Probes

```
V18-specific:
FAM-ATCCAGCAGGTAGTGCGAGG-MGB   (SEQ ID NO: 796)

V19-specific:
FAM-CACTGTGACATCGGCCCAA-MGB    (SEQ ID NO: 797)
```

RNaseP Primers and Probe

```
RNaseP forward primer:
AGATTTGGACCTGCGAGC          (SEQ ID NO: 840)

RNaseP reverse primer:
GAGCGGCTGTCTCCACAAGT        (SEQ ID NO: 841)

RNaseP-VIC probe:
CCGCGCAGAGCCTTC             (SEQ ID NO: 842)
```

Assay Reagents:

The reaction mixture contained 900 nM V18-specific forward primer (or V19-specific forward primer), 900 nM each of the 13 J region reverse primers, 900 nM RNaseP forward primer, 900 nM RNaseP reverse primer, 250 nM V18-specific TAQMAN™ probe (or V19-specific probe) with FAM fluorophore, 900 nM RNaseP probe with VIC fluorophore, 0-100 ng sample DNA, and ddPCR supermix (Catalogue No. 186-3027 from Bio-RAD, Hercules, USA). Bulk reaction volumes were converted into 1 nL droplet-in-oil immersions with the QX100 ddPCR System Droplet Generator (Bio-Rad) via the standard vendor's protocol. Droplets were cycled with the following conditions: 95° C. for 10 min, followed by 50 cycles of 94° C. for 30 sec and 61° C. for 1 min, then held at 10° C. Droplets were individually analyzed for fluorescence by flow cytometry in the QX100 ddPCR System Droplet Reader (Bio-Rad) according to the manufacturer's instructions. A threshold was set between highly fluorescent droplets (containing target molecules) and less fluorescent droplets (without target molecules), and the concentrations of target molecules were calculated by Poisson statistics to quantify T cells (FAM) and total cells (VIC) in each well.

Data Analysis:

The data were analyzed using QUANTASOFT™ software. QUANTASOFT™ calculated FAM and VIC concentration values for each well. Florescence thresholds were set so that they were above the negative droplets and below the positive droplets.

The data can be reported in two different ways. The first reports the ratio of genomes with rearranged TCRB genes to total diploid genomes. This ratio is computed by dividing the number of molecules with a TCRB rearrangement, as determined by PCR amplification and V specific probes, by half the number of RNaseP genes, as determined by PCR amplification and RNaseP specific probes. The factor of a half is required because each diploid genome has two RNaseP genes. Data reported in this manner are described in this example.

Alternatively, a second set of data can be reported. This is output as an estimation of the fraction of T cells in a sample. Approximately 80% of αβ T cells have only one of their two TCRβ alleles rearranged. The other 20% have both alleles rearranged, with one of the two being productively rearranged and the other non-productively rearranged. Other cell types lack the TCRβ rearrangement. Hence, an accurate count of the number of TCRβ rearrangements in a sample of cells is directly proportional to the number of T cells within that mix. To approximate the number of T cells in the sample, the total count of TCRB rearrangements is divided by 1.2. So, this second data analysis is equal to the first count described above divided by 1.2.

Figure 3:
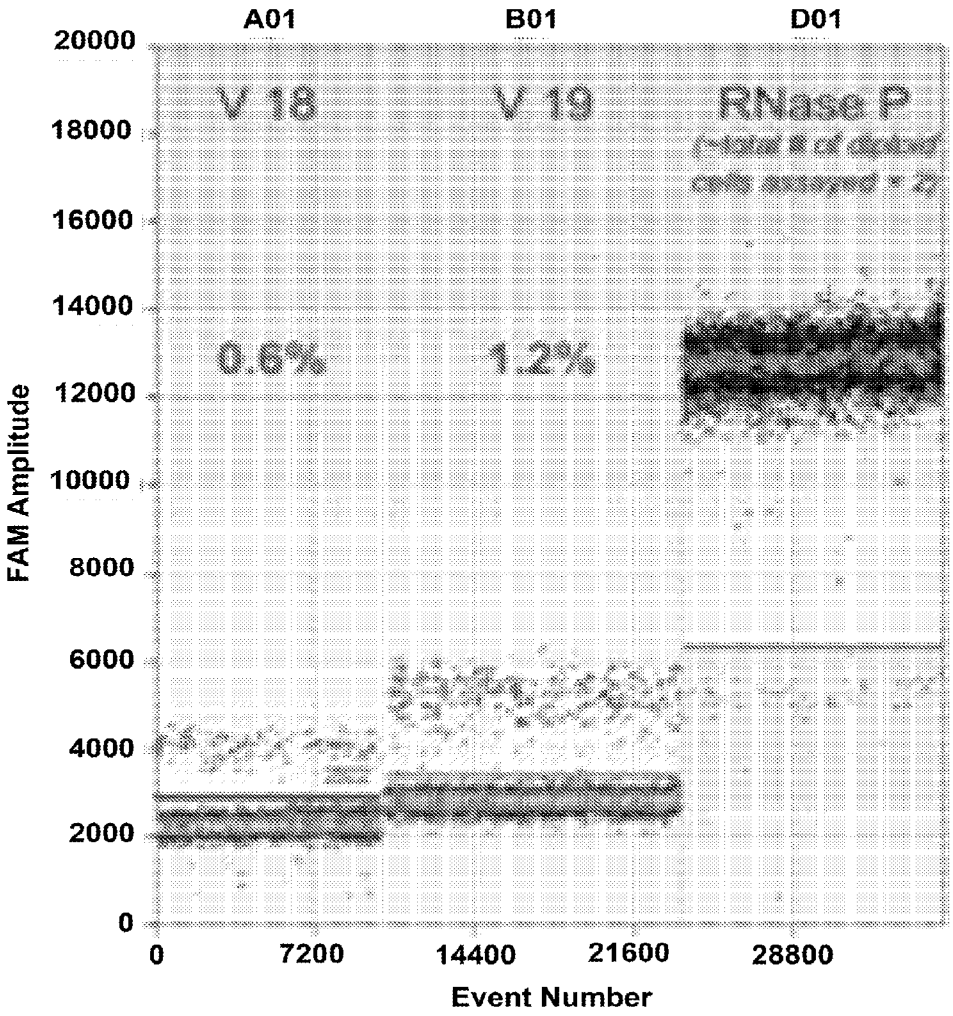
FIG. 3 shows dPCR results using TCRV18, TCRV19 or RNase P specific probes and buffy coat DNA as the template. Each data point represents a single dPCR specific reaction for the V18, V19, or RNase P specific probe. Droplets are assigned as positive (above horizontal separation lines) or negative (below horizontal separation lines) based on their fluorescence amplitude. The number of positive and negative droplets in each channel is used to calculate the concentration of target molecules and the Poisson-based confidence intervals to enumerate the V gene segment-specific T lymphocyte population (0.6% for the V18 segment and 1.2% for the V19 segment).

FIG. 3 shows a sample output from a TIL dPCR experiment using buffy coat DNA as the template. Each data point represents a single dPCR specific reaction for the V18, V19 or RNaseP gene segment. Droplets were assigned as positive or negative based on their fluorescence amplitudes. The number of positive and negative droplets in each channel was used to calculate the concentration of target molecules and the Poisson-based confidence intervals to enumerate the V gene segment-specific T lymphocyte population. In this sample, 0.6% of the sample was composed of V18-specific T lymphocytes, while 1.2% of the sample was V19-specific T lymphocytes.

Example 5 dPCR-Based Detection of Tumor-Infiltrating Lymphocytes

Tumor-infiltrating T lymphocytes were quantified by detecting rearranged DNA encoding TCRB using a digital droplet PCR (dPCR) assay with the RNase P gene as an internal control as follows.

Equipment:

QX100 Droplet Digital PCR System (Bio-rad, Item No. 186-3001)

Heat Sealer (Eppendorf, Item No. 951023078)

Primer and Probe Sequences: The following primers and probes were used for the dPCR assay:

V Region (Forward) Primers

| No. | Name | Sequence (5' to 3') | SEQ ID NO. |
|---|---|---|---|
| 1 | V02 | TTC GAT GAT CAA TTC TCA GTT GAA AGG CC | 844 |
| 2 | V03-1 | CCT AAA TCT CCA GAC AAA GCT CAC TTA AA | 845 |
| 3 | V04-1 | CTG AAT GCC CCA ACA GCT CTC TCT TAA AC | 846 |
| 4 | V04-2/3 | CTG AAT GCC CCA ACA GCT CTC ACT TAT TC | 847 |
| 5 | V05-1 | TGG TCG ATT CTC AGG GCG CCA GTT CTC TA | 848 |
| 6 | V05-3 | TAA TCG ATT CTC AGG GCG CCA GTT CCA TG | 849 |
| 7 | V05-4 | TCC TAG ATT CTC AGG TCT CCA GTT CCC TA | 850 |
| 8 | V05-5 | AAG AGG AAA CTT CCC TGA TCG ATT CTC AGC | 694 |
| 9 | V05-6 | GGC AAC TTC CCT GAT CGA TTC TCA GGT CA | 851 |
| 10 | V05-8 | GGA AAC TTC CCT CCT AGA TTT TCA GGT CG | 852 |
| 11 | V06-1 | GTC CCC AAT GGC TAC AAT GTC TCC AGA TT | 661 |
| 12 | V06-2/3 | GCC AAA GGA GAG GTC CCT GAT GGC TAC AA | 853 |
| 13 | V06-4 | GTC CCT GAT GGT TAT AGT GTC TCC AGA GC | 854 |
| 14 | V06-5 | AAG GAG AAG TCC CCA ATG GCT ACA ATG TC | 693 |
| 15 | V06-6 | GAC AAA GGA GAA GTC CCG AAT GGC TAC AAC | 675 |
| 16 | V06-7 | GTT CCC AAT GGC TAC AAT GTC TCC AGA TC | 855 |
| 17 | V06-8 | CTC TAG ATT AAA CAC AGA GGA TTT CCC AC | 856 |
| 18 | V06-9 | AAG GAG AAG TCC CCG ATG GCT ACA ATG TA | 692 |

-continued

| No. | Name | Sequence (5' to 3') | SEQ ID NO. |
|---|---|---|---|
| 19 | V07-1 | TCC CCG TGA TCG GTT CTC TGC ACA GAG GT | 857 |
| 20 | V07-2 | AGT GAT CGC TTC TCT GCA GAG AGG ACT GG | 858 |
| 21 | V07-3 | GGC TGC CCA ACG ATC GGT TCT TTG CAG T | 859 |
| 22 | V07-4 | GGC GGC CCA GTG GTC GGT TOT CTG CAG AG | 860 |
| 23 | V07-6/7 | ATG ATC GGT TCT CTG CAG AGA GGC CTG AGG | 861 |
| 24 | V07-8 | GCT GCC CAG TGA TCG CTT CTT TGC AGA AA | 862 |
| 25 | V07-9 | GGT TCT CTG CAG AGA GGC CTA AGG GAT CT | 863 |
| 26 | V09 | GTT CCC TGA CTT GCA CTC TGA ACT AAA C | 864 |
| 27 | V10-1 | AAC AAA GGA GAA GTC TCA GAT GGC TAC AG | 865 |
| 28 | V10-2 | GAT AAA GGA GAA GTC CCC GAT GGC TAT GT | 866 |
| 29 | V10-3 | GAC AAA GGA GAA GTC TCA GAT GGC TAT AG | 867 |
| 30 | V11-1/2/3 | CTA AGG ATC GAT TTT CTG CAG AGA GGC TC | 868 |
| 31 | V12-3/4 | TCG ATT CTC AGC TAA GAT GCC TAA TGC | 869 |
| 32 | V12-5 | TTC TCA GCA GAG ATG CCT GAT GCA ACT TTA | 870 |
| 33 | V13 | CTG ATC GAT TCT CAG CTC AAC AGT TCA GT | 871 |
| 34 | V14 | TCT TAG CTG AAA GGA CTG GAG GGA CGT AT | 650 |
| 35 | V15 | GCC GAA CAC TTC TTT CTG CTT TCT TGA C | 872 |
| 36 | V16 | TTC AGC TAA GTG CCT CCC AAA TTC ACC CT | 873 |
| 37 | V18 | ATT TTC TGC TGA ATT TCC CAA AGA GGG CC | 686 |
| 38 | V19 | TAT AGC TGA AGG GTA CAG CGT CTC TCG GG | 874 |
| 39 | V20-1 | ATG CAA GCC TGA CCT TGT CCA CTC TGA CA | 875 |
| 40 | V24-1 | ATC TCT GAT GGA TAC AGT GTC TCT CGA CA | 876 |
| 41 | V25-1 | TTT CCT CTG AGT CAA CAG TCT CCA GAA TA | 877 |
| 42 | V27 | TCC TGA AGG GTA CAA AGT CTC TCG AAA AG | 878 |
| 43 | V28 | TCC TGA GGG GTA CAG TGT CTC TAG AGA GA | 652 |
| 44 | V29-1 | CAT CAG CCG CCC AAA CCT AAC ATT CTC AA | 685 |
| 45 | V30 | GAC CCC AGG ACC GGC AGT TCA TCC TGA GT | 879 |

J Region (Reverse) Primers

The J region reverse primers were the same as in Example 4.

TCRB V Region Probes

All probes included a minor groove binder (MGB) and had a FAM fluorophore on the 5' end.

| No. | Name | Specific to | Sequence (5' to 3') | SEQ ID NO. |
|---|---|---|---|---|
| 1 | V02 | V02 | TCCGGTCCACAAAGCTGGAG | 908 |
| 2 | V03 | V03-1, V03-2p | CTGGAGCTTGGTGACTCTGC | 909 |
| 3 | V04a | V04-1 | TCACCTACACGCCCTGC | 835 |

-continued

| No. | Name | Specific to | Sequence (5' to 3') | SEQ ID NO. |
|---|---|---|---|---|
| 4 | V04b | V04-2, V04-3 | ACACACCCTGCAGCCAG | 836 |
| 5 | V05a1 | V05-1 | AGCACCTTGGAGCTGGG | 821 |
| 6 | V05a2 | V05-3 | TGAGTGCCTTGGAGCTGG | 822 |
| 7 | V05b | V05-4, V05-5, V05-6, V05-7, V05-8 | TGAGCTGAATGTGAACGCCTT | 778 |

-continued

| No. | Name | Specific to | Sequence (5' to 3') | SEQ ID NO. |
|---|---|---|---|---|
| 8 | V06a | V06-1, V06-2, V06-3 | TGGAGTCGGCTGCTCC | 809 |
| 9 | V06b | V06-7, V06-9 | CTGGAGTCAGCTGCTCCC | 823 |
| 10 | V06c | V06-4 | CACAGATGATTTCCCCCTC | 837 |
| 11 | V06d | V06-1, V06-5, V06-6, V06-8, V06-9 | TGCTCCCTCCCAGACATC | 811 |
| 12 | V07a1 | V07-1 | CTGAAGTTCCAGCGCACA | 838 |
| 13 | V07a2 | V07-2 | TCCGTCTCCACTCTGACGA | 839 |
| 14 | V07b | V07-3, V07-4, V07-8 | ACTCTGAAGATCCAGCGCA | 824 |
| 15 | V07c | V07-4, V07-6, V07-9 | TCCAGCGCACAGAGCA | 828 |
| 16 | V07d | V07-7 | CAGCGGGACTCAGCCA | 829 |
| 17 | V09 | V09 | TGAGCTCTCTGGAGCTGG | 815 |
| 18 | V10a1 | V10-1 | TCAAACACAGAGGACCTCCC | 830 |
| 19 | V10a2 | V10-2 | CACTCTGGAGTCAGCTACCC | 831 |
| 20 | V10b | V10-3 | TCACTCTGGAGTCCGCTACC | 787 |
| 21 | V11 | V11-1, V11-2, V11-3 | AGTAGACTCCACTCTCAAGATCCA | 788 |
| 22 | V12c | V12-3, V12-4, V12-5 | ATCCAGCCCTCAGAACCCAG | 791 |
| 23 | V13 | V13 | ACATGAGCTCCTTGGAGCTG | 792 |
| 24 | V14 | V14 | TGCAGAACTGGAGGATTCTGG | 793 |
| 25 | V15 | V15 | TGTACCTGTGTGCCACCAGC | 794 |
| 26 | V16 | V16 | CCTTGAGATCCAGGCTACG | 816 |
| 27 | V18 | V18 | ATCCAGCAGGTAGTGCGAGG | 796 |
| 28 | V19 | V19 | CACTGTGACATCGGCCCAA | 797 |
| 29 | V20 | V20-1 | CAGTGCCCATCCTGAAGACA | 798 |
| 30 | V24 | V24-1 | TGTCCCTAGAGTCTGCCATCC | 800 |
| 31 | V25 | V25-1 | CAGGCCCTCACATACCTCTC | 801 |
| 32 | V27 | V27-1 | TGGAGTCGCCCAGCC | 818 |
| 33 | V28 | V28 | AGGAGCGCTTCTCCCTG | 819 |
| 34 | V29 | V29-1 | TGTGAGCAACATGAGCCCTG | 804 |
| 35 | V30 | V30 | TCCTTCTCAGTGACTCTGGC | 820 |

RNaseP Primers and Probe.

The RNase P primers and probe were the same as in Example 4.

Assay Reagents:

The assay reagents were prepared as follows:

V Region Primer/Probe Mix

The V region (forward) primers and Taqman probes were assigned to 8 different subgroups (A through H). Each subgroup contained 3 to 4 probes and 4 to 7 corresponding primers, allowing each subgroup to specifically detect a subset of T-cell rearrangements. The subgroups were as follows:

| Subgroup | Probes | Primers |
|---|---|---|
| A | V02 | V02 |
| | V14 | V14 |
| | V15 | V15 |
| | V29 | V29-1 |
| B | V05a1 | V05-1 |
| | V06a | V06-1 |
| | | V06-2 |
| | | V06-3 |
| | V13 | V13 |
| | V28 | V28 |
| C | V05b | V05-4 |
| | | V05-5 |
| | | V05-6 |
| | | V05-7 |
| | | V05-8 |
| | V09 | V09 |
| | V25 | V25-1 |
| | V27 | V27-1 |
| D | V06b | V06-7 |
| | | V06-9 |
| | V06d | V06-1 |
| | | V06-5 |
| | | V06-6 |
| | | V06-8 |
| | | (V06-9) |
| | V18 | V18 |
| | V20 | V20-1 |
| E | V05a2 | V05-3 |
| | V12c | V12-3 |
| | | V12-4 |
| | | V12-5 |
| | V24 | V24-1 |
| | V30 | V30 |
| F | V07c | V07-4 |
| | | V07-6 |
| | | V07-9 |
| | V07d | V07-7 |
| | V10a1 | V10-1 |
| | V10a2 | V10-2 |
| G | V11 | V11-1 |
| | | V11-2 |
| | | V11-3 |
| | V16 | V16 |
| | V19 | V19 |
| H | V03 | V03-1 |
| | V07b | V07-3 |
| | | V07-4 |
| | | V07-8 |
| | V10b | V10-3 |

Although eight subgroups (A-H) were prepared as described herein with subsets of primers and probes, other embodiments are contemplated in which all probes and primers may be present in a single reaction or in 7, 6, 5, 4, 3 or 2 reactions, or alternatively in a greater number of reactions, where the number of reactions may vary as a function of herein described parameters that may be altered for particular assay configurations, such as concentrations of the assay components, amplification cycle steps, instrumentation capacity and capabilities, and other factors. For each subgroup described in this example, a 20× stock mix was made. Primer concentrations were 18 μM each in the stock, and 900 nM in the final reaction volume. Probe concentrations were 5 μM each in the stock, and 250 nM in the final reaction volume.

For example, a recipe for a 20× stock of the subgroup A primer/probe mix was as follows:

| | Volume added (μL) |
|---|---|
| V02 forward primer (1000 μM) | 3.6 |
| V14 forward primer (1000 μM) | 3.6 |
| V15 forward primer (1000 μM) | 3.6 |
| V29-1 forward primer (1000 μM) | 3.6 |
| V02-FAM Taqman probe (1000 μM) | 10 |
| V14-FAM Taqman probe (1000 μM) | 10 |
| V15-FAM Taqman probe (1000 μM) | 10 |
| V29-FAM Taqman probe (1000 μM) | 10 |
| Nuclease-free water | 145.6 |
| Total | 200 |

J Region Primer Mix

All 13 J region (reverse) primers were combined into a 20× stock. Primer concentrations were 18 μM each in the stock, and 900 nM in the final reaction volume. The recipe was as follows:

| | Volume added (μL) |
|---|---|
| J1-1 reverse primer (1000 μM) | 3.6 |
| J1-2 reverse primer (1000 μM) | 3.6 |
| J1-3 reverse primer (1000 μM) | 3.6 |
| J1-4 reverse primer (1000 μM) | 3.6 |
| J1-5 reverse primer (1000 μM) | 3.6 |
| J1-6 reverse primer (1000 μM) | 3.6 |
| J2-1 reverse primer (1000 μM) | 3.6 |
| J2-2 reverse primer (1000 μM) | 3.6 |
| J2-3 reverse primer (1000 μM) | 3.6 |
| J2-4 reverse primer (1000 μM) | 3.6 |
| J2-5 reverse primer (1000 μM) | 3.6 |
| J2-6 reverse primer (1000 μM) | 3.6 |
| J2-7 reverse primer (1000 μM) | 3.6 |
| Nuclease-free water | 153.2 |
| Total | 200 |

RNaseP Reference Assay Mix

RNaseP was used as a reference gene to quantify the number of cells interrogated. The RNaseP gene was known to be present at two copies per diploid genome.

The 20× RNaseP reference assay stock was prepared as follows:

| | Volume added (μL) |
|---|---|
| RNaseP forward primer (100 μM) | 36 |
| RNaseP reverse primer (100 μM) | 36 |
| RNaseP-VIC Taqman probe (100 μM) | 36 |
| Nuclease-free water | 92 |
| Total | 200 |

Bulk dPCR Volumes

Before droplet generation, bulk dPCR volumes were prepared. A plate of bulk dPCRs was prepared with each well having the following recipe:

| Reagent | 1X |
|---|---|
| dPCR Supermix (2X) | 12.5 μL |
| V primer/probe mix (20X) | 1.25 μL |
| J primer mix (20X) | 1.25 μL |
| RNaseP reference mix (20X) | 1.25 μL |
| DNA (20 ng/μL) | 5 μL |
| Nuclease-free water | 3.75 μL |
| Total | 25 μL |

-continued

Figure 4:
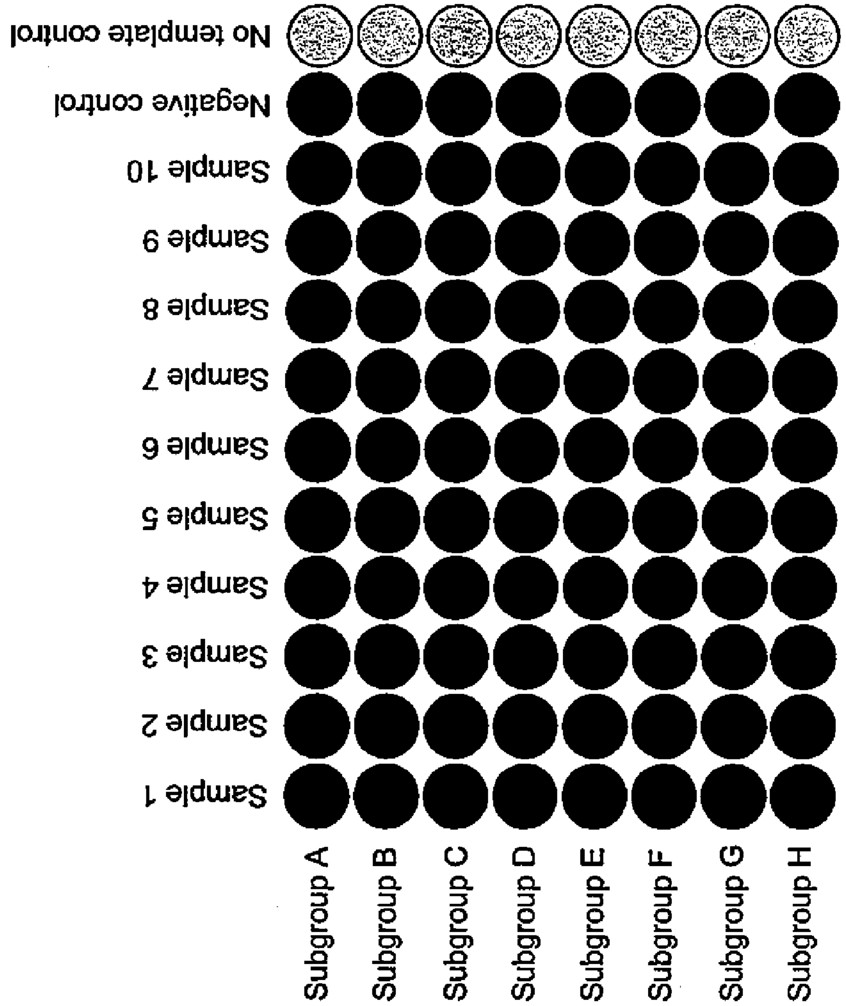
FIG. 4 shows an exemplary assay plate for using dPCR to quantify tumor infiltrating lymphocytes in samples.

A typical plate was configured as shown in FIG. 4. Samples 1 through 10 were the experimental samples. The negative control was genomic DNA from a source where no detection of T-cell rearrangements was expected (e.g., HT29 human colon adenocarcinoma cells, a non-lymphoid cancer cell line, catalogue number HTB-38™, American Type Culture Colleciton, Manassas, Va.), and the "no template control" (NTC) group used water in the place of DNA.

1) To set-up the plate, primary mastermix was created:

| Reagent | 1X | 106X |
|---|---|---|
| dPCR Supermix (2X) | 12.5 μL | 1325 μL |
| V primer/probe mix (20X) | 1.25 μL | — |
| J primer mix (20X) | 1.25 μL | 132.5 μL |
| RNaseP reference mix (20X) | 1.25 μL | 132.5 μL |
| DNA (20 ng/!L) | 5 μL | — |
| Nuclease-free water | 3.75 μL | 397.5 μL |
| Total | 25 μL | 1987.5 μL |

2) Then individual mastermixes for each assay subgroup were created:

| Reagent | 13X |
|---|---|
| Primary mastermix (see above) | 243.75 |
| V primer/probe mix (20X) | 16.25 |
| Total | 260 μL |

3) Each subgroup mastermix was pipetted into all appropriate wells, and then the sample DNA (or water for NTC wells) was pipetted in each well of the indicated column:

| Reagent | 1X |
|---|---|
| Subgroup mastermix | 20 μL |
| DNA (20 ng/μL) | 5 μL |
| Total (final) | 25 μL |

4) The plate was sealed with a removable foil PCR sheet and briefly spun in a centrifuge (e.g., 1000×g for 5 seconds) to make sure the dPCR bulk reaction volumes were at the bottom of each well.

Droplet Generation:

Wells of a DG8 cartrige were each loaded with 20 μL of reaction mixture. Droplets were generated and transferred into a fresh Eppendorf twin.tec PCR plate (Eppendorf, Order No. 0030 128.648). The plate was then heat-sealed.

Thermal Cycling Conditions:

The thermal cycling conditions were the same as described above in Example 4.

Data Analysis:

The data were analyzed using QUANTASOFT™ software (Bio-Rad, Hercules, Calif.). QUANTASOFT™ calculated FAM and VIC concentration values for each well. Florescence thresholds were set so that they were above the negative droplets and below the positive droplets. To determine the fraction of cells with TCRs of a given subgroup in a given well, the following formula was used:

$$\text{Fraction of Cells with TCRs(subgroup } X)=2^*(\text{FAM concentration})/(\text{VIC concentration})$$

The above formula was applied to a sample data set to determine % TIL and the results were as follows:

| Subgroup | FAM concentration (TCRs) | VIC concentration (RNaseP) | Fraction of Cells with TCRs from Subgroup |
|---|---|---|---|
| A | 16.3 | 728 | 0.04 |
| B | 30.5 | 810 | 0.08 |
| C | 27.9 | 708 | 0.08 |
| D | 36.9 | 690 | 0.11 |
| E | 30.6 | 741 | 0.08 |
| F | 34.4 | 782 | 0.09 |
| G | 17.9 | 735 | 0.05 |
| H | 13.8 | 715 | 0.04 |
| | Total fraction of cells with TCRs = | | 0.56 |

Figure 5A:
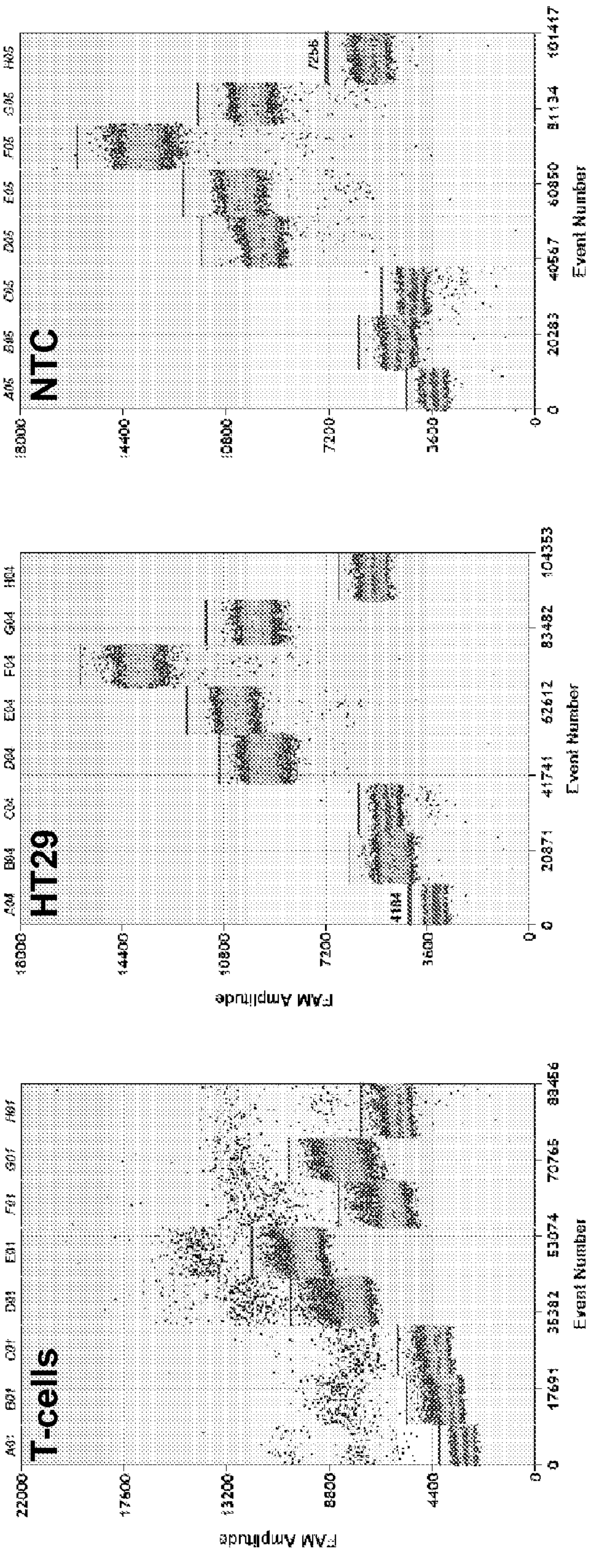
FIGS. 5A-5C show dPCR results using eight different subgroups of probes and primers (A through H). Each data point represents a single dPCR specific reaction for the probes of subgroups A through H. Droplets were assigned as positive (above horizontal separation lines) or negative (below horizontal separation lines) based on their fluorescence amplitude. The number of positive and negative droplets in each channel was used to calculate the concentration of target molecules and the Poisson-based confidence intervals to enumerate the V gene segment-specific T lymphocyte population.

Example 6 dPCR-Based Detection and Characterization of Tumor-Infiltating Lymphocytes in a Leukemia Patient Digital PCR reactions in this example were performed essentially as described above in Examples 4 and 5. In pilot studies, subgroups A-H mastermixes were processed for thermal cycling as described above using template DNA (20 ng/μL) from either isolated human peripheral blood T cells of a healthy donor or from HT29 cells, or no-template controls (NTC), with FAM signal for TCR and VIC for the internal control Rnase P gene as described above. FIG. 5A shows representative data for the eight subgroups, in which pronounced detection of amplification products can be seen when T cell DNA templates were present, with virtually no background signal detectable when non-lymphoid HT29 DNA was used as the template, or when no template was present (NTC). Each data point represents a single dPCR specific reaction for the probes of subgroups A through H. Droplets are assigned as positive (above horizontal separation lines) or negative (below horizontal separation lines) based on their fluorescence amplitudes. The number of positive and negative droplets in each channel was used to calculate the concentration of target molecules and the Poisson-based confidence intervals to enumerate the V gene segment-specific T lymphocyte population.

Figure 5B:
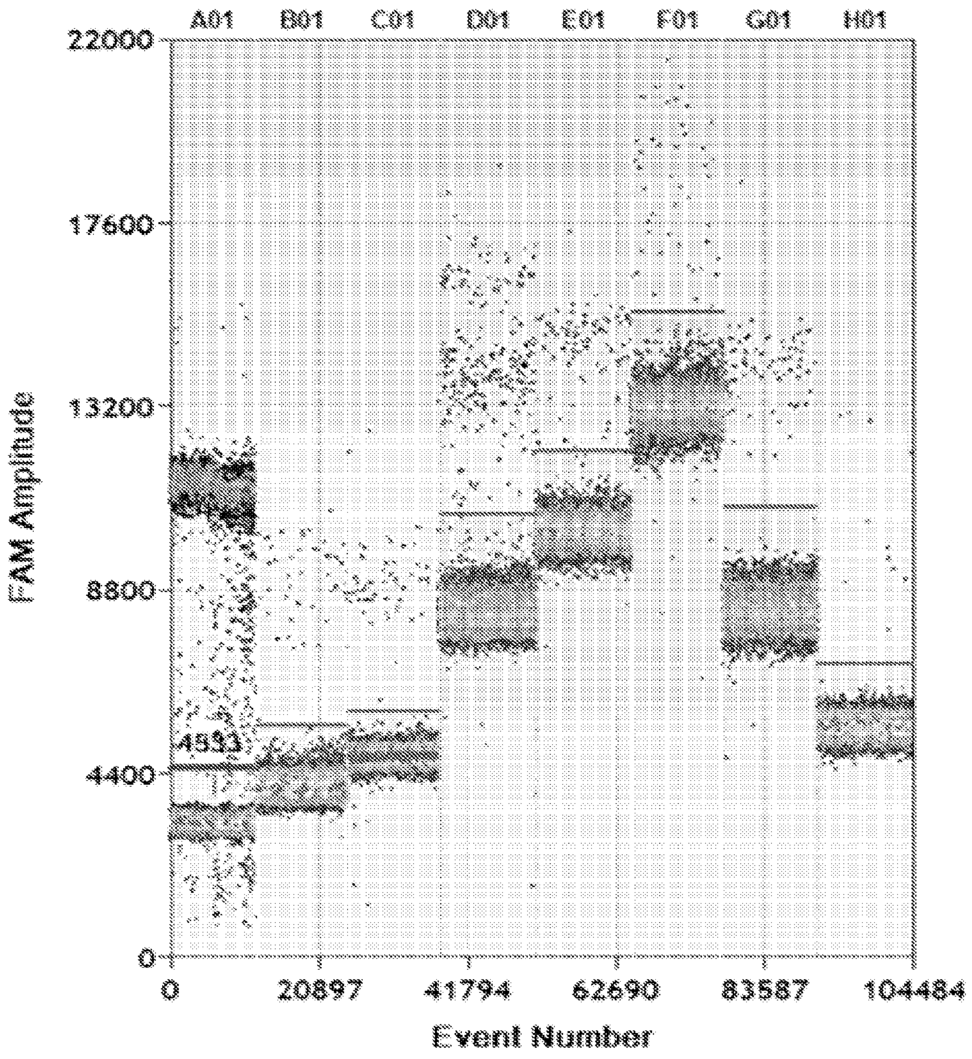
Figure 5C:
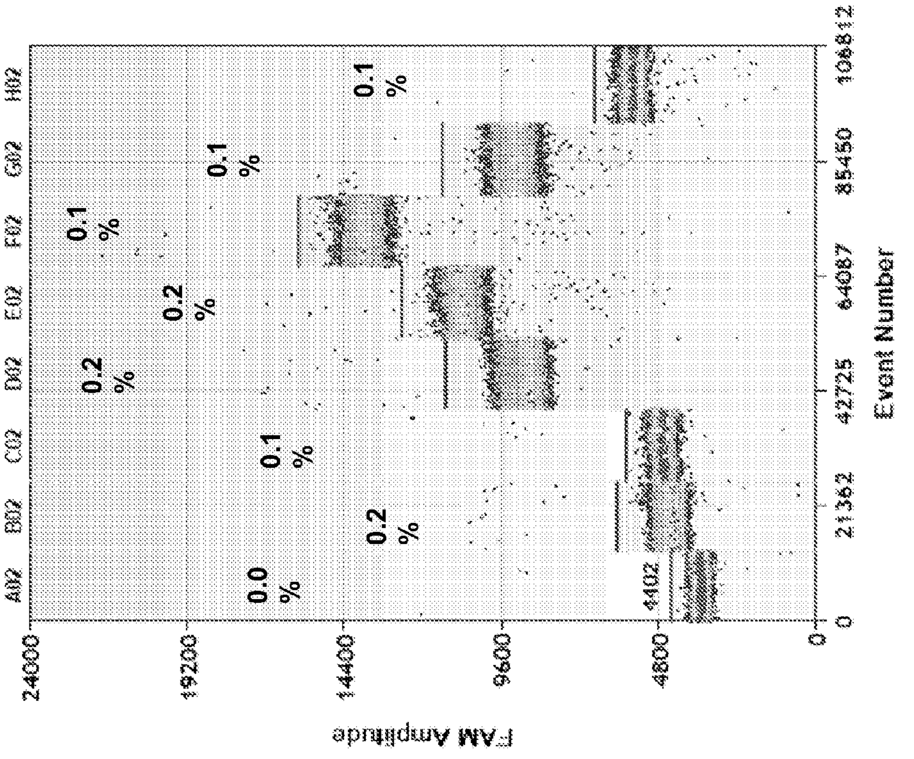

Tumor-infiltrating T lymphocytes in a sample from a patient with T cell acute lymphocytic leukemia (T-ALL) were quantified using a dPCR assay with the RNase P gene as an internal control, essentially as described above according to Example 5. For use as amplification template, DNA was extracted from a bone marrow sample taken prior to treatment of the patient. The results of dPCR using 8 different subgroups of probes and primers (A through H) and DNA from the sample are shown in FIG. 5B. Each data point represents a single dPCR specific reaction for the probes of subgroups A through H. Droplets are assigned as positive (above horizontal separation lines) or negative (below horizontal separation lines) based on their fluorescence amplitudes. The number of positive and negative droplets in each channel was used to calculate the concentration of target molecules and the Poisson-based confidence intervals to enumerate the V gene segment-specific T lymphocyte population. The results showed that a majority (79.7%) of the cells from the sample of the patient had the rearranged Vβ segment(s) of subgroup A. Similar evidence of clonal overrepresentation within a subgroup was also independently observed when template DNA from another T-ALL patient was analyzed in the dPCR assay for quantifying T cells in the sample by TCRB rearrangement; in that patient a pronounced signal representing >90% of cells was detected in subgroup B. By contrast, when template DNA from a patient diagnosed with early thymic precursor (ETP) T-ALL was used in the dPCR method, substantially no rearranged TCRB FAM signal was detectable, consistent with TCR gene rearrangement not having yet taken place in ETP cells that occur as the predominant clonal population in ETP T-ALL (FIG. 5C).

Example 7

Preferential Use of Different Vβ Gene Segments by CD4+ and CD8+ Cells

For each Vβ segment, the frequency is calculated with which productively rearranged TCR sequences in each of the CD4+ samples are used (CD4+ and CD8+ T cell populations were sorted using a FacsARIA, BD Biosciences, San Jose, Calif.), and the mean value of these frequencies is taken to be the population mean usage for that Vβ segment. This value is compared to the usage of each segment in CD8+ T cells. Many of the individual Vβ segments are preferentially used more frequently in either CD4+ cells relative to their usage in CD8+ cells, or in CD8+ cells relative to their usage in CD4+ cells. To assess statistical significance of such preferential usage, a two-tailed unpaired t-test for difference of means is performed. 21 of 48 measured Vβ segments have differential usage between CD4+ and CD8+ samples, indicating that T cell subpopulation differentiative pathways influence the frequency with which TCR gene rearrangements bearing certain particular V gene segments survive the selection process.

Having established the existence of TCR sequence features that distinguish CD4+ from CD8+ T cells, a computational method was developed to estimate the proportion of T cells that are CD4+ in an unknown sample using TCR sequence data alone. Briefly, a usage frequency for each Vβ segment was calculated for CD4+ and CD8+ T cells using flow-sorted samples from 42 subjects. These values were used to train a likelihood model which treats each observed TCR sequence as independent and uses the observed means as generative probabilities.

To determine the likelihood of new data under this model, a proportion of CD4+ T cells, p, is assumed. The observed mean usage for each Vβ segment in the training data for CD4+ T cells is taken to be the same as the probability of an unknown CD4+ T cell using that segment, and likewise for CD8+ T cells. Thus, the likelihood of observing in new data a single sequence with a given Vβ segment is calculated as:

$$[p^*P(V|CD4)]+[(1-p)^*P(V|CD8)]$$

The likelihood of a dataset is calculated as the product of the likelihoods of its constituent sequences. To determine the proportion of CD4+ T cells in new data, the likelihood of the new data is calculated at each p from 0 to 1 with a granularity of 0.01, and the value of p leading to the highest likelihood of the observed data is chosen as the estimate of the proportion of CD4+ T cells in the sample.

Figure 6:
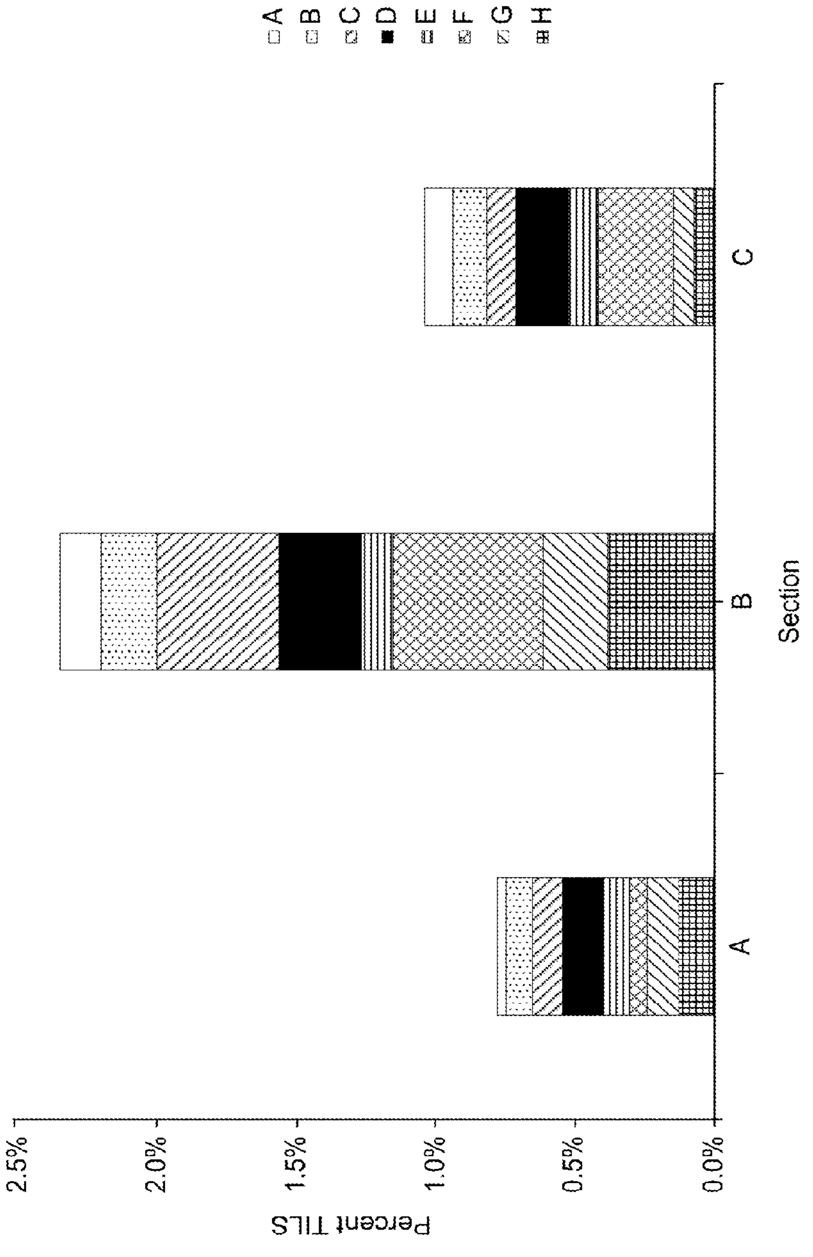
FIG. 6 is a graph showing low variation in TIL percentage and clonality in three different biopsies from a large cervical tumor. Shading represents percentage of TIL identified with indicated pooled primer subgroup.

Example 8 dPCR-Based Detection and Clonality Analysis of Tumor-Infiltrating Lymphocytes in Cervical Tumor Biopsies This example describes quantitative digital droplet PCR quantification of TIL in three fresh-frozen solid human ovarian tumor samples obtained from distinct sites of the same tumor from the same cervical cancer patient. Genomic DNA was extracted from tumor punch biopsies using a proteinase K digest and solid-phase reversible immobilization, magnetic bead technology (Agencourt #A41497) on a BIOMEK™ FX workstation according to the manufacturers' instructions. Following extraction, the DNA yield and purity were assessed using UV spectral analysis on a TRINEAN DROPSENSE™ spectrophotometer by measuring the UV absorbance at 260 nm ($A_{260}$) and 280 nm ($A_{280}$). DNA samples were then processed for quantitative digital droplet PCR. Tumor-infiltrating T lymphocytes in these three biopsies were quantified using a dPCR assay with the RNase P as an internal control and eight subgroups of TCRB probes and primers (subgroups A through H), essentially as described above in Example 5. The results are summarized in FIG. 6, which shows low variability in the TIL percentages and degrees of clonality that were detected according to the herein described methods in these three different biopsy samples, despite their being obtained from distinct sites in the tumor. These results demonstrate that there was low variation in TIL percentage (0.8%-2.3%) and low variation between biopsy samples as indicated by the degree of T cell receptor sequence, and hence T cell clonal, diversity (shown as the percent of each T cell class in A-H).

Example 9

Determining Accuracy of dPCR-Based Assay Across a Large Sensitivity Range

Figure 7:
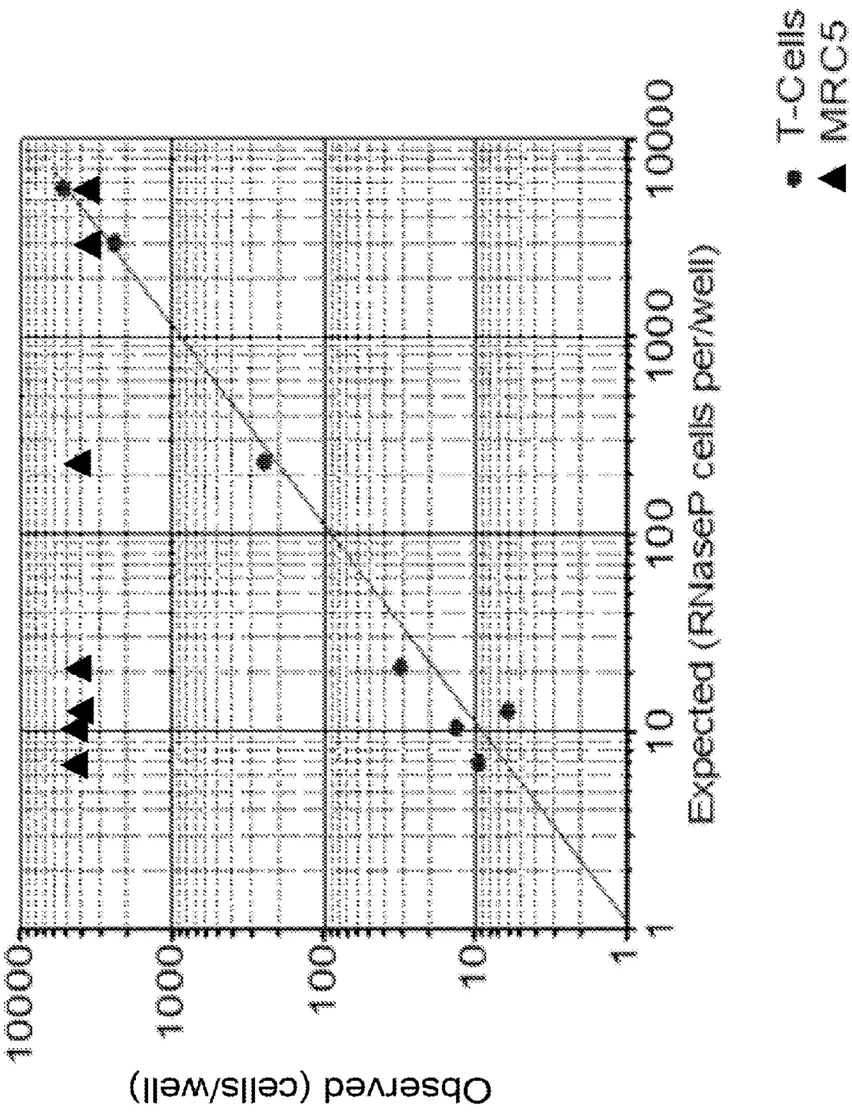
FIG. 7 is a graph showing that an assay measuring RNaseP+ cell concentrations using dPCR was accurate across a large dynamic range (from 1 to $10^4$ RNaseP+ cells per well).

The accuracy of dPCR-based TIL quantification was performed using DNA from various dilutions of T cells, either in the presence or absence of 4000 MRC5 cells (a normal human lung cell line), to simulate a range of TIL detection down to roughly one T cell in a background of 1000 human cells. Digital PCR was performed using TCRB- and RNase P-specific primers essentially as described above in Examples 4 and 5. FIG. 7 shows that dPCR-based TIL quantification was accurate across a large dynamic range of T cell representation in a mixed cell population.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for determining a relative quantity of tumor-infiltrating lymphocytes in a solid tumor, comprising:

(a) obtaining a sample comprising a solid tumor tissue;

(b) amplifying by PCR at least 80% of all rearranged TCR or Ig CDR3-encoding regions present in said sample using a plurality of V-segment oligonucleotide primers comprising sequences selected from the group consisting of SEQ ID NOs: 1-52, 221-238, 255-260, 262-267, 269, 272, 283, 286, 291, 292, 294-297, 301-326, 330, 338, 382, 405, 447-484, 644-695, and 843-879 and a plurality of J-segment oligonucleotide primers comprising sequences selected from the group consisting of 53-63, 65, 215-220, and 247 to produce a plurality of rearranged DNA amplicons;

(c) amplifying by PCR a control sequence present in said sample using a pair of control sequence primers, wherein said control sequence primers are capable of amplifying a control sequence that is not an adaptive immune receptor gene and present in all cells in said sample;

(d) quantifying a number of adaptive immune receptor sequence reads in said sample generated from high-throughput sequencing (HTS) of said plurality of rearranged DNA amplicons;

(e) quantifying a number of control sequence reads in said sample using said amplified control sequence; and (f) comparing said number of adaptive immune receptor sequence reads and said number of control sequence reads to estimate a relative quantity of tumor-infiltrating lymphocytes in said solid tumor.

2. The method of claim 1, further comprising quantifying a number of unique sequence reads generated from said HTS, wherein each unique sequence read comprises a sequence distinct from the other sequence reads.

3. The method of claim 1, wherein said number of control sequence reads represents a total number of diploid genomes in said sample.

4. The method of claim 3, wherein said comparing comprises dividing said number of control sequence reads in half and determining a ratio between said number of adaptive immune receptor sequence reads and half of said number of control sequence reads.

5. The method of claim 1, wherein said comparing comprises estimating a total number of adaptive immune cells in said sample by dividing said number of adaptive immune receptor sequence reads by a numerical factor.

6. The method of claim 1, wherein said plurality of rearranged DNA amplicons comprises at least $10^6$ DNA molecules.

7. The method of claim 1, wherein said plurality of rearranged DNA amplicons comprises at least $10^5$ DNA molecules.

8. The method of claim 1, wherein each V-segment oligonucleotide primer comprises a nucleotide sequence of at least 15 contiguous nucleotides that is complementary to at least one functional TCR or Ig V-encoding gene segment, and wherein said V-segment oligonucleotide primers specifically hybridize to at least 80% of all functional TCR or Ig V-encoding gene segments that are present in said sample.

9. The method of claim 1, wherein each J-segment oligonucleotide primer comprises a nucleotide sequence of at least 15 contiguous nucleotides that is complementary to at least one functional TCR or Ig J-encoding gene segment, and wherein said J-segment oligonucleotide primers specifically hybridize to at least 80% of all functional TCR or Ig J-encoding gene segments that are present in said test sample.

10. The method of claim 1, wherein each amplified rearranged TCR or Ig CDR3-encoding region is less than 600 nucleotides in length.

11. The method of claim 1, wherein each of said rearranged TCR or Ig CDR3-encoding regions encode a T cell receptor (TCR) V-region polypeptide or an immunoglobulin (Ig) V-region polypeptide comprising a V gene recombination signal sequence (RSS) and a T cell receptor (TCR) J-region polypeptide or an immunoglobulin (Ig) J-region polypeptide comprising a J gene RSS, and wherein each rearranged DNA amplicon comprises (i) at least 10, 20, 30 or 40 contiguous nucleotides of a sense strand of a TCR or Ig V-encoding gene segment, said at least 10, 20, 30 or 40 contiguous nucleotides being situated 5' to said V gene RSS and (ii) at least 10, 20 or 30 contiguous nucleotides of a sense strand of a TCR or Ig J-encoding gene segment, said at least 10, 20 or 30 contiguous nucleotides being situated 3' to said J gene RSS.

12. The method of claim 1, wherein said tumor-infiltrating lymphocytes are T cells or B cells.

13. The method of claim 1, wherein said rearranged TCR or Ig CDR3-encoding regions are selected from the group consisting of rearranged TCRα CDR3-encoding regions, TCRβ CDR3-encoding regions, TCRγ CDR3-encoding regions, TCRδ CDR3-encoding regions, IgH CDR3-encoding regions, Igκ CDR3-encoding regions, and Igλ CDR3-encoding regions.

14. A method for quantifying a relative representation of tumor infiltrating T cells in a solid tissue tumor sample, comprising:

obtaining DNA templates from said sample;

amplifying rearranged T cell receptor DNA molecules utilizing a plurality of V-segment oligonucleotide primers comprising sequences selected from the group consisting of SEQ ID NOs: 1-52, 221-238, 255-260, 262-267, 269, 272, 283, 286, 291, 292, 294-297, 301-326, 330, 338, 382, 405, 447-484, 644-695 and 843-879 and a plurality of J-segment oligonucleotide primers comprising sequences selected from the group consisting of 53-63, 65, 215-220, and 247 in a single multiplex PCR from said DNA templates to produce a multiplicity of amplified rearranged DNA molecules;

sequencing said multiplicity of amplified rearranged DNA molecules by high-throughput sequencing (HTS) to produce rearranged T cell receptor sequence reads;

determining a number of rearranged T cell receptor DNA molecules from said rearranged T cell receptor sequence reads, wherein said number of T cell receptor DNA molecules is proportional to a number of T cells in said sample;

determining a number of diploid genomes in the sample, wherein said number of diploid genomes represents a number of total cells in the sample; and quantifying a ratio of the relative representation of tumor infiltrating T cells in said sample by comparing said number of T cells by said number of total cells in the sample.

15. The method of claim 14, wherein each V-segment oligonucleotide primer comprises a nucleotide sequence of at least 15 contiguous nucleotides that is complementary to at least one functional TCR V-encoding gene segment, and wherein said V-segment oligonucleotide primers specifically hybridize to at least 80% of all functional TCR V-encoding gene segments that are present in said sample.

16. The method of claim 15, wherein each J-segment oligonucleotide primer comprises a nucleotide sequence of at least 15 contiguous nucleotides that is complementary to at least one functional TCR J-encoding gene segment, and wherein said J-segment oligonucleotide primers specifically hybridize to at least 80% of all functional TCR J-encoding gene segments that are present in said test sample.

17. The method of claim 14, wherein each of said rearranged TCR encodes a T cell receptor (TCR) V-region polypeptide comprising a V gene recombination signal sequence (RSS) and a T cell receptor (TCR) J-region polypeptide comprising a J gene RSS, and wherein each rearranged DNA molecule comprises (i) at least 10, 20, 30 or 40 contiguous nucleotides of a sense strand of a TCR V-encoding gene segment, said at least 10, 20, 30 or 40 contiguous nucleotides being situated 5' to said V gene RSS and (ii) at least 10, 20 or 30 contiguous nucleotides of a sense strand of a TCR J-encoding gene segment, said at least 10, 20 or 30 contiguous nucleotides being situated 3' to said J gene RSS.

18. The method of claim 14, wherein said number of diploid genomes in said sample is determined by contacting said sample with a pair of control sequence primers and by amplifying a control sequence from said DNA templates, wherein said control sequence primers are capable of amplifying a control sequence present in all cells in said sample.

19. The method of claim 14, further comprising quantifying a number of unique sequence reads generated from said HTS, wherein each unique sequence read comprises a sequence distinct from the other sequence reads.

20. The method of claim 14, wherein said comparing comprises dividing said number of T cells by a numerical factor.

21. The method of claim 14, wherein said rearranged DNA molecules are selected from the group consisting of rearranged TCRα CDR3-encoding regions, TCRβ CDR3-encoding regions, TCRγ CDR3-encoding regions, and TCRδ CDR3-encoding regions.

22. The method of claim 1, wherein the amplifying steps of (b) and (c) are performed in the same PCR reaction.

23. The method of claim 1, wherein the amplifying steps of (b) and (c) are performed in separate PCR reactions.

* * * * *

SEQUENCE LISTING

```
<160> NUMBER OF SEQ ID NOS: 909

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV25-1_RN2v3
<220> FEATURE:
<221> NAME/KEY: modified_base
<222> LOCATION: (37)..(37)
<223> OTHER INFORMATION: Ribonucleotide base
<220> FEATURE:
<223> OTHER INFORMATION: 3' 3SpC3

<400> SEQUENCE: 1

ggagatcttt cctctgagtc aacagtctcc agaataagga c                    41


<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
```

-continued

<220> FEATURE:
<223> OTHER INFORMATION: TRBV12-1_RN2v3
<220> FEATURE:
<221> NAME/KEY: modified_base
<222> LOCATION: (31)..(31)
<223> OTHER INFORMATION: Ribonucleotide base
<220> FEATURE:
<223> OTHER INFORMATION: 3' 3SpC3

<400> SEQUENCE: 2
ggattgattc tcagcacaga tgcctgatgt atcat 35

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV12-5_RN2v3
<220> FEATURE:
<221> NAME/KEY: modified_base
<222> LOCATION: (33)..(33)
<223> OTHER INFORMATION: Ribonucleotide base
<220> FEATURE:
<223> OTHER INFORMATION: 3' 3SpC3

<400> SEQUENCE: 3
gattctcagc agagatgcct gatgcaactt tagccac 37

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV2_RN2v3
<220> FEATURE:
<223> OTHER INFORMATION: 3' 3SpC3

<400> SEQUENCE: 4
aagtctgaaa tattcgatga tcaattctca gttgaaaggc cugatg 46

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV16_RN2v3
<220> FEATURE:
<221> NAME/KEY: modified_base
<222> LOCATION: (27)..(27)
<223> OTHER INFORMATION: Ribonucleotide base
<220> FEATURE:
<223> OTHER INFORMATION: 3' 3SpC3

<400> SEQUENCE: 5

-continued agctaagtgc ctcccaaatt caccctgtag c 31

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV5-1_RN2v3
<220> FEATURE:
<221> NAME/KEY: modified_base
<222> LOCATION: (26)..(26)
<223> OTHER INFORMATION: Ribonucleotide base
<220> FEATURE:
<223> OTHER INFORMATION: 3' 3SpC3

<400> SEQUENCE: 6
cgattctcag ggcgccagtt ctctaactct 30

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV14_RN2v3
<220> FEATURE:
<223> OTHER INFORMATION: 3' 3SpC3

<400> SEQUENCE: 7
tcttagctga aaggactgga gggacgtatu ctac 34

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV12-4_RN2v3
<220> FEATURE:
<221> NAME/KEY: modified_base
<222> LOCATION: (33)..(33)
<223> OTHER INFORMATION: Ribonucleotide base
<220> FEATURE:
<223> OTHER INFORMATION: 3' 3SpC3

<400> SEQUENCE: 8
gaggatcgat tctcagctaa gatgcctaat gcatcat 37

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:

-continued

<223> OTHER INFORMATION: Description of Combined DNA/RNA Molecule:
      Synthetic primer
<220> FEATURE:
<223> OTHER INFORMATION: TRBV28_RN2v3
<220> FEATURE:
<221> NAME/KEY: modified_base
<222> LOCATION: (30)..(30)
<223> OTHER INFORMATION: Ribonucleotide base
<220> FEATURE:
<223> OTHER INFORMATION: 3' 3SpC3

<400> SEQUENCE: 9
tcctgagggg tacagtgtct ctagagagaa gaag 34

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV27_RN2v3
<220> FEATURE:
<221> NAME/KEY: modified_base
<222> LOCATION: (35)..(35)
<223> OTHER INFORMATION: Ribonucleotide base
<220> FEATURE:
<223> OTHER INFORMATION: 3' 3SpC3

<400> SEQUENCE: 10
gatgttcctg aagggtacaa agtctctcga aaagagaag 39

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV5-4_RN2v3
<220> FEATURE:
<221> NAME/KEY: modified_base
<222> LOCATION: (31)..(31)
<223> OTHER INFORMATION: Ribonucleotide base
<220> FEATURE:
<223> OTHER INFORMATION: 3' 3SpC3

<400> SEQUENCE: 11
ctcctagatt ctcaggtctc cagttcccta attat 35

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV7-1_RN2v3
<220> FEATURE:
<221> NAME/KEY: modified_base
<222> LOCATION: (26)..(26)

<223> OTHER INFORMATION: Ribonucleotide base
<220> FEATURE:
<223> OTHER INFORMATION: 3' 3SpC3

<400> SEQUENCE: 12
cgtgatcggt tctctgcaca gaggtctgag 30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV19_RN2v3
<220> FEATURE:
<221> NAME/KEY: modified_base
<222> LOCATION: (26)..(26)
<223> OTHER INFORMATION: Ribonucleotide base
<220> FEATURE:
<223> OTHER INFORMATION: 3' 3SpC3

<400> SEQUENCE: 13
gctgaagggt acagcgtctc tcgggagaag 30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV5-3_RN2v3
<220> FEATURE:
<221> NAME/KEY: modified_base
<222> LOCATION: (26)..(26)
<223> OTHER INFORMATION: Ribonucleotide base
<220> FEATURE:
<223> OTHER INFORMATION: 3' 3SpC3

<400> SEQUENCE: 14
cgattctcag ggcgccagtt ccatgactgt 30

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV9_RN2v3
<220> FEATURE:
<221> NAME/KEY: modified_base
<222> LOCATION: (34)..(34)
<223> OTHER INFORMATION: Ribonucleotide base
<220> FEATURE:
<223> OTHER INFORMATION: 3' 3SpC3

<400> SEQUENCE: 15
caacagttcc ctgacttgca ctctgaacta aacctgag 38

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV6-7_RN2v3
<220> FEATURE:
<221> NAME/KEY: modified_base
<222> LOCATION: (34)..(34)
<223> OTHER INFORMATION: Ribonucleotide base
<220> FEATURE:
<223> OTHER INFORMATION: 3' 3SpC3

<400> SEQUENCE: 16
agaagttccc aatggctaca atgtctccag atcaaaca 38

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV6-4_RN2v3
<220> FEATURE:
<221> NAME/KEY: modified_base
<222> LOCATION: (32)..(32)
<223> OTHER INFORMATION: Ribonucleotide base
<220> FEATURE:
<223> OTHER INFORMATION: 3' 3SpC3

<400> SEQUENCE: 17
aagtccctga tggttatagt gtctccagag caaaca 36

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV6-1_RN2v3
<220> FEATURE:
<221> NAME/KEY: modified_base
<222> LOCATION: (30)..(30)
<223> OTHER INFORMATION: Ribonucleotide base
<220> FEATURE:
<223> OTHER INFORMATION: 3' 3SpC3

<400> SEQUENCE: 18
gtccccaatg gctacaatgt ctccagatta aaca 34

<210> SEQ ID NO 19
<211> LENGTH: 32
<212> TYPE: DNA
<213> ORGANISM: Artificial Sequence
<220> FEATURE:

-continued

<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV7-9_RN2v3
<220> FEATURE:
<221> NAME/KEY: modified_base
<222> LOCATION: (28)..(28)
<223> OTHER INFORMATION: Ribonucleotide base
<220> FEATURE:
<223> OTHER INFORMATION: 3' 3SpC3

<400> SEQUENCE: 19
ttctctgcag agaggcctaa gggatctctc tc 32

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV7-9_RN2v3
<220> FEATURE:
<221> NAME/KEY: modified_base
<222> LOCATION: (25)..(25)
<223> OTHER INFORMATION: Ribonucleotide base
<220> FEATURE:
<223> OTHER INFORMATION: 3' 3SpC3

<400> SEQUENCE: 20
gcccaacgat cggttctttg cagtcaggc 29

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV7-4_RN2v3
<220> FEATURE:
<221> NAME/KEY: modified_base
<222> LOCATION: (24)..(24)
<223> OTHER INFORMATION: Ribonucleotide base
<220> FEATURE:
<223> OTHER INFORMATION: 3' 3SpC3

<400> SEQUENCE: 21
ccagtggtcg gttctctgca gagaggcc 28

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV5-6_RN2v3

<220> FEATURE:
<221> NAME/KEY: modified_base
<222> LOCATION: (29)..(29)
<223> OTHER INFORMATION: Ribonucleotide base
<220> FEATURE:
<223> OTHER INFORMATION: 3' 3SpC3

<400> SEQUENCE: 22
gcaacttccc tgatcgattc tcaggtcacc agt 33

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV5-6_RN2v3
<220> FEATURE:
<221> NAME/KEY: modified_base
<222> LOCATION: (34)..(34)
<223> OTHER INFORMATION: Ribonucleotide base
<220> FEATURE:
<223> OTHER INFORMATION: 3' 3SpC3

<400> SEQUENCE: 23
cagaggaaac ttccctccta gattttcagg tcgccagt 38

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV7-8_RN2v3
<220> FEATURE:
<221> NAME/KEY: modified_base
<222> LOCATION: (27)..(27)
<223> OTHER INFORMATION: Ribonucleotide base
<220> FEATURE:
<223> OTHER INFORMATION: 3' 3SpC3

<400> SEQUENCE: 24
gcccagtgat cgcttctttg cagaaaggcc t 31

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV12-2_RN2v3
<220> FEATURE:
<221> NAME/KEY: modified_base
<222> LOCATION: (27)..(27)
<223> OTHER INFORMATION: Ribonucleotide base
<220> FEATURE:
<223> OTHER INFORMATION: 3' 3SpC3

<400> SEQUENCE: 25
cgattctcag ctgagaggcc tgatggatca t 31

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV15_RN2v3
<220> FEATURE:
<221> NAME/KEY: modified_base
<222> LOCATION: (31)..(31)
<223> OTHER INFORMATION: Ribonucleotide base
<220> FEATURE:
<223> OTHER INFORMATION: 3' 3SpC3

<400> SEQUENCE: 26
aggccgaaca cttctttctg ctttcttgac atccg 35

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV6-2_RN2v3
<220> FEATURE:
<223> OTHER INFORMATION: 3' 3SpC3

<400> SEQUENCE: 27
caaaggagag gtccctgatg gctacaaugt ct 32

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV23-1_RN2v3
<220> FEATURE:
<221> NAME/KEY: modified_base
<222> LOCATION: (29)..(29)
<223> OTHER INFORMATION: Ribonucleotide base
<220> FEATURE:
<223> OTHER INFORMATION: 3' 3SpC3

<400> SEQUENCE: 28
gattctcatc tcaatgcccc aagaacgcac cct 33

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV10-2_RN2v3
<220> FEATURE:
<223> OTHER INFORMATION: 3' 3SpC3

<400> SEQUENCE: 29
cagataaagg agaagtcccc gatggctatg tugtct 36

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV30_RN2v3
<220> FEATURE:
<223> OTHER INFORMATION: 3' 3SpC3

<400> SEQUENCE: 30
caggaccggc agttcatcct gagtuctaa 29

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV10-3_RN2v3
<220> FEATURE:
<223> OTHER INFORMATION: 3' 3SpC3

<400> SEQUENCE: 31
agatactgac aaaggagaag tctcagatgg ctatagugtc t 41

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV6-6_RN2v3
<220> FEATURE:
<221> NAME/KEY: modified_base
<222> LOCATION: (31)..(31)
<223> OTHER INFORMATION: Ribonucleotide base
<220> FEATURE:
<223> OTHER INFORMATION: 3' 3SpC3

<400> SEQUENCE: 32
gacaaaggag aagtcccgaa tggctacaac gtctc 35

<210> SEQ ID NO 33

-continued

<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV13_RN2v3
<220> FEATURE:
<221> NAME/KEY: modified_base
<222> LOCATION: (32)..(32)
<223> OTHER INFORMATION: Ribonucleotide base
<220> FEATURE:
<223> OTHER INFORMATION: 3' 3SpC3

<400> SEQUENCE: 33
ccctgatcga ttctcagctc aacagttcag tgacta 36

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV4-1_RN2v3
<220> FEATURE:
<221> NAME/KEY: modified_base
<222> LOCATION: (31)..(31)
<223> OTHER INFORMATION: Ribonucleotide base
<220> FEATURE:
<223> OTHER INFORMATION: 3' 3SpC3

<400> SEQUENCE: 34
cctgaatgcc ccaacagctc tctcttaaac cttca 35

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV4-3_RN2v3
<220> FEATURE:
<221> NAME/KEY: modified_base
<222> LOCATION: (31)..(31)
<223> OTHER INFORMATION: Ribonucleotide base
<220> FEATURE:
<223> OTHER INFORMATION: 3' 3SpC3

<400> SEQUENCE: 35
cctgaatgcc ccaacagctc tcacttattc cttca 35

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
<220> FEATURE:

<223> OTHER INFORMATION: Description of Combined DNA/RNA Molecule:
Synthetic primer
<220> FEATURE:
<223> OTHER INFORMATION: TRBV26_RN2v3
<220> FEATURE:
<221> NAME/KEY: modified_base
<222> LOCATION: (38)..(38)
<223> OTHER INFORMATION: Ribonucleotide base
<220> FEATURE:
<223> OTHER INFORMATION: 3' 3SpC3

<400> SEQUENCE: 36
ggagatgtct ctgagaggta tcatgtttct tgaaatacta ta 42

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer
<220> FEATURE:
<223> OTHER INFORMATION: TRBV6-8_RN2v3
<220> FEATURE:
<223> OTHER INFORMATION: 3' 3SpC3

<400> SEQUENCE: 37
tacaatgtct ctagattaaa cacagaggat ttcccacuca gg 42

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer
<220> FEATURE:
<223> OTHER INFORMATION: TRBV3-2_RN2v3
<220> FEATURE:
<223> OTHER INFORMATION: 3' 3SpC3

<400> SEQUENCE: 38
ttctcacctg actctccaga caaagctcat utaaa 35

<210> SEQ ID NO 39
<211> LENGTH: 35
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer
<220> FEATURE:
<223> OTHER INFORMATION: TRBV11-2_RN2v3
<220> FEATURE:
<221> NAME/KEY: modified_base
<222> LOCATION: (31)..(31)
<223> OTHER INFORMATION: Ribonucleotide base
<220> FEATURE:
<223> OTHER INFORMATION: 3' 3SpC3

<400> SEQUENCE: 39
cctaaggatc gattttctgc agagaggctc aaagg 35

-continued

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV2_RN2v3
<220> FEATURE:
<221> NAME/KEY: modified_base
<222> LOCATION: (30)..(30)
<223> OTHER INFORMATION: Ribonucleotide base
<220> FEATURE:
<223> OTHER INFORMATION: 3' 3SpC3

<400> SEQUENCE: 40
cctgaatgcc ctgacagctc tcgcttatac cttc 34

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV3-1_RN2v3
<220> FEATURE:
<223> OTHER INFORMATION: 3' 3SpC3

<400> SEQUENCE: 41
gcttctcacc taaatctcca gacaaagctc acttaaauct tc 42

<210> SEQ ID NO 42
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV29-1_RN2v3
<220> FEATURE:
<221> NAME/KEY: modified_base
<222> LOCATION: (30)..(30)
<223> OTHER INFORMATION: Ribonucleotide base
<220> FEATURE:
<223> OTHER INFORMATION: 3' 3SpC3

<400> SEQUENCE: 42
catcagccgc ccaaacctaa cattctcaac tctg 34

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

```
<220> FEATURE:
<223> OTHER INFORMATION: TRBV18_RN2v3
<220> FEATURE:
<221> NAME/KEY: modified_base
<222> LOCATION: (30)..(30)
<223> OTHER INFORMATION: Ribonucleotide base
<220> FEATURE:
<223> OTHER INFORMATION: 3' 3SpC3

<400> SEQUENCE: 43

attttctgct gaatttccca aagagggccc cagc                              34


<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV17_RN2v3
<220> FEATURE:
<221> NAME/KEY: modified_base
<222> LOCATION: (30)..(30)
<223> OTHER INFORMATION: Ribonucleotide base
<220> FEATURE:
<223> OTHER INFORMATION: 3' 3SpC3

<400> SEQUENCE: 44

attcacagct gaaagaccta acggaacgtc ttcc                              34


<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV20-1_RN2v3
<220> FEATURE:
<221> NAME/KEY: modified_base
<222> LOCATION: (27)..(27)
<223> OTHER INFORMATION: Ribonucleotide base
<220> FEATURE:
<223> OTHER INFORMATION: 3' 3SpC3

<400> SEQUENCE: 45

caagcctgac cttgtccact ctgacagtga c                                 31


<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBV7-6_RN2v3
<220> FEATURE:
<221> NAME/KEY: modified_base
<222> LOCATION: (25)..(25)
<223> OTHER INFORMATION: Ribonucleotide base
<220> FEATURE:
```

<223> OTHER INFORMATION: 3' 3SpC3

<400> SEQUENCE: 46
ggttctctgc agagaggcct gagggatcc 29

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV24-1_RN2v3
<220> FEATURE:
<221> NAME/KEY: modified_base
<222> LOCATION: (35)..(35)
<223> OTHER INFORMATION: Ribonucleotide base
<220> FEATURE:
<223> OTHER INFORMATION: 3' 3SpC3

<400> SEQUENCE: 47
gagagatctc tgatggatac agtgtctctc gacaggcac 39

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV7-2_RN2v3
<220> FEATURE:
<221> NAME/KEY: modified_base
<222> LOCATION: (27)..(27)
<223> OTHER INFORMATION: Ribonucleotide base
<220> FEATURE:
<223> OTHER INFORMATION: 3' 3SpC3

<400> SEQUENCE: 48
gatcgcttct ctgcagagag gactggggga t 31

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBV6-9_RN2v3
<220> FEATURE:
<223> OTHER INFORMATION: 3' 3SpC3

<400> SEQUENCE: 49
aaggagaagt ccccgatggc tacaatgtau ccag 34

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer
<220> FEATURE:
<223> OTHER INFORMATION: TRBV6-5_RN2v3
<220> FEATURE:
<223> OTHER INFORMATION: 3' 3SpC3

<400> SEQUENCE: 50
aaggagaagt ccccaatggc tacaatgtcu ccag 34

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer
<220> FEATURE:
<223> OTHER INFORMATION: TRBV5-5_RN2v3
<220> FEATURE:
<223> OTHER INFORMATION: 3' 3SpC3

<400> SEQUENCE: 51
aagaggaaac ttccctgatc gattctcagc ucgcc 35

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer
<220> FEATURE:
<223> OTHER INFORMATION: TRBV10-1_RN2v3
<220> FEATURE:
<223> OTHER INFORMATION: 3' 3SpC3

<400> SEQUENCE: 52
gacactaaca aaggagaagt ctcagatggc tacagugtct 40

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Description of Combined DNA/RNA Molecule:
Synthetic primer
<220> FEATURE:
<223> OTHER INFORMATION: TRBJ1-1_RN2v3
<220> FEATURE:
<221> NAME/KEY: modified_base
<222> LOCATION: (36)..(36)
<223> OTHER INFORMATION: Ribonucleotide base
<220> FEATURE:
<223> OTHER INFORMATION: 3' 3SpC3

<400> SEQUENCE: 53
ttacctacaa ctgtgagtct ggtgccttgt ccaaagaaag 40

-continued

<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBJ1-2_RN2v3
<220> FEATURE:
<221> NAME/KEY: modified_base
<222> LOCATION: (31)..(31)
<223> OTHER INFORMATION: Ribonucleotide base
<220> FEATURE:
<223> OTHER INFORMATION: 3' 3SpC3

<400> SEQUENCE: 54
tacaacggtt aacctggtcc ccgaaccgaa ggtgt 35

<210> SEQ ID NO 55
<211> LENGTH: 39
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBJ1-3_RN2v3
<220> FEATURE:
<223> OTHER INFORMATION: 3' 3SpC3

<400> SEQUENCE: 55
acctacaaca gtgagccaac ttccctctcc aaaauatat 39

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBJ1-4_RN2v3
<220> FEATURE:
<221> NAME/KEY: modified_base
<222> LOCATION: (32)..(32)
<223> OTHER INFORMATION: Ribonucleotide base
<220> FEATURE:
<223> OTHER INFORMATION: 3' 3SpC3

<400> SEQUENCE: 56
caagacagag agctgggttc cactgccaaa aaacag 36

<210> SEQ ID NO 57
<211> LENGTH: 38
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBJ1-5_RN2v3
<220> FEATURE:
<221> NAME/KEY: modified_base
<222> LOCATION: (34)..(34)
<223> OTHER INFORMATION: Ribonucleotide base
<220> FEATURE:
<223> OTHER INFORMATION: 3' 3SpC3

<400> SEQUENCE: 57
acctaggatg gagagtcgag tcccatcacc aaaatgct 38

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBJ1-6_RN2v3
<220> FEATURE:
<221> NAME/KEY: modified_base
<222> LOCATION: (29)..(29)
<223> OTHER INFORMATION: Ribonucleotide base
<220> FEATURE:
<223> OTHER INFORMATION: 3' 3SpC3

<400> SEQUENCE: 58
tcacagtgag cctggtcccg ttcccaaagt gga 33

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBJ2-1_RN2v3
<220> FEATURE:
<221> NAME/KEY: modified_base
<222> LOCATION: (26)..(26)
<223> OTHER INFORMATION: Ribonucleotide base
<220> FEATURE:
<223> OTHER INFORMATION: 3' 3SpC3

<400> SEQUENCE: 59
cggtgagccg tgtccctggc ccgaagaact 30

<210> SEQ ID NO 60
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBJ2_2RN2v3
<220> FEATURE:
<221> NAME/KEY: modified_base
<222> LOCATION: (32)..(32)
<223> OTHER INFORMATION: Ribonucleotide base
<220> FEATURE:

<223> OTHER INFORMATION: 3' 3SpC3

<400> SEQUENCE: 60
ccagtacggt cagcctagag ccttctccaa aaaaca 36

<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBJ2-3_RN2v3
<220> FEATURE:
<221> NAME/KEY: modified_base
<222> LOCATION: (27)..(27)
<223> OTHER INFORMATION: Ribonucleotide base
<220> FEATURE:
<223> OTHER INFORMATION: 3' 3SpC3

<400> SEQUENCE: 61
actgtcagcc gggtgcctgg gccaaaatac t 31

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBJ2-3_RN2v3
<220> FEATURE:
<221> NAME/KEY: modified_base
<222> LOCATION: (23)..(23)
<223> OTHER INFORMATION: Ribonucleotide base
<220> FEATURE:
<223> OTHER INFORMATION: 3' 3SpC3

<400> SEQUENCE: 62
agagccgggt cccggcgccg aagtact 27

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: TRBJ2-5_RN2v3
<220> FEATURE:
<221> NAME/KEY: modified_base
<222> LOCATION: (23)..(23)
<223> OTHER INFORMATION: Ribonucleotide base
<220> FEATURE:
<223> OTHER INFORMATION: 3' 3SpC3

<400> SEQUENCE: 63
ggagccgcgt gcctggcccg aagtact 27

```
<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBJ2-6_RN2v3
<220> FEATURE:
<221> NAME/KEY: modified_base
<222> LOCATION: (24)..(24)
<223> OTHER INFORMATION: Ribonucleotide base
<220> FEATURE:
<223> OTHER INFORMATION: 3' 3SpC3

<400> SEQUENCE: 64

gtcagcctgc tgccggcccc gaaagtca                                         28


<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: TRBJ2-7_RN2v3
<220> FEATURE:
<221> NAME/KEY: modified_base
<222> LOCATION: (24)..(24)
<223> OTHER INFORMATION: Ribonucleotide base
<220> FEATURE:
<223> OTHER INFORMATION: 3' 3SpC3

<400> SEQUENCE: 65

gtgagcctgg tgcccggccc gaagtact                                         28


<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: TCRB V7 family-specific real time PCR probe
<220> FEATURE:
<223> OTHER INFORMATION: 3' TET(tetrachlorofluorescein) or 3BHQ_1(4-(2-
      nitro-4-toloyldiazo)-2'-methoxy-5'-methyl-azobenzene-4"-(N-ethyl)-
      N-ethyl-2-cyanoethyl-(N,N-diisopropyl)-phosphoramidite)

<400> SEQUENCE: 66

gggactcagc ygtgtatctc tgtgcc                                           26


<210> SEQ ID NO 67
<211> LENGTH: 284
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV1*01

<400> SEQUENCE: 67
```

gatactggaa ttacccagac accaaaatac ctggtcacag caatggggag taaaaggaca 60
atgaaacgtg agcatctggg acatgattct atgtattggt acagacagaa agctaagaaa 120
tccctggagt tcatgtttta ctacaactgt aaggaattca ttgaaaacaa gactgtgcca 180
aatcacttca cacctgaatg ccctgacagc tctcgcttat accttcatgt ggtcgcactg 240
cagcaagaag actcagctgc gtatctctgc accagcagcc aaga 284

<210> SEQ ID NO 68
<211> LENGTH: 289
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV2*01

<400> SEQUENCE: 68
gaacctgaag tcacccagac tcccagccat caggtcacac agatgggaca ggaagtgatc 60
ttgcgctgtg tccccatctc taatcactta tacttctatt ggtacagaca aatcttgggc 120
agaaagtcga gtttctggtt tccttttata ataatgaaat ctcagagaag tctgaaatat 180
tcgatgatca attctcagtt gaaaggcctg atggatcaaa tttcactctg aagatccggt 240
ccacaaagct ggaggactca gccatgtact tctgtgccag cagtgaagc 289

<210> SEQ ID NO 69
<211> LENGTH: 288
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV2*03

<400> SEQUENCE: 69
gaacctgaag tcacccagac tcccagccat caggtcacac agatgggaca ggaagtgatc 60
ttgcgctgtg tccccatctc taatcactta tacttctatt ggtacagaca aatcttgggg 120
cagaaagtcg agtttctggt ttccttttat aataatgaaa tctcagagaa gtctgaaata 180
ttcgatgatc aattctcagt tgagaggcct gatggatcaa atttcactct gaagatccgg 240
tccacaaagc tggaggactc agccatgtac ttctgtgcca gcagtgaa 288

<210> SEQ ID NO 70
<211> LENGTH: 287
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV3-1*01

<400> SEQUENCE: 70
gacacagctg tttcccagac tccaaaatac ctggtcacac agatgggaaa cgacaagtcc 60
attaaatgtg aacaaaatct gggccatgat actatgtatt ggtataaaca ggactctaag 120
aaatttctga agataatgtt tagctacaat aataaggagc tcattataaa tgaaacagtt 180
ccaaatcgct tctcacctaa atctccagac aaagctcact taaatcttca catcaattcc 240
ctggagcttg gtgactctgc tgtgtatttc tgtgccagca gccaaga 287

<210> SEQ ID NO 71
<211> LENGTH: 279
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV3-1*02

<400> SEQUENCE: 71
gacacagctg tttcccagac tccaaaatac ctggtcacac agatgggaaa cgacaagtcc 60
attaaatgtg aacaaaatct gggccatgat actatgtatt ggtataaaca ggactctaag 120
aaatttctga agataatgtt tagctacaat aacaaggaga tcattataaa tgaaacagtt 180
ccaaatcgat tctcacctaa atctccagac aaagctaaat taaatcttca catcaattcc 240
ctggagcttg gtgactctgc tgtgtatttc tgtgccagc 279

<210> SEQ ID NO 72
<211> LENGTH: 287
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV3-2*01

<400> SEQUENCE: 72
gacacagccg tttcccagac tccaaaatac ctggtcacac agatgggaaa aaaggagtct 60
cttaaatgag aacaaaatct gggccataat gctatgtatt ggtataaaca ggactctaag 120
aaatttctga agacaatgtt tatctacagt aacaaggagc caattttaaa tgaaacagtt 180
ccaaatcgct tctcacctga ctctccagac aaagctcatt taaatcttca catcaattcc 240
ctggagcttg gtgactctgc tgtgtatttc tgtgccagca gccaaga 287

<210> SEQ ID NO 73
<211> LENGTH: 287
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV3-2*02

<400> SEQUENCE: 73
gacacagccg tttcccagac tccaaaatac ctggtcacac agatgggaaa aaaggagtct 60
cttaaatgag aacaaaatct gggccataat gctatgtatt ggtataaaca ggactctaag 120
aaatttctga agacaatgtt tatctacagt aacaaggagc caattttaaa tgaaacagtt 180
ccaaatcgct tctcacctga ctctccagac aaagttcatt taaatcttca catcaattcc 240
ctggagcttg gtgactctgc tgtgtatttc tgtgccagca gccaaga 287

<210> SEQ ID NO 74
<211> LENGTH: 285
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV3-2*03

<400> SEQUENCE: 74
gacacagccg tttcccagac tccaaaatac ctggtcacac agacgggaaa aaaggagtct 60
cttaaatgag aacaaaatct gggccataat gctatgtatt ggtataaaca ggactctaag 120
aaatttctga agacaatgtt tatctacagt aacaaggagc caattttaaa tgaaacagtt 180
ccaaatcgct tctcacctga ctctccagac aaagttcatt taaatcttca catcaattcc 240
ctggagcttg gtgactctgc tgtgtatttc tgtgccagca gccaa 285

<210> SEQ ID NO 75
<211> LENGTH: 287
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV4-1*01

<400> SEQUENCE: 75
gacactgaag ttacccagac accaaaacac ctggtcatgg gaatgacaaa taagaagtct 60
ttgaaatgtg aacaacatat ggggcacagg gctatgtatt ggtacaagca gaaagctaag 120
aagccaccgg agctcatgtt tgtctacagc tatgagaaac tctctataaa tgaaagtgtg 180
ccaagtcgct tctcacctga atgccccaac agctctctct taaaccttca cctacacgcc 240
ctgcagccag aagactcagc cctgtatctc tgcgccagca gccaaga 287

<210> SEQ ID NO 76
<211> LENGTH: 258
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV4-1*02

<400> SEQUENCE: 76
cacctggtca tgggaatgac aaataagaag tctttgaaat gtgaacaaca tatggggcac 60
agggcaatgt attggtacaa gcagaaagct aagaagccac cggagctcat gtttgtctac 120
agctatgaga aactctctat aaatgaaagt gtgccaagtc gcttctcacc tgaatgcccc 180
aacagctctc tcttaaacct tcacctacac gccctgcagc cagaagactc agccctgtat 240
ctctgcgcca gcagccaa 258

<210> SEQ ID NO 77
<211> LENGTH: 287
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV4-2*01

<400> SEQUENCE: 77
gaaacgggag ttacgcagac accaagacac ctggtcatgg gaatgacaaa taagaagtct 60
ttgaaatgtg aacaacatct ggggcataac gctatgtatt ggtacaagca aagtgctaag 120
aagccactgg agctcatgtt tgtctacaac tttaaagaac agactgaaaa caacagtgtg 180
ccaagtcgct tctcacctga atgccccaac agctctcact tattccttca cctacacacc 240
ctgcagccag aagactcggc cctgtatctc tgtgccagca gccaaga 287

<210> SEQ ID NO 78
<211> LENGTH: 282
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV4-2*02

<400> SEQUENCE: 78
gaaacgggag ttacgcagac accaagacac ctggtcatgg gaatgacaaa taagaagtct 60
ttgaaatgtg aacaacatct ggggcataac gctatgtatt ggtacaagca aagtgctaag 120
aagccactgg agctcatgtt tgtctacaac tttaaagaac agactgaaaa caacagtgtg 180
ccaagtcgct tctcacctga atgccccaac agctctcact tatgccttca cctacacacc 240
ctgcagccag aagactcggc cctgtatctc tgtgccagca cc 282

<210> SEQ ID NO 79
<211> LENGTH: 287
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV4-3*01

<400> SEQUENCE: 79
gaaacgggag ttacgcagac accaagacac ctggtcatgg gaatgacaaa taagaagtct 60
ttgaaatgtg aacaacatct gggtcataac gctatgtatt ggtacaagca aagtgctaag 120
aagccactgg agctcatgtt tgtctacagt cttgaagaac gggttgaaaa caacagtgtg 180
ccaagtcgct tctcacctga atgccccaac agctctcact tattccttca cctacacacc 240
ctgcagccag aagactcggc cctgtatctc tgcgccagca gccaaga 287

<210> SEQ ID NO 80
<211> LENGTH: 282
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV4-3*02

<400> SEQUENCE: 80
gaaacgggag ttacgcagac accaagacac ctggtcatgg gaatgacaaa taagaagtct 60
ttgaaatgtg aacaacatct gggtcataac gctatgtatt ggtacaagca aagtgctaag 120
aagccactgg agctcatgtt tgtctacagt cttgaagaac gggttgaaaa caacagtgtg 180
ccaagtcgct tctcacctga atgccccaac agctctcact tatcccttca cctacacacc 240
ctgcagccag aagactcggc cctgtatctc tgcgccagca gc 282

<210> SEQ ID NO 81
<211> LENGTH: 282
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV4-3*3

<400> SEQUENCE: 81
gaaacgggag ttacgcagac accaagacac ctggtcatgg gaatgacaaa taagaagtct 60
ttgaaatgtg aacaacatct gggtcataac gctatgtatt ggtacaagca aagtgctaag 120
aagccactgg agctcatgtt tgtctacagt cttgaagaac gtgttgaaaa caacagtgtg 180
ccaagtcgct tctcacctga atgccccaac agctctcact tattccttca cctacacacc 240
ctgcagccag aagactcggc cctgtatctc tgcgccagca gc 282

<210> SEQ ID NO 82
<211> LENGTH: 231
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV4-3*04

<400> SEQUENCE: 82
aagaagtctt tgaaatgtga acaacatctg ggcataacg ctatgtattg gtacaagcaa 60
agtgctaaga agccactgga gctcatgttt gtctacagtc ttgaagaacg ggttgaaaac 120
aacagtgtgc caagtcgctt ctcacctgaa tgccccaaca gctctcactt attccttcac 180
ctacacaccc tgcagccaga agactcggcc ctgtatctct gcgccagcag c 231

<210> SEQ ID NO 83
<211> LENGTH: 286
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV5-1*01

<400> SEQUENCE: 83
aaggctggag tcactcaaac tccaagatat ctgatcaaaa cgagaggaca gcaagtgaca 60
ctgagctgct cccctatctc tgggcatagg agtgtatcct ggtaccaaca gaccccagga 120
cagggccttc agttcctctt tgaatacttc agtgagacac agagaaacaa aggaaacttc 180
cctggtcgat tctcagggcg ccagttctct aactctcgct ctgagatgaa tgtgagcacc 240
ttggagctgg gggactcggc cctttatctt tgcgccagca gcttgg 286

<210> SEQ ID NO 84
<211> LENGTH: 285
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV5-1*02

<400> SEQUENCE: 84
agggctgggg tcactcaaac tccaagacat ctgatcaaaa cgagaggaca gcaagtgaca 60
ctgggctgct cccctatctc tgggcatagg agtgtatcct ggtaccaaca gaccctagga 120
cagggccttc agttcctctt tgaatacttc agtgagacac agagaaacaa aggaaacttc 180

-continued cttggtcgat tctcagggcg ccagttctct aactctcgct ctgagatgaa tgtgagcacc 240
ttggagctgg gggactcggc cctttatctt tgcgccagcg cttgc 285

<210> SEQ ID NO 85
<211> LENGTH: 286
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV5-3*01

<400> SEQUENCE: 85
gaggctggag tcacccaaag tcccacacac ctgatcaaaa cgagaggaca gcaagtgact 60
ctgagatgct ctcctatctc tgggcacagc agtgtgtcct ggtaccaaca ggccccgggt 120
caggggcccc agtttatctt tgaatatgct aatgagttaa ggagatcaga aggaaacttc 180
cctaatcgat tctcagggcg ccagttccat gactgttgct ctgagatgaa tgtgagtgcc 240
ttggagctgg gggactcggc cctgtatctc tgtgccagaa gcttgg 286

<210> SEQ ID NO 86
<211> LENGTH: 286
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV5-3*02

<400> SEQUENCE: 86
gaggctggag tcacccaaag tcccacacac ctgatcaaaa cgagaggaca gcaagtgact 60
ctgagatgct ctcctatctc tgggcacagc agtgtgtcct ggtaccaaca ggccccgggt 120
caggggcccc agtttatctt tgaatatgct aatgagttaa ggagatcaga aggaaacttc 180
cctaatcgat tctcagggcg ccagttccat gactattgct ctgagatgaa tgtgagtgcc 240
ttggagctgg gggactcggc cctgtatctc tgtgccagaa gcttgg 286

<210> SEQ ID NO 87
<211> LENGTH: 286
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV5-4*01

<400> SEQUENCE: 87
gagactggag tcacccaaag tcccacacac ctgatcaaaa cgagaggaca gcaagtgact 60
ctgagatgct cttctcagtc tgggcacaac actgtgtcct ggtaccaaca ggccctgggt 120
caggggcccc agtttatctt tcagtattat agggaggaag agaatggcag aggaaacttc 180
cctcctagat tctcaggtct ccagttccct aattatagct ctgagctgaa tgtgaacgcc 240
ttggagctgg acgactcggc cctgtatctc tgtgccagca gcttgg 286

<210> SEQ ID NO 88
<211> LENGTH: 282
<212> TYPE: DNA
<213> ORGANISM: Artificial Sequence
<220> FEATURE:

-continued

<223> OTHER INFORMATION: Description of Artificial Sequence: Synthetic
      polynucleotide
<220> FEATURE:
<223> OTHER INFORMATION: TRBV5-4*02

<400> SEQUENCE: 88
gagactggag tcacccaaag tcccacacac ctgatcaaaa cgagaggaca gcaagtgact 60
ctgagatgct cttctcagtc tgggcacaac actgtgtcct ggtaccaaca ggccctgggt 120
caggggcccc agtttatctt tcagtattat agggaggaag agaatggcag aggaaacttc 180
cctcctagat tctcaggtct ccagttccct aattataact ctgagctgaa tgtgaacgcc 240
ttggagctgg acgactcggc cctgtatctc tgtgccagca gc 282

<210> SEQ ID NO 89
<211> LENGTH: 234
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV5-4*03

<400> SEQUENCE: 89
cagcaagtga cactgagatg ctcttctcag tctgggcaca acactgtgtc ctggtaccaa 60
caggccctgg gtcaggggcc ccagtttatc tttcagtatt atagggagga agagaatggc 120
agaggaaact tccctcctag attctcaggt ctccagttcc ctaattatag ctctgagctg 180
aatgtgaacg ccttggagct ggacgactcg gccctgtatc tctgtgccag cagc 234

<210> SEQ ID NO 90
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV5-4*04

<400> SEQUENCE: 90
actgtgtcct ggtaccaaca ggccctgggt caggggcccc agtttatctt tcagtattat 60
agggaggaag agaatggcag aggaaactcc cctcctagat tctcaggtct ccagttccct 120
aattatagct ctgagctgaa tgtgaacgcc ttggagctgg acgactcggc cctgtatctc 180
tgtgccagca gc 192

<210> SEQ ID NO 91
<211> LENGTH: 286
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV5-5*01

<400> SEQUENCE: 91
gacgctggag tcacccaaag tcccacacac ctgatcaaaa cgagaggaca gcaagtgact 60
ctgagatgct ctcctatctc tgggcacaag agtgtgtcct ggtaccaaca ggtcctgggt 120
caggggcccc agtttatctt tcagtattat gagaaagaag agagaggaag aggaaacttc 180
cctgatcgat tctcagctcg ccagttccct aactatagct ctgagctgaa tgtgaacgcc 240
ttgttgctgg gggactcggc cctgtatctc tgtgccagca gcttgg 286

<210> SEQ ID NO 92
<211> LENGTH: 282
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV5-5*02

<400> SEQUENCE: 92
gacgctggag tcacccaaag tcccacacac ctgatcaaaa cgagaggaca gcacgtgact 60
ctgagatgct ctcctatctc tgggcacaag agtgtgtcct ggtaccaaca ggtcctgggt 120
caggggcccc agtttatctt tcagtattat gagaaagaag agagaggaag aggaaacttc 180
cctgatcgat tctcagctcg ccagttccct aactatagct ctgagctgaa tgtgaacgcc 240
ttgttgctgg gggactcggc cctgtatctc tgtgccagca gc 282

<210> SEQ ID NO 93
<211> LENGTH: 282
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV5-5*03

<400> SEQUENCE: 93
gacgctggag tcacccaaag tcccacacac ctgatcaaaa cgagaggaca gcaagtgact 60
ctgagatgct ctcctatctc tgagcacaag agtgtgtcct ggtaccaaca ggtcctgggt 120
caggggcccc agtttatctt tcagtattat gagaaagaag agagaggaag aggaaacttc 180
cctgatcgat tctcagctcg ccagttccct aactatagct ctgagctgaa tgtgaacgcc 240
ttgttgctgg gggactcggc cctgtatctc tgtgccagca gc 282

<210> SEQ ID NO 94
<211> LENGTH: 286
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV5-6*01

<400> SEQUENCE: 94
gacgctggag tcacccaaag tcccacacac ctgatcaaaa cgagaggaca gcaagtgact 60
ctgagatgct ctcctaagtc tgggcatgac actgtgtcct ggtaccaaca ggccctgggt 120
caggggcccc agtttatctt tcagtattat gaggaggaag agagacagag aggcaacttc 180
cctgatcgat tctcaggtca ccagttccct aactatagct ctgagctgaa tgtgaacgcc 240
ttgttgctgg gggactcggc cctctatctc tgtgccagca gcttgg 286

<210> SEQ ID NO 95
<211> LENGTH: 286
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV5-7*01

<400> SEQUENCE: 95
gacgctggag tcacccaaag tcccacacac ctgatcaaaa cgagaggaca gcacgtgact 60
ctgagatgct ctcctatctc tgggcacacc agtgtgtcct cgtaccaaca ggccctgggt 120
caggggcccc agtttatctt tcagtattat gagaaagaag agagaggaag aggaaacttc 180
cctgatcaat tctcaggtca ccagttccct aactatagct ctgagctgaa tgtgaacgcc 240
ttgttgctag ggactcggc cctctatctc tgtgccagca gcttgg 286

<210> SEQ ID NO 96
<211> LENGTH: 286
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV5-8*01

<400> SEQUENCE: 96
gaggctggag tcacacaaag tcccacacac ctgatcaaaa cgagaggaca gcaagcgact 60
ctgagatgct ctcctatctc tgggcacacc agtgtgtact ggtaccaaca ggccctgggt 120
ctgggcctcc agttcctcct ttggtatgac gagggtgaag agagaaacag aggaaacttc 180
cctcctagat tttcaggtcg ccagttccct aattatagct ctgagctgaa tgtgaacgcc 240
ttggagctgg aggactcggc cctgtatctc tgtgccagca gcttgg 286

<210> SEQ ID NO 97
<211> LENGTH: 238
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV5-8*02

<400> SEQUENCE: 97
aggacagcaa gcgactctga gatgctctcc tatctctggg cacaccagtg tgtactggta 60
ccaacaggcc ctgggtctgg gcctccagct cctcctttgg tatgacgagg gtgaagagag 120
aaacagagga aacttccctc ctagattttc aggtcgccag ttccctaatt atagctctga 180
gctgaatgtg aacgccttgg agctggagga ctcggccctg tatctctgtg ccagcagc 238

<210> SEQ ID NO 98
<211> LENGTH: 287
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV6-1*01

<400> SEQUENCE: 98
aatgctggtg tcactcagac cccaaaattc caggtcctga agacaggaca gagcatgaca 60
ctgcagtgtg cccaggatat gaaccataac tccatgtact ggtatcgaca agacccaggc 120
atgggactga ggctgattta ttactcagct tctgagggta ccactgacaa aggagaagtc 180

-continued cccaatggct acaatgtctc cagattaaac aaacgggagt tctcgctcag gctggagtcg 240
gctgctccct cccagacatc tgtgtacttc tgtgccagca gtgaagc 287

<210> SEQ ID NO 99
<211> LENGTH: 287
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV6-2*01

<400> SEQUENCE: 99
aatgctggtg tcactcagac cccaaaattc cgggtcctga agacaggaca gagcatgaca 60
ctgctgtgtg cccaggatat gaaccatgaa tacatgtact ggtatcgaca agacccaggc 120
atggggctga ggctgattca ttactcagtt ggtgagggta caactgccaa aggagaggtc 180
cctgatggct acaatgtctc cagattaaaa aaacagaatt tcctgctggg gttggagtcg 240
gctgctccct cccaaacatc tgtgtacttc tgtgccagca gttactc 287

<210> SEQ ID NO 100
<211> LENGTH: 287
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV6-3*01

<400> SEQUENCE: 100
aatgctggtg tcactcagac cccaaaattc cgggtcctga agacaggaca gagcatgaca 60
ctgctgtgtg cccaggatat gaaccatgaa tacatgtact ggtatcgaca agacccaggc 120
atggggctga ggctgattca ttactcagtt ggtgagggta caactgccaa aggagaggtc 180
cctgatggct acaatgtctc cagattaaaa aaacagaatt tcctgctggg gttggagtcg 240
gctgctccct cccaaacatc tgtgtacttc tgtgccagca gttactc 287

<210> SEQ ID NO 101
<211> LENGTH: 287
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV6-4*01

<400> SEQUENCE: 101
attgctggga tcacccaggc accaacatct cagatcctgg cagcaggacg gcgcatgaca 60
ctgagatgta cccaggatat gagacataat gccatgtact ggtatagaca agatctagga 120
ctggggctaa ggctcatcca ttattcaaat actgcaggta ccactggcaa aggagaagtc 180
cctgatggtt atagtgtctc cagagcaaac acagatgatt tcccccctcac gttggcgtct 240 gctgtaccct ctcagacatc tgtgtacttc tgtgccagca gtgactc 287

<210> SEQ ID NO 102
<211> LENGTH: 287
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: TRBV6-4*02

<400> SEQUENCE: 102
actgctggga tcacccaggc accaacatct cagatcctgg cagcaggacg gagcatgaca     60
ctgagatgta cccaggatat gagacataat gccatgtact ggtatagaca agatctagga    120
ctggggctaa ggctcatcca ttattcaaat actgcaggta ccactggcaa aggagaagtc    180
cctgatggtt atagtgtctc cagagcaaac acagatgatt tccccctcac gttggcgtct    240
gctgtaccct ctcagacatc tgtgtacttc tgtgccagca gtgactc                 287

<210> SEQ ID NO 103
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV6-5*01

<400> SEQUENCE: 103
aatgctggtg tcactcagac cccaaaattc caggtcctga agacaggaca gagcatgaca     60
ctgcagtgtg cccaggatat gaaccatgaa tacatgtcct ggtatcgaca agacccaggc    120
atggggctga ggctgattca ttactcagtt ggtgctggta tcactgacca aggagaagtc    180
cccaatggct acaatgtctc cagatcaacc acagaggatt tcccgctcag gctgctgtcg    240
gctgctccct cccagacatc tgtgtacttc tgtgccagca gttactc                 287

<210> SEQ ID NO 104
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV6-6*01

<400> SEQUENCE: 104
aatgctggtg tcactcagac cccaaaattc cgcatcctga agataggaca gagcatgaca     60
ctgcagtgta cccaggatat gaaccataac tacatgtact ggtatcgaca agacccaggc    120
atggggctga agctgattta ttattcagtt ggtgctggta tcactgataa aggagaagtc    180
ccgaatggct acaacgtctc cagatcaacc acagaggatt tcccgctcag gctggagttg    240
gctgctccct cccagacatc tgtgtacttc tgtgccagca gttactc                 287

<210> SEQ ID NO 105
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV6-6*02

<400> SEQUENCE: 105
aatgctggtg tcactcagac cccaaaattc cgcatcctga agataggaca gagcatgaca     60
ctgcagtgtg cccaggatat gaaccataac tacatgtact ggtatcgaca agacccaggc    120

-continued

```
atggggctga agctgattta ttattcagtt ggtgctggta tcactgacaa aggagaagtc    180

ccgaatggct acaacgtctc cagatcaacc acagaggatt tcccgctcag gctggagttg    240

gctgctccct cccagacatc tgtgtacttc tgtgccagca gt                       282


<210> SEQ ID NO 106
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV6-6*03

<400> SEQUENCE: 106

aatgctggtg tcactcagac cccaaaattc cgcatcctga agataggaca gagcatgaca     60

ctgcagtgtg cccaggatat gaaccataac tacatgtact ggtatcgaca agacccaggc    120

atggggctga agctgattta ttattcagtt ggtgctggta tcactgataa aggagaagtc    180

ccgaatggct acaacgtctc cagatcaacc acagaggatt tcccgctcag gctggagttg    240

gctgctccct cccagacatc tgtgtacttc tgtgccagca gt                       282


<210> SEQ ID NO 107
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV6-6*04

<400> SEQUENCE: 107

aatgctggtg tcactcagac cccaaaattc cgcatcctga agataggaca gagcatgaca     60

ctgcagtgta cccaggatat gaaccatgaa tacatgtact ggtatcgaca agacccaggc    120

atggggctga agctgattta ttattcagtt ggtgctggta tcactgataa aggagaagtc    180

ccgaatggct acaatgtctc cagatcaacc acagaggatt tcccgctcag gctggagttg    240

gctgctccct cccagacatc tgtgtacttc tgtgccagca gtcga                    285


<210> SEQ ID NO 108
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV6-6*05

<400> SEQUENCE: 108

aatgctggtg tcactcagac cccaaaattc cgcatcctga agataggaca gagcatgaca     60

ctgcagtgtg cccaggatat gaaccataac tacatgtact ggtatcgaca agacccaggc    120

atggggctga agctgattta ttattcagtt ggtgctggta tcactgacaa aggagaagtc    180

ccgaatggct acaacgtctc cagatcaacc acagaggatt tcccgctcag gctggagttg    240

gctgctgcct cccagacatc tgtgtacttc tgtgccagca gc                       282


<210> SEQ ID NO 109
<211> LENGTH: 287
```

<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV6-7*01

<400> SEQUENCE: 109
aatgctggtg tcactcagac cccaaaattc cacgtcctga agacaggaca gagcatgact 60
ctgctgtgtg cccaggatat gaaccatgaa tacatgtatc ggtatcgaca agacccaggc 120
aaggggctga ggctgattta ctactcagtt gctgctgctc tcactgacaa aggagaagtt 180
cccaatggct acaatgtctc cagatcaaac acagaggatt tcccccctcaa gctggagtca 240 gctgctccct ctcagacttc tgtttacttc tgtgccagca gttactc 287

<210> SEQ ID NO 110
<211> LENGTH: 284
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV6-8*01

<400> SEQUENCE: 110
aatgctggtg tcactcagac cccaaaattc cacatcctga agacaggaca gagcatgaca 60
ctgcagtgtg cccaggatat gaaccatgga tacatgtcct ggtatcgaca agacccaggc 120
atggggctga gactgattta ctactcagct gctgctggta ctactgacaa agaagtcccc 180
aatggctaca atgtctctag attaaacaca gaggatttcc cactcaggct ggtgtcggct 240
gctccctccc agacatctgt gtacttgtgt gccagcagtt actc 284

<210> SEQ ID NO 111
<211> LENGTH: 287
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV6-9*01

<400> SEQUENCE: 111
aatgctggtg tcactcagac cccaaaattc cacatcctga agacaggaca gagcatgaca 60
ctgcagtgtg cccaggatat gaaccatgga tacttgtcct ggtatcgaca agacccaggc 120
atggggctga ggcgcattca ttactcagtt gctgctggta tcactgacaa aggagaagtc 180
cccgatggct acaatgtatc cagatcaaac acagaggatt tcccgctcag gctggagtca 240
gctgctccct cccagacatc tgtatacttc tgtgccagca gttattc 287

<210> SEQ ID NO 112
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-01*01

<400> SEQUENCE: 112

```
ggtgctggag tctcccagtc cctgagacac aaggtagcaa agaagggaaa ggatgtagct     60

ctcagatatg atccaatttc aggtcataat gccctttatt ggtaccgaca gagcctgggg    120

cagggcctgg agtttccaat ttacttccaa ggcaaggatg cagcagacaa atcggggctt    180

ccccgtgatc ggttctctgc acagaggtct gagggatcca tctccactct gaagttccag    240

cgcacacagc agggggactt ggctgtgtat ctctgtgcca gcagctcagc              290


<210> SEQ ID NO 113
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV7-2*01

<400> SEQUENCE: 113

ggagctggag tctcccagtc ccccagtaac aaggtcacag agaagggaaa ggatgtagag     60

ctcaggtgtg atccaatttc aggtcatact gccctttact ggtaccgaca gagcctgggg    120

cagggcctgg agtttttaat ttacttccaa ggcaacagtg caccagacaa atcagggctg    180

cccagtgatc gcttctctgc agagaggact gggggatccg tctccactct gacgatccag    240

cgcacacagc aggaggactc ggccgtgtat ctctgtgcca gcagcttagc              290


<210> SEQ ID NO 114
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV7-2*02

<400> SEQUENCE: 114

ggagctggag tctcccagtc ccccagtaac aaggtcacag agaagggaaa ggatgtagag     60

ctcaggtgtg atccaatttc aggtcatact gccctttact ggtaccgaca gaggctgggg    120

cagggcctgg agtttttaat ttacttccaa ggcaacagtg caccagacaa atcagggctg    180

cccagtgatc gcttctctgc agagaggact ggggaatccg tctccactct gacgatccag    240

cgcacacagc aggaggactc ggccgtgtat ctctgtgcca gcagcttagc              290


<210> SEQ ID NO 115
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV7-2*03

<400> SEQUENCE: 115

ggagctggag tctcccagtc ccccagtaac aaggtcacag agaagggaaa ggatgtagag     60

ctcaggtgtg atccaatttc aggtcatact gccctttact ggtaccgaca gaggctgggg    120

cagggcctgg agtttttaat ttacttccaa ggcaacagtg caccagacaa atcagggctg    180

cccagtgatc gcttctctgc agagaggact ggggaatccg tctccactct gacgatccag    240

cgcacacagc aggaggactc ggccgtgtat ctctgtacca gcagcttagc              290
```

<210> SEQ ID NO 116
<211> LENGTH: 288
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-2*04

<400> SEQUENCE: 116
ggagctggag tttcccagtc ccccagtaac aaggtcacag agaagggaaa ggatgtagag 60
ctcaggtgtg atccaatttc aggtcatact gccctttact ggtaccgaca gagcctgggg 120
cagggcctgg agtttttaat ttacttccaa ggcaacagtg caccagacaa atcagggctg 180
cccagtgatc gcttctctgc agagaggact gggggatccg tctccactct gacgatccag 240
cgcacacagc aggaggactc ggccgtgtat ctctgtgcca gcagctta 288

<210> SEQ ID NO 117
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-3*01

<400> SEQUENCE: 117
ggtgctggag tctcccagac ccccagtaac aaggtcacag agaagggaaa atatgtagag 60
ctcaggtgtg atccaatttc aggtcatact gccctttact ggtaccgaca aagcctgggg 120
cagggcccag agtttctaat ttacttccaa ggcacgggtg cggcagatga ctcagggctg 180
cccaacgatc ggttctttgc agtcaggcct gagggatccg tctctactct gaagatccag 240
cgcacagagc gggggactc agccgtgtat ctctgtgcca gcagcttaac 290

<210> SEQ ID NO 118
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-3*02

<400> SEQUENCE: 118
ggtgctggag tctcccagac ccccagtaac aaggtcacag agaagggaaa agatgtagag 60
ctcaggtgtg atccaatttc aggtcatact gccctttact ggtaccgaca aagcctgggg 120
cagggcccag agtttctaat ttacttccaa ggcacgggtg cggcagatga ctcagggctg 180
cccaaagatc ggttctttgc agtcaggcct gagggatccg tctctactct gaagatccag 240
cgcacagagc agggggactc agccgtgtat ctccgtgcca gcagcttaac 290

<210> SEQ ID NO 119
<211> LENGTH: 288
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-3*03

<400> SEQUENCE: 119
ggtgctggag tctcccagac ccccagtaac aaggtcacag agaagggaaa agatgtagag 60
ctcaggtgtg atccaatttc aggtcatact gccctttact ggtaccgaca aagcctgggg 120
cagggcccag agtttctaat ttacttccaa ggcacgggtg cggcagatga ctcagggctg 180
cccaaagatc ggttctttgc agtcaggcct gagggatccg tctctactct gaagatccag 240
cgcacagagc agggggactc agccgcgtat ctccgtgcca gcagctta 288

<210> SEQ ID NO 120
<211> LENGTH: 285
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-3*04

<400> SEQUENCE: 120
ggtgctggag tctcccagac ccccagtaac aaggtcacag agaagggaaa atatgtagag 60
ctcaggtgtg atccaatttc aggtcatact gccctttact ggtaccgaca aagcctgggg 120
cagggcccag agtttctaat ttacttccaa ggcacgggtg cggcagatga ctcagggctg 180
cccaacgatc ggttctttgc agtcaggcct gagggatccg tctctactct gaagatccag 240
cgcacagagc ggggggactc tgccgtgtat ctctgtgcca gcagc 285

<210> SEQ ID NO 121
<211> LENGTH: 231
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-3*05

<400> SEQUENCE: 121
tgggagctca ggtgtgatcc aatttcaggt catactgccc tttactggta ccgacaaagc 60
ctggggcagg gcccagagct tctaatttac ttccaaggca cgggtgcggc agatgactca 120
gggctgccca acgatcggtt ctttgcagtc aggcctgagg gatccgtctc tactctgaag 180
atccagcgca cagagcgggg ggactcagcc gtgtatctct gtgccagcag c 231

<210> SEQ ID NO 122
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-4*01

<400> SEQUENCE: 122
ggtgctggag tctcccagtc cccaaggtac aaagtcgcaa agaggggacg ggatgtagct 60
ctcaggtgtg attcaatttc gggtcatgta accctttatt ggtaccgaca gaccctgggg 120
cagggctcag aggttctgac ttactcccag agtgatgctc aacgagacaa atcagggcgg 180
cccagtggtc ggttctctgc agagaggcct gagagatccg tctccactct gaagatccag 240
cgcacagagc agggggactc agctgtgtat ctctgtgcca gcagcttagc 290

<210> SEQ ID NO 123
<211> LENGTH: 288
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-5*01

<400> SEQUENCE: 123
ggtgctggag tctcccagtc cccaaggtac gaagtcacac agaggggaca ggatgtagct 60
cccaggtgtg atccaatttc gggtcaggta accctttatt ggtaccgaca gaccctgggg 120
cagggccaag agtttctgac ttccttccag gatgaaactc aacaagataa atcagggctg 180
ctcagtgatc aattctccac agagaggtct gaggatcttt ctccacctga agatccagcg 240
cacagagcaa gggcgactcg gctgtgtatc tctgtgccag aagcttag 288

<210> SEQ ID NO 124
<211> LENGTH: 289
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-5*02

<400> SEQUENCE: 124
ggtgctggag tctcccagtc cccaaggtac gaagtcacac agaggggaca ggatgtagct 60
cccaggtgtg atccaatttc gggtcaggta accctttatt ggtaccgaca gaccctgggg 120
cagggccaag agtttctgac ttccttccag gatgaaactc aacaagataa atcagggctg 180
ctcagtgatc aattctccac agagaggtct gaggatcttt ctccacctga agatccagcg 240
cacagagcaa gggcgactcg gctgtgtatc tctgtgtcag aagcttagc 289

<210> SEQ ID NO 125
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-6*01

<400> SEQUENCE: 125
ggtgctggag tctcccagtc tcccaggtac aaagtcacaa agaggggaca ggatgtagct 60
ctcaggtgtg atccaatttc gggtcatgta tccctttatt ggtaccgaca ggccctgggg 120
cagggcccag agtttctgac ttacttcaat tatgaagccc aacaagacaa atcagggctg 180
cccaatgatc ggttctctgc agagaggcct gagggatcca tctccactct gacgatccag 240
cgcacagagc agcgggactc ggccatgtat cgctgtgcca gcagcttagc 290

<210> SEQ ID NO 126
<211> LENGTH: 285
<212> TYPE: DNA
<213> ORGANISM: Artificial Sequence
<220> FEATURE:
<223> OTHER INFORMATION: Description of Artificial Sequence: Synthetic polynucleotide
<220> FEATURE:

<223> OTHER INFORMATION: TRBV7-6*02

<400> SEQUENCE: 126

```
ggtgctggag tctcccagtc tcccaggtac aaagtcacaa agaggggaca ggatgtagct      60

ctcaggtgtg atccaatctc gggtcatgta tcccttt att ggtaccgaca ggccctgggg    120

cagggcccag agtttctgac ttacttcaat tatgaagccc aacaagacaa atcagggctg    180

cccaatgatc ggttctctgc agagaggcct gagggatcca tctccactct gacgatccag    240

cgcacagagc agcgggactc ggccatgtat cgctgtgcca gcagc                     285
```

<210> SEQ ID NO 127
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV7-7*01

<400> SEQUENCE: 127

```
ggtgctggag tctcccagtc tcccaggtac aaagtcacaa agaggggaca ggatgtaact      60

ctcaggtgtg atccaatttc gagtcatgca acccttt att ggtatcaaca ggccctgggg    120

cagggcccag agtttctgac ttacttcaat tatgaagctc aaccagacaa atcagggctg    180

cccagtgatc ggttctctgc agagaggcct gagggatcca tctccactct gacgattcag    240

cgcacagagc agcgggactc agccatgtat cgctgtgcca gcagcttagc                290
```

<210> SEQ ID NO 128
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV7-7*02

<400> SEQUENCE: 128

```
ggtgctggag tctcccagtc tcccaggtac aaagtcacaa agaggggaca ggatgtaact      60

ctcaggtgtg atccaatttc gagtcatgta acccttt att ggtatcaaca ggccctgggg    120

cagggcccag agtttctgac ttacttcaat tatgaagctc aaccagacaa atcagggctg    180

cccagtgatc ggttctctgc agagaggcct gagggatcca tctccactct gacgattcag    240

cgcacagagc agcgggactc agccatgtat cgctgtgcca gcagc                     285
```

<210> SEQ ID NO 129
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV7-8*01

<400> SEQUENCE: 129

```
ggtgctggag tctcccagtc ccctaggtac aaagtcgcaa agagaggaca ggatgtagct      60

ctcaggtgtg atccaatttc gggtcatgta tcccttttt t ggtaccaaca ggccctgggg    120

caggggccag agtttctgac ttatttccag aatgaagctc aactagacaa atcggggctg    180
```

-continued

```
cccagtgatc gcttctttgc agaaaggcct gagggatccg tctccactct gaagatccag    240

cgcacacagc aggaggactc cgccgtgtat ctctgtgcca gcagcttagc               290


<210> SEQ ID NO 130
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV7-8*02

<400> SEQUENCE: 130

ggtgctggag tctcccagtc ccctaggtac aaagtcgcaa agagaggaca ggatgtagct     60

ctcaggtgtg atccaatttc gggtcatgta tccctttttt ggtaccaaca ggccctgggg    120

caggggccag agtttctgac ttatttccag aatgaagctc aactagacaa atcggggctg    180

cccagtgatc gcttctttgc agaaaggcct gagggatccg tctccactct gaagatccag    240

cgcacacaga aggaggactc cgccgtgtat ctctgtgcca gcagcttagc               290


<210> SEQ ID NO 131
<211> LENGTH: 288
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV7-8*03

<400> SEQUENCE: 131

ggtgctggag tctcccagtc ccctaggtac aaagtcgcaa agagaggaca ggatgtagct     60

ctcaggtgtg atccaatttc gggtcatgta tccctttttt ggtaccaaca ggccctcggg    120

caggggccag agtttctgac ttatttccag aatgaagctc aactagacaa atcggggctg    180

cccagtgatc gcttctttgc agaaaggcct gagggatccg tctccactct gaagatccag    240

cgcacacagc aggaggactc cgccgtgtat ctctgtgcca gcagccga                 288


<210> SEQ ID NO 132
<211> LENGTH: 288
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV7-9*05

<400> SEQUENCE: 132

gatactggag tctcccagaa ccccagacac aagatcacaa agaggggaca gaatgtaact     60

ttcaggtgtg atccaatttc tgaacacaac cgcctttatt ggtaccgaca gaccctgggg    120

cagggcccag agtttctgac ttacttccag aatgaagctc aactagaaaa atcaaggctg    180

ctcagtgatc ggttctctgc agagaggcct aagggatctc tctccacctt ggagatccag    240

cgcacagagc agggggactc ggccatgtat ctctgtgcca gcaccaaa                 288


<210> SEQ ID NO 133
<211> LENGTH: 288
<212> TYPE: DNA
<213> ORGANISM: Artificial Sequence
<220> FEATURE:
```

<223> OTHER INFORMATION: Description of Artificial Sequence: Synthetic
polynucleotide
<220> FEATURE:
<223> OTHER INFORMATION: TRBV7-9*06

<400> SEQUENCE: 133
gatactggag tctcccagaa ccccagacac aagatcacaa agaggggaca gaatgtaact 60
ttcaggtgtg atccaatttc tgaacacaac cgcctttatt ggtaccgaca gaccctgggg 120
cagggcccag agtttctgac ttacttccag aatgaagctc aactagaaaa atcaaggctg 180
ctcagtgatc ggttctctgc agagaggcct aagggatctc tttccacctt ggagatccag 240
cgcacagagc agggggactc ggccatgtat ctctgtgcca gcacgttg 288

<210> SEQ ID NO 134
<211> LENGTH: 285
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV7-9*03

<400> SEQUENCE: 134
gatactggag tctcccagga ccccagacac aagatcacaa agaggggaca gaatgtaact 60
ttcaggtgtg atccaatttc tgaacacaac cgcctttatt ggtaccgaca gaccctgggg 120
cagggcccag agtttctgac ttacttccag aatgaagctc aactagaaaa atcaaggctg 180
ctcagtgatc ggttctctgc agagaggcct aagggatctt tctccacctt ggagatccag 240
cgcacagagc agggggactc ggccatgtat ctctgtgcca gcagc 285

<210> SEQ ID NO 135
<211> LENGTH: 290
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV7-9*01

<400> SEQUENCE: 135
gatactggag tctcccagaa ccccagacac aagatcacaa agaggggaca gaatgtaact 60
ttcaggtgtg atccaatttc tgaacacaac cgcctttatt ggtaccgaca gaccctgggg 120
cagggcccag agtttctgac ttacttccag aatgaagctc aactagaaaa atcaaggctg 180
ctcagtgatc ggttctctgc agagaggcct aagggatctt tctccacctt ggagatccag 240
cgcacagagc agggggactc ggccatgtat ctctgtgcca gcagcttagc 290

<210> SEQ ID NO 136
<211> LENGTH: 288
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV7-9*02

<400> SEQUENCE: 136
gatactggag tctcccagaa ccccagacac aacatcacaa agaggggaca gaatgtaact 60
ttcaggtgtg atccaatttc tgaacacaac cgcctttatt ggtaccgaca gaccctgggg 120

```
cagggcccag agtttctgac ttacttccag aatgaagctc aactagaaaa atcaaggctg    180

ctcagtgatc ggttctctgc agagaggcct aagggatctt tctccacctt ggagatccag    240

cgcacagagc agggggactc ggccatgtat ctctgtgcca gcagctta                288
```

<210> SEQ ID NO 137
<211> LENGTH: 207
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-9*07

<400> SEQUENCE: 137

```
cacaaccgcc tttattggta ccgacagacc ctggggcagg gcccagagtt tctgacttac     60

ttccagaatg aagctcaact agaaaaatca aggctgctca gtgatcggtt ctctgcagag    120

aggcctaagg gatctttctc caccttggag atccagcgca cagaggaggg ggactcggcc    180

atgtatctct gtgccagcag cagcagt                                        207
```

<210> SEQ ID NO 138
<211> LENGTH: 288
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV7-9*04

<400> SEQUENCE: 138

```
atatctggag tctcccacaa ccccagacac aagatcacaa agaggggaca gaatgtaact     60

ttcaggtgtg atccaatttc tgaacacaac cgcctttatt ggtaccgaca gaaccctggg    120

cagggcccag agtttctgac ttacttccag aatgaagctc aactggaaaa atcagggctg    180

ctcagtgatc ggatctctgc agagaggcct aagggatctt tctccacctt ggagatccag    240

cgcacagagc agggggactc ggccatgtat ctctgtgcca gcagctct                288
```

<210> SEQ ID NO 139
<211> LENGTH: 279
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV8-1*01

<400> SEQUENCE: 139

```
gaggcaggga tcagccagat accaagatat cacagacaca cagggaaaaa gatcatcctg     60

aaatatgctc agattaggaa ccattattca gtgttctgtt atcaataaga ccaagaatag    120

gggctgaggc tgatccatta ttcaggtagt attggcagca tgaccaaagg cggtgccaag    180

gaagggtaca atgtctctgg aaacaagctc aagcattttc cctcaaccct ggagtctact    240

agcaccagcc agacctctgt acctctgtgg cagtgcatc                           279
```

<210> SEQ ID NO 140
<211> LENGTH: 271
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV8-2*01

<400> SEQUENCE: 140
gatgctggga tcacccagat gccaagatat cacattgtac agaagaaaga gatgatcctg 60
gaatgtgctc aggttaggaa cagtgttctg atatcgacag gacccaagac gggggctgaa 120
gcttatccac tattcaggca gtggtcacag caggaccaaa gttgatgtca cagaggggta 180
ctgtgtttct tgaaacaagc ttgagcattt ccccaatcct ggcatccacc agcaccagcc 240
agacctatct gtaccactgt ggcagcacat c 271

<210> SEQ ID NO 141
<211> LENGTH: 286
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV9*01

<400> SEQUENCE: 141
gattctggag tcacacaaac cccaaagcac ctgatcacag caactggaca gcgagtgacg 60
ctgagatgct cccctaggtc tggagacctc tctgtgtact ggtaccaaca gagcctggac 120
cagggcctcc agttcctcat tcagtattat aatggagaag agagagcaaa aggaaacatt 180
cttgaacgat tctccgcaca acagttccct gacttgcact ctgaactaaa cctgagctct 240
ctggagctgg gggactcagc tttgtatttc tgtgccagca gcgtag 286

<210> SEQ ID NO 142
<211> LENGTH: 282
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV9*03

<400> SEQUENCE: 142
gattctggag tcacacaaac cccaaagcac ctgatcacag caactggaca gcgagtgacg 60
ctgagatgct cccctaggtc tggagacctc tctgtgtact ggtaccaaca gagcctggac 120
cagggcctcc agttcctcat tcaatattat aatggagaag agagagcaaa aggaaacatt 180
cttgaacgat tctccgcaca acagttccct gacttgcact ctgaactaaa cctgagctct 240
ctggagctgg gggactcagc tttgtatttc tgtgccagca gc 282

<210> SEQ ID NO 143
<211> LENGTH: 286
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV9*02

<400> SEQUENCE: 143
gattctggag tcacacaaac cccaaagcac ctgatcacag caactggaca gcgagtgacg 60

```
ctgagatgct cccctaggtc tggagacctc tctgtgtact ggtaccaaca gagcctggac    120

cagggcctcc agttcctcat tcactattat aatggagaag agagagcaaa aggaaacatt    180

cttgaacgat tctccgcaca acagttccct gacttgcact ctgaactaaa cctgagctct    240

ctggagctgg gggactcagc tttgtatttc tgtgccagca gcgtag                   286


<210> SEQ ID NO 144
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV10-1*01

<400> SEQUENCE: 144

gatgctgaaa tcacccagag cccaagacac aagatcacag agacaggaag gcaggtgacc     60

ttggcgtgtc accagacttg gaaccacaac aatatgttct ggtatcgaca agacctggga    120

catgggctga ggctgatcca ttactcatat ggtgttcaag acactaacaa aggagaagtc    180

tcagatggct acagtgtctc tagatcaaac acagaggacc tccccctcac tctggagtct    240

gctgcctcct cccagacatc tgtatatttc tgcgccagca gtgagtc                  287


<210> SEQ ID NO 145
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV10-1*02

<400> SEQUENCE: 145

gatgctgaaa tcacccagag cccaagacac aagatcacag agacaggaag gcaggtgacc     60

ttggcgtgtc accagacttg gaaccacaac aatatgttct ggtatcgaca agacctggga    120

catgggctga ggctgatcca ttactcatat ggtgttcacg acactaacaa aggagaagtc    180

tcagatggct acagtgtctc tagatcaaac acagaggacc tccccctcac tctggagtct    240

gctgcctcct cccagacatc tgtatatttc tgcgccagca gt                       282


<210> SEQ ID NO 146
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV10-2*01

<400> SEQUENCE: 146

gatgctggaa tcacccagag cccaagatac aagatcacag agacaggaag gcaggtgacc     60

ttgatgtgtc accagacttg gagccacagc tatatgttct ggtatcgaca agacctggga    120

catgggctga ggctgatcta ttactcagca gctgctgata ttacagataa aggagaagtc    180

cccgatggct atgttgtctc cagatccaag acagagaatt tccccctcac tctggagtca    240

gctacccgct cccagacatc tgtgtatttc tgcgccagca gtgagtc                  287


<210> SEQ ID NO 147
```

<211> LENGTH: 217
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV10-2*02

<400> SEQUENCE: 147
aaggcaggtg accttgatgt gtcaccagac ttggagccac agctatatgt tctggtatcg 60
acaagacctg ggacatgggc tgaggctgat ctattactca gcagctgctg atattacaga 120
taaaggagaa gtccccgatg gctacgttgt ctccagatcc aagacagaga atttccccct 180
cactctggag tcagctaccc gctcccagac atctgtg 217

<210> SEQ ID NO 148
<211> LENGTH: 273
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV10-3*03

<400> SEQUENCE: 148
gatgctggaa tcacccagag cccaagacac aaggtcacag agacaggaac accagtgact 60
ctgagatgtc accagactga gaaccaccgc tacatgtact ggtatcgaca agacccgggg 120
catgggctga ggctaatcca ttactcatat ggtgttaaag atactgacaa aggagaagtc 180
tcagatggct atagtgtctc tagatcaaag acagaggatt tcctcctcac tctggagtcc 240
gctaccagct cccagacatc tgtgtacttc tgt 273

<210> SEQ ID NO 149
<211> LENGTH: 273
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV10-3*04

<400> SEQUENCE: 149
gatgctggaa tcacccagag cccaagacac aaggtcacag agacaggaac accagtgact 60
ctgagatgtc accagactga gaaccaccgc tacatgtact ggtatcgaca agacccgggg 120
catgggctga ggctgatcca ttactcatat ggtgttaaag atactgacaa aggagaagtc 180
tcagatggct atagtgtctc tagatcaaag acagaggatt tcctcctcac tctggagtcc 240
gctaccagct cccagacatc tgtgtacttc tgt 273

<210> SEQ ID NO 150
<211> LENGTH: 287
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV10-3*01

<400> SEQUENCE: 150
gatgctggaa tcacccagag cccaagacac aaggtcacag agacaggaac accagtgact 60
ctgagatgtc accagactga gaaccaccgc tatatgtact ggtatcgaca agacccgggg 120
catgggctga ggctgatcca ttactcatat ggtgttaaag atactgacaa aggagaagtc 180
tcagatggct atagtgtctc tagatcaaag acagaggatt tcctcctcac tctggagtcc 240
gctaccagct cccagacatc tgtgtacttc tgtgccatca gtgagtc 287

<210> SEQ ID NO 151
<211> LENGTH: 287
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV10-3*02

<400> SEQUENCE: 151
gatgctggaa tcacccagag cccaagacac aaggtcacag agacaggaac accagtgact 60
ctgagatgtc atcagactga gaaccaccgc tatatgtact ggtatcgaca agacccgggg 120
catgggctga ggctgatcca ttactcatat ggtgttaaag atactgacaa aggagaagtc 180
tcagatggct atagtgtctc tagatcaaag acagaggatt tcctcctcac tctggagtcc 240
gctaccagct cccagacatc tgtgtacttc tgtgccatca gtgagtc 287

<210> SEQ ID NO 152
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV11-1*01

<400> SEQUENCE: 152
gaagctgaag ttgcccagtc ccccagatat aagattacag agaaaagcca ggctgtggct 60
ttttggtgtg atcctatttc tggccatgct accctttact ggtaccggca gatcctggga 120
cagggcccgg agcttctggt tcaatttcag gatgagagtg tagtagatga ttcacagttg 180
cctaaggatc gattttctgc agagaggctc aaaggagtag actccactct caagatccag 240
cctgcagagc ttggggactc ggccatgtat ctctgtgcca gcagcttagc 290

<210> SEQ ID NO 153
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV11-3*01

<400> SEQUENCE: 153
gaagctggag tggttcagtc tcccagatat aagattatag agaaaaaaca gcctgtggct 60
ttttggtgca atcctatttc tggccacaat accctttact ggtacctgca gaacttggga 120
cagggcccgg agcttctgat tcgatatgag aatgaggaag cagtagacga ttcacagttg 180
cctaaggatc gattttctgc agagaggctc aaaggagtag actccactct caagatccag 240
cctgcagagc ttggggactc ggccgtgtat ctctgtgcca gcagcttaga 290

<210> SEQ ID NO 154
<211> LENGTH: 285
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV11-3*02

<400> SEQUENCE: 154
gaagctggag tggttcagtc tcccagatat aagattatag agaaaaagca gcctgtggct 60
ttttggtgca atcctatttc tggccacaat accctttact ggtaccggca gaacttggga 120
cagggcccgg agcttctgat tcgatatgag aatgaggaag cagtagacga ttcacagttg 180
cctaaggatc gattttctgc agagaggctc aaaggagtag actccactct caagatccag 240
cctgcagagc ttggggactc ggccgtgtat ctctgtgcca gcagc 285

<210> SEQ ID NO 155
<211> LENGTH: 269
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV11-3*03

<400> SEQUENCE: 155
ggtctcccag atataagatt atagagaaga aacagcctgt ggctttttgg tgcaatccaa 60
tttctggcca caatacccctt tactggtacc tgcagaactt gggacagggc ccggagcttc 120
tgattcgata tgagaatgag gaagcagtag acgattcaca gttgcctaag gatcgatttt 180
ctgcagagag gctcaaagga gtagactcca ctctcaagat ccagccagca gagcttgggg 240
actcggccat gtatctctgt gccagcagc 269

<210> SEQ ID NO 156
<211> LENGTH: 290
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV11-2*01

<400> SEQUENCE: 156
gaagctggag ttgcccagtc tcccagatat aagattatag agaaaaggca gagtgtggct 60
ttttggtgca atcctatatc tggccatgct accctttact ggtaccagca gatcctggga 120
cagggcccaa agcttctgat tcagtttcag aataacggtg tagtggatga ttcacagttg 180
cctaaggatc gattttctgc agagaggctc aaaggagtag actccactct caagatccag 240
cctgcaaagc ttgaggactc ggccgtgtat ctctgtgcca gcagcttaga 290

<210> SEQ ID NO 157
<211> LENGTH: 285
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV11-2*03

<400> SEQUENCE: 157
gaagctggag ttgcccagtc tcccagatat aagattatag agaaaaggca gagtgtggct 60
ttttggtgca atcctatatc tggccatgct accctttact ggtaccagca gatcctggga 120
cagggcccaa agcttctgat tcagtttcag aataacggtg tagtggatga ttcacagttg 180
cctaaggatc gattttctgc agagaggctc aaaggagtag actccactct caagatccaa 240
cctgcaaagc ttgaggactc ggccgtgtat ctctgtgcca gcagc 285

<210> SEQ ID NO 158
<211> LENGTH: 285
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV11-2*02

<400> SEQUENCE: 158
gaagctggag ttgcccagtc tcccagatat aagattatag agaaaaggca gagtgtggct 60
ttttggtgca atcctatatc tggccatgct accctttact ggtaccagca gatcctggga 120
cagggcccaa agcttctgat tcagtttcag aataacggtg tagtggatga ttcacagttg 180
cctaaggatc gattttctgc agagaggctc aaaggagtag actccactct caagatccag 240
cctgcaaagc ttgagaactc ggccgtgtat ctctgtgcca gcagt 285

<210> SEQ ID NO 159
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV12-1*01

<400> SEQUENCE: 159
gatgctggtg ttatccagtc acccaggcac aaagtgacag agatgggaca atcagtaact 60
ctgagatgcg aaccaatttc aggccacaat gatcttctct ggtacagaca gacctttgtg 120
cagggactgg aattgctgaa ttacttctgc agctggaccc tcgtagatga ctcaggagtg 180
tccaaggatt gattctcagc acagatgcct gatgtatcat tctccactct gaggatccag 240
cccatggaac ccagggactt gggcctatat ttctgtgcca gcagctttgc 290

<210> SEQ ID NO 160
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV12-2*01

<400> SEQUENCE: 160
gatgctggca ttatccagtc acccaagcat gaggtgacag aaatgggaca aacagtgact 60
ctgagatgtg agccaatttt tggccacaat ttcctttttct ggtacagaga taccttcgtg 120
cagggactgg aattgctgag ttacttccgg agctgatcta ttatagataa tgcaggtatg 180
cccacagagc gattctcagc tgagaggcct gatggatcat tctctactct gaagatccag 240
cctgcagagc agggggactc ggccgtgtat gtctgtgcaa gtcgcttagc 290

<210> SEQ ID NO 161
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV12-4*01

<400> SEQUENCE: 161
gatgctggag ttatccagtc accccggcac gaggtgacag agatgggaca agaagtgact 60
ctgagatgta aaccaatttc aggacacgac tacctttttct ggtacagaca gaccatgatg 120
cggggactgg agttgctcat ttactttaac aacaacgttc cgatagatga ttcagggatg 180
cccgaggatc gattctcagc taagatgcct aatgcatcat tctccactct gaagatccag 240
ccctcagaac ccagggactc agctgtgtac ttctgtgcca gcagtttagc 290

<210> SEQ ID NO 162
<211> LENGTH: 288
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV12-4*02

<400> SEQUENCE: 162
gatgctggag ttatccagtc accccggcac gaggtgacag agatgggaca agaagtgact 60
ctgagatgta aaccaatttc aggacatgac tacctttttct ggtacagaca gaccatgatg 120
cggggactgg agttgctcat ttactttaac aacaacgttc cgatagatga ttcagggatg 180
cccgaggatc gattctcagc taagatgcct aatgcatcat tctccactct gaggatccag 240
ccctcagaac ccagggactc agctgtgtac ttctgtgcca gcagttta 288

<210> SEQ ID NO 163
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV12-3*01

<400> SEQUENCE: 163
gatgctggag ttatccagtc accccgccat gaggtgacag agatgggaca agaagtgact 60
ctgagatgta aaccaatttc aggccacaac tccctttttct ggtacagaca gaccatgatg 120
cggggactgg agttgctcat ttactttaac aacaacgttc cgatagatga ttcagggatg 180
cccgaggatc gattctcagc taagatgcct aatgcatcat tctccactct gaagatccag 240
ccctcagaac ccagggactc agctgtgtac ttctgtgcca gcagtttagc 290

<210> SEQ ID NO 164
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide

<220> FEATURE:
<223> OTHER INFORMATION: TRBV12-5*01

<400> SEQUENCE: 164
gatgctagag tcacccagac accaaggcac aaggtgacag agatgggaca agaagtaaca 60
atgagatgtc agccaatttt aggccacaat actgttttct ggtacagaca gaccatgatg 120
caaggactgg agttgctggc ttacttccgc aaccgggctc ctctagatga ttcggggatg 180
ccgaaggatc gattctcagc agagatgcct gatgcaactt tagccactct gaagatccag 240
ccctcagaac ccagggactc agctgtgtat ttttgtgcta gtggtttggt 290

<210> SEQ ID NO 165
<211> LENGTH: 287
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV12*01

<400> SEQUENCE: 165
gctgctggag tcatccagtc cccaagacat ctgatcaaag aaaagaggga aacagccact 60
ctgaaatgct atcctatccc tagacacgac actgtctact ggtaccagca gggtccaggt 120
caggaccccc agttcctcat ttcgttttat gaaaagatgc agagcgataa aggaagcatc 180
cctgatcgat tctcagctca acagttcagt gactatcatt ctgaactgaa catgagctcc 240
ttggagctgg gggactcagc cctgtacttc tgtgccagca gcttagg 287

<210> SEQ ID NO 166
<211> LENGTH: 282
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV13*02

<400> SEQUENCE: 166
gctgctggag tcatccagtc cccaagacat ctgatcagag aaaagaggga aacagccact 60
ctgaaatgct atcctatccc tagacacgac actgtctact ggtaccagca gggcccaggt 120
caggaccccc agttcttcat ttcgttttat gaaaagatgc agagcgataa aggaagcatc 180
cctgatcgat tctcagctca acagttcagt gactatcatt ctgaactgaa catgagctcc 240
ttggagctgg gggactcagc cctgtacttc tgtgccagca gc 282

<210> SEQ ID NO 167
<211> LENGTH: 290
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV14*01

<400> SEQUENCE: 167
gaagctggag ttactcagtt ccccagccac agcgtaatag agaagggcca gactgtgact 60
ctgagatgtg acccaatttc tggacatgat aatctttatt ggtatcgacg tgttatggga 120
aaagaaataa aatttctgtt acattttgtg aaagagtcta aacaggatga gtccggtatg 180

-continued

```
cccaacaatc gattcttagc tgaaaggact ggagggacgt attctactct gaaggtgcag    240

cctgcagaac tggaggattc tggagtttat ttctgtgcca gcagccaaga               290


<210> SEQ ID NO 168
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV14*02

<400> SEQUENCE: 168

gaagctggag ttactcagtt ccccagccac agcgtaatag agaagggcca gactgtgact     60

ctgagatgtg acccaatttc tggacatgat aatctttatt ggtatcgacg tgttatggga    120

aaagaaataa aatttctgtt acattttgtg aaagagtcta aacaggatga atccggtatg    180

cccaacaatc gattcttagc tgaaaggact ggagggacgt attctactct gaaggtgcag    240

cctgcagaac tggaggattc tggagtttat ttctgtgcca gcagc                    285


<210> SEQ ID NO 169
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV15*01

<400> SEQUENCE: 169

gatgccatgg tcatccagaa cccaagatac caggttaccc agtttggaaa gccagtgacc     60

ctgagttgtt ctcagacttt gaaccataac gtcatgtact ggtaccagca gaagtcaagt    120

caggccccaa agctgctgtt ccactactat gacaaagatt ttaacaatga agcagacacc    180

cctgataact tccaatccag gaggccgaac acttctttct gctttcttga catccgctca    240

ccaggcctgg gggacacagc catgtacctg tgtgccacca gcagaga                  287


<210> SEQ ID NO 170
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV15*03

<400> SEQUENCE: 170

gatgccatgg tcatccagaa cccaagatac cgggttaccc agtttggaaa gccagtgacc     60

ctgagttgtt ctcagacttt gaaccataac gtcatgtact ggtaccagca gaagtcaagt    120

caggccccaa agctgctgtt ccactactat aacaaagatt ttaacaatga agcagacacc    180

cctgataact tccaatccag gaggccgaac acttctttct gctttctaga catccgctca    240

ccaggcctgg gggacgcagc catgtaccag tgtgccacca gc                       282


<210> SEQ ID NO 171
<211> LENGTH: 282
<212> TYPE: DNA
<213> ORGANISM: Artificial Sequence
```

<220> FEATURE:
<223> OTHER INFORMATION: Description of Artificial Sequence: Synthetic
      polynucleotide
<220> FEATURE:
<223> OTHER INFORMATION: TRBV15*02

<400> SEQUENCE: 171
gatgccatgg tcatccagaa cccaagatac caggttaccc agtttggaaa gccagtgacc     60
ctgagttgtt ctcagacttt gaaccataac gtcatgtact ggtaccagca gaagtcaagt    120
caggccccaa agctgctgtt ccactactat gacaaagatt ttaacaatga agcagacacc    180
cctgataact tccaatccag gaggccgaac acttctttct gctttcttga catccgctca    240
ccaggcctgg gggacgcagc catgtacctg tgtgccacca gc                       282

<210> SEQ ID NO 172
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV16*01

<400> SEQUENCE: 172
ggtgaagaag tcgcccagac tccaaaacat cttgtcagag ggaaggaca gaaagcaaaa     60 ttatattgtg ccccaataaa aggacacagt tatgtttttt ggtaccaaca ggtcctgaaa    120
aacgagttca agttcttgat ttccttccag aatgaaaatg tctttgatga aacaggtatg    180
cccaaggaaa gattttcagc taagtgcctc ccaaattcac cctgtagcct tgagatccag    240
gctacgaagc ttgaggattc agcagtgtat ttttgtgcca gcagccaatc               290

<210> SEQ ID NO 173
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV16*02

<400> SEQUENCE: 173
ggtgaagaag tcgcccagac tccaaaacat cttgtcagag gggaaggaca gaaagcaaaa     60
ttatattgtg ccccaataaa aggacacagt taggtttttt ggtaccaaca ggtcctgaaa    120
aacgagttca agttcttgat ttccttccag aatgaaaatg tctttgatga aacaggtatg    180
cccaaggaaa gattttcagc taagtgcctc ccaaattcac cctgtagcct tgagatccag    240
gctacgaagc ttgaggattc agcagtgtat ttttgtgcca gcagccaatc               290

<210> SEQ ID NO 174
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV16*03

<400> SEQUENCE: 174
ggtgaagaag tcgcccagac tccaaaacat cttgtcagag gggaaggaca gaaagcaaaa     60

-continued

```
ttatattgtg ccccaataaa aggacacagt tatgtttttt ggtaccaaca ggtcctgaaa    120

aacgagttca agttcttggt ttccttccag aatgaaaatg tctttgatga aacaggtatg    180

cccaaggaaa gattttcagc taagtgcctc ccaaattcac cctgtagcct tgagatccag    240

gctacgaagc ttgaggattc agcagtgtat ttttgtgcca gcagc                    285
```

<210> SEQ ID NO 175
<211> LENGTH: 287
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV17*01

<400> SEQUENCE: 175

```
gagcctggag tcagccagac ccccagacac aaggtcacca acatgggaca ggaggtgatt     60

ctgaggtgcg atccatcttc tggtcacatg tttgttcact ggtaccgaca gaatctgagg    120

caagaaatga agttgctgat ttccttccag taccaaaaca ttgcagttga ttcagggatg    180

cccaaggaac gattcacagc tgaaagacct aacggaacgt cttccacgct gaagatccat    240

cccgcagagc cgagggactc agccgtgtat ctctacagta gcggtgg                  287
```

<210> SEQ ID NO 176
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV18*01

<400> SEQUENCE: 176

```
aatgccggcg tcatgcagaa cccaagacac ctggtcagga ggaggggaca ggaggcaaga     60

ctgagatgca gcccaatgaa aggacacagt catgtttact ggtatcggca gctcccagag    120

gaaggtctga aattcatggt ttatctccag aaagaaaata tcatagatga gtcaggaatg    180

ccaaaggaac gattttctgc tgaatttccc aaagagggcc ccagcatcct gaggatccag    240

caggtagtgc gaggagattc ggcagcttat ttctgtgcca gctcaccacc               290
```

<210> SEQ ID NO 177
<211> LENGTH: 287
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV19*01

<400> SEQUENCE: 177

```
gatggtggaa tcactcagtc cccaaagtac ctgttcagaa aggaaggaca gaatgtgacc     60

ctgagttgtg aacagaattt gaaccacgat gccatgtact ggtaccgaca ggacccaggg    120

caagggctga gattgatcta ctactcacag atagtaaatg actttcagaa aggagatata    180

gctgaagggt acagcgtctc tcgggagaag aaggaatcct ttcctctcac tgtgacatcg    240

gcccaaaaga acccgacagc tttctatctc tgtgccagta gtataga                  287
```

<210> SEQ ID NO 178

<211> LENGTH: 287
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV19*02

<400> SEQUENCE: 178
gatggtggaa tcactcagtc cccaaagtac ctgttcagaa aggaaggaca gaatgtgacc 60
ctgagttgtg aacagaattt gaaccacgat gccatgtact ggtaccgaca ggtcccaggg 120
caagggctga gattgatcta ctactcacac atagtaaatg actttcagaa aggagatata 180
gctgaagggt acagcgtctc tcgggagaag aaggaatcct ttcctctcac tgtgacatcg 240
gcccaaaaga acccgacagc tttctatctc tgtgccagta gtataga 287

<210> SEQ ID NO 179
<211> LENGTH: 282
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV19*03

<400> SEQUENCE: 179
gatggtggaa tcactcagtc cccaaagtac ctgttcagaa aggaaggaca gaatgtgacc 60
ctgagttgtg aacagaattt gaaccacgat gccatgtact ggtaccgaca ggacccaggg 120
caagggctga gattgatcta ctactcacac atagtaaatg actttcagaa aggagatata 180
gctgaagggt acagcgtctc tcgggagaag aaggaatcct ttcctctcac tgtgacatcg 240
gcccaaaaga acccgacagc tttctatctc tgtgccagta gc 282

<210> SEQ ID NO 180
<211> LENGTH: 291
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV20-1*05

<400> SEQUENCE: 180
ggtgctgtcg tctctcaaca tccgagcagg gttatctgta agagtggaac ctctgtgaag 60
atcgagtgcc gttccctgga ctttcaggcc acaactatgt tttggtatcg tcagttcccg 120
aaaaagagtc tcatgctgat ggcaacttcc aatgagggct ccaaggccac atacgagcaa 180
ggcgtcgaga aggacaagtt tctcatcaac catgcaagcc tgaccttgtc cactctgaca 240
gtgaccagtg cccatcctga agacagcagc ttctacatct gcagtgctag a 291

<210> SEQ ID NO 181
<211> LENGTH: 291
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV20-1*07

<400> SEQUENCE: 181

```
ggtgctgtcg tctctcaaca tccgagcagg gttatctgta agagtggaac ctctgtgaag     60

atcgagtgcc gttccctgga ctttcaggcc acaactatgt tttggtatcg tcagttcccg    120

aaaaagagtc tcatgcagat cgcaacttcc aatgagggct ccaaggccac atacgagcaa    180

ggcgtcgaga aggacaagtt tctcatcaac catgcaagcc tgaccttgtc cactctgaca    240

gtgaccagtg cccatcctga agacagcagc ttctacatct gcagtgctag a             291
```

<210> SEQ ID NO 182
<211> LENGTH: 291
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV20-1*04

<400> SEQUENCE: 182

```
ggtgctgtcg tctctcaaca tccgagcagg gttatctgta agagtggaac ctctgtgaag     60

atcgagtgcc gttccttgga ctttcaggcc acaactatgt tttggtatcg tcagttcccg    120

aaaaagagtc tcatgctgat ggcaacttcc aatgagggct ccaaggccac atacgagcaa    180

ggcgtcgaga aggacaagtt tctcatcaac catgcaagcc tgaccttgtc cactctgaca    240

gtgaccagtg cccatcctga agacagcagc ttctacatct gcagtgctag t             291
```

<210> SEQ ID NO 183
<211> LENGTH: 288
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV20-1*06

<400> SEQUENCE: 183

```
ggtgctgtcg tctctcaaca tccgagtagg gttatctgta agagtggaac ctctgtgaag     60

atcgagtgcc gttccctgga ctttcaggcc acaactatgt tttggtatcg tcagttcccg    120

aaaaagagtc tcatgctgat ggcaacttcc aatgagggct ccaaggccac atacgagcaa    180

ggcgtcgaga aggacaagtt tctcatcaac catgcaagcc tgaccttgtc cactctgaca    240

gtgaccagtg cccatcctga agacagcagc ttctacatct gcagtgct                 288
```

<210> SEQ ID NO 184
<211> LENGTH: 288
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV20-1*02

<400> SEQUENCE: 184

```
ggtgctgtcg tctctcaaca tccgagcagg gttatctgta agagtggaac ctctgtgaag     60

atcgagtgcc gttccctgga ctttcaggcc acaactatgt tttggtatcg tcagttcccg    120

aaacagagtc tcatgctgat ggcaacttcc aatgagggct ccaaggccac atacgagcaa    180

ggcgtcgaga aggacaagtt tctcatcaac catgcaagcc tgaccttgtc cactctgaca    240

gtgaccagtg cccatcctga agacagcagc ttctacatct gcagtgct                 288
```

<210> SEQ ID NO 185
<211> LENGTH: 293
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV20-1*01

<400> SEQUENCE: 185
ggtgctgtcg tctctcaaca tccgagctgg gttatctgta agagtggaac ctctgtgaag 60
atcgagtgcc gttccctgga ctttcaggcc acaactatgt tttggtatcg tcagttcccg 120
aaacagagtc tcatgctgat ggcaacttcc aatgagggct ccaaggccac atacgagcaa 180
ggcgtcgaga aggacaagtt tctcatcaac catgcaagcc tgaccttgtc cactctgaca 240
gtgaccagtg cccatcctga agacagcagc ttctacatct gcagtgctag aga 293

<210> SEQ ID NO 186
<211> LENGTH: 288
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV20-1*03

<400> SEQUENCE: 186
ggtgctgtcg tctctcaaca tccgagctgg gttatctgta agagtggaac ctctgtgaag 60
atcgagtgcc gttccctgga ctttcaggcc acaactatgt tttggtatcg tcagttcccg 120
aaacagagtc tcatgctgat ggcaacttcc aatgagggct gcaaggccac atacgagcaa 180
ggcgtcgaga aggacaagtt tctcatcaac catgcaagcc tgaccttgtc cactctgaca 240
gtgaccagtg cccatcctga agacagcagc ttctacatct gcagtgct 288

<210> SEQ ID NO 187
<211> LENGTH: 290
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV21-1*01

<400> SEQUENCE: 187
gacaccaagg tcacccagag acctagactt ctggtcaaag caagtgaaca gaaagcaaag 60
atggattgtg ttcctataaa agcacatagt tatgtttact ggtatcgtaa gaagctggaa 120
gaagagctca agtttttggt ttactttcag aatgaagaac ttattcagaa agcagaaata 180
atcaatgagc gatttttagc ccaatgctcc aaaaactcat cctgtacctt ggagatccag 240
tccacggagt caggggacac agcactgtat ttctgtgcca gcagcaaagc 290

<210> SEQ ID NO 188
<211> LENGTH: 288
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:

-continued

<223> OTHER INFORMATION: TRBV22-1*01

<400> SEQUENCE: 188
gatgctgaca tctatcagat gccattccag ctcactgggg ctggatggga tgtgactctg 60
gagtggaaac ggaatttgag acacaatgac atgtactgct actggtactg gcaggaccca 120
aagcaaaatc tgagactgat ctattactca agggttgaaa aggatattca gagaggagat 180
ctaactgaag gctacgtgtc tgccaagagg agaaggggct atttcttctc agggtgaagt 240
tggcccacac cagccaaaca gctttgtact tctgtcctgg gagcgcac 288

<210> SEQ ID NO 189
<211> LENGTH: 290
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV23-1*01

<400> SEQUENCE: 189
catgccaaag tcacacagac tccaggacat ttggtcaaag gaaaaggaca gaaaacaaag 60
atggattgta cccccgaaaa aggacatact tttgtttatt ggtatcaaca gaatcagaat 120
aaagagttta tgcttttgat ttcctttcag aatgaacaag ttcttcaaga aacggagatg 180
cacaagaagc gattctcatc tcaatgcccc aagaacgcac cctgcagcct ggcaatcctg 240
tcctcagaac cgggagacac ggcactgtat ctctgcgcca gcagtcaatc 290

<210> SEQ ID NO 190
<211> LENGTH: 288
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV24-1*01

<400> SEQUENCE: 190
gatgctgatg ttacccagac cccaaggaat aggatcacaa agacaggaaa gaggattatg 60
ctggaatgtt ctcagactaa gggtcatgat agaatgtact ggtatcgaca agacccagga 120
ctgggcctac ggttgatcta ttactccttt gatgtcaaag atataaacaa aggagagatc 180
tctgatggat acagtgtctc tcgacaggca caggctaaat tctccctgtc cctagagtct 240
gccatcccca accagacagc tctttacttc tgtgccacca gtgatttg 288

<210> SEQ ID NO 191
<211> LENGTH: 287
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: TRBV25-1*01

<400> SEQUENCE: 191
gaagctgaca tctaccagac cccaagatac cttgttatag ggacaggaaa gaagatcact 60
ctggaatgtt ctcaaaccat gggccatgac aaaatgtact ggtatcaaca agatccagga 120
atggaactac acctcatcca ctattcctat ggagttaatt ccacagagaa gggagatctt 180

```
tcctctgagt caacagtctc cagaataagg acggagcatt ttcccctgac cctggagtct    240

gccaggccct cacatacctc tcagtacctc tgtgccagca gtgaata                  287


<210> SEQ ID NO 192
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV26*01

<400> SEQUENCE: 192

gatgctgtag ttacacaatt cccaagacac agaatcattg ggacaggaaa ggaattcatt     60

ctacagtgtt cccagaatat gaatcatgtt acaatgtact ggtatcgaca ggacccagga    120

cttggactga agctggtcta ttattcacct ggcactggga gcactgaaaa aggagatatc    180

tctgaggggt atcatgtttc ttgaaatact atagcatctt ttcccctgac cctgaagtct    240

gccagcacca accagacatc tgtgtatctc tatgccagca gttcatc                  287


<210> SEQ ID NO 193
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV27*01

<400> SEQUENCE: 193

gaagcccaag tgacccagaa cccaagatac ctcatcacag tgactggaaa gaagttaaca     60

gtgacttgtt ctcagaatat gaaccatgag tatatgtcct ggtatcgaca agacccaggg    120

ctgggcttaa ggcagatcta ctattcaatg aatgttgagg tgactgataa gggagatgtt    180

cctgaagggt acaaagtctc tcgaaaagag aagaggaatt tcccccctgat cctggagtcg    240

cccagcccca accagacctc tctgtacttc tgtgccagca gtttatc                  287


<210> SEQ ID NO 194
<211> LENGTH: 287
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV28*01

<400> SEQUENCE: 194

gatgtgaaag taacccagag ctcgagatat ctagtcaaaa ggacgggaga gaaagttttt     60

ctggaatgtg tccaggatat ggaccatgaa aatatgttct ggtatcgaca agacccaggt    120

ctggggctac ggctgatcta tttctcatat gatgttaaaa tgaaagaaaa aggagatatt    180

cctgaggggt acagtgtctc tagagagaag aaggagcgct tctccctgat tctggagtcc    240

gccagcacca accagacatc tatgtacctc tgtgccagca gtttatg                  287


<210> SEQ ID NO 195
<211> LENGTH: 290
<212> TYPE: DNA
<213> ORGANISM: Artificial Sequence
<220> FEATURE:
```

<223> OTHER INFORMATION: Description of Artificial Sequence: Synthetic
      polynucleotide
<220> FEATURE:
<223> OTHER INFORMATION: TRBV29-1*01

<400> SEQUENCE: 195
agtgctgtca tctctcaaaa gccaagcagg gatatctgtc aacgtggaac ctccctgacg     60
atccagtgtc aagtcgatag ccaagtcacc atgatgttct ggtaccgtca gcaacctgga    120
cagagcctga cactgatcgc aactgcaaat cagggctctg aggccacata tgagagtgga    180
tttgtcattg acaagtttcc catcagccgc ccaaacctaa cattctcaac tctgactgtg    240
agcaacatga gccctgaaga cagcagcata tatctctgca gcgttgaaga               290

<210> SEQ ID NO 196
<211> LENGTH: 288
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV29-1*02

<400> SEQUENCE: 196
agtgctgtca tctctcaaaa gccaagcagg gatatctgtc aacgtggaac ctccctgacg     60
atccagtgtc aagtcgatag ccaagtcacc atgatgttct ggtaccgtca gcaacctgga    120
cagagcctga cactgatcgc aactgcaaat cagggctctg aggccacata tgagagtgga    180
tttgtcattg acaagtttcc catcagccgc ccaaacctaa cattctcaag tctgactgtg    240
agcaacatga gccctgaaga cagcagcata tatctctgca gcgttgaa                 288

<210> SEQ ID NO 197
<211> LENGTH: 231
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV29-1*03

<400> SEQUENCE: 197
acgatccagt gtcaagtcga tagccaagtc accatgatat tctggtaccg tcagcaacct     60
ggacagagcc tgacactgat cgcaactgca aatcagggct ctgaggccac atatgagagt    120
ggatttgtca ttgacaagtt tcccatcagc cgcccaaacc taacattctc aactctgact    180
gtgagcaaca tgagccctga agacagcagc atatatctct gcagcgcggg c             231

<210> SEQ ID NO 198
<211> LENGTH: 284
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TRBV30*02

<400> SEQUENCE: 198
tctcagacta ttcatcaatg gccagcgacc ctggtgcagc ctgtgggcag cccgctctct     60
ctggagtgca ctgtggaggg aacatcaaac cccaacctat actggtaccg acaggctgca    120
ggcaggggcc tccagctgct cttctactcc gttggtattg gccagatcag ctctgaggtg    180
ccccagaatc tctcagcctc cagaccccag gaccggcagt tcatcctgag ttctaagaag 240
ctcctcctca gtgactctgg cttctatctc tgtgcctgga gtgt 284

<210> SEQ ID NO 199
<211> LENGTH: 282
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV30*05

<400> SEQUENCE: 199
tctcagacta ttcatcaatg gccagcgacc ctggtgcagc ctgtgggcag cccgctctcc 60
ctggagtgca ctgtggaggg aacatcaaac cccaacctat actggtaccg acaggctgca 120
ggacggggcc tccagctgct cttctactcc gttggtattg gccagatcag ctctgaggtg 180
ccccagaatc tctcagcctc cagaccccag gaccggcagt tcatcctgag ttctaagaag 240
ctccttctca gtgactctgg cttctatctc tgtgcctggg ga 282

<210> SEQ ID NO 200
<211> LENGTH: 284
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV30*01

<400> SEQUENCE: 200
tctcagacta ttcatcaatg gccagcgacc ctggtgcagc ctgtgggcag cccgctctct 60
ctggagtgca ctgtggaggg aacatcaaac cccaacctat actggtaccg acaggctgca 120
ggcaggggcc tccagctgct cttctactcc gttggtattg gccagatcag ctctgaggtg 180
ccccagaatc tctcagcctc cagaccccag gaccggcagt tcatcctgag ttctaagaag 240
ctccttctca gtgactctgg cttctatctc tgtgcctgga gtgt 284

<210> SEQ ID NO 201
<211> LENGTH: 276
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TRBV30*04

<400> SEQUENCE: 201
actattcatc aatggccagc gaccctggtg cagcctgtgg gcagcccgct ctctctggag 60
tgcactgtgg agggaacatc aaaccccaac ctatactggt accgacaggc tgcaggcagg 120
ggcctccagc tgctcttcta ctccattggt attgaccaga tcagctctga ggtgccccag 180
aatctctcag cctccagacc ccaggaccgg cagttcattc tgagttctaa gaagctcctc 240
ctcagtgact ctggcttcta tctctgtgcc tggagt 276

<210> SEQ ID NO 202
<211> LENGTH: 448
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ1S1

<400> SEQUENCE: 202

```
ttgaaaaagg aacctaggac cctgtggatg gactctgtca ttctccatgg tcctaaaaag     60
caaaagtcaa agtgttcttc tgtgtaatac ccataaagca caggaggaga tttcttagct    120
cactgtcctc catcctagcc agggccctct cccctctcta tgccttcaat gtgattttca    180
ccttgacccc tgtcactgtg tgaacactga agctttcttt ggacaaggca ccagactcac    240
agttgtaggt aagacatttt tcaggttctt ttgcagatcc gtcacaggga aaagtgggtc    300
cacagtgtcc cttttagagt ggctatattc ttatgtgcta actatggcta caccttcggt    360
tcggggacca ggttaaccgt tgtaggtaag gctgggggtc tctaggaggg gtgcgatgag    420
ggaggactct gtcctgggaa atgtcaaa                                       448
```

<210> SEQ ID NO 203
<211> LENGTH: 448
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ1S2

<400> SEQUENCE: 203

```
gccagggccc tctcccctct ctatgccttc aatgtgattt tcaccttgac ccctgtcact     60
gtgtgaacac tgaagctttc tttggacaag gcaccagact cacagttgta ggtaagacat    120
ttttcaggtt cttttgcaga tccgtcacag ggaaaagtgg gtccacagtg tcccttttag    180
agtggctata ttcttatgtg ctaactatgg ctacaccttc ggttcgggga ccaggttaac    240
cgttgtaggt aaggctgggg gtctctagga ggggtgcgat gagggaggac tctgtcctgg    300
gaaatgtcaa agagaacaga gatcccagct cccggagcca gactgaggga gacgtcatgt    360
catgtcccgg gattgagttc aggggaggct ccctgtgagg gcgaatccac ccaggcttcc    420
cagaggctct gagcagtcac agctgagc                                       448
```

<210> SEQ ID NO 204
<211> LENGTH: 450
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ1S3

<400> SEQUENCE: 204

```
gattttatag gaggccactc tgtgtctctt tttgtcacct gcctgagtct tgggcaagct     60
ctggaaggga acacagagta ctggaagcag agctgctgtc cctgtgaggg aagagttccc    120
atgaactccc aacctctgcc tgaatcccag ctgtgctcag cagagactgg ggggttttga    180
agtggccctg ggaggctgtg ctctggaaac accatatatt ttggagaggg aagttggctc    240
actgttgtag gtgagtaagt caaggctgga cagctgggaa cttgcaaaaa ggggctggaa    300
tccagacgga gcctttgtct ctagtgctta ggtgaaagtg tatttttgtc aggaaggcct    360
atgaggcaga tgaggagggg atagcctccc tctcctctcg actattttgt agactgcctg    420
```

tgccaagtta ggttccccta ctgagagatg 450

<210> SEQ ID NO 205
<211> LENGTH: 451
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ1S4

<400> SEQUENCE: 205
cagaagaggg aacttggggg atcacacggg gcctaattgg tctgctgacc accgcatttt 60
gggttgtacc attgtctacc cctctaccca ccagggttaa aattctacta aggaacagga 120
gaggacctgg caggtggact tggggaggca ggagtggaag gcagcaggtc gcggttttcc 180
ttccagtctt taatgttgtg caactaatga aaaactgttt tttggcagtg gaacccagct 240
ctctgtcttg ggtatgtaaa agacttcttt cgggatagtg tatcataagg tcggagttcc 300
aggaggaccc cttgcgggag ggcagaaact gagaacacag ccaagaaaag ctcataaaat 360
gtgggtcagt ggagtgtgtg gtggggcccc aagagttctg tgtgtaagca gcttctggaa 420
ggaagggccc acaccagctc ctctggggtt t 451

<210> SEQ ID NO 206
<211> LENGTH: 450
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ1S5

<400> SEQUENCE: 206
gatagtgtat cataaggtcg gagttccagg aggacccctt gcgggagggc agaaactgag 60
aacacagcca agaaaagctc ataaaatgtg ggtcagtgga gtgtgtggtg gggccccaag 120
agttctgtgt gtaagcagct tctggaagga agggcccaca ccagctcctc tggggtttgc 180
cacactcatg atgcactgtg tagcaatcag ccccagcatt ttggtgatgg gactcgactc 240
tccatcctag gtaagttgca gaatcagggt ggtatggcca ttgtcccttg aaggcagagt 300
tctctgcttc tcctcccggt gctggtgagg cagattgagt aaaatctctt accccatggg 360
gtaagagctg tgcctgtgcc tgcgttccct ttggtgtgtc ttggttgact cctctatttc 420
tcttctctaa gtcttcagtc cataatctgc 450

<210> SEQ ID NO 207
<211> LENGTH: 453
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ1S6

<400> SEQUENCE: 207
atggctctgc ctctcctaag cctcttcctc ttgcgcctta tgctgcacag tatgcttagg 60
cctttttcct aacagaatcc ctttggtcca gagccatgaa tccaggcaga gaaaggcagc 120
catcctgctg tcagggagct aagacttgcc ctctgactgg agatcgccgg gtgggtttta 180
tctaagcctc tgcagctgtg ctcctataat tcacccctcc actttgggaa cgggaccagg 240
ctcactgtga caggtatggg ggctccactc ttgactcggg ggtgcctggg tttgactgca 300
atgatcagtt gctgggaagg gaattgagtg taagaacgga ggtcagggtc accccttctt 360
acctggagca ctgtgccctc tcctcccctc cctggagctc ttccagcttg ttgctctgct 420
gtgttgcctg cagttcctca gctgtagagc tcc 453

<210> SEQ ID NO 208
<211> LENGTH: 449
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ2S1

<400> SEQUENCE: 208
aatccactgt gttgtccccc agccaagtgg attctcctct gcaaattggt ggtggcctca 60
tgcaagatcc agttaccgtg tccagctaac tcgagacagg aaaagatagg ctcaggaaag 120
agaggaaggg tgtgccctct gtctgtgcta agggaggtgg ggaaggagaa ggaattctgg 180
gcagcccctt cccactgtgc tcctacaatg agcagttctt cgggccaggg acacggctca 240
ccgtgctagg taagaagggg gctccaggtg ggagagaggg tgagcagccc agcctgcacg 300
accccagaac cctgttctta ggggagtgga cactgggcaa tccagggccc tcctcgaggg 360
aagcggggtt tgcgccaggg tccccagggc tgtgcgaaca ccggggagct gtttttttgga 420 gaaggctcta ggctgaccgt actgggtaa 449

<210> SEQ ID NO 209
<211> LENGTH: 451
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ2S2

<400> SEQUENCE: 209
ctgtgctcct acaatgagca gttcttcggg ccagggacac ggctcaccgt gctaggtaag 60
aagggggctc caggtgggag agagggtgag cagcccagcc tgcacgaccc cagaaccctg 120
ttcttagggg agtggacact gggcaatcca gggccctcct cgagggaagc ggggtttgcg 180
ccagggtccc cagggctgtg cgaacaccgg ggagctgttt tttggagaag gctctaggct 240
gaccgtactg ggtaaggagg cggttggggc tccggagagc tccgagaggg cgggatgggc 300
agaggtaagc agctgcccca ctctgagagg ggctgtgctg agaggcgctg ctgggcgtct 360
gggcggagga ctcctggttc tgggtgctgg gagagcgatg gggctctcag cggtgggaag 420
gacccgagct gagtctggga cagcagagcg g 451

<210> SEQ ID NO 210
<211> LENGTH: 449
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ2S3

<400> SEQUENCE: 210
gggcgggatg ggcagaggta agcagctgcc ccactctgag aggggctgtg ctgagaggcg 60
ctgctgggcg tctgggcgga ggactcctgg ttctgggtgc tgggagagcg atggggctct 120
cagcggtggg aaggacccga gctgagtctg ggacagcaga gcgggcagca ccggtttttg 180
tcctgggcct ccaggctgtg agcacagata cgcagtattt tggcccaggc acccggctga 240
cagtgctcgg taagcggggg ctcccgctga agccccggaa ctggggaggg ggcgccccgg 300
gacgccgggg gcgtcgcagg gccagtttct gtgccgcgtc tcggggctgt gagccaaaaa 360
cattcagtac ttcggcgccg ggacccggct ctcagtgctg ggtaagctgg ggccgccggg 420
ggaccgggga cgagactgcg ctcgggttt 449

<210> SEQ ID NO 211
<211> LENGTH: 450
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ2S4

<400> SEQUENCE: 211
gacagcagag cgggcagcac cggtttttgt cctgggcctc caggctgtga gcacagatac 60
gcagtatttt ggcccaggca cccggctgac agtgctcggt aagcgggggc tcccgctgaa 120
gccccggaac tggggagggg gcgccccggg acgccggggg cgtcgcaggg ccagtttctg 180
tgccgcgtct cggggctgtg agccaaaaac attcagtact tcggcgccgg gacccggctc 240
tcagtgctgg gtaagctggg gccgccgggg gaccggggac gagactgcgc tcgggttttt 300
gtgcggggct cgggggccgt gaccaagaga cccagtactt cgggccaggc acgcggctcc 360
tggtgctcgg tgagcgcggg ctgctggggc gcgggcgcgg gcggcttggg tctggttttt 420
gcggggagtc cccgggctgt gctctggggc 450

<210> SEQ ID NO 212
<211> LENGTH: 448
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ2S5

<400> SEQUENCE: 212
ccccggaact ggggaggggg cgccccggga cgccgggggc gtcgcagggc cagtttctgt 60
gccgcgtctc ggggctgtga gccaaaaaca ttcagtactt cggcgccggg acccggctct 120
cagtgctggg taagctgggg ccgccggggg accggggacg agactgcgct cgggtttttg 180
tgcggggctc gggggccgtg accaagagac ccagtacttc gggccaggca cgcggctcct 240
ggtgctcggt gagcgcgggc tgctggggcg cgggcgcggg cggcttgggt ctggtttttg 300
cggggagtcc ccgggctgtg ctctggggcc aacgtcctga ctttcggggc cggcagcagg 360
ctgaccgtgc tgggtgagtt ttcgcgggac cacccgggcg gcgggattca ggtggaaggc 420
ggcggctgct tcgcggcacc cggtccgg 448

<210> SEQ ID NO 213

<211> LENGTH: 453
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ2S6

<400> SEQUENCE: 213
cagtgctggg taagctgggg ccgccggggg accggggacg agactgcgct cgggtttttg 60
tgcggggctc gggggccgtg accaagagac ccagtacttc gggccaggca cgcggctcct 120
ggtgctcggt gagcgcgggc tgctggggcg cgggcgcggg cggcttgggt ctggtttttg 180
cggggagtcc ccgggctgtg ctctggggcc aacgtcctga ctttcggggc cggcagcagg 240
ctgaccgtgc tgggtgagtt ttcgcgggac cacccgggcg gcgggattca ggtggaaggc 300
ggcggctgct tcgcggcacc cggtccggcc ctgtgctggg agacctgggc tgggtcccca 360
gggtgggcag gagctcgggg agccttagag gtttgcatgc gggggtgcac ctccgtgctc 420
ctacgagcag tacttcgggc cgggcaccag gct 453

<210> SEQ ID NO 214
<211> LENGTH: 447
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: TCRBJ2S7

<400> SEQUENCE: 214
tgactttcgg ggccggcagc aggctgaccg tgctgggtga gttttcgcgg gaccacccgg 60
gcggcgggat tcaggtggaa ggcggcggct gcttcgcggc acccggtccg gccctgtgct 120
gggagacctg ggctgggtcc ccagggtggg caggagctcg gggagcctta gaggtttgca 180
tgcgggggtg cacctccgtg ctcctacgag cagtacttcg ggccgggcac caggctcacg 240
gtcacaggtg agattcgggc gtctccccac cttccagccc ctcggtcccc ggagtcggag 300
ggtggaccgg agctggagga gctgggtgtc cggggtcagc tctgcaaggt cacctccccg 360
ctcctgggga aagactgggg aagagggagg gggtggggag gtgctcagag tccggaaagc 420
tgagcagagg gcgaggccac ttttaat 447

<210> SEQ ID NO 215
<211> LENGTH: 50
<212> TYPE: DNA
<213> ORGANISM: Homo sapiens

<400> SEQUENCE: 215
gaattattat aagaaactct ttggcagtgg aacaacactg gttgtcacag 50

<210> SEQ ID NO 216
<211> LENGTH: 50
<212> TYPE: DNA
<213> ORGANISM: Homo sapiens

<400> SEQUENCE: 216
gaattattat aagaaactct ttggcagtgg aacaacactt gttgtcacag 50

<210> SEQ ID NO 217
<211> LENGTH: 47

<212> TYPE: DNA
<213> ORGANISM: Homo sapiens

<400> SEQUENCE: 217
ttattataag aaactctttg gcagtggaac aacacttgtt gtcacag 47

<210> SEQ ID NO 218
<211> LENGTH: 60
<212> TYPE: DNA
<213> ORGANISM: Homo sapiens

<400> SEQUENCE: 218
tgggcaagag ttgggcaaaa aaatcaaggt atttggtccc ggaacaaagc ttatcattac 60

<210> SEQ ID NO 219
<211> LENGTH: 60
<212> TYPE: DNA
<213> ORGANISM: Homo sapiens

<400> SEQUENCE: 219
ataccactgg ttggttcaag atatttgctg aagggactaa gctcatagta acttcacctg 60

<210> SEQ ID NO 220
<211> LENGTH: 60
<212> TYPE: DNA
<213> ORGANISM: Homo sapiens

<400> SEQUENCE: 220
atagtagtga ttggatcaag acgtttgcaa aagggactag gctcatagta acttcgcctg 60

<210> SEQ ID NO 221
<211> LENGTH: 300
<212> TYPE: DNA
<213> ORGANISM: Homo sapiens

<400> SEQUENCE: 221
tcttccaact tggaagggag aacgaagtca gtcatcaggc agactgggtc atctgctgaa 60
atcacttgtg atcttgctga aggaagtaac ggctacatcc actggtacct acaccaggag 120
gggaaggccc cacagcgtct tcagtactat gactcctaca actccaaggt tgtgttggaa 180
tcaggagtca gtccagggaa gtattatact tacgcaagca caaggaacaa cttgagattg 240
atactgcgaa atctaattga aaatgactct ggggtctatt actgtgccac ctgggacggg 300

<210> SEQ ID NO 222
<211> LENGTH: 297
<212> TYPE: DNA
<213> ORGANISM: Homo sapiens

<400> SEQUENCE: 222
tcttccaact tggaagggag aacgaagtca gtcatcaggc agactgggtc atctgctgaa 60
atcacttgtg atcttgctga aggaagtaac ggctacatcc actggtacct acaccaggag 120
gggaaggccc cacagcgtct tcagtactat gactcctaca actccaaggt tgtgttggaa 180
tcaggagtca gtccagggaa gtattatact tacgcaagca caaggaacaa cttgagattg 240
atactgcaaa atctaattga aaatgactct ggggtctatt actgtgccac ctgggac 297

<210> SEQ ID NO 223
<211> LENGTH: 300
<212> TYPE: DNA
<213> ORGANISM: Homo sapiens

<400> SEQUENCE: 223
tcttccaact tggaagggag aacgaagtca gtcatcaggc agactgggtc atctgctgaa 60
atcacttgtg atcttgctga aggaagtacc ggctacatcc actggtacct acaccaggag 120
gggaaggccc cacagcgtct tctgtactat gactcctaca cctccagcgt tgtgttggaa 180
tcaggaatca gcccagggaa gtatgatact tatggaagca caaggaagaa cttgagaatg 240
atactgcgaa atcttattga aaatgactct ggagtctatt actgtgccac ctgggatggg 300

<210> SEQ ID NO 224
<211> LENGTH: 300
<212> TYPE: DNA
<213> ORGANISM: Homo sapiens

<400> SEQUENCE: 224
tcttccaact tggaagggag aacgaagtca gtcatcaggc agactgggtc atctgctgaa 60
atcacttgtg atcttgctga aggaagtacc ggctacatcc actggtacct acaccaggag 120
gggaaggccc cacagcgtct tctgtactat gactcctaca cctccagcgt tgtgttggaa 180
tcaggaatca gcccagggaa gtatgatact tacggaagca caaggaagaa cttgagaatg 240
atactgcgaa atcttattga aaatgactct ggagtctatt actgtgccac ctgggatggg 300

<210> SEQ ID NO 225
<211> LENGTH: 300
<212> TYPE: DNA
<213> ORGANISM: Homo sapiens

<400> SEQUENCE: 225
tcttccaact tggaagggag aacaaagtca gtcaccaggc caactgggtc atcagctgta 60
atcacttgtg atcttcctgt agaaaatgcc gtctacaccc actggtacct acaccaggag 120
gggaaggccc cacagcgtct tctgtactat gactcctaca actccagggt tgtgttggaa 180
tcaggaatca gtcgagaaaa gtatcatact tatgcaagca cagggaagag ccttaaattt 240
atactggaaa atctaattga acgtgactct ggggtctatt actgtgccac ctgggatagg 300

<210> SEQ ID NO 226
<211> LENGTH: 297
<212> TYPE: DNA
<213> ORGANISM: Homo sapiens

<400> SEQUENCE: 226
tcttccaact tggaagggag aacgaagtca gtcaccaggc tgactgggtc atctgctgaa 60
atcacctgtg atcttcctgg agcaagtacc ttatacatcc actggtacct gcaccaggag 120
gggaaggccc cacagtgtct tctgtactat gaaccctact actccagggt tgtgctggaa 180
tcaggaatca ctccaggaaa gtatgacact ggaagcacaa ggagcaattg gaatttgaga 240
ctgcaaaatc taattaaaaa tgattctggg ttctattact gtgccacctg ggacagg 297

<210> SEQ ID NO 227
<211> LENGTH: 300
<212> TYPE: DNA
<213> ORGANISM: Homo sapiens

<400> SEQUENCE: 227
tcttccaact tggaagggag aacgaagtca gtcaccaggc agactgggtc atctgctgaa 60
atcacttgcg atcttactgt aacaaatacc ttctacatcc actggtacct acaccaggag 120
gggaaggccc cacagcgtct tctgtactat gacgtctcca ccgcaaggga tgtgttggaa 180
tcaggactca gtccaggaaa gtattatact catacaccca ggaggtggag ctggatattg 240
agactgcaaa atctaattga aaatgattct ggggtctatt actgtgccac ctgggacagg 300

<210> SEQ ID NO 228
<211> LENGTH: 299
<212> TYPE: DNA
<213> ORGANISM: Homo sapiens

<400> SEQUENCE: 228
tcttccaact tggaagggag aacgaagtca gtcaccaggc agactgggtc atctgctgaa 60
atcacttgcg atcttactgt aacaaatacc ttctacatcc actggtacct acaccaggag 120
gggaaggccc cacagcgtct tctgtactat gacgtctcca ctgcaaggga tgtgttggaa 180
tcaggactca gtccaggaaa gtattatact catacaccca ggaggtggag ctggatattg 240
agactgcaaa atctaattga aaatgattct ggggtctatt actgtgccac ctgggacag 299

<210> SEQ ID NO 229
<211> LENGTH: 300
<212> TYPE: DNA
<213> ORGANISM: Homo sapiens

<400> SEQUENCE: 229
tcttccaact tggaagggag aatgaagtca gtcaccaggc cgactgggtc atctgctgaa 60
atcacttgtg accttactgt aataaatgcc gtctacatcc actggtacct acagcaggag 120
gggaagaccc cacagcatct tctgcactat gaagtctcca actcaaggga tgtgttggaa 180
tcaggtctca gtcttggaaa gtattatact catacaccga ggaggtggag ctggaatttg 240
agactgcaaa atctaattga aaatgattct ggggtctatt actgtgccac ctggggcagg 300

<210> SEQ ID NO 230
<211> LENGTH: 300
<212> TYPE: DNA
<213> ORGANISM: Homo sapiens

<400> SEQUENCE: 230
tcttccaact tggaagggag aatgaagtca gtcaccaggc cgactgggtc atctgctgaa 60
atcacttgtg accttactgt aataaatgcc gtctacatcc actggtacct acagcaggag 120
gggaagaccc cacagcatct tctgcactat gatgtctcca actcaaggga tgtgttggaa 180
tcaggtctca gtcttggaaa gtattatact catacaccga ggaggtggag ctggaatttg 240
agactgcaaa atctaattga aaatgattct ggggtctatt actgtgccac ctggggcagg 300

<210> SEQ ID NO 231
<211> LENGTH: 300
<212> TYPE: DNA
<213> ORGANISM: Homo sapiens

<400> SEQUENCE: 231
tcttccaact tggaaggggg aacgaagtca gtcacgaggc cgactaggtc atctgctgaa 60
atcacttgtg accttactgt aataaatgcc ttctacatcc actggtacct acaccaggag 120
gggaaggccc cacagcgtct tctgtactat gacgtctcca actcaaagga tgtgttggaa 180
tcaggactca gtccaggaaa gtattatact catacaccca ggaggtggag ctggatattg 240
atactacgaa atctaattga aaatgattct ggggtctatt actgtgccac ctgggacagg 300

<210> SEQ ID NO 232

<211> LENGTH: 311
<212> TYPE: DNA
<213> ORGANISM: Homo sapiens

<400> SEQUENCE: 232
ttatcaaaag tggagcagtt ccagctatcc atttccacgg aagtcaagaa aagtattgac 60
ataccttgca agatatcgag cacaaggttt gaaacagatg tcattcactg gtaccggcag 120
aaaccaaatc aggctttgga gcacctgatc tatattgtct caacaaaatc cgcagctcga 180
cgcagcatgg gtaagacaag caacaaagtg gaggcaagaa agaattctca aactctcact 240
tcaatcctta ccatcaagtc cgtagagaaa gaagacatgg ccgtttacta ctgtgctgcg 300
tggtgggtgg c 311

<210> SEQ ID NO 233
<211> LENGTH: 308
<212> TYPE: DNA
<213> ORGANISM: Homo sapiens

<400> SEQUENCE: 233
ttatcaaaag tggagcagtt ccagctatcc atttccacgg aagtcaagaa aagtattgac 60
ataccttgca agatatcgag cacaaggttt gaaacagatg tcattcactg gtaccggcag 120
aaaccaaatc aggctttgga gcacctgatc tatattgtct caacaaaatc cgcagctcga 180
cgcagcatgg gtaagacaag caacaaagtg gaggcaagaa agaattctca aactctcact 240
tcaatcctta ccatcaagtc cgtagagaaa gaagacatgg ccgtttacta ctgtgctgcg 300
tgggatta 308

<210> SEQ ID NO 234
<211> LENGTH: 309
<212> TYPE: DNA
<213> ORGANISM: Homo sapiens

<400> SEQUENCE: 234
cttgggcagt tggaacaacc tgaaatatct atttccagac cagcaaataa gagtgcccac 60
atatcttgga aggcatccat ccaaggcttt agcagtaaaa tcatacactg gtactggcag 120
aaaccaaaca aaggcttaga atatttatta catgtcttct tgacaatctc tgctcaagat 180
tgctcaggtg ggaagactaa gaaacttgag gtaagtaaaa atgctcacac ttccacttcc 240
actttgaaaa taaagttctt agagaaagaa gatgaggtgg tgtaccactg tgcctgctgg 300
attaggcac 309

<210> SEQ ID NO 235
<211> LENGTH: 309
<212> TYPE: DNA
<213> ORGANISM: Homo sapiens

<400> SEQUENCE: 235
cttgggcagt tggaacaacc tgaaatatct atttccagac cagcaaataa gagtgcccac 60
atatcttgga aggcatccat ccaaggcttt agcagtaaaa tcatacactg gtactggcag 120
aaaccaaaca aaggcttaga atatttatta catgtcttct tgacaatctc tgctcaagat 180
tgctcaggtg ggaagactaa gaaacttgag ataagtaaaa atgctcacac ttccacttcc 240
actttgaaaa taaagttctt agagaaagaa gatgaggtgg tgtaccactg tgcctgctgg 300
attaggcac 309

<210> SEQ ID NO 236
<211> LENGTH: 306
<212> TYPE: DNA
<213> ORGANISM: Homo sapiens

<400> SEQUENCE: 236
gcaggtcacc tagagcaacc tcaaatttcc agtactaaaa cgctgtcaaa aacagcccgc 60
ctggaatgtg tggtgtctgg aataacaatt tctgcaacat ctgtatattg gtatcgagag 120
agacctggtg aagtcataca gttcctggtg tccatttcat atgacggcac tgtcagaaag 180
gaatccggca ttccgtcagg caaatttgag gtggatagga tacctgaaac gtctacatcc 240
actctcacca ttcacaatgt agagaaacag gacatagcta cctactactg tgccttgtgg 300
gaggtg 306

<210> SEQ ID NO 237
<211> LENGTH: 306
<212> TYPE: DNA
<213> ORGANISM: Homo sapiens

<400> SEQUENCE: 237
gcaggtcacc tagagcaacc tcaaatttcc agtactaaaa cgctgtcaaa aacagcccgc 60
ctggaatgtg tggtgtctgg aataaaaatt tctgcaacat ctgtatattg gtatcgagag 120
agacctggtg aagtcataca gttcctggtg tccatttcat atgacggcac tgtcagaaag 180
gaatctggca ttccgtcagg caaatttgag gtggatagga tacctgaaac gtctacatcc 240
actctcacca ttcacaatgt agagaaacag gacatagcta cctactactg tgccttgtgg 300
gaggtg 306

<210> SEQ ID NO 238
<211> LENGTH: 285
<212> TYPE: DNA
<213> ORGANISM: Homo sapiens

<400> SEQUENCE: 238
ctcatcaggc cggagcagct ggcccatgtc ctggggcact agggaagctt ggtcatcctg 60
cagtgcgtgg tccgcaccag gatcagctac acccactggt accagcagaa gggccaggtc 120
cctgaggcac tccaccagct ggccatgtcc aagttggatg tgcagtggga ttccatcctg 180
aaagcagata aaatcatagc caaggatggc agcagctcta tcttggcagt actgaagttg 240
gagacaggca tcgagggcat gaactactgc acaacctggg ccctg 285

<210> SEQ ID NO 239
<211> LENGTH: 48
<212> TYPE: DNA
<213> ORGANISM: Homo sapiens

<400> SEQUENCE: 239
actactttga ctactggggc caaggaaccc tggtcaccgt ctcctcag 48

<210> SEQ ID NO 240
<211> LENGTH: 48
<212> TYPE: DNA
<213> ORGANISM: Homo sapiens

<400> SEQUENCE: 240
gctactttga ctactggggc caagggaccc tggtcaccgt ctcctcag 48

<210> SEQ ID NO 241

<211> LENGTH: 48
<212> TYPE: DNA
<213> ORGANISM: Homo sapiens

<400> SEQUENCE: 241
actactttga ctactggggc cagggaaccc tggtcaccgt ctcctcag 48

<210> SEQ ID NO 242
<211> LENGTH: 50
<212> TYPE: DNA
<213> ORGANISM: Homo sapiens

<400> SEQUENCE: 242
tgatgctttt gatgtctggg gccaagggac aatggtcacc gtctcttcag 50

<210> SEQ ID NO 243
<211> LENGTH: 50
<212> TYPE: DNA
<213> ORGANISM: Homo sapiens

<400> SEQUENCE: 243
tgatgctttt gatatctggg gccaagggac aatggtcacc gtctcttcag 50

<210> SEQ ID NO 244
<211> LENGTH: 63
<212> TYPE: DNA
<213> ORGANISM: Homo sapiens

<400> SEQUENCE: 244
attactacta ctactacggt atggacgtct gggggcaagg gaccacggtc accgtctcct 60
cag 63

<210> SEQ ID NO 245
<211> LENGTH: 62
<212> TYPE: DNA
<213> ORGANISM: Homo sapiens

<400> SEQUENCE: 245
attactacta ctactacggt atggacgtct ggggccaagg gaccacggtc accgtctcct 60
ca 62

<210> SEQ ID NO 246
<211> LENGTH: 63
<212> TYPE: DNA
<213> ORGANISM: Homo sapiens

<400> SEQUENCE: 246
attactacta ctactacggt atggacgtct ggggcaaagg gaccacggtc accgtctcct 60
cag 63

<210> SEQ ID NO 247
<211> LENGTH: 62
<212> TYPE: DNA
<213> ORGANISM: Homo sapiens

<400> SEQUENCE: 247
attactacta ctactactac atggacgtct ggggcaaagg gaccacggtc accgtctcct 60
ca 62

<210> SEQ ID NO 248
<211> LENGTH: 53

-continued

<212> TYPE: DNA
<213> ORGANISM: Homo sapiens

<400> SEQUENCE: 248
ctactggtac ttcgatctct ggggccgtgg caccctggtc actgtctcct cag 53

<210> SEQ ID NO 249
<211> LENGTH: 51
<212> TYPE: DNA
<213> ORGANISM: Homo sapiens

<400> SEQUENCE: 249
acaactggtt cgactcctgg ggccaaggaa ccctggtcac cgtctcctca g 51

<210> SEQ ID NO 250
<211> LENGTH: 51
<212> TYPE: DNA
<213> ORGANISM: Homo sapiens

<400> SEQUENCE: 250
acaactggtt cgacccctgg ggccagggaa ccctggtcac cgtctcctca g 51

<210> SEQ ID NO 251
<211> LENGTH: 52
<212> TYPE: DNA
<213> ORGANISM: Homo sapiens

<400> SEQUENCE: 251
gctgaatact tccagcactg gggccagggc accctggtca ccgtctcctc ag 52

<210> SEQ ID NO 252
<211> LENGTH: 61
<212> TYPE: DNA
<213> ORGANISM: Homo sapiens

<400> SEQUENCE: 252
gctacaagtg cttggagcac tggggcaggg cagcccggac accgtctccc tgggaacgtc 60
a 61

<210> SEQ ID NO 253
<211> LENGTH: 54
<212> TYPE: DNA
<213> ORGANISM: Homo sapiens

<400> SEQUENCE: 253
aaaggtgctg gggtcccct gaacccgacc cgccctgaga ccgcagccac atca 54

<210> SEQ ID NO 254
<211> LENGTH: 52
<212> TYPE: DNA
<213> ORGANISM: Homo sapiens

<400> SEQUENCE: 254
cttgcggttg gacttcccag ccgacagtgg tggtctggct tctgaggggt ca 52

<210> SEQ ID NO 255
<211> LENGTH: 296
<212> TYPE: DNA
<213> ORGANISM: Homo sapiens

<400> SEQUENCE: 255
caggttcagc tggtgcagtc tggagctgag gtgaagaagc ctggggcctc agtgaaggtc 60

-continued tcctgcaagg cttctggtta cacctttacc agctatggta tcagctgggt gcgacaggcc 120
cctggacaag ggcttgagtg gatgggatgg atcagcgctt acaatggtaa cacaaactat 180
gcacagaagc tccagggcag agtcaccatg accacagaca catccacgag cacagcctac 240
atggagctga ggagcctgag atctgacgac acggccgtgt attactgtgc gagaga 296

<210> SEQ ID NO 256
<211> LENGTH: 276
<212> TYPE: DNA
<213> ORGANISM: Homo sapiens

<400> SEQUENCE: 256
caggttcagc tggtgcagtc tggagctgag gtgaagaagc ctggggcctc agtgaaggtc 60
tcctgcaagg cttctggtta cacctttacc agctatggta tcagctgggt gcgacaggcc 120
cctggacaag ggcttgagtg gatgggatgg atcagcgctt acaatggtaa cacaaactat 180
gcacagaagc tccagggcag agtcaccatg accacagaca catccacgag cacagcctac 240
atggagctga ggagcctaag atctgacgac acggcc 276

<210> SEQ ID NO 257
<211> LENGTH: 296
<212> TYPE: DNA
<213> ORGANISM: Homo sapiens

<400> SEQUENCE: 257
caggtgcagc tggtgcagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggacgg atcaacccta acagtggtgg cacaaactat 180
gcacagaagt ttcagggcag ggtcaccagt accagggaca cgtccatcag cacagcctac 240
atggagctga gcaggctgag atctgacgac acggtcgtgt attactgtgc gagaga 296

<210> SEQ ID NO 258
<211> LENGTH: 296
<212> TYPE: DNA
<213> ORGANISM: Homo sapiens

<400> SEQUENCE: 258
caggtgcagc tggtgcagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggatgg atcaacccta acagtggtgg cacaaactat 180
gcacagaagt ttcagggcag ggtcaccatg accagggaca cgtccatcag cacagcctac 240
atggagctga gcaggctgag atctgacgac acggccgtgt attactgtgc gagaga 296

<210> SEQ ID NO 259
<211> LENGTH: 296
<212> TYPE: DNA
<213> ORGANISM: Homo sapiens
<220> FEATURE:
<221> NAME/KEY: modified_base
<222> LOCATION: (113)..(113)
<223> OTHER INFORMATION: a, c, t or g

<400> SEQUENCE: 259
caggtgcagc tggtgcagtc tggggctgag gtgaagaagc ttggggcctc agtgaaggtc 60
tcctgcaagg cttctggata caccttcacc ggctactata tgcactgggt gcnacaggcc 120
cctggacaag ggcttgagtg gatgggatgg atcaacccta acagtggtgg cacaaactat 180
gcacagaagt ttcagggcag ggtcaccatg accagggaca cgtccatcag cacagcctac 240
atggagctga gcaggctgag atctgacgac acggccgtgt attactgtgc gagaga 296

<210> SEQ ID NO 260
<211> LENGTH: 294
<212> TYPE: DNA
<213> ORGANISM: Homo sapiens

<400> SEQUENCE: 260
caggtgcagc tggtgcagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggatgg atcaacccta acagtggtgg cacaaactat 180
gcacagaagt ttcagggctg ggtcaccatg accagggaca cgtccatcag cacagcctac 240
atggagctga gcaggctgag atctgacgac acggccgtgt attactgtgc gaga 294

<210> SEQ ID NO 261
<211> LENGTH: 296
<212> TYPE: DNA
<213> ORGANISM: Homo sapiens

<400> SEQUENCE: 261
caggtccagc tggtacagtc tggggctgag gtgaagaagc ctggggcctc agtgaaggtc 60
tcctgcaagg tttccggata caccctcact gaattatcca tgcactgggt gcgacaggct 120
cctggaaaag ggcttgagtg gatgggaggt tttgatcctg aagatggtga aacaatctac 180
gcacagaagt tccagggcag agtcaccatg accgaggaca catctacaga cacagcctac 240
atggagctga gcagcctgag atctgaggac acggccgtgt attactgtgc aacaga 296

<210> SEQ ID NO 262
<211> LENGTH: 296
<212> TYPE: DNA
<213> ORGANISM: Homo sapiens

<400> SEQUENCE: 262
caggtccagc ttgtgcagtc tggggctgag gtgaagaagc ctggggcctc agtgaaggtt 60
tcctgcaagg cttctggata caccttcact agctatgcta tgcattgggt gcgccaggcc 120
cccggacaaa ggcttgagtg gatgggatgg atcaacgctg gcaatggtaa cacaaaatat 180
tcacagaagt tccagggcag agtcaccatt accagggaca catccgcgag cacagcctac 240
atggagctga gcagcctgag atctgaagac acggctgtgt attactgtgc gagaga 296

<210> SEQ ID NO 263
<211> LENGTH: 296
<212> TYPE: DNA
<213> ORGANISM: Homo sapiens

<400> SEQUENCE: 263
caggttcagc tggtgcagtc tggggctgag gtgaagaagc ctggggcctc agtgaaggtt 60
tcctgcaagg cttctggata caccttcact agctatgcta tgcattgggt gcgccaggcc 120
cccggacaaa ggcttgagtg gatgggatgg agcaacgctg gcaatggtaa cacaaaatat 180
tcacaggagt tccagggcag agtcaccatt accagggaca catccgcgag cacagcctac 240
atggagctga gcagcctgag atctgaggac atggctgtgt attactgtgc gagaga 296

<210> SEQ ID NO 264

<211> LENGTH: 296
<212> TYPE: DNA
<213> ORGANISM: Homo sapiens
<220> FEATURE:
<221> NAME/KEY: modified_base
<222> LOCATION: (295)..(295)
<223> OTHER INFORMATION: a, c, t or g

<400> SEQUENCE: 264
cagatgcagc tggtgcagtc tggggctgag gtgaagaaga ctgggtcctc agtgaaggtt 60
tcctgcaagg cttccggata caccttcacc taccgctacc tgcactgggt gcgacaggcc 120
cccggacaag cgcttgagtg gatgggatgg atcacacctt tcaatggtaa caccaactac 180
gcacagaaat tccaggacag agtcaccatt actagggaca ggtctatgag cacagcctac 240
atggagctga gcagcctgag atctgaggac acagccatgt attactgtgc aagana 296

<210> SEQ ID NO 265
<211> LENGTH: 296
<212> TYPE: DNA
<213> ORGANISM: Homo sapiens

<400> SEQUENCE: 265
cagatgcagc tggtgcagtc tggggctgag gtgaagaaga ctgggtcctc agtgaaggtt 60
tcctgcaagg cttccggata caccttcacc taccgctacc tgcactgggt gcgacaggcc 120
cccggacaag cgcttgagtg gatgggatgg atcacacctt tcaatggtaa caccaactac 180
gcacagaaat tccaggacag agtcaccatt accagggaca ggtctatgag cacagcctac 240
atggagctga gcagcctgag atctgaggac acagccatgt attactgtgc aagata 296

<210> SEQ ID NO 266
<211> LENGTH: 260
<212> TYPE: DNA
<213> ORGANISM: Homo sapiens

<400> SEQUENCE: 266
agaagactgg gtcctcagtg aaggtttcct gcaaggcttc cggatacacc ttcacctacc 60
gctacctgca ctgggtgcga caggccccca gacaagcgct tgagtggatg ggatggatca 120
cacctttcaa tggtaacacc aactacgcac agaaattcca ggacagagtc accattacca 180
gggacaggtc tatgagcaca gcctacatgg agctgagcag cctgagatct gaggacacag 240
ccatgtatta ctgtgcaaga 260

<210> SEQ ID NO 267
<211> LENGTH: 296
<212> TYPE: DNA
<213> ORGANISM: Homo sapiens

<400> SEQUENCE: 267
caggtgcagc tggtgcagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcctgag atctgaggac acggccgtgt attactgtgc gagaga 296

<210> SEQ ID NO 268
<211> LENGTH: 296
<212> TYPE: DNA
<213> ORGANISM: Homo sapiens

<400> SEQUENCE: 268
caggtgcagc tggtgcagtc tggggctgag gtgaagaagc ctggggcctc agtgaaggtt 60
tcctgcaagg catctggata caccttcaac agctactata tgcactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcctgag atctgaggac acggccgtgt attactgtgc gagaga 296

<210> SEQ ID NO 269
<211> LENGTH: 296
<212> TYPE: DNA
<213> ORGANISM: Homo sapiens

<400> SEQUENCE: 269
caggtgcagc tggtgcagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcctgag atctgaggac acggccgtgt attactgtgc tagaga 296

<210> SEQ ID NO 270
<211> LENGTH: 296
<212> TYPE: DNA
<213> ORGANISM: Homo sapiens

<400> SEQUENCE: 270
caaatgcagc tggtgcagtc tgggcctgag gtgaagaagc ctgggacctc agtgaaggtc 60
tcctgcaagg cttctggatt cacctttact agctctgctg tgcagtgggt gcgacaggct 120
cgtggacaac gccttgagtg gataggatgg atcgtcgttg gcagtggtaa cacaaactac 180
gcacagaagt tccaggaaag agtcaccatt accagggaca tgtccacaag cacagcctac 240
atggagctga gcagcctgag atccgaggac acggccgtgt attactgtgc ggcaga 296

<210> SEQ ID NO 271
<211> LENGTH: 296
<212> TYPE: DNA
<213> ORGANISM: Homo sapiens

<400> SEQUENCE: 271
caaatgcagc tggtgcagtc tgggcctgag gtgaagaagc ctgggacctc agtgaaggtc 60
tcctgcaagg cttctggatt cacctttact agctctgcta tgcagtgggt gcgacaggct 120
cgtggacaac gccttgagtg gataggatgg atcgtcgttg gcagtggtaa cacaaactac 180
gcacagaagt tccaggaaag agtcaccatt accagggaca tgtccacaag cacagcctac 240
atggagctga gcagcctgag atccgaggac acggccgtgt attactgtgc ggcaga 296

<210> SEQ ID NO 272
<211> LENGTH: 296
<212> TYPE: DNA
<213> ORGANISM: Homo sapiens

<400> SEQUENCE: 272
caggtgcagc tggggcagtc tgaggctgag gtaaagaagc ctggggcctc agtgaaggtc 60
tcctgcaagg cttccggata caccttcact tgctgctcct tgcactggtt gcaacaggcc 120
cctggacaag ggcttgaaag gatgagatgg atcacacttt acaatggtaa caccaactat 180
gcaaagaagt tccagggcag agtcaccatt accagggaca tgtccctgag gacagcctac 240
atagagctga gcagcctgag atctgaggac tcggctgtgt attactgggc aagata 296

<210> SEQ ID NO 273
<211> LENGTH: 296
<212> TYPE: DNA
<213> ORGANISM: Homo sapiens

<400> SEQUENCE: 273
caggtgcagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt attactgtgc gagaga 296

<210> SEQ ID NO 274
<211> LENGTH: 294
<212> TYPE: DNA
<213> ORGANISM: Homo sapiens

<400> SEQUENCE: 274
caggtccagc tggtgcaatc tggggctgag gtgaagaagc ctgggtcctc ggtgaaggtc 60
tcctgcaagg cttctggagg caccttcagc agctatacta tcagctgggt gcgacaggcc 120
cctggacaag ggcttgagtg gatgggaagg atcatcccta tccttggtat agcaaactac 180
gcacagaagt tccagggcag agtcacgatt accgcggaca aatccacgag cacagcctac 240
atggagctga gcagcctgag atctgaggac acggccgtgt attactgtgc gaga 294

<210> SEQ ID NO 275
<211> LENGTH: 275
<212> TYPE: DNA
<213> ORGANISM: Homo sapiens

<400> SEQUENCE: 275
caggtgcagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgatgac acggc 275

<210> SEQ ID NO 276
<211> LENGTH: 296
<212> TYPE: DNA
<213> ORGANISM: Homo sapiens

<400> SEQUENCE: 276
caggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaagg atcatcccta tccttggtat agcaaactac 180
gcacagaagt tccagggcag agtcacgatt accgcggaca aatccacgag cacagcctac 240
atggagctga gcagcctgag atctgaggac acggccgtgt attactgtgc gagaga 296

-continued

<210> SEQ ID NO 277
<211> LENGTH: 294
<212> TYPE: DNA
<213> ORGANISM: Homo sapiens

<400> SEQUENCE: 277
caggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accacggacg aatccacgag cacagcctac 240
atggagctga gcagcctgag atctgaggac acggccgtgt attactgtgc gaga 294

<210> SEQ ID NO 278
<211> LENGTH: 296
<212> TYPE: DNA
<213> ORGANISM: Homo sapiens

<400> SEQUENCE: 278
caggtgcagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggaca aatccacgag cacagcctac 240
atggagctga gcagcctgag atctgaggac acggccgtgt attactgtgc gagaga 296

<210> SEQ ID NO 279
<211> LENGTH: 233
<212> TYPE: DNA
<213> ORGANISM: Homo sapiens

<400> SEQUENCE: 279
agaagcctgg gtcctcggtg aaggtctcct gcaaggcttc tggaggcacc ttcagcagct 60
atgctatcag ctgggtgcga caggcccctg gacaagggct tgagtggatg ggaaggatca 120
tccctatctt tggtacagca aactacgcac agaagttcca gggcagagtc acgattaccg 180
cggacgaatc cacgagcaca gcctacatgg agctgagcag cctgagatct gag 233

<210> SEQ ID NO 280
<211> LENGTH: 296
<212> TYPE: DNA
<213> ORGANISM: Homo sapiens

<400> SEQUENCE: 280
caggtccagc tggtgcaatc tggggctgag gtgaagaagc ctgggtcctc ggtgaaggtc 60
tcctgcaagg cttctggagg caccttcagc agctatacta tcagctgggt gcgacaggcc 120
cctggacaag ggcttgagtg gatgggaagg atcatcccta tccttggtac agcaaactac 180
gcacagaagt tccagggcag agtcacgatt accgcggaca aatccacgag cacagcctac 240
atggagctga gcagcctgag atctgaggac acggccgtgt attactgtgc gagaga 296

<210> SEQ ID NO 281
<211> LENGTH: 296
<212> TYPE: DNA
<213> ORGANISM: Homo sapiens

<400> SEQUENCE: 281
caggtgcagc tggtgcagtc tggggctgag gtgaagaagc ctgggtcctc ggtgaaggtc 60

-continued

```
tcctgcaagg cttctggagg caccttcagc agctatgcta tcagctgggt gcgacaggcc    120

cctggacaag ggcttgagtg gatgggaagg atcatcccta tccttggtat agcaaactac    180

gcacagaagt tccagggcag agtcacgatt accgcggaca aatccacgag cacagcctac    240

atggagctga gcagcctgag atctgaggac acggccgtgt attactgtgc gagaga       296


<210> SEQ ID NO 282
<211> LENGTH: 296
<212> TYPE: DNA
<213> ORGANISM: Homo sapiens

<400> SEQUENCE: 282

caggtccagc tggtgcagtc tggggctgag gtgaagaagc ctgggtcctc agtgaaggtc     60

tcctgcaagg cttctggagg caccttcagc agctatgcta tcagctgggt gcgacaggcc    120

cctggacaag ggcttgagtg gatgggaggg atcatcccta tccttggtat agcaaactac    180

gcacagaagt tccagggcag agtcacgatt accgcggaca aatccacgag cacagcctac    240

atggagctga gcagcctgag atctgaggac acggccgtgt attactgtgc gagaga       296


<210> SEQ ID NO 283
<211> LENGTH: 296
<212> TYPE: DNA
<213> ORGANISM: Homo sapiens

<400> SEQUENCE: 283

caggtccagc tggtgcagtc tggggctgag gtgaagaagc ctgggtcctc ggtgaaggtc     60

tcctgcaagg cttctggagg caccttcagc agctatgcta tcagctgggt gcgacaggcc    120

cctggacaag ggcttgagtg gatgggaagg atcatcccta tccttggtac agcaaactac    180

gcacagaagt tccagggcag agtcacgatt accgcggacg aatccacgag cacagcctac    240

atggagctga gcagcctgag atctgaggac acggccgtgt attactgtgc gagaga       296


<210> SEQ ID NO 284
<211> LENGTH: 296
<212> TYPE: DNA
<213> ORGANISM: Homo sapiens

<400> SEQUENCE: 284

caggtccagc tggtgcagtc tggggctgag gtgaagaagc ctgggtcctc ggtgaaggtc     60

tcctgcaagg cttctggagg caccttcagc agctatgcta tcagctgggt gcgacaggcc    120

cctggacaag ggcttgagtg gatgggaggg atcatcccta tctttggtac agcaaactac    180

gcacagaagt tccagggcag agtcacgatt accgcggacg aatccacgag cacagcctac    240

atggagctga gcagcctgag atctgaggac acggccgtgt attactgtgc gagaga       296


<210> SEQ ID NO 285
<211> LENGTH: 296
<212> TYPE: DNA
<213> ORGANISM: Homo sapiens

<400> SEQUENCE: 285

caggtccagc tggtgcagtc tggggctgag gtgaagaagc ctgggtcctc agtgaaggtc     60

tcctgcaagg cttctggagg caccttcagc agctatgcta tcagctgggt gcgacaggcc    120

cctggacaag ggcttgagtg gatgggaggg atcatcccta tctttggtac agcaaactac    180

gcacagaagt tccagggcag agtcacgatt accgcggacg aatccacgag cacagcctac    240

atggagctga gcagcctgag atctgaggac acggccgtgt attactgtgc gagaga       296
```

<210> SEQ ID NO 286
<211> LENGTH: 296
<212> TYPE: DNA
<213> ORGANISM: Homo sapiens

<400> SEQUENCE: 286
caggtgcagc tggtgcagtc tggggctgag gtgaagaagc ctggggcctc agtgaaggtc 60
tcctgcaagg cttctggata caccttcacc agttatgata tcaactgggt gcgacaggcc 120
actggacaag ggcttgagtg gatgggatgg atgaacccta acagtggtaa cacaggctat 180
gcacagaagt tccagggcag agtcaccatg accaggaaca cctccataag cacagcctac 240
atggagctga gcagcctgag atctgaggac acggccgtgt attactgtgc gagagg 296

<210> SEQ ID NO 287
<211> LENGTH: 296
<212> TYPE: DNA
<213> ORGANISM: Homo sapiens
<220> FEATURE:
<221> NAME/KEY: modified_base
<222> LOCATION: (136)..(136)
<223> OTHER INFORMATION: a, c, t or g
<220> FEATURE:
<221> NAME/KEY: modified_base
<222> LOCATION: (253)..(253)
<223> OTHER INFORMATION: a, c, t or g

<400> SEQUENCE: 287
caggttcagc tgttgcagcc tggggtccag gtgaagaagc ctgggtcctc agtgaaggtc 60
tcctgctagg cttccagata caccttcacc aaatacttta cacggtgggt gtgacaaagc 120
cctggacaag ggcatnagtg gatgggatga atcaaccctt acaacgataa cacacactac 180
gcacagacgt tctggggcag agtcaccatt accagtgaca ggtccatgag cacagcctac 240
atggagctga gcngcctgag atccgaagac atggtcgtgt attactgtgt gagaga 296

<210> SEQ ID NO 288
<211> LENGTH: 260
<212> TYPE: DNA
<213> ORGANISM: Homo sapiens

<400> SEQUENCE: 288
ggaagtctgg ggcctcagtg aaagtctcct gtagtttttc tgggtttacc atcaccagct 60
acggtataca ttgggtgcaa cagtcccctg gacaagggct tgagtggatg ggatggatca 120
accctggcaa tggtagccca agctatgcca agaagtttca gggcagattc accatgacca 180
gggacatgtc cacaaccaca gcctacacag acctgagcag cctgacatct gaggacatgg 240
ctgtgtatta ctatgcaaga 260

<210> SEQ ID NO 289
<211> LENGTH: 294
<212> TYPE: DNA
<213> ORGANISM: Homo sapiens

<400> SEQUENCE: 289
gaggtccagc tggtacagtc tggggctgag gtgaagaagc ctggggctac agtgaaaatc 60
tcctgcaagg tttctggata caccttcacc gactactaca tgcactgggt gcaacaggcc 120
cctggaaaag ggcttgagtg gatgggactt gttgatcctg aagatggtga aacaatatac 180
gcagagaagt tccagggcag agtcaccata accgcggaca cgtctacaga cacagcctac 240
atggagctga gcagcctgag atctgaggac acggccgtgt attactgtgc aaca 294

<210> SEQ ID NO 290
<211> LENGTH: 233
<212> TYPE: DNA
<213> ORGANISM: Homo sapiens

<400> SEQUENCE: 290
agaagcctgg ggctacagtg aaaatctcct gcaaggtttc tggatacacc ttcaccgact 60
actacatgca ctgggtgcaa caggcccctg gaaaagggct tgagtggatg ggacttgttg 120
atcctgaaga tggtgaaaca atatatgcag agaagttcca gggcagagtc accataaccg 180
cggacacgtc tacagacaca gcctacatgg agctgagcag cctgagatct gag 233

<210> SEQ ID NO 291
<211> LENGTH: 294
<212> TYPE: DNA
<213> ORGANISM: Homo sapiens

<400> SEQUENCE: 291
caggtgcagc tggtgcagtc tggggctgag gtgaagaagc ctggggcctc agtgaaggtc 60
tcctgcaagg cttctggata catcttcacc gactactata tgcactgggt gcgacaggcc 120
cctggacaag agcttgggtg gatgggacgg atcaacccta acagtggtgg cacaaactat 180
gcacagaagt ttcagggcag agtcaccatg accagggaca cgtccatcag cacagcctac 240
acggagctga gcagcctgag atctgaggac acggccacgt attactgtgc gaga 294

<210> SEQ ID NO 292
<211> LENGTH: 296
<212> TYPE: DNA
<213> ORGANISM: Homo sapiens

<400> SEQUENCE: 292
caggtgcagc tggtgcagtc tggggctgag gtgaagaagc ctggggcctc agtgaaggtc 60
tcctgcaagg cttctggata catcttcacc gactactata tgcactgggt gcgacaggcc 120
cctggacaag agcttgggtg gatgggacgg atcaacccta acagtggtgg cacaaactat 180
gcacagaagt ttcagggcag agtcaccatg accagggaca cgtccatcag cacagcctgc 240
acggagctga gcagcctgag atctgaggac acggccacgt attactgtgc gagaga 296

<210> SEQ ID NO 293
<211> LENGTH: 296
<212> TYPE: DNA
<213> ORGANISM: Homo sapiens

<400> SEQUENCE: 293
caggtgcagc tggtgcagtc tggagctgag gtgaagaagc ctagagcctc agtgaaggtc 60
tcctgcaagg cttctggtta cacctttacc agctactata tgcactgggt gtgacaggcc 120
cctgaacaag ggcttgagtg gatgggatgg atcaacactt acaatggtaa cacaaactac 180
ccacagaagc tccagggcag agtcaccatg accagagaca catccacgag cacagcctac 240
atggagctga gcaggctgag atctgacgac atggccgtgt attactgtgc gagaga 296

<210> SEQ ID NO 294
<211> LENGTH: 294
<212> TYPE: DNA
<213> ORGANISM: Homo sapiens

<400> SEQUENCE: 294
caggtccaac tggtgtagtc tggagctgag gtgaagaagc ctggggcctc agtgaaggtc 60
tcctgcaagg cttctggata caccttcacc gactacttta tgaactggat gcgccaggcc 120
cctggacaaa ggcttgagtg gatgggatgg atcaacgctg gcaatggtaa cacaaaatat 180
tcacagaagc tccagggcag agtcaccatt accagggaca catcttcgag cacagcctac 240
atgcagctga gcagcctgag atctgaggac acggccgtgt attactgtgc gaga 294

<210> SEQ ID NO 295
<211> LENGTH: 260
<212> TYPE: DNA
<213> ORGANISM: Homo sapiens

<400> SEQUENCE: 295
agaagcctgg ggcctcagtg aaggtctcct gcaaggcttc tggatacacc ttcaccgact 60
actttatgaa ctggatgcgc caggcccctg gacaaaggct tgagtggatg ggatggatca 120
acgctggcaa tggtaacaca aaatattcac agaagctcca gggcagagtc accattacca 180
gggacacatc tgcgagcaca gcctacatgc agctgagcag cctgagatct gaggacacgg 240
ccgtgtatta ctgtgcgaga 260

<210> SEQ ID NO 296
<211> LENGTH: 294
<212> TYPE: DNA
<213> ORGANISM: Homo sapiens

<400> SEQUENCE: 296
caggtccaac tggtgtagtc tggagctgag gtgaagaagc ctggggcctc agtgaaggtc 60
tcctgcaagg cttctggata caccttcacc agctactata tgaactggat gcgccaggcc 120
cctggacaag gcttcgagtg gatgggatgg atcaacgctg gcaatggtaa cacaaagtat 180
tcacagaagc tccagggcag agtcaccatt accagggaca catctgcgag cacagcctac 240
atgcagctga gcagcctgag atctgaggac acggccgtgt attactgtgc gaga 294

<210> SEQ ID NO 297
<211> LENGTH: 294
<212> TYPE: DNA
<213> ORGANISM: Homo sapiens

<400> SEQUENCE: 297
caggaccagt tggtgcagtc tggggctgag gtgaagaagc ctctgtcctc agtgaaggtc 60
tccttcaagg cttctggata caccttcacc aacaacttta tgcactgggt gtgacaggcc 120
cctggacaag gacttgagtg gatgggatgg atcaatgctg gcaatggtaa cacaacatat 180
gcacagaagt tccagggcag agtcaccata accagggaca cgtccatgag cacagcctac 240
acggagctga gcagcctgag atctgaggac acggccgtgt attactgtgc gaga 294

<210> SEQ ID NO 298
<211> LENGTH: 260
<212> TYPE: DNA
<213> ORGANISM: Homo sapiens

<400> SEQUENCE: 298
agaagcctgg ggcctcagtg aaggtctcct gcaaggcttc tggatacacc ttcaccagct 60
actgtatgca ctgggtgcac caggtccatg cacaagggct tgagtggatg ggattggtgt 120
gccctagtga tggcagcaca agctatgcac agaagttcca ggccagagtc accataacca 180
gggacacatc catgagcaca gcctacatgg agctaagcag tctgagatct gaggacacgg 240
ccatgtatta ctgtgtgaga 260

<210> SEQ ID NO 299
<211> LENGTH: 294
<212> TYPE: DNA
<213> ORGANISM: Homo sapiens

<400> SEQUENCE: 299
caggtacagc tggtgcagtc tggggctgag gtgaagaagc ctggggcctc agtgaaggtc 60
tcctgcaagg cttctggata caccttcacc aactactgta tgcactgggt gcgccaggtc 120
catgcacaag ggcttgagtg gatgggattg gtgtgcccta gtgatggcag cacaagctat 180
gcacaaaagt tccaggccag agtcaccata accagggaca catccatgag cacagcctac 240
atggagctaa gcagtctgag atctgaggac acggccatgt attactgtgt gaga 294

<210> SEQ ID NO 300
<211> LENGTH: 296
<212> TYPE: DNA
<213> ORGANISM: Homo sapiens

<400> SEQUENCE: 300
caggtacagc tgatgcagtc tggggctgag gtgaagaagc ctggggcctc agtgaggatc 60
tcctgcaagg cttctggata caccttcacc agctactgta tgcactgggt gtgccaggcc 120
catgcacaag ggcttgagtg gatgggattg gtgtgcccta gtgatggcag cacaagctat 180
gcacagaagt tccagggcag agtcaccata accagggaca catccatggg cacagcctac 240
atggagctaa gcagcctgag atctgaggac acggccatgt attactgtgt gagaga 296

<210> SEQ ID NO 301
<211> LENGTH: 301
<212> TYPE: DNA
<213> ORGANISM: Homo sapiens

<400> SEQUENCE: 301
caggtcacct tgaaggagtc tggtcctgca ctggtgaaac ccacacagac cctcatgctg 60
acctgcacct tctctgggtt ctcactcagc acttctggaa tgggtgtggg ttagatctgt 120
cagccctcag caaaggccct ggagtggctt gcacacattt attagaatga taataaatac 180
tacagcccat ctctgaagag taggctcatt atctccaagg acacctccaa gaatgaagtg 240
gttctaacag tgatcaacat ggacattgtg gacacagcca cacattactg tgcaaggaga 300
c 301

<210> SEQ ID NO 302
<211> LENGTH: 301
<212> TYPE: DNA
<213> ORGANISM: Homo sapiens

<400> SEQUENCE: 302
caggtcacct tgaaggagtc tggtcctgtg ctggtgaaac ccacagagac cctcacgctg 60
acctgcaccg tctctgggtt ctcactcagc aatgctagaa tgggtgtgag ctggatccgt 120
cagcccccag ggaaggccct ggagtggctt gcacacattt tttcgaatga cgaaaaatcc 180
tacagcacat ctctgaagag caggctcacc atctccaagg acacctccaa aagccaggtg 240
gtccttacca tgaccaacat ggaccctgtg gacacagcca catattactg tgcacggata 300
c 301

<210> SEQ ID NO 303
<211> LENGTH: 302
<212> TYPE: DNA
<213> ORGANISM: Homo sapiens

<400> SEQUENCE: 303
cagatcacct tgaaggagtc tggtcctacg ctggtgaaac ccacacagac cctcacgctg 60
acctgcacct tctctgggtt ctcactcagc actagtggag tgggtgtggg ctggatccgt 120
cagcccccag gaaaggccct ggagtggctt gcactcattt attggaatga tgataagcgc 180
tacagcccat ctctgaagag caggctcacc atcaccaagg acacctccaa aaaccaggtg 240
gtccttacaa tgaccaacat ggaccctgtg gacacagcca catattactg tgcacacaga 300
cc 302

<210> SEQ ID NO 304
<211> LENGTH: 124
<212> TYPE: DNA
<213> ORGANISM: Homo sapiens

<400> SEQUENCE: 304
actagtggag tgggtgtggg ctggatccgt cagcccccag gaaaggccct ggagtggctt 60
gcactcattt attgggatga tgataagcgc tacagcccat ctctgaagag caggctcacc 120
atca 124

<210> SEQ ID NO 305
<211> LENGTH: 210
<212> TYPE: DNA
<213> ORGANISM: Homo sapiens

<400> SEQUENCE: 305
gctggtgaaa cccacacaga ccctcacgct gacctgcacc ttctctgggt tctcactcag 60
cactagtgga gtgggtgtgg gctggatccg tcagccccca ggaaaggccc tggagtggct 120
tgcactcatt tattgggatg atgataagcg ctacagccca tctctgaaga gcaggctcac 180
cattaccaag gacacctcca aaaaccaggt 210

<210> SEQ ID NO 306
<211> LENGTH: 297
<212> TYPE: DNA
<213> ORGANISM: Homo sapiens

<400> SEQUENCE: 306
cagatcacct tgaaggagtc tggtcctacg ctggtgaaac ccacacagac cctcacgctg 60
acctgcacct tctctgggtt ctcactcagc actagtggag tgggtgtggg ctggatccgt 120
cagcccccag gaaaggccct ggagtggctt gcactcattt attggaatga tgataagcgc 180
tacagcccat ctctgaagag caggctcacc atcaccaagg acacctccaa aaaccaggtg 240
gtccttacaa tgaccaacat ggaccctgtg gacacaggca catattactg tgtacgg 297

<210> SEQ ID NO 307
<211> LENGTH: 301
<212> TYPE: DNA
<213> ORGANISM: Homo sapiens

<400> SEQUENCE: 307
cagatcacct tgaaggagtc tggtcctacg ctggtgaaac ccacacagac cctcacgctg 60

-continued

```
acctgcacct tctctgggtt ctcactcagc actagtggag tgggtgtggg ctggatccgt    120

cagcccccag gaaaggccct ggagtggctt gcactcattt attgggatga tgataagcgc    180

tacggcccat ctctgaagag caggctcacc atcaccaagg acacctccaa aaaccaggtg    240

gtccttacaa tgaccaacat ggaccctgtg gacacagcca catattactg tgcacacaga    300

c                                                                    301


<210> SEQ ID NO 308
<211> LENGTH: 300
<212> TYPE: DNA
<213> ORGANISM: Homo sapiens

<400> SEQUENCE: 308

cagatcacct tgaaggagtc tggtcctacg ctggtaaaac ccacacagac cctcacgctg     60

acctgcacct tctctgggtt ctcactcagc actagtggag tgggtgtggg ctggatccgt    120

cagcccccag gaaaggccct ggagtggctt gcactcattt attgggatga tgataagcgc    180

tacggcccat ctctgaagag caggctcacc atcaccaagg acacctccaa aaaccaggtg    240

gtccttacaa tgaccaacat ggaccctgtg gacacagcca catattactg tgcacacaga    300


<210> SEQ ID NO 309
<211> LENGTH: 294
<212> TYPE: DNA
<213> ORGANISM: Homo sapiens

<400> SEQUENCE: 309

cagatcacct tgaaggagtc tggtcctacg ctggtgaaac ccacacagac cctcacgctg     60

acctgcacct tctctgggtt ctcactcagc actagtggag tgggtgtggg ctggatccgt    120

cagcccccag gaaaggccct ggagtggctt gcactcattt attggaatga tgataagcgc    180

tacagcccat ctctgaagag caggctcacc atcaccaagg acacctccaa aaaccaggtg    240

gtccttacaa tgaccaacat ggaccctgtg gacacaggca catattactg tgta          294


<210> SEQ ID NO 310
<211> LENGTH: 301
<212> TYPE: DNA
<213> ORGANISM: Homo sapiens

<400> SEQUENCE: 310

caggtcacct tgaaggagtc tggtcctgcg ctggtgaaac ccacacagac cctcacactg     60

acctgcacct tctctgggtt ctcactcagc actagtggaa tgcgtgtgag ctggatccgt    120

cagcccccag gaaaggccct ggagtggctt gcactcattt attgggatga tgataagcgc    180

tacagcccat ctctgaagag caggctcacc atcaccaagg acacctccaa aaaccaggtg    240

gtccttacaa tgaccaacat ggaccctgtg gacacagcca catattactg tgcacacaga    300

c                                                                    301


<210> SEQ ID NO 311
<211> LENGTH: 301
<212> TYPE: DNA
<213> ORGANISM: Homo sapiens

<400> SEQUENCE: 311

caggtcacct tgaaggagtc tggtcctacg ctggtgaaac ccacacagac cctcacgctg     60

acctgcacct tctctgggtt ctcactcagc actagtggag tgggtgtggg ctggatccgt    120

cagcccccag gaaaggccct ggagtggctt gcactcattt attgggatga tgataagcgc    180
```

tacggcccat ctctgaagag caggctcacc atcaccaagg acacctccaa aaaccaggtg 240
gtccttacaa tgaccaacat ggaccctgtg gacacagcca catattactg tgcacacaga 300
c 301

<210> SEQ ID NO 312
<211> LENGTH: 297
<212> TYPE: DNA
<213> ORGANISM: Homo sapiens

<400> SEQUENCE: 312
cagatcacct tgaaggagtc tggtcctacg ctggtgaaac ccacacagac cctcacgctg 60
acctgcacct tctctgggtt ctcactcagc actagtggag tgggtgtggg ctggatccgt 120
cagcccccag gaaaggccct ggagtggctt gcactcattt attgggatga tgataagcgc 180
tacagcccat ctctgaagag caggctcacc atcaccaagg acacctccaa aaaccaggtg 240
gtccttacaa tgaccaacat ggaccctgtg gacacagcca catattactg tgcacgg 297

<210> SEQ ID NO 313
<211> LENGTH: 301
<212> TYPE: DNA
<213> ORGANISM: Homo sapiens

<400> SEQUENCE: 313
caggtcacct tgagggagtc tggtcctgcg ctggtgaaac ccacacagac cctcacactg 60
acctgcacct tctctgggtt ctcactcagc actagtggaa tgtgtgtgag ctggatccgt 120
cagcccccag ggaaggccct ggagtggctt gcactcattg attgggatga tgataaatac 180
tacagcacat ctctgaagac caggctcacc atctccaagg acacctccaa aaaccaggtg 240
gtccttacaa tgaccaacat ggaccctgtg gacacagcca cgtattactg tgcacggata 300
c 301

<210> SEQ ID NO 314
<211> LENGTH: 290
<212> TYPE: DNA
<213> ORGANISM: Homo sapiens

<400> SEQUENCE: 314
caggtcacct tgagggagtc tggtcctgcg ctggtgaaac ccacacagac cctcacactg 60
acctgcacct tctctgggtt ctcactcagc actagtggaa tgtgtgtgag ctggatccgt 120
cagcccccag ggaaggccct ggagtggctt gcactcattg attgggatga tgataaatac 180
tacagcacat ctctgaagac caggctcacc atctccaagg acacctccaa aaaccaggtg 240
gtccttacaa tgaccaacat ggaccctgtg gacacggccg tgtattactg 290

<210> SEQ ID NO 315
<211> LENGTH: 290
<212> TYPE: DNA
<213> ORGANISM: Homo sapiens

<400> SEQUENCE: 315
caggtcacct tgaaggagtc tggtcctgcg ctggtgaaac ccacacagac cctcacactg 60
acctgcacct tctctgggtt ctcactcagc actagtggaa tgcgtgtgag ctggatccgt 120
cagcccccag ggaaggccct ggagtggctt gcacgcattg attgggatga tgataaattc 180
tacagcacat ctctgaagac caggctcacc atctccaagg acacctccaa aaaccaggtg 240
gtccttacaa tgaccaacat ggaccctgtg gacacggccg tgtattactg 290

<210> SEQ ID NO 316
<211> LENGTH: 288
<212> TYPE: DNA
<213> ORGANISM: Homo sapiens

<400> SEQUENCE: 316
caggtcacct tgaaggagtc tggtcctgcg ctggtgaaac ccacacagac cctcacactg 60
acctgcacct tctctgggtt ctcactcagc actagtggaa tgcgtgtgag ctggatccgt 120
cagcccccag ggaaggccct ggagtggctt gcacgcattg attgggatga tgataaattc 180
tacagcacat ctctgaagac caggctcacc atctccaagg acacctccaa aaaccaggtg 240
gtccttacaa tgaccaacat ggaccctgtg gacacagcca cgtattac 288

<210> SEQ ID NO 317
<211> LENGTH: 237
<212> TYPE: DNA
<213> ORGANISM: Homo sapiens

<400> SEQUENCE: 317
tgcgctggtg aaacccacac agaccctcac actgacctgc accttctctg ggttctcact 60
cagcactagt ggaatgcgtg cgagctggat ccgtcagccc ccagggaagg ccctggagtg 120
gcttgcacgc attgattggg atgatgataa attctacagc acatctctga agaccaggct 180
caccatctcc aaggacacct ccaaaaacca ggtggtcctt acaatgacca acatgga 237

<210> SEQ ID NO 318
<211> LENGTH: 290
<212> TYPE: DNA
<213> ORGANISM: Homo sapiens

<400> SEQUENCE: 318
caggtcacct tgaaggagtc tggtcctgcg ctggtgaaac ccacacagac cctcacactg 60
acctgcacct tctctgggtt ctcactcagc actagtggaa tgcgtgtgag ctggatccgt 120
cagcccccag ggaaggccct ggagtggctt gcacgcattg attgggatga tgataaattc 180
tacagcacat ccctgaagac caggctcacc atctccaagg acacctccaa aaaccaggtg 240
gtccttacaa tgaccaacat ggaccctgtg gacacggccg tgtattactg 290

<210> SEQ ID NO 319
<211> LENGTH: 290
<212> TYPE: DNA
<213> ORGANISM: Homo sapiens

<400> SEQUENCE: 319
caggtcacct tgagggagtc tggtcctgcg ctggtgaaac ccacacagac cctcacactg 60
acctgcacct tctctgggtt ctcactcagc actagtggaa tgtgtgtgag ctggatccgt 120
cagcccccgg ggaaggccct ggagtggctt gcactcattg attgggatga tgataaatac 180
tacagcacat ctctgaagac caggctcacc atctccaagg acacctccaa aaaccaggtg 240
gtccttacaa tgaccaacat ggaccctgtg gacacggccg tgtattactg 290

<210> SEQ ID NO 320
<211> LENGTH: 290
<212> TYPE: DNA
<213> ORGANISM: Homo sapiens

<400> SEQUENCE: 320

```
caggtcacct tgagggagtc tggtcctgcg ctggtgaaac ccacacagac cctcacactg     60

acctgcgcct tctctgggtt ctcactcagc actagtggaa tgtgtgtgag ctggatccgt    120

cagcccccag ggaaggccct ggagtggctt gcacgcattg attgggatga tgataaatac    180

tacagcacat ctctgaagac caggctcacc atctccaagg acacctccaa aaaccaggtg    240

gtccttacaa tgaccaacat ggaccctgtg gacacggccg tgtattactg              290


<210> SEQ ID NO 321
<211> LENGTH: 297
<212> TYPE: DNA
<213> ORGANISM: Homo sapiens

<400> SEQUENCE: 321

cagatcacct tgaaggagtc tggtcctacg ctggtgaaac ccacacagac cctcacgctg     60

acccgcacct tctctgggtt ctcactcagc actagtggaa tgtgtgtgag ctggatccgt    120

cagcccccag ggaaggccct ggagtggctt gcactcattg attgggatga tgataaatac    180

tacagcacat ctctgaacac caggctcacc atctccaagg acacctccaa aaaccaggtg    240

gtccttacaa tgaccaacat ggaccctgtg gacacaggca catattactg tgtacgg      297


<210> SEQ ID NO 322
<211> LENGTH: 301
<212> TYPE: DNA
<213> ORGANISM: Homo sapiens

<400> SEQUENCE: 322

caggtcacct tgaaggagtc tggtcctgcg ctggtgaaac ccacacagac cctcacactg     60

acctgcacct tctctgggtt ctcactcagc actagtggaa tgcgtgtgag ctggatccgt    120

cagcccccag ggaaggccct ggagtggatt gcacgcattg attgggatga tgataaatac    180

tacagcacat ctctgaagac caggctcacc atctccaagg acacctccaa aaaccaggtg    240

gtccttacaa tgaccaacat ggaccctgtg gacacagcca cgtattactg tgcacggata    300

c                                                                    301


<210> SEQ ID NO 323
<211> LENGTH: 301
<212> TYPE: DNA
<213> ORGANISM: Homo sapiens

<400> SEQUENCE: 323

cagatcacct tgaaggagtc tggtcctacg ctggtgaaac ccacacagac cctcacgctg     60

acctgcacct tctctgggtt ctcactcagc actagtggaa tgtgtgtgag ctggatccgt    120

cagcccccag ggaaggccct ggagtggctt gcactcattg attgggatga tgataaatac    180

tacagcacat ctctgaagac caggctcacc atctccaagg acacctccaa aaaccaggtg    240

gtccttacaa tgaccaacat ggaccctgtg gacacagcca catattactg tgcacacaga    300

c                                                                    301


<210> SEQ ID NO 324
<211> LENGTH: 301
<212> TYPE: DNA
<213> ORGANISM: Homo sapiens

<400> SEQUENCE: 324

caggtcacct tgagggagtc tggtcctgcg ctggtgaaac ccacacagac cctcacactg     60
```

acctgcacct tctctgggtt ctcactcagc actagtggaa tgtgtgtgag ctggatccgt 120
cagcccccag ggaaggccct ggagtggctt gcactcattg attgggatga tgataaatac 180
tacagcacat ctctgaagac caggctcacc atctccaagg acacctccaa aaaccaggtg 240
gtccttacaa tgaccaacat ggaccctgtg gacacagcca cgtattattg tgcacggata 300
c 301

<210> SEQ ID NO 325
<211> LENGTH: 301
<212> TYPE: DNA
<213> ORGANISM: Homo sapiens

<400> SEQUENCE: 325
caggtcacct tgagggagtc tggtcctgcg ctggtgaaac ccacacagac cctcacactg 60
acctgcacct tctctgggtt ctcactcagc actagtggaa tgtgtgtgag ctggatccgt 120
cagcccccag ggaaggccct ggagtggctt gcactcattg attgggatga tgataaatac 180
tacagcacat ctctgaagac caggctcacc atctccaagg acacctccaa aaaccaggtg 240
gtccttacaa tgaccaacat ggaccctgtg gacacagcca cgtattattg tgcacggata 300
c 301

<210> SEQ ID NO 326
<211> LENGTH: 298
<212> TYPE: DNA
<213> ORGANISM: Homo sapiens

<400> SEQUENCE: 326
caggtcacct tgaaggagtc tggtcctgcg ctggtgaaac ccacagagac cctcacgctg 60
acctgcactc tctctgggtt ctcactcagc acttctggaa tgggtatgag ctggatccgt 120
cagcccccag ggaaggccct ggagtggctt gctcacattt ttttgaatga caaaaaatcc 180
tacagcacgt ctctgaagaa caggctcatc atctccaagg acacctccaa aagccaggtg 240
gtccttacca tgaccaacat ggaccctgtg gacacagcca cgtattactg tgcatgga 298

<210> SEQ ID NO 327
<211> LENGTH: 296
<212> TYPE: DNA
<213> ORGANISM: Homo sapiens

<400> SEQUENCE: 327
caggtgcagc tggtggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtggtagtac catatactac 180
gcagactctg tgaagggccg attcaccatc tccagggaca acgccaagaa ctcactgtat 240
ctgcaaatga acagcctgag agccgaggac acggccgtgt attactgtgc gagaga 296

<210> SEQ ID NO 328
<211> LENGTH: 294
<212> TYPE: DNA
<213> ORGANISM: Homo sapiens

<400> SEQUENCE: 328
caggtgcagc tgttggagtc tgggggaggc ttggtcaagc ctggagggtc cctgagactc 60
tcctgtgcag cctctggatt caccttcagt gactactaca tgagctggat ccgccaggct 120
ccagggaagg ggctggagtg ggtttcatac attagtagta gtagtagtta cacaaactac 180
gcagactctg tgaagggccg attcaccatc tccagagaca acgccaagaa ctcactgtat 240
ctgcaaatga acagcctgag agccgaggac acggccgtgt attactgtgc gaga 294

<210> SEQ ID NO 329
<211> LENGTH: 293
<212> TYPE: DNA
<213> ORGANISM: Homo sapiens

<400> SEQUENCE: 329
gaggtgcatc tggtggagtc tgggggaggc ttggtacagc ctgggggggc cctgagactc 60
tcctgtgcag cctctggatt caccttcagt aactacgaca tgcactgggt ccgccaagct 120
acaggaaaag gtctggagtg ggtctcagcc aatggtactg ctggtgacac atactatcca 180
ggctccgtga aggggcgatt caccatctcc agagaaaatg ccaagaactc cttgtatctt 240
caaatgaaca gcctgagagc cggggacacg gctgtgtatt actgtgcaag aga 293

<210> SEQ ID NO 330
<211> LENGTH: 293
<212> TYPE: DNA
<213> ORGANISM: Homo sapiens

<400> SEQUENCE: 330
gaggtgcatc tggtggagtc tgggggaggc ttggtacagc ctgggggggc cctgagactc 60
tcctgtgcag cctctggatt caccttcagt aactacgaca tgcactgggt ccgccaagct 120
acaggaaaag gtctggagtg ggtctcagcc aatggtactg ctggtgacac atactatcca 180
ggctccgtga aggggcgatt caccatctcc agagaaaatg ccaagaactc cttgtatctt 240
caaatgaaca gcctgagagc cggggacacg gctgtgtatt actgtgcaag aga 293

<210> SEQ ID NO 331
<211> LENGTH: 291
<212> TYPE: DNA
<213> ORGANISM: Homo sapiens

<400> SEQUENCE: 331
gaggtgcagc tggtggagtc tgggggaggc ttggtacagc ctggggggtc cctgagactc 60
tcctgtgcag cctgtggatt caccttcagt agctacgaca tgcactgggt ccgccaagct 120
acaggaaaag gtctggagtg ggtctcagct attggtactg ctggtgacac atactatcca 180
ggctccgtga agggccaatt caccatctcc agagaaaatg ccaagaactc cttgtatctt 240
caaatgaaca gcctgagagc cggggacacg gctgtgtatt actgtgcaag a 291

<210> SEQ ID NO 332
<211> LENGTH: 302
<212> TYPE: DNA
<213> ORGANISM: Homo sapiens

<400> SEQUENCE: 332
gaggtgcagc tggtggagtc tgggggagcc ttggtaaagc ctggggggtc ccttagactc 60
tcctgtgcag cctctggatt cactttcagt aacgcctgga tgagctgggt ccgccaggct 120
ccagggaagg ggctggagtg ggttggccgt attaaaagca aaactgatgg tgggacaaca 180
gactacgctg cacccgtgaa aggcagattc accatctcaa gagatgattc aaaaaacacg 240
ctgtatctgc aaatgaacag cctgaaaacc gaggacacag ccgtgtatta ctgtaccaca 300
ga 302

<210> SEQ ID NO 333
<211> LENGTH: 302
<212> TYPE: DNA
<213> ORGANISM: Homo sapiens

<400> SEQUENCE: 333
gaggtgcagc tggtggagtc tgccggagcc ttggtacagc ctgggggtc ccttagactc 60 tcctgtgcag cctctggatt cacttgcagt aacgcctgga tgagctgggt ccgccaggct 120
ccagggaagg ggctggagtg ggttggccgt attaaaagca aagctaatgg tgggacaaca 180
gactacgctg cacctgtgaa aggcagattc accatctcaa gagttgattc aaaaaacacg 240
ctgtatctgc aaatgaacag cctgaaaacc gaggacacag ccgtgtatta ctgtaccaca 300
ga 302

<210> SEQ ID NO 334
<211> LENGTH: 302
<212> TYPE: DNA
<213> ORGANISM: Homo sapiens

<400> SEQUENCE: 334
gaggtgcagc tggtggagtc tgggggaggc ttggtaaagc ctgggggtc ccttagactc 60 tcctgtgcag cctctggatt cactttcagt aacgcctgga tgagctgggt ccgccaggct 120
ccagggaagg ggctggagtg ggttggccgt attgaaagca aaactgatgg tgggacaaca 180
gactacgctg cacccgtgaa aggcagattc accatctcaa gagatgattc aaaaaacacg 240
ctgtatctgc aaatgaacag cctgaaaacc gaggacacag ccgtgtatta ctgtaccaca 300
ga 302

<210> SEQ ID NO 335
<211> LENGTH: 302
<212> TYPE: DNA
<213> ORGANISM: Homo sapiens

<400> SEQUENCE: 335
gaggtgcagc tggtggagtc tgggggaggc ttggtaaagc ctgggggtc ccttagactc 60 tcctgtgcag cctctggatt cactttcagt aacgcctgga tgagctgggt ccgccaggct 120
ccagggaagg ggctggagtg ggttggccgt attaaaagca aaactgatgg tgggacaaca 180
gactacgctg cacccgtgaa aggcagattc accatctcaa gagatgattc aaaaaacacg 240
ctgtatctgc aaatgaacag tctgaaaacc gaggacacag ccgtgtatta ctgtaccaca 300
ga 302

<210> SEQ ID NO 336
<211> LENGTH: 302
<212> TYPE: DNA
<213> ORGANISM: Homo sapiens

<400> SEQUENCE: 336
gaggtgcagc tggtggagtc tgggggaggc ttggtaaagc ctgggggtc ccttagactc 60 tcctgtgcag cctctggatt cactttcagt aacgcctgga tgagctgggt ccgccaggct 120
ccagggaagg ggctggagtg ggtcggccgt attaaaagca aaactgatgg tgggacaaca 180
aactacgctg cacccgtgaa aggcagattc accatctcaa gagatgattc aaaaaacacg 240
ctgtatctgc aaatgaacag cctgaaaacc gaggacacag ccgtgtatta ctgtaccaca 300
ga 302

<210> SEQ ID NO 337
<211> LENGTH: 302
<212> TYPE: DNA
<213> ORGANISM: Homo sapiens

<400> SEQUENCE: 337
gaggtgcagc tggtggagtc tgggggaggc ttggtaaagc ctggggggtc ccttagactc 60
tcctgtgcag cctctggttt cactttcagt aacgcctgga tgaactgggt ccgccaggct 120
ccagggaagg ggctggagtg ggtcggccgt attaaaagca aaactgatgg tgggacaaca 180
gactacgctg cacccgtgaa aggcagattc accatctcaa gagatgattc aaaaaacacg 240
ctgtatctgc aaatgaacag cctgaaaacc gaggacacag ccgtgtatta ctgtaccaca 300
ga 302

<210> SEQ ID NO 338
<211> LENGTH: 302
<212> TYPE: DNA
<213> ORGANISM: Homo sapiens

<400> SEQUENCE: 338
gaggtgcagc tggtggagtc tgggggaggc ttggtaaagc ctggggggtc ccttagactc 60
tcctgtgcag cctctggttt cactttcagt aacgcctgga tgaactgggt ccgccaggct 120
ccagggaagg ggctggagtg ggtcggccgt attaaaagca aaactgatgg tgggacaaca 180
gactacgctg cacccgtgaa aggcagattc accatctcaa gagatgattc aaaaaacacg 240
ctgtatctgc aaatgaacag cctgaaaacc gaggacacag ccgtgtatta ctgtaccaca 300
ga 302

<210> SEQ ID NO 339
<211> LENGTH: 302
<212> TYPE: DNA
<213> ORGANISM: Homo sapiens

<400> SEQUENCE: 339
gaggtgcagc tggtggagtc tgcgggaggc ttggtacagc ctggggggtc ccttagactc 60
tcctgtgcag cctctggatt cacttgcagt aacgcctgga tgagctgggt ccgccaggct 120
ccagggaagg ggctggagtg ggttggctgt attaaaagca aagctaatgg tgggacaaca 180
gactacgctg cacctgtgaa aggcagattc accatctcaa gagatgattc aaaaaacacg 240
ctgtatctgc aaatgatcag cctgaaaacc gaggacacgg ccgtgtatta ctgtaccaca 300
gg 302

<210> SEQ ID NO 340
<211> LENGTH: 296
<212> TYPE: DNA
<213> ORGANISM: Homo sapiens

<400> SEQUENCE: 340
gaggtacaac tggtggagtc tgggggaggc ttggtacagc ctggggggtc cctgagactc 60
tcctgtgcag cctctggatt caccttcagt aacagtgaca tgaactgggc ccgcaaggct 120
ccaggaaagg ggctggagtg ggtatcgggt gttagttgga atggcagtag gacgcactat 180
gtggactccg tgaagcgccg attcatcatc tccagagaca attccaggaa ctccctgtat 240
ctgcaaaaga acagacggag agccgaggac atggctgtgt attactgtgt gagaaa 296

<210> SEQ ID NO 341
<211> LENGTH: 296
<212> TYPE: DNA
<213> ORGANISM: Homo sapiens

<400> SEQUENCE: 341
gaggtgcagc tggtggagtc tgggggaggc ttggtacagc ctggggggtc cctgagactc 60
tcctgtgcag cctctggatt caccttcagt aacagtgaca tgaactgggc ccgcaaggct 120
ccaggaaagg ggctggagtg ggtatcgggt gttagttgga atggcagtag gacgcactat 180
gtggactccg tgaagcgccg attcatcatc tccagagaca attccaggaa ctccctgtat 240
ctgcaaaaga acagacggag agccgaggac atggctgtgt attactgtgt gagaaa 296

<210> SEQ ID NO 342
<211> LENGTH: 296
<212> TYPE: DNA
<213> ORGANISM: Homo sapiens

<400> SEQUENCE: 342
acagtgcagc tggtggagtc tgggggaggc ttggtagagc ctggggggtc cctgagactc 60
tcctgtgcag cctctggatt caccttcagt aacagtgaca tgaactgggt ccgccaggct 120
ccaggaaagg ggctggagtg ggtatcgggt gttagttgga atggcagtag gacgcactat 180
gcagactctg tgaagggccg attcatcatc tccagagaca attccaggaa cttcctgtat 240
cagcaaatga acagcctgag gcccgaggac atggctgtgt attactgtgt gagaaa 296

<210> SEQ ID NO 343
<211> LENGTH: 296
<212> TYPE: DNA
<213> ORGANISM: Homo sapiens

<400> SEQUENCE: 343
gaggtgcagc tggtggagtc tgggggaggt gtggtacggc ctggggggtc cctgagactc 60
tcctgtgcag cctctggatt cacctttgat gattatggca tgagctgggt ccgccaagct 120
ccagggaagg ggctggagtg ggtctctggt attaattgga atggtggtag cacaggttat 180
gcagactctg tgaagggccg attcaccatc tccagagaca acgccaagaa ctccctgtat 240
ctgcaaatga acagtctgag agccgaggac acggccttgt atcactgtgc gagaga 296

<210> SEQ ID NO 344
<211> LENGTH: 296
<212> TYPE: DNA
<213> ORGANISM: Homo sapiens

<400> SEQUENCE: 344
gaggtgcagc tggtggagtc tgggggaggc ctggtcaagc ctggggggtc cctgagactc 60
tcctgtgcag cctctggatt caccttcagt agctatagca tgaactgggt ccgccaggct 120
ccagggaagg ggctggagtg ggtctcatcc attagtagta gtagtagtta catatactac 180
gcagactcag tgaagggccg attcaccatc tccagagaca acgccaagaa ctcactgtat 240
ctgcaaatga acagcctgag agccgaggac acggctgtgt attactgtgc gagaga 296

<210> SEQ ID NO 345
<211> LENGTH: 296
<212> TYPE: DNA
<213> ORGANISM: Homo sapiens

<400> SEQUENCE: 345
gaggtgcaac tggtggagtc tgggggaggc ctggtcaagc ctggggggtc cctgagactc 60
tcctgtgcag cctctggatt caccttcagt agctatagca tgaactgggt ccgccaggct 120
ccagggaagg ggctggagtg ggtctcatcc attagtagta gtagtagtta catatactac 180
gcagactcag tgaagggccg attcaccatc tccagagaca acgccaagaa ctcactgtat 240
ctgcaaatga acagcctgag agccgaggac acggctgtgt attactgtgc gagaga 296

<210> SEQ ID NO 346
<211> LENGTH: 302
<212> TYPE: DNA
<213> ORGANISM: Homo sapiens

<400> SEQUENCE: 346
gaggtgcatc tggtggagtc tgggggagcc ttggtacagc ctggggggtc cctgagactc 60
tcctgtgcag cctctggatt caccttcagt tactactaca tgagcggggt ccgccaggct 120
cccgggaagg ggctggaatg ggtaggtttc attagaaaca aagctaatgg tgggacaaca 180
gaatagacca cgtctgtgaa aggcagattc acaatctcaa gagatgattc caaaagcatc 240
acctatctgc aaatgaagag cctgaaaacc gaggacacgg ccgtgtatta ctgttccaga 300
ga 302

<210> SEQ ID NO 347
<211> LENGTH: 302
<212> TYPE: DNA
<213> ORGANISM: Homo sapiens

<400> SEQUENCE: 347
gaggtgcagc tggtggagtc tgggggaggc ttggtacagc ctggggggtc cctgagactc 60
tcctgtgcag cctctggatt caccttcagt tactactaca tgagcggggt ccgccaggct 120
cccgggaagg ggctggaatg ggtaggtttc attagaaaca aagctaatgg tgggacaaca 180
gaatagacca cgtctgtgaa aggcagattc acaatctcaa gagatgattc caaaagcatc 240
acctatctgc aaatgaagag cctgaaaacc gaggacacgg ccgtgtatta ctgttccaga 300
ga 302

<210> SEQ ID NO 348
<211> LENGTH: 296
<212> TYPE: DNA
<213> ORGANISM: Homo sapiens

<400> SEQUENCE: 348
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gaaaga 296

<210> SEQ ID NO 349
<211> LENGTH: 296
<212> TYPE: DNA
<213> ORGANISM: Homo sapiens

<400> SEQUENCE: 349
gaggtgcagc tgttggagtc tgggggaggc ttggtacagc ctggggggtc cctgagactc 60

-continued

```
tcctgtgcag cctctggatt cacctttagc agctatgcca tgagctgggt ccgccaggct    120

ccagggaagg ggctggagtg ggtctcagct attagtggta gtggtggtag cacatactac    180

ggagactccg tgaagggccg gttcaccatc tcaagagaca attccaagaa cacgctgtat    240

ctgcaaatga acagcctgag agccgaggac acggccgtat attactgtgc gaaaga        296


<210> SEQ ID NO 350
<211> LENGTH: 294
<212> TYPE: DNA
<213> ORGANISM: Homo sapiens

<400> SEQUENCE: 350

gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagtt atttatagcg gtggtagtag cacatactat    180

gcagactccg tgaagggccg gttcaccatc tccagagata attccaagaa cacgctgtat    240

ctgcaaatga acagcctgag agccgaggac acggccgtat attactgtgc gaaa          294


<210> SEQ ID NO 351
<211> LENGTH: 296
<212> TYPE: DNA
<213> ORGANISM: Homo sapiens

<400> SEQUENCE: 351

gaggtgcagc tggtggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaggac acggccgtat attactgtgc gaaaga        296


<210> SEQ ID NO 352
<211> LENGTH: 294
<212> TYPE: DNA
<213> ORGANISM: Homo sapiens

<400> SEQUENCE: 352

gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct atttatagca gtggtagtag cacatactat    180

gcagactccg tgaagggccg gttcaccatc tccagagaca attccaagaa cacgctgtat    240

ctgcaaatga acagcctgag agccgaggac acggccgtat attactgtgc gaaa          294


<210> SEQ ID NO 353
<211> LENGTH: 296
<212> TYPE: DNA
<213> ORGANISM: Homo sapiens

<400> SEQUENCE: 353

gagatgcagc tggtggagtc tgggggaggc ttgcaaaagc ctgcgtggtc cccgagactc     60

tcctgtgcag cctctcaatt caccttcagt agctactaca tgaactgtgt ccgccaggct    120

ccagggaatg ggctggagtt ggtttgacaa gttaatccta atgggggtag cacatacctc    180

atagactccg gtaaggaccg attcaatacc tccagagata acgccaagaa cacacttcat    240

ctgcaaatga acagcctgaa aaccgaggac acggccctct attagtgtac cagaga        296
```

<210> SEQ ID NO 354
<211> LENGTH: 296
<212> TYPE: DNA
<213> ORGANISM: Homo sapiens

<400> SEQUENCE: 354
gagatgcagc tggtggagtc tgggggaggc ttggcaaagc ctgcgtggtc cccgagactc 60
tcctgtgcag cctctcaatt caccttcagt agctactaca tgaactgtgt ccgccaggct 120
ccagggaatg ggctggagtt ggtttgacaa gttaatccta atgggggtag cacatacctc 180
atagactccg gtaaggaccg attcaatacc tccagagata acgccaagaa cacacttcat 240
ctgcaaatga acagcctgaa aaccgaggac acggccctct attagtgtac cagaga 296

<210> SEQ ID NO 355
<211> LENGTH: 294
<212> TYPE: DNA
<213> ORGANISM: Homo sapiens

<400> SEQUENCE: 355
gagatgcagc tggtggagtc tgggggaggc ttggcaaagc ctgcgtggtc cccgagactc 60
tcctgtgcag cctctcaatt caccttcagt agctactaca tgaactgtgt ccgccaggct 120
ccagggaatg ggctggagtt ggttggacaa gttaatccta atgggggtag cacatacctc 180
atagactccg gtaaggaccg attcaatacc tccagagata acgccaagaa cacacttcat 240
ctgcaaatga acagcctgaa aaccgaggac acggccctgt attagtgtac caga 294

<210> SEQ ID NO 356
<211> LENGTH: 296
<212> TYPE: DNA
<213> ORGANISM: Homo sapiens

<400> SEQUENCE: 356
caggtgcagc tggtggagtc tgggggaggc gtggtccagc ctgggaggtc cctgagactc 60
tcctgtgcag cctctggatt caccttcagt agctatgcta tgcactgggt ccgccaggct 120
ccaggcaagg ggctagagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgaggac acggctgtgt attactgtgc gagaga 296

<210> SEQ ID NO 357
<211> LENGTH: 296
<212> TYPE: DNA
<213> ORGANISM: Homo sapiens

<400> SEQUENCE: 357
caggtgcagc tggtggagtc tgggggaggc gtggtccagc ctgggggtc cctgagactc 60 tcctgtgcag cgtctggatt caccttcagt agctatggca tgcactgggt ccgccaggct 120
ccaggcaagg ggctggagtg ggtggcattt atacggtatg atggaagtaa taaatactat 180
gcagactccg tgaagggccg attcaccatc tccagagaca attccaagaa cacgctgtat 240
ctgcaaatga acagcctgag agctgaggac acggctgtgt attactgtgc gaaaga 296

<210> SEQ ID NO 358
<211> LENGTH: 296
<212> TYPE: DNA
<213> ORGANISM: Homo sapiens

<400> SEQUENCE: 358
caggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agctgaggac acggctgtgt attactgtgc gagaga 296

<210> SEQ ID NO 359
<211> LENGTH: 296
<212> TYPE: DNA
<213> ORGANISM: Homo sapiens

<400> SEQUENCE: 359
caggtgcagc tggtggagtc tgggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgaggac acggctgtgt attactgtgc gagaga 296

<210> SEQ ID NO 360
<211> LENGTH: 296
<212> TYPE: DNA
<213> ORGANISM: Homo sapiens

<400> SEQUENCE: 360
caggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctagagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgagggc acggctgtgt attactgtgc gagaga 296

<210> SEQ ID NO 361
<211> LENGTH: 296
<212> TYPE: DNA
<213> ORGANISM: Homo sapiens

<400> SEQUENCE: 361
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctagagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgaggac acggctgtgt attactgtgc gagaga 296

<210> SEQ ID NO 362
<211> LENGTH: 296
<212> TYPE: DNA
<213> ORGANISM: Homo sapiens

<400> SEQUENCE: 362
caggtgcagc tggtggagtc tgggggaggc gtggtccagc ctgggaggtc cctgagactc 60
tcctgtgcag cctctggatt caccttcagt agctatgcta tgcactgggt ccgccaggct 120
ccaggcaagg ggctagagtg ggtggcagtt atatcatatg atggaagtaa taaatactac 180
gcagactccg tgaagggccg attcaccatc tccagagaca attccaagaa cacgctgtat 240
ctgcaaatga acagcctgag agccgaggac acggctgtgt attactgtgc gagaga 296

<210> SEQ ID NO 363
<211> LENGTH: 294
<212> TYPE: DNA
<213> ORGANISM: Homo sapiens

<400> SEQUENCE: 363
caggtgcagc tggtggactc tgggggaggc gtggtccagc ctgggaggtc cctgagactc 60
tcctgtgcag cctctgcatt caccttcagt agctatgcta tgcactgggt ccgccaggct 120
ccaggcaagg ggctagagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgaggac acggctgtgt attactgtgc gaga 294

<210> SEQ ID NO 364
<211> LENGTH: 296
<212> TYPE: DNA
<213> ORGANISM: Homo sapiens

<400> SEQUENCE: 364
caggtgcagc tggtggagtc tgggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atggaagtaa taaatactac 180
gcagactccg tgaagggccg attcgccatc tccagagaca attccaagaa cacgctgtat 240
ctgcaaatga acagcctgag agctgaggac acggctgtgt attactgtgc gagaga 296

<210> SEQ ID NO 365
<211> LENGTH: 296
<212> TYPE: DNA
<213> ORGANISM: Homo sapiens

<400> SEQUENCE: 365
caggtgcagc tggtggagtc tgggggaggc gtggtccagc ctgggaggtc cctgagactc 60
tcctgtgcag cctctggatt caccttcagt agctatgcta tgcactgggt ccgccaggct 120
ccaggcaagg ggctagagtg ggtggcagtt atatcatatg atggaagtaa taaatactac 180
acagactccg tgaagggccg attcaccatc tccagagaca attccaagaa cacgctgtat 240
ctgcaaatga acagcctgag agctgaggac acggctgtgt attactgtgc gagaga 296

<210> SEQ ID NO 366
<211> LENGTH: 296
<212> TYPE: DNA
<213> ORGANISM: Homo sapiens

<400> SEQUENCE: 366
caggtgcagc tggtggagtc tgggggaggc gtggtccagc ctgggaggtc cctgagactc 60
tcctgtgcag cgtctggatt caccttcagt agctatgcta tgcactgggt ccgccaggct 120
ccaggcaagg ggctagagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgaggac acggctgtgt attactgtgc gagaga 296

<210> SEQ ID NO 367

<211> LENGTH: 296
<212> TYPE: DNA
<213> ORGANISM: Homo sapiens

<400> SEQUENCE: 367
caggtgcagc tggtggagtc tggggggggc gtggtccagc ctgggaggtc cctgagactc    60
tcctgtgcag cgtctggatt caccttcagt agctatggca tgcactgggt ccgccaggct   120
ccaggcaagg ggctagagtg ggtggcagtt atatcatatg atggaagtaa taaatactac   180
gcagactccg tgaagggccg attcaccatc tccagagaca attccaagaa cacgctgtat   240
ctgcaaatga acagcctgag agccgaggac acggctgtgt attactgtgc gagaga       296

<210> SEQ ID NO 368
<211> LENGTH: 296
<212> TYPE: DNA
<213> ORGANISM: Homo sapiens

<400> SEQUENCE: 368
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctagagtg ggtggcagtt atatcatatg atggaagtaa taaatactac   180
gcagactccg tgaagggccg attcaccatc tccagagaca attccaagaa caggctgtat   240
ctgcaaatga acagcctgag agctgaggac acggctgtgt attactgtgc gagaga       296

<210> SEQ ID NO 369
<211> LENGTH: 296
<212> TYPE: DNA
<213> ORGANISM: Homo sapiens

<400> SEQUENCE: 369
caggtgcagc tggtggagtc tgggggaggc gtggtccagc ctgggaggtc cctgagactc    60
tcctgtgcag cctctggatt caccttcagt agctatgcta tgcactgggt ccgccaggct   120
ccaggcaagg ggctggagtg ggtggcagtt atatcatatg atggaagtaa taaatactac   180
gcagactccg tgaagggccg attcaccatc tccagagaca attccaagaa cacgctgtat   240
cttcaaatga acagcctgag agctgaggac acggctgtgt attactgtgc gagaga       296

<210> SEQ ID NO 370
<211> LENGTH: 296
<212> TYPE: DNA
<213> ORGANISM: Homo sapiens

<400> SEQUENCE: 370
caggtgcagc tggtggagtc tgggggaggc gtggtccagc ctgggaggtc cctgagactc    60
tcctgtgcag cctctggatt caccttcagt agctatgcta tgcactgggt ccgccaggct   120
ccaggcaagg ggctagagtg ggtggcagtt atatcatatg atggaagtaa taaatactac   180
gcagactccg tgaagggccg attcaccatc tccagagaca attccaagaa cacgctgtat   240
ctgcaaatga gcagcctgag agctgaggac acggctgtgt attactgtgc gagaga       296

<210> SEQ ID NO 371
<211> LENGTH: 296
<212> TYPE: DNA
<213> ORGANISM: Homo sapiens

<400> SEQUENCE: 371
caggtgcagc tggtggagtc tgggggaggc gtggtccagc ctgggaggtc cctgagactc    60
tcctgtgcag cctctggatt caccttcagt agctatgcta tgcactgggt ccgccaggcc 120
ccaggcaagg ggctagagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgaggac acggctgtgt attactgtgc gagaga 296

<210> SEQ ID NO 372
<211> LENGTH: 296
<212> TYPE: DNA
<213> ORGANISM: Homo sapiens

<400> SEQUENCE: 372
caggtgcagc tggtggagtc tgggggaggc gtggtccagc ctgggaggtc cctgagactc 60
tcctgtgcag cctctggatt caccttcagt agctatgcta tgcactgggt ccgccaggct 120
ccgggcaagg ggctagagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgaggac acggctgtgt attactgtgc gagaga 296

<210> SEQ ID NO 373
<211> LENGTH: 296
<212> TYPE: DNA
<213> ORGANISM: Homo sapiens

<400> SEQUENCE: 373
caggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agctgaggac acggctgtgt attactgtgc gaaaga 296

<210> SEQ ID NO 374
<211> LENGTH: 296
<212> TYPE: DNA
<213> ORGANISM: Homo sapiens

<400> SEQUENCE: 374
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatcatatg atggaagtaa taaatactac 180
gcagactccg tgaagggccg attcaccatc tccagagaca attccaagaa cacgctgtat 240
ctgcaaatga acagcctgag agctgaggac acggctgtgt attactgtgc gagaga 296

<210> SEQ ID NO 375
<211> LENGTH: 294
<212> TYPE: DNA
<213> ORGANISM: Homo sapiens

<400> SEQUENCE: 375
caggtgcagc tggtggagtc tgggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atggaagcaa taaatactac 180
gcagactccg tgaagggccg attcaccatc tccagagaca attccaagaa cacgctgtat 240
ctgcaaatga acagcctgag agctgaggac acggctgtgt attactgtgc gaga 294

<210> SEQ ID NO 376
<211> LENGTH: 296
<212> TYPE: DNA
<213> ORGANISM: Homo sapiens

<400> SEQUENCE: 376
caggtgcagc tggtggagtc tgggggaggc gtggtccagc ctgggaggtc cctgagactc 60
tcctgtgcag cgtctggatt caccttcagt agctatgcta tgcactgggt ccgccaggct 120
ccaggcaagg ggctggagtg ggtggcagtt atatcatatg atggaagcaa taaatactac 180
gcagactccg tgaagggccg attcaccatc tccagagaca attccaagaa cacgctgtat 240
ctgcaaatga acagcctgag agctgaggac acggctgtgt attactgtgc gaaaga 296

<210> SEQ ID NO 377
<211> LENGTH: 298
<212> TYPE: DNA
<213> ORGANISM: Homo sapiens

<400> SEQUENCE: 377
gaggtggagc tgatagagtc catagaggac ctgagacaac ctgggaagtt cctgagactc 60
tcctgtgtag cctctagatt cgccttcagt agcttctgaa tgagccgagt tcaccagtct 120
ccaggcaagg ggctggagtg agtaatagat ataaaagatg atggaagtca gatacaccat 180
gcagactctg tgaagggcag attctccatc tccaaagaca atgctaagaa ctctctgtat 240
ctgcaaatga acactcagag agctgaggac gtggccgtgt atggctatac ataaggtc 298

<210> SEQ ID NO 378
<211> LENGTH: 296
<212> TYPE: DNA
<213> ORGANISM: Homo sapiens

<400> SEQUENCE: 378
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggtatg atggaagtaa taaatactat 180
gcagactccg tgaagggccg attcaccatc tccagagaca attccaagaa cacgctgtat 240
ctgcaaatga acagcctgag agccgaggac acggctgtgt attactgtgc gagaga 296

<210> SEQ ID NO 379
<211> LENGTH: 296
<212> TYPE: DNA
<213> ORGANISM: Homo sapiens

<400> SEQUENCE: 379
caggtacagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggtatg atggaagtaa taaatactat 180
gcagactccg cgaagggccg attcaccatc tccagagaca attccacgaa cacgctgttt 240
ctgcaaatga acagcctgag agccgaggac acggctgtgt attactgtgc gagaga 296

<210> SEQ ID NO 380
<211> LENGTH: 296
<212> TYPE: DNA
<213> ORGANISM: Homo sapiens

<400> SEQUENCE: 380
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggtatg atggaagtaa taaatactat 180
gcagactccg tgaagggccg attcaccatc tccagagaca actccaagaa cacgctgtat 240
ctgcaaatga acagcctgag agccgaggac acggctgtgt attactgtgc gaaaga 296

<210> SEQ ID NO 381
<211> LENGTH: 296
<212> TYPE: DNA
<213> ORGANISM: Homo sapiens

<400> SEQUENCE: 381
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agccgaggac acggctgtgt attactgtgc gagaga 296

<210> SEQ ID NO 382
<211> LENGTH: 296
<212> TYPE: DNA
<213> ORGANISM: Homo sapiens

<400> SEQUENCE: 382
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agccgaggac acggctgtgt attactgtgc gagaga 296

<210> SEQ ID NO 383
<211> LENGTH: 296
<212> TYPE: DNA
<213> ORGANISM: Homo sapiens

<400> SEQUENCE: 383
gaggtgcagc tggtggagtc tgggggaggc ttggtacagc ctgggggatc cctgagactc 60
tcctgtgcag cctctggatt caccttcagt aacagtgaca tgaactgggt ccatcaggct 120
ccaggaaagg ggctggagtg ggtatcgggt gttagttgga atggcagtag gacgcactat 180
gcagactctg tgaagggccg attcatcatc tccagagaca attccaggaa caccctgtat 240
ctgcaaacga atagcctgag ggccgaggac acggctgtgt attactgtgt gagaaa 296

<210> SEQ ID NO 384
<211> LENGTH: 292
<212> TYPE: DNA
<213> ORGANISM: Homo sapiens

<400> SEQUENCE: 384
gaggtgcagc tggtggagtc tgggggaggc ttggtacagc ctagggggtc cctgagactc 60
tcctgtgcag cctctggatt caccgtcagt agcaatgaga tgagctggat ccgccaggct 120
ccagggaagg ggctggagtg ggtctcatcc attagtggtg gtagcacata ctacgcagac 180
tccaggaagg gcagattcac catctccaga gacaattcca agaacacgct gtatcttcaa 240
atgaacaacc tgagagctga gggcacggcc gcgtattact gtgccagata ta 292

<210> SEQ ID NO 385
<211> LENGTH: 292
<212> TYPE: DNA
<213> ORGANISM: Homo sapiens

<400> SEQUENCE: 385
gaggtgcagc tggtggagtc tgggggaggc ttggtacagc ctagggggtc cctgagactc 60
tcctgtgcag cctctggatt caccgtcagt agcaatgaga tgagctggat ccgccaggct 120
ccagggaagg ggctggagtg ggtctcatcc attagtggtg gtagcacata ctacgcagac 180
tccaggaagg gcagattcac catctccaga gacaattcca agaacacgct gtatcttcaa 240
atgaacaacc tgagagctga gggcacggcc gtgtattact gtgccagata ta 292

<210> SEQ ID NO 386
<211> LENGTH: 298
<212> TYPE: DNA
<213> ORGANISM: Homo sapiens

<400> SEQUENCE: 386
gaagtgcagc tggtggagtc tgggggagtc gtggtacagc ctggggggtc cctgagactc 60
tcctgtgcag cctctggatt cacctttgat gattatacca tgcactgggt ccgtcaagct 120
ccggggaagg gtctggagtg ggtctctctt attagttggg atggtggtag cacatactat 180
gcagactctg tgaagggccg attcaccatc tccagagaca acagcaaaaa ctccctgtat 240
ctgcaaatga acagtctgag aactgaggac accgccttgt attactgtgc aaaagata 298

<210> SEQ ID NO 387
<211> LENGTH: 294
<212> TYPE: DNA
<213> ORGANISM: Homo sapiens

<400> SEQUENCE: 387
gaagtgcagc tggtggagtc tgggggaggc gtggtacagc ctggggggtc cctgagactc 60
tcctgtgcag cctctggatt cacctttgat gattatgcca tgcactgggt ccgtcaagct 120
ccagggaagg gtctggagtg ggtctctctt attagtgggg atggtggtag cacatactat 180
gcagactctg tgaagggccg attcaccatc tccagagaca acagcaaaaa ctccctgtat 240
ctgcaaatga acagtctgag aactgaggac accgccttgt attactgtgc aaaa 294

<210> SEQ ID NO 388
<211> LENGTH: 291
<212> TYPE: DNA
<213> ORGANISM: Homo sapiens

<400> SEQUENCE: 388
gaggatcagc tggtggagtc tgggggaggc ttggtacagc ctggggggtc cctgcgaccc 60
tcctgtgcag cctctggatt cgccttcagt agctatgctc tgcactgggt tcgccgggct 120
ccagggaagg gtctggagtg ggtatcagct attggtactg gtggtgatac atactatgca 180
gactccgtga tgggccgatt caccatctcc agagacaacg ccaagaagtc cttgtatctt 240
catatgaaca gcctgatagc tgaggacatg gctgtgtatt attgtgcaag a 291

<210> SEQ ID NO 389
<211> LENGTH: 293
<212> TYPE: DNA
<213> ORGANISM: Homo sapiens

<400> SEQUENCE: 389
gaggatcagc tggtggagtc tgggggaggc ttggtacagc ctgggggtc cctgagaccc 60 tcctgtgcag cctctggatt cgccttcagt agctatgttc tgcactgggt tcgccgggct 120
ccagggaagg gtccggagtg ggtatcagct attggtactg gtggtgatac atactatgca 180
gactccgtga tgggccgatt caccatctcc agagacaacg ccaagaagtc cttgtatctt 240
caaatgaaca gcctgatagc tgaggacatg gctgtgtatt attgtgcaag aga 293

<210> SEQ ID NO 390
<211> LENGTH: 282
<212> TYPE: DNA
<213> ORGANISM: Homo sapiens

<400> SEQUENCE: 390
gaggatcagc tggtggagtc tgggggaggc ttggtacagc ctgggggtc cctgagaccc 60 tcctgtgcag cctctggatt cgccttcagt agctatgttc tgcactgggt tcgccgggct 120
ccagggaagg gtccggagtg ggtatcagct attggtactg gtggtgatac atactatgca 180
gactccgtga tgggccgatt caccatctcc agagacaacg ccaagaagtc cttgtatctc 240
aaatgaacag cctgatagct gaggacatgg ctgtgtatta tg 282

<210> SEQ ID NO 391
<211> LENGTH: 296
<212> TYPE: DNA
<213> ORGANISM: Homo sapiens

<400> SEQUENCE: 391
gaggtgcagc tggtggagtc tgggggaggc ttggtacagc ctgggggtc cctgagactc 60 tcctgtgcag cctctggatt caccttcagt agctatagca tgaactgggt ccgccaggct 120
ccagggaagg ggctggagtg ggtttcatac attagtagta gtagtagtac catatactac 180
gcagactctg tgaagggccg attcaccatc tccagagaca atgccaagaa ctcactgtat 240
ctgcaaatga acagcctgag agccgaggac acggctgtgt attactgtgc gagaga 296

<210> SEQ ID NO 392
<211> LENGTH: 296
<212> TYPE: DNA
<213> ORGANISM: Homo sapiens

<400> SEQUENCE: 392
gaggtgcagc tggtggagtc tgggggaggc ttggtacagc ctgggggtc cctgagactc 60 tcctgtgcag cctctggatt caccttcagt agctatagca tgaactgggt ccgccaggct 120
ccagggaagg ggctggagtg ggtttcatac attagtagta gtagtagtac catatactac 180
gcagactctg tgaagggccg attcaccatc tccagagaca atgccaagaa ctcactgtat 240
ctgcaaatga acagcctgag agacgaggac acggctgtgt attactgtgc gagaga 296

<210> SEQ ID NO 393
<211> LENGTH: 296
<212> TYPE: DNA
<213> ORGANISM: Homo sapiens

<400> SEQUENCE: 393
gaggtgcagc tggtggagtc tgggggaggc ttggtacagc ctggagggtc cctgagactc 60
tcctgtgcag cctctggatt caccttcagt agttatgaaa tgaactgggt ccgccaggct 120
ccagggaagg ggctggagtg ggtttcatac attagtagta gtggtagtac catatactac 180
gcagactctg tgaagggccg attcaccatc tccagagaca acgccaagaa ctcactgtat 240
ctgcaaatga acagcctgag agccgaggac acggctgttt attactgtgc gagaga 296

<210> SEQ ID NO 394
<211> LENGTH: 302
<212> TYPE: DNA
<213> ORGANISM: Homo sapiens

<400> SEQUENCE: 394
gaggtgcagc tggtggagtc tgggggaggc ttggtacagc cagggcggtc cctgagactc 60
tcctgtacag cttctggatt cacctttggt gattatgcta tgagctggtt ccgccaggct 120
ccagggaagg ggctggagtg ggtaggtttc attagaagca aagcttatgg tgggacaaca 180
gaatacaccg cgtctgtgaa aggcagattc accatctcaa gagatggttc caaaagcatc 240
gcctatctgc aaatgaacag cctgaaaacc gaggacacag ccgtgtatta ctgtactaga 300
ga 302

<210> SEQ ID NO 395
<211> LENGTH: 302
<212> TYPE: DNA
<213> ORGANISM: Homo sapiens

<400> SEQUENCE: 395
gaggtgcagc tggtggagtc tgggggaggc ttggtacagc cagggccgtc cctgagactc 60
tcctgtacag cttctggatt cacctttggg tattatccta tgagctgggt ccgccaggct 120
ccagggaagg ggctggagtg ggtaggtttc attagaagca aagcttatgg tgggacaaca 180
gaatacgccg cgtctgtgaa aggcagattc accatctcaa gagatgattc caaaagcatc 240
gcctatctgc aaatgaacag cctgaaaacc gaggacacag ccgtgtatta ctgtactaga 300
ga 302

<210> SEQ ID NO 396
<211> LENGTH: 302
<212> TYPE: DNA
<213> ORGANISM: Homo sapiens

<400> SEQUENCE: 396
gaggtgcagc tggtggagtc tgggggaggc ttggtacagc cagggcggtc cctgagactc 60
tcctgtacag cttctggatt cacctttggt gattatgcta tgagctggtt ccgccaggct 120
ccagggaagg ggctggagtg ggtaggtttc attagaagca aagcttatgg tgggacaaca 180
gaatacgccg cgtctgtgaa aggcagattc accatctcaa gagatgattc caaaagcatc 240
gcctatctgc aaatgaacag cctgaaaacc gaggacacag ccgtgtatta ctgtactaga 300
ga 302

<210> SEQ ID NO 397
<211> LENGTH: 302
<212> TYPE: DNA
<213> ORGANISM: Homo sapiens

<400> SEQUENCE: 397
gaggtgcagc tggtggagtc tgggggaggc ttggtacagc cagggcggtc cctgagactc 60
tcctgtacag cttctggatt cacctttggt gattatgcta tgagctgggt ccgccaggct 120
ccagggaagg ggctggagtg ggtaggtttc attagaagca aagcttatgg tgggacaaca 180
gaatacgccg cgtctgtgaa aggcagattc accatctcaa gagatgattc caaaagcatc 240
gcctatctgc aaatgaacag cctgaaaacc gaggacacag ccgtgtatta ctgtactaga 300
ga 302

<210> SEQ ID NO 398
<211> LENGTH: 302
<212> TYPE: DNA
<213> ORGANISM: Homo sapiens

<400> SEQUENCE: 398
gaggtgcagc tggtggagtc tgggggaggc ttggtaaagc cagggcggtc cctgagactc 60
tcctgtacag cttctggatt cacctttggt gattatgcta tgagctggtt ccgccaggct 120
ccagggaagg ggctggagtg ggtaggtttc attagaagca aagcttatgg tgggacaaca 180
gaatacgccg cgtctgtgaa aggcagattc accatctcaa gagatgattc caaaagcatc 240
gcctatctgc aaatgaacag cctgaaaacc gaggacacag ccgtgtatta ctgtactaga 300
ga 302

<210> SEQ ID NO 399
<211> LENGTH: 296
<212> TYPE: DNA
<213> ORGANISM: Homo sapiens

<400> SEQUENCE: 399
gaggtgcagc tggtggagtc tgggtgaggc ttggtacagc ctggagggtc cctgagactc 60
tcctgtgcag cctctggatt caccttcagt agctcctgga tgcactgggt ctgccaggct 120
ccggagaagg ggctggagtg ggtggccgac ataaagtgtg acggaagtga gaaatactat 180
gtagactctg tgaagggccg attgaccatc tccagagaca atgccaagaa ctccctctat 240
ctgcaagtga acagcctgag agctgaggac atgaccgtgt attactgtgt gagagg 296

<210> SEQ ID NO 400
<211> LENGTH: 294
<212> TYPE: DNA
<213> ORGANISM: Homo sapiens

<400> SEQUENCE: 400
gaggtgcagc tggtggagtc tgggtgaggc ttggtacagc ctggagggtc cctgagactc 60
tcctgtgcag cctctggatt caccttcagt agctcctgga tgcactgggt ctgccaggct 120
ccggagaagg ggcaggagtg ggtggccgac ataaagtgtg acggaagtga gaaatactat 180
gtagactctg tgaagggccg attgaccatc tccagagaca atgccaagaa ctccctctat 240
ctgcaagtga acagcctgag agctgaggac atgaccgtgt attactgtgt gaga 294

<210> SEQ ID NO 401
<211> LENGTH: 294
<212> TYPE: DNA
<213> ORGANISM: Homo sapiens

<400> SEQUENCE: 401
gaggtgcagc tggtcgagtc tgggtgaggc ttggtacagc ctggagggtc cctgagactc 60
tcctgtgcag cctctggatt caccttcagt agctcctgga tgcactgggt ctgccaggct 120
ccggagaagg ggctggagtg ggtggccgac ataaagtgtg acggaagtga gaaatactat 180
gtagactctg tgaagggccg attgaccatc tccagagaca atgccaagaa ctccctctat 240
ctgcaagtga acagcctgag agctgaggac atgaccgtgt attactgtgt gaga 294

<210> SEQ ID NO 402
<211> LENGTH: 293
<212> TYPE: DNA
<213> ORGANISM: Homo sapiens

<400> SEQUENCE: 402
gaggtgcagc tggtggagtc tggaggaggc ttgatccagc ctggggggtc cctgagactc 60
tcctgtgcag cctctgggtt caccgtcagt agcaactaca tgagctgggt ccgccaggct 120
ccagggaagg ggctggagtg ggtctcagtt atttatagcg gtggtagcac atactacgca 180
gactccgtga agggccgatt caccatctcc agagacaatt ccaagaacac gctgtatctt 240
caaatgaaca gcctgagagc cgaggacacg gccgtgtatt actgtgcgag aga 293

<210> SEQ ID NO 403
<211> LENGTH: 291
<212> TYPE: DNA
<213> ORGANISM: Homo sapiens

<400> SEQUENCE: 403
gaggtgcagc tggtggagac tggaggaggc ttgatccagc ctggggggtc cctgagactc 60
tcctgtgcag cctctgggtt caccgtcagt agcaactaca tgagctgggt ccgccaggct 120
ccagggaagg ggctggagtg ggtctcagtt atttatagcg gtggtagcac atactacgca 180
gactccgtga agggccgatt caccatctcc agagacaatt ccaagaacac gctgtatctt 240
caaatgaaca gcctgagagc cgaggacacg gccgtgtatt actgtgcgag a 291

<210> SEQ ID NO 404
<211> LENGTH: 293
<212> TYPE: DNA
<213> ORGANISM: Homo sapiens

<400> SEQUENCE: 404
gaggtgcagc tggtggagtc tggaggaggc ttgatccagc ctggggggtc cctgagactc 60
tcctgtgcag cctctgggtt caccgtcagt agcaactaca tgagctgggt ccgccagcct 120
ccagggaagg ggctggagtg ggtctcagtt atttatagcg gtggtagcac atactacgca 180
gactctgtga agggccgatt caccatctcc agagacaatt ccaagaacac gctgtatctt 240
caaatgaaca gcctgagagc cgaggacacg gccgtgtatt actgtgctag gga 293

<210> SEQ ID NO 405
<211> LENGTH: 296
<212> TYPE: DNA
<213> ORGANISM: Homo sapiens

<400> SEQUENCE: 405
gaggtacagc tggtggagtc tgaagaaaac caaagacaac ttgggggatc cctgagactc 60
tcctgtgcag actctggatt aaccttcagt agctactgaa tgagctcaga ttcccaagct 120
ccagggaagg ggctggagtg agtagtagat atatagtagg atagaagtca gctatgttat 180
gcacaatctg tgaagagcag attcaccatc tccaaagaaa atgccaagaa ctcactctgt 240
ttgcaaatga acagtctgag agcagagggc acggccgtgt attactgtat gtgagy 296

<210> SEQ ID NO 406
<211> LENGTH: 296
<212> TYPE: DNA
<213> ORGANISM: Homo sapiens

<400> SEQUENCE: 406
gaggtacagc tggtggagtc tgaagaaaac caaagacaac ttgggggatc cctgagactc 60
tcctgtgcag actctggatt aaccttcagt agctactgaa tgagctcaga ttcccaggct 120
ccagggaagg ggctggagtg agtagtagat atatagtacg atagaagtca gatatgttat 180
gcacaatctg tgaagagcag attcaccatc tccaaagaaa atgccaagaa ctcactccgt 240
ttgcaaatga acagtctgag agcagagggc acggccgtgt attactgtat gtgagg 296

<210> SEQ ID NO 407
<211> LENGTH: 296
<212> TYPE: DNA
<213> ORGANISM: Homo sapiens

<400> SEQUENCE: 407
gaggtacagc tggtggagtc tgaagaaaac caaagacaac ttgggggatc cctgagactc 60
tcctgtgcag actctggatt aaccttcagt agctactgaa tgagctcaga ttcccaggct 120
ccagggaagg ggctggagtg agtagtagat atatagtagg atagaagtca gctatgttat 180
gcacaatctg tgaagagcag attcaccatc tccaaagaaa atgccaagaa ctcactctgt 240
ttgcaaatga acagtctgag agcagagggc acggccgtgt attactgtat gtgagt 296

<210> SEQ ID NO 408
<211> LENGTH: 296
<212> TYPE: DNA
<213> ORGANISM: Homo sapiens

<400> SEQUENCE: 408
gaggtgcagc tggtggagtc tggggaaggc ttggtccagc ctggggggtc cctgagactc 60
tcctgtgcag cctctggatt caccttcagt agctctgcta tgcactgggt ccgccaggct 120
ccaagaaagg gtttgtagtg ggtctcagtt attagtacaa gtggtgatac cgtactctac 180
acagactctg tgaagggccg attcaccatc tccagagaca atgcccagaa ttcactgtct 240
ctgcaaatga acagcctgag agccgagggc acagttgtgt actactgtgt gaaaga 296

<210> SEQ ID NO 409
<211> LENGTH: 298
<212> TYPE: DNA
<213> ORGANISM: Homo sapiens

<400> SEQUENCE: 409
gaggtggagc tgatagagtc catagagggc ctgagacaac ttgggaagtt cctgagactc 60
tcctgtgtag cctctggatt caccttcagt agctactgaa tgagctgggt caatgagact 120
ctagggaagg ggctggaggg agtaatagat gtaaaatatg atggaagtca gatataccat 180
gcagactctg tgaagggcag attcaccatc tccaaagaca atgctaagaa ctcaccgtat 240
ctccaaacga acagtctgag agctgaggac atgaccatgc atggctgtac ataaggtt 298

<210> SEQ ID NO 410
<211> LENGTH: 294
<212> TYPE: DNA
<213> ORGANISM: Homo sapiens

<400> SEQUENCE: 410
gaggtggagc tgatagagtc catagagggc ctgagacaac ttgggaagtt cctgagactc 60
tcctgtgtag cctctggatt caccttcagt agctactgaa tgagctgggt caatgagact 120
ctagggaagg ggctggaggg agtaatagat gtaaaatatg atggaagtca gatataccat 180
gcagactctg tgaagggcag attcaccatc tccaaagaca atgctaagaa ctcaccgtat 240
ctgcaaacga acagtctgag agctgaggac atgaccatgc atggctgtac ataa 294

<210> SEQ ID NO 411
<211> LENGTH: 296
<212> TYPE: DNA
<213> ORGANISM: Homo sapiens

<400> SEQUENCE: 411
gaggtgcagc tggtggagtc tgggggaggc ttggtccagc ctggggggtc cctgagactc 60
tcctgtgcag cctctggatt caccttcagt agctatgcta tgcactgggt ccgccaggct 120
ccagggaagg gactggaata tgtttcagct attagtagta atgggggtag cacatattat 180
gcaaactctg tgaagggcag attcaccatc tccagagaca attccaagaa cacgctgtat 240
cttcaaatgg gcagcctgag agctgaggac atggctgtgt attactgtgc gagaga 296

<210> SEQ ID NO 412
<211> LENGTH: 296
<212> TYPE: DNA
<213> ORGANISM: Homo sapiens

<400> SEQUENCE: 412
gaggtgcagc tggtggagtc tggggaaggc ttggtccagc ctggggggtc cctgagactc 60
tcctgtgcag cctctggatt caccttcagt agctatgcta tgcactgggt ccgccaggct 120
ccagggaagg gactggaata tgtttcagct attagtagta atgggggtag cacatattat 180
gcagactctg tgaagggcag attcaccatc tccagagaca attccaagaa cacgctgtat 240
cttcaaatgg gcagcctgag agctgaggac atggctgtgt attactgtgc gagaga 296

<210> SEQ ID NO 413
<211> LENGTH: 296
<212> TYPE: DNA
<213> ORGANISM: Homo sapiens

<400> SEQUENCE: 413
gaggtgcagc tggtggagtc tgggggaggc ttggtccagc ctggggggtc cctgagactc 60
tcctgttcag cctctggatt caccttcagt agctatgcta tgcactgggt ccgccaggct 120
ccagggaagg gactggaata tgtttcagct attagtagta atgggggtag cacatactac 180
gcagactcag tgaagggcag attcaccatc tccagagaca attccaagaa cacgctgtat 240
gtccaaatga gcagtctgag agctgaggac acggctgtgt attactgtgt gaaaga 296

<210> SEQ ID NO 414
<211> LENGTH: 296
<212> TYPE: DNA
<213> ORGANISM: Homo sapiens

<400> SEQUENCE: 414
caggtgcagc tggtggagtc tgggggaggc ttggtccagc ctggggggtc cctgagactc 60
tcctgttcag cctctggatt caccttcagt agctatgcta tgcactgggt ccgccaggct 120
ccagggaagg gactggaata tgtttcagct attagtagta atgggggtag cacatactac 180
gcagactcag tgaagggcag attcaccatc tccagagaca attccaagaa cacgctgtat 240
ctgcaaatga acagcctgag agctgaggac acggctgtgt attactgtgc gagaga 296

<210> SEQ ID NO 415
<211> LENGTH: 296
<212> TYPE: DNA
<213> ORGANISM: Homo sapiens

<400> SEQUENCE: 415
gaggtgcagc tggtggagtc tgggggaggc ttggtccagc ctgggggtc cctgagactc 60 tcctgttcag cctctggatt caccttcagt agctatgcta tgcactgggt ccgccaggct 120
ccagggaagg gactggaata tgtttcagct attagtagta atgggggtag cacatactac 180
gcagactcag tgaagggcag attcaccatc tccagagaca attccaagaa cacgctgtat 240
gttcaaatga gcagtctgag agctgaggac acggctgtgt attactgtgt gaaaga 296

<210> SEQ ID NO 416
<211> LENGTH: 293
<212> TYPE: DNA
<213> ORGANISM: Homo sapiens

<400> SEQUENCE: 416
gaggtgcagc tggtggagtc tgggggaggc ttggtccagc ctgggggtc cctgagactc 60 tcctgtgcag cctctggatt caccgtcagt agcaactaca tgagctgggt ccgccaggct 120
ccagggaagg ggctggagtg ggtctcagtt atttatagcg gtggtagcac atactacgca 180
gactccgtga agggcagatt caccatctcc agagacaatt ccaagaacac gctgtatctt 240
caaatgaaca gcctgagagc cgaggacacg gctgtgtatt actgtgcgag aga 293

<210> SEQ ID NO 417
<211> LENGTH: 291
<212> TYPE: DNA
<213> ORGANISM: Homo sapiens

<400> SEQUENCE: 417
gaggtgcagc tggtggagtc tgggggaggc ttggtccagc ctgggggtc cctgagactc 60 tcctgtgcag cctctggatt caccgtcagt agcaactaca tgagctgggt ccgccaggct 120
ccagggaagg ggctggagtg ggtctcagtt atttatagcg gtggtagcac atactacgca 180
gactccgtga agggccgatt caccatctcc agagacaatt ccaagaacac gctgtatctt 240
caaatgaaca gcctgagagc tgaggacacg gctgtgtatt actgtgcgag a 291

<210> SEQ ID NO 418
<211> LENGTH: 293
<212> TYPE: DNA
<213> ORGANISM: Homo sapiens

<400> SEQUENCE: 418
gaggtgcagc tggtggagtc tggaggaggc ttgatccagc ctgggggtc cctgagactc 60 tcctgtgcag cctctgggtt caccgtcagt agcaactaca tgagctgggt ccgccaggct 120
ccagggaagg ggctggagtg ggtctcagtt atttatagct gtggtagcac atactacgca 180
gactccgtga agggccgatt caccatctcc agagacaatt ccaagaacac gctgtatctt 240
caaatgaaca gcctgagagc tgaggacacg gctgtgtatt actgtgcgag aga 293

<210> SEQ ID NO 419
<211> LENGTH: 293
<212> TYPE: DNA

<213> ORGANISM: Homo sapiens

<400> SEQUENCE: 419
gaggtgcagc tggtggagtc tgggggaggc ttggtccagc ctggggggtc cctgagactc 60
tcctgtgcag cctctggatt caccgtcagt agcaactaca tgagctgggt ccgccaggct 120
ccagggaagg ggctggagtg ggtctcagtt atttatagcg gtggtagcac atactacgca 180
gactccgtga agggcagatt caccatctcc agagacaatt ccaagaacac gctgtatctt 240
caaatgaaca gcctgagagc cgaggacacg gctgtgtatt actgtgcgag aca 293

<210> SEQ ID NO 420
<211> LENGTH: 296
<212> TYPE: DNA
<213> ORGANISM: Homo sapiens

<400> SEQUENCE: 420
gaggtgcagc tggtggagtc tgggggaggc ttggtccagc ctggggggtc cctgagactc 60
tcctgtgcag cctctggatt cacctttagt agctattgga tgagctgggt ccgccaggct 120
ccagggaagg ggctggagtg ggtggccaac ataaagcaag atggaagtga gaaatactat 180
gtggactctg tgaagggccg attcaccatc tccagagaca acgccaagaa ctcactgtat 240
ctgcaaatga acagcctgag agccgaggac acggctgtgt attactgtgc gagaga 296

<210> SEQ ID NO 421
<211> LENGTH: 294
<212> TYPE: DNA
<213> ORGANISM: Homo sapiens

<400> SEQUENCE: 421
gaggtgcagc tggtggagtc tgggggaggc ttggtccagc ctggggggtc cctgagactc 60
tcctgtgcag cctctggatt cacctttagt agctattgga tgagctgggt ccgccaggct 120
ccagggaaag ggctggagtg ggtggccaac ataaagcaag atggaagtga gaaatactat 180
gtggactctg tgaagggccg attcaccatc tccagagaca acgccaagaa ctcactgtat 240
ctgcaaatga acagcctgag agccgaggac acggctgtgt attactgtgc gaga 294

<210> SEQ ID NO 422
<211> LENGTH: 302
<212> TYPE: DNA
<213> ORGANISM: Homo sapiens

<400> SEQUENCE: 422
gaggtgcagc tggtggagtc cgggggaggc ttggtccagc ctggggggtc cctgagactc 60
tcctgtgcag cctctggatt caccttcagt gactactaca tgagctgggt ccgccaggct 120
cccgggaagg ggctggagtg ggtaggtttc attagaaaca aagctaatgg tgggacaaca 180
gaatagacca cgtctgtgaa aggcagattc acaatctcaa gagatgattc caaaagcatc 240
acctatctgc aaatgaacag cctgagagcc gaggacacgg ccgtgtatta ctgtgcgaga 300
ga 302

<210> SEQ ID NO 423
<211> LENGTH: 302
<212> TYPE: DNA
<213> ORGANISM: Homo sapiens

<400> SEQUENCE: 423
gaggtgcagc tggtggagtc tgggggaggc ttggtccagc ctggagggtc cctgagactc 60
tcctgtgcag cctctggatt caccttcagt gaccactaca tggactgggt ccgccaggct 120
ccagggaagg ggctggagtg ggttggccgt actagaaaca aagctaacag ttacaccaca 180
gaatacgccg cgtctgtgaa aggcagattc accatctcaa gagatgattc aaagaactca 240
ctgtatctgc aaatgaacag cctgaaaacc gaggacacgg ccgtgtatta ctgtgctaga 300
ga 302

<210> SEQ ID NO 424
<211> LENGTH: 165
<212> TYPE: DNA
<213> ORGANISM: Homo sapiens

<400> SEQUENCE: 424
accttcagtg accactacat ggactgggtc cgccaggctc cagggaaggg gctggagtgg 60
gttggccgta ctagaaacaa agctaacagc tacaccacag aatacgccgc gtctgtgaaa 120
ggcagattca ccatctcaag agatgattca aagaactcac tgtat 165

<210> SEQ ID NO 425
<211> LENGTH: 302
<212> TYPE: DNA
<213> ORGANISM: Homo sapiens

<400> SEQUENCE: 425
gaggtgcagc tggtggagtc tgggggaggc ttggtccagc ctggggggtc cctgaaactc 60
tcctgtgcag cctctgggtt caccttcagt ggctctgcta tgcactgggt ccgccaggct 120
tccgggaaag ggctggagtg ggttggccgt attagaagca aagctaacag ttacgcgaca 180
gcatatgctg cgtcggtgaa aggcaggttc accatctcca gagatgattc aaagaacacg 240
gcgtatctgc aaatgaacag cctgaaaacc gaggacacgg ccgtgtatta ctgtactaga 300
ca 302

<210> SEQ ID NO 426
<211> LENGTH: 302
<212> TYPE: DNA
<213> ORGANISM: Homo sapiens

<400> SEQUENCE: 426
gaggtgcagc tggtggagtc cgggggaggc ttggtccagc ctggggggtc cctgaaactc 60
tcctgtgcag cctctgggtt caccttcagt ggctctgcta tgcactgggt ccgccaggct 120
tccgggaaag ggctggagtg ggttggccgt attagaagca aagctaacag ttacgcgaca 180
gcatatgctg cgtcggtgaa aggcaggttc accatctcca gagatgattc aaagaacacg 240
gcgtatctgc aaatgaacag cctgaaaacc gaggacacgg ccgtgtatta ctgtactaga 300
ca 302

<210> SEQ ID NO 427
<211> LENGTH: 296
<212> TYPE: DNA
<213> ORGANISM: Homo sapiens

<400> SEQUENCE: 427
gaggtgcagc tggtggagtc cgggggaggc ttagttcagc ctggggggtc cctgagactc 60
tcctgtgcag cctctggatt caccttcagt agctactgga tgcactgggt ccgccaagct 120
ccagggaagg ggctggtgtg ggtctcacgt attaatagtg atgggagtag cacaagctac 180

-continued

```
gcggactccg tgaagggccg attcaccatc tccagagaca acgccaagaa cacgctgtat    240

ctgcaaatga acagtctgag agccgaggac acggctgtgt attactgtgc aagaga        296
```

<210> SEQ ID NO 428
<211> LENGTH: 294
<212> TYPE: DNA
<213> ORGANISM: Homo sapiens

<400> SEQUENCE: 428

```
gaggtgcagc tggtggagtc tgggggaggc ttagttcagc ctggggggtc cctgagactc     60

tcctgtgcag cctctggatt caccttcagt agctactgga tgcactgggt ccgccaagct    120

ccagggaagg ggctggtgtg ggtctcacgt attaatagtg atgggagtag cacaagctac    180

gcggactccg tgaagggccg attcaccatc tccagagaca acgccaagaa cacgctgtat    240

ctgcaaatga acagtctgag agccgaggac acggctgtgt attactgtgc aaga          294
```

<210> SEQ ID NO 429
<211> LENGTH: 296
<212> TYPE: DNA
<213> ORGANISM: Homo sapiens

<400> SEQUENCE: 429

```
gaggtgcagc tggtggagtc cgggggaggc ttagttcagc ctggggggtc cctgagactc     60

tcctgtgcag cctctggatt caccttcagt agctactgga tgcactgggt ccgccaagct    120

ccagggaagg ggctggtgtg ggtctcacgt attaatagtg atgggagtag cacaacgtac    180

gcggactccg tgaagggccg attcaccatc tccagagaca acgccaagaa cacgctgtat    240

ctgcaaatga acagtctgag agccgaggac acggctgtgt attactgtgc aagaga        296
```

<210> SEQ ID NO 430
<211> LENGTH: 298
<212> TYPE: DNA
<213> ORGANISM: Homo sapiens

<400> SEQUENCE: 430

```
gaagtgcagc tggtggagtc tgggggaggc ttggtacagc ctggcaggtc cctgagactc     60

tcctgtgcag cctctggatt cacctttgat gattatgcca tgcactgggt ccggcaagct    120

ccagggaagg gcctggagtg ggtctcaggt attagttgga atagtggtag cataggctat    180

gcggactctg tgaagggccg attcaccatc tccagagaca acgccaagaa ctccctgtat    240

ctgcaaatga acagtctgag agctgaggac acggccttgt attactgtgc aaaagata      298
```

<210> SEQ ID NO 431
<211> LENGTH: 288
<212> TYPE: DNA
<213> ORGANISM: Homo sapiens

<400> SEQUENCE: 431

```
gaggtgcagc tggtggagtc tcggggagtc ttggtacagc ctggggggtc cctgagactc     60

tcctgtgcag cctctggatt caccgtcagt agcaatgaga tgagctgggt ccgccaggct    120

ccagggaagg gtctggagtg ggtctcatcc attagtggtg gtagcacata ctacgcagac    180

tccaggaagg gcagattcac catctccaga gacaattcca agaacacgct gcatcttcaa    240

atgaacagcc tgagagctga ggacacggct gtgtattact gtaagaaa                288
```

<210> SEQ ID NO 432
<211> LENGTH: 293

<212> TYPE: DNA
<213> ORGANISM: Homo sapiens

<400> SEQUENCE: 432
gaggtgcagc tggtggagtc tgggggaggc ttggtaaagc ctggggggtc cctgagactc 60
tcctgtgcag cctctggatt caccttcagt gactactaca tgaactgggt ccgccaggct 120
ccagggaagg ggctggagtg ggtctcatcc attagtagta gtagtaccat atactacgca 180
gactctgtga agggccgatt caccatctcc agagacaacg ccaagaactc actgtatctg 240
caaatgaaca gcctgagagc cgaggacacg gctgtgtatt actgtgcgag aga 293

<210> SEQ ID NO 433
<211> LENGTH: 293
<212> TYPE: DNA
<213> ORGANISM: Homo sapiens

<400> SEQUENCE: 433
gaggtgcagc tggtggagtc tgggggaggc ttggtaaagc ctggggggtc cctgagactc 60
tcctgtgcag cctctggatt caccttcagt gactactaca tgaactgggt ccgccaggct 120
ccagggaagg ggctggagtg ggtctcatcc attagtagta gtagtaccat atactacgca 180
gactctgtga agggccgatt caccatctcc agagacaacg ccaagaactc actgtatctg 240
caaatgaaca gcctgagagc cgaggacacg gctgtttatt actgtgcgag aga 293

<210> SEQ ID NO 434
<211> LENGTH: 300
<212> TYPE: DNA
<213> ORGANISM: Homo sapiens

<400> SEQUENCE: 434
gaggtgcagc tggtggagtc tgggggaggc ttggtccagc ctggggggttc tctgagactc 60 tcatgtgcag cctctggatt caccttcagt gaccactaca tgagctgggt ccgccaggct 120
caagggaaag ggctagagtt ggtaggttta ataagaaaca aagctaacag ttacacgaca 180
gaatatgctg cgtctgtgaa aggcagactt accatctcaa gagaggattc aaagaacacg 240
atgtatctgc aaatgagcaa cctgaaaacc gaggacttgg ccgtgtatta ctgtgctaga 300

<210> SEQ ID NO 435
<211> LENGTH: 300
<212> TYPE: DNA
<213> ORGANISM: Homo sapiens

<400> SEQUENCE: 435
gaggtgcagc tgttggagtc tgggggaggc ttggtccagc ctgggggttc tctgagactc 60
tcatgtgctg cctctggatt caccttcagt gaccactaca tgagctgggt ccgccaggct 120
caagggaaag ggctagagtt ggtaggttta ataagaaaca aagctaacag ttacacgaca 180
gaatatgctg cgtctgtgaa aggcagactt accatctcaa gagaggattc aaagaacacg 240
ctgtatctgc aaatgagcag cctgaaaacc gaggacttgg ccgtgtatta ctgtgctaga 300

<210> SEQ ID NO 436
<211> LENGTH: 300
<212> TYPE: DNA
<213> ORGANISM: Homo sapiens

<400> SEQUENCE: 436
gaggtgcagc tggtggagtc tgggggaggc ttggtccagc ctgggggttc tctgagactc 60
tcatgtgcag cctctggatt caccttcagt gaccactaca tgagctgggt ccgccaggct 120
caagggaaag ggctagagtt ggtaggttta ataagaaaca aagctaacag ttacacgaca 180
gaatatgctg cgtctgtgaa aggcagactt accatctcaa gagaggattc aaagaacacg 240
ctgtatctgc aaatgagcag cctgaaaacc gaggacttgg ccgtgtatta ctgtgctaga 300

<210> SEQ ID NO 437
<211> LENGTH: 291
<212> TYPE: DNA
<213> ORGANISM: Homo sapiens

<400> SEQUENCE: 437
gaggttcagc tggtgcagtc tgggggaggc ttggtacatc ctgggggggtc cctgagactc 60 tcctgtgcag gctctggatt caccttcagt agctatgcta tgcactgggt tcgccaggct 120
ccaggaaaag gtctggagtg ggtatcagct attggtactg gtggtggcac atactatgca 180
gactccgtga agggccgatt caccatctcc agagacaatg ccaagaactc cttgtatctt 240
caaatgaaca gcctgagagc cgaggacatg gctgtgtatt actgtgcaag a 291

<210> SEQ ID NO 438
<211> LENGTH: 291
<212> TYPE: DNA
<213> ORGANISM: Homo sapiens

<400> SEQUENCE: 438
gaggttcagc tggtgcagtc tgggggaggc ttggtacagc ctgggggggtc cctgagactc 60 tcctgtgcag gctctggatt caccttcagt agctatgcta tgcactgggt tcgccaggct 120
ccaggaaaag gtctggagtg ggtatcagct attggtactg gtggtggcac atactatgca 180
gactccgtga agggccgatt caccatctcc agagacaatg ccaagaactc cttgtatctt 240
caaatgaaca gcctgagagc cgaggacatg gctgtgtatt actgtgcaag a 291

<210> SEQ ID NO 439
<211> LENGTH: 294
<212> TYPE: DNA
<213> ORGANISM: Homo sapiens

<400> SEQUENCE: 439
gaggtgcagc tggtagagtc tgggagaggc ttggcccagc ctgggggggta cctaaaactc 60 tccggtgcag cctctggatt caccgtcggt agctggtaca tgagctggat ccaccaggct 120
ccagggaagg gtctggagtg ggtctcatac attagtagta gtggttgtag cacaaactac 180
gcagactctg tgaagggcag attcaccatc tccacagaca actcaaagaa cacgctctac 240
ctgcaaatga acagcctgag agtggaggac acggccgtgt attactgtgc aaga 294

<210> SEQ ID NO 440
<211> LENGTH: 294
<212> TYPE: DNA
<213> ORGANISM: Homo sapiens

<400> SEQUENCE: 440
gaggtgcagc tggtggagtc tgggggaggc ttagtacagc ctggagggtc cctgagactc 60
tcctgtgcag cctctggatt caccttcagt agctactgga tgcactgggt ccgccaagct 120
ccagggaagg ggctggtgtg ggtctcacgt attaatagtg atgggagtag cacaagctac 180
gcagactcca tgaagggcca attcaccatc tccagagaca atgctaagaa cacgctgtat 240
ctgcaaatga acagtctgag agctgaggac atggctgtgt attactgtac taga 294

<210> SEQ ID NO 441
<211> LENGTH: 294
<212> TYPE: DNA
<213> ORGANISM: Homo sapiens

<400> SEQUENCE: 441
gaggtgcagc tggaggagtc tgggggaggc ttagtacagc ctggagggtc cctgagactc 60
tcctgtgcag cctctggatt caccttcagt agctactgga tgcactgggt ccgccaatct 120
ccagggaagg ggctggtgtg agtctcacgt attaatagtg atgggagtag cacaagctac 180
gcagactcct tgaagggcca attcaccatc tccagagaca atgctaagaa cacgctgtat 240
ctgcaaatga acagtctgag agctgaggac atggctgtgt attactgtac taga 294

<210> SEQ ID NO 442
<211> LENGTH: 296
<212> TYPE: DNA
<213> ORGANISM: Homo sapiens

<400> SEQUENCE: 442
gaagtgcagc tggtggagtc tgggggaggc ttggtccagc ctggggggtc cctgagactc 60
tcctgtgcag cctctgtatt caccttcagt aacagtgaca taaactgggt cctctaggct 120
ccaggaaagg ggctggagtg ggtctcgggt attagttgga atggcggtaa gacgcactat 180
gtggactccg tgaagggcca attttccatc tccagagaca attccagcaa gtccctgtat 240
ctgcaaaaga acagacagag agccaaggac atggccgtgt attactgtgt gagaaa 296

<210> SEQ ID NO 443
<211> LENGTH: 294
<212> TYPE: DNA
<213> ORGANISM: Homo sapiens

<400> SEQUENCE: 443
gaggtgcagc tggtggagtc tgggggaggc ttggtccagc ctggggggtc cctgagacac 60
tcctgtgcag cctctggatt caccttcagt aacagtgaca tgaactgggt cctctaggct 120
ccaggaaagg ggctggagtg ggtctcgggt attagttgga atggcggtaa gacgcactat 180
gtggactccg tgaagggcca atttaccatc tccagagaca attccagcaa gtccctgtat 240
ctgcaaaaga acagacagag agccaaagac atggccgtgt attactgtgt gaga 294

<210> SEQ ID NO 444
<211> LENGTH: 294
<212> TYPE: DNA
<213> ORGANISM: Homo sapiens

<400> SEQUENCE: 444
gaggtgcagc tggtggagtc tgggggaggc ttggtccagc ctggggggtc cctgagacac 60
tcctgtgcag cctctggatt caccttcagt aacagtgaca tgaactgggt cctctaggct 120
ccaggaaagg ggctggagtg ggtctcggat attagttgga atggcggtaa gacgcactat 180
gtggactccg tgaagggcca atttaccatc tccagagaca attccagcaa gtccctgtat 240
ctgcaaaaga acagacagag agccaaggac atggccgtgt attactgtgt gaga 294

<210> SEQ ID NO 445
<211> LENGTH: 292
<212> TYPE: DNA
<213> ORGANISM: Homo sapiens

<400> SEQUENCE: 445
gaggtgcagc tggtggagtc tgggggaggc ttggtacagc ctggggggtc cctgagactg 60
tcctgtccag cctctggatt caccttcagt aaccactaca tgagctgggt ccgccaggct 120
ccagggaagg gactggagtg ggtttcatac attagtggtg atagtggtta cacaaactac 180
gcagactctg tgaagggccg attcaccatc tccagggaca acgccaataa ctcaccgtat 240
ctgcaaatga acagcctgag agctgaggac acggctgtgt attactgtgt ga 292

<210> SEQ ID NO 446
<211> LENGTH: 292
<212> TYPE: DNA
<213> ORGANISM: Homo sapiens

<400> SEQUENCE: 446
gaggtgcagc tggtggagtc tggaggaggc ttggtacagc ctggggggtc cctgagactc 60
tcctgtgcag cctctggatt caccttcagt aaccactaca cgagctgggt ccgccaggct 120
ccagggaagg gactggagtg ggtttcatac agtagtggta atagtggtta cacaaactac 180
gcagactctg tgaaaggccg attcaccatc tccagggaca acgccaagaa ctcactgtat 240
ctgcaaatga acagcctgag agccgaggac acggctgtgt attactgtgt ga 292

<210> SEQ ID NO 447
<211> LENGTH: 296
<212> TYPE: DNA
<213> ORGANISM: Homo sapiens

<400> SEQUENCE: 447
caggtgcagc tgcaggagtc gggcccagga ctggtgaagc cttcggacac cctgtccctc 60
acctgcgctg tctctggtta ctccatcagc agtagtaact ggtggggctg gatccggcag 120
cccccaggga agggactgga gtggattggg tacatctatt atagtgggag cacctactac 180
aacccgtccc tcaagagtcg agtcaccatg tcagtagaca cgtccaagaa ccagttctcc 240
ctgaagctga gctctgtgac cgccgtggac acggccgtgt attactgtgc gagaaa 296

<210> SEQ ID NO 448
<211> LENGTH: 296
<212> TYPE: DNA
<213> ORGANISM: Homo sapiens

<400> SEQUENCE: 448
caggtgcagc tgcaggagtc gggcccagga ctggtgaagc cttcacagac cctgtccctc 60
acctgcgctg tctctggtta ctccatcagc agtagtaact ggtggggctg gatccggcag 120
cccccaggga agggactgga gtggattggg tacatctatt atagtgggag catctactac 180
aacccgtccc tcaagagtcg agtcaccatg tcagtagaca cgtccaagaa ccagttctcc 240
ctgaagctga gctctgtgac cgccgtggac acggccgtgt attactgtgc gagaaa 296

<210> SEQ ID NO 449
<211> LENGTH: 296
<212> TYPE: DNA
<213> ORGANISM: Homo sapiens

<400> SEQUENCE: 449
caggtgcagc tgcaggagtc gggcccagga ctggtgaagc cttcggacac cctgtccctc 60
acctgcgctg tctctggtta ctccatcagc agtagtaact ggtggggctg gatccggcag 120
cccccaggga agggactgga gtggattggg tacatctatt atagtgggag cacctactac 180
aacccgtccc tcaagagtcg agtcaccatg tcagtagaca cgtccaagaa ccagttctcc 240
ctgaagctga gctctgtgac cgccgtggac acggccgtgt attactgtgc gagaga 296

<210> SEQ ID NO 450
<211> LENGTH: 294
<212> TYPE: DNA
<213> ORGANISM: Homo sapiens

<400> SEQUENCE: 450
caggtgcagc tgcaggagtc gggcccagga ctggtgaagc cttcggacac cctgtccctc 60
acctgcgctg tctctggtta ctccatcagc agtagtaact ggtggggctg gatccggcag 120
cccccaggga agggactgga gtggattggg tacatctatt atagtgggag cacctactac 180
aacccgtccc tcaagagtcg agtcaccatg tcagtagaca cgtccaagaa ccagttctcc 240
ctgaagctga gctctgtgac cgccgtggac accggcgtgt attactgtgc gaga 294

<210> SEQ ID NO 451
<211> LENGTH: 287
<212> TYPE: DNA
<213> ORGANISM: Homo sapiens

<400> SEQUENCE: 451
caggtgcagc tgcaggagtc gggcccagga ctggtgaagc cttcggacac cctgtccctc 60
acctgcgctg tctctggtta ctccatcagc agtagtaact ggtggggctg gatccggcag 120
cccccaggga agggactgga gtggattggg tacatctatt atagtgggag catctactac 180
aacccgtccc tcaagagtcg agtcaccatg tcagtagaca cgtccaagaa ccagttctcc 240
ctgaagctga gctctgtgac cgccgtggac acggccgtgt attactg 287

<210> SEQ ID NO 452
<211> LENGTH: 299
<212> TYPE: DNA
<213> ORGANISM: Homo sapiens

<400> SEQUENCE: 452
cagctgcagc tgcaggagtc cggctcagga ctggtgaagc cttcacagac cctgtccctc 60
acctgcgctg tctctggtgg ctccatcagc agtggtggtt actcctggag ctggatccgg 120
cagccaccag ggaagggcct ggagtggatt gggtacatct atcatagtgg gagcacctac 180
tacaacccgt ccctcaagag tcgagtcacc atatcagtag acaggtccaa gaaccagttc 240
tccctgaagc tgagctctgt gaccgccgcg gacacggccg tgtattactg tgccagaga 299

<210> SEQ ID NO 453
<211> LENGTH: 294
<212> TYPE: DNA
<213> ORGANISM: Homo sapiens

<400> SEQUENCE: 453
cagctgcagc tgcaggagtc cggctcagga ctggtgaagc cttcacagac cctgtccctc 60
acctgcgctg tctctggtgg ctccatcagc agtggtggtt actcctggag ctggatccgg 120
cagccaccag ggaagggcct ggagtggatt gggtacatct atcatagtgg gagcacctac 180
tacaacccgt ccctcaagag tcgagtcacc atatcagtag acaggtccaa gaaccagttc 240
tccctgaagc tgagctctgt gaccgctgcg gacacggccg tgtattactg tgcg 294

<210> SEQ ID NO 454

<211> LENGTH: 299
<212> TYPE: DNA
<213> ORGANISM: Homo sapiens

<400> SEQUENCE: 454
cagctgcagc tgcaggagtc cggctcagga ctggtgaagc cttcacagac cctgtccctc 60
acctgcgctg tctctggtgg ctccatcagc agtggtggtt actcctggag ctggatccgg 120
cagccaccag ggaagggcct ggagtggatt gggagtatct attatagtgg gagcacctac 180
tacaacccgt ccctcaagag tcgagtcacc atatccgtag acacgtccaa gaaccagttc 240
tccctgaagc tgagctctgt gaccgctgca gacacggctg tgtattactg tgcgagaca 299

<210> SEQ ID NO 455
<211> LENGTH: 227
<212> TYPE: DNA
<213> ORGANISM: Homo sapiens

<400> SEQUENCE: 455
tctggtggct ccatcagcag tggtggttac tcctggagct ggatccggca gccaccaggg 60
aagggcctgg agtggattgg gtacatctat catagtggga gcacctacta caacccgtcc 120
ctcaagagtc gagtcaccat atcagtagac acgtccaaga accagttctc cctgaagctg 180
agctctgtga ccgccgcaga cacggccgtg tattactgtg cgagaga 227

<210> SEQ ID NO 456
<211> LENGTH: 299
<212> TYPE: DNA
<213> ORGANISM: Homo sapiens

<400> SEQUENCE: 456
caggtgcagc tgcaggagtc gggcccagga ctggtgaagc cttcacagac cctgtccctc 60
acctgcactg tctctggtgg ctccatcagc agtggtgatt actactggag ttggatccgc 120
cagcccccag ggaagggcct ggagtggatt gggtacatct attacagtgg gagcacctac 180
tacaacccgt ccctcaagag tcgagttacc atatcagtag acacgtccaa gaaccagttc 240
tccctgaagc tgagctctgt gactgccgca gacacggccg tgtattactg tgccagaga 299

<210> SEQ ID NO 457
<211> LENGTH: 299
<212> TYPE: DNA
<213> ORGANISM: Homo sapiens

<400> SEQUENCE: 457
caggtgcagc tgcaggagtc gggcccagga ctggtgaagc cttcggacac cctgtccctc 60
acctgcactg tctctggtgg ctccatcagc agtggtgatt actactggag ttggatccgc 120
cagcccccag ggaagggcct ggagtggatt gggtacatct attacagtgg gagcacctac 180
tacaacccgt ccctcaagag tcgagttacc atatcagtag acacgtccaa gaaccagttc 240
tccctgaagc tgagctctgt gactgcagca gacacggccg tgtattactg tgccagaga 299

<210> SEQ ID NO 458
<211> LENGTH: 290
<212> TYPE: DNA
<213> ORGANISM: Homo sapiens

<400> SEQUENCE: 458
caggtgcagc tgcaggagtc gggcccagga ctggtgaagc cttcacagac cctgtccctc 60
acctgcactg tctctggtgg ctccatcagc agtggtgatt actactggag ttggatccgc 120

```
cagcccccag ggaagggcct ggagtggatt gggtacatct attacagtgg gagcacctac    180

tacaacccgt ccctcaagag tcgagttacc atatcagtag acacgtccaa gaaccagttc    240

tccctgaagc tgagctctgt gactgccgcg gacacggccg tgtattactg               290


<210> SEQ ID NO 459
<211> LENGTH: 290
<212> TYPE: DNA
<213> ORGANISM: Homo sapiens

<400> SEQUENCE: 459

caggtgcagc tgcaggactc gggcccagga ctggtgaagc cttcacagac cctgtccctc     60

acctgcactg tctctggtgg ctccatcagc agtggtgatt actactggag ttggatccgc    120

cagcccccag ggaagggcct ggagtggatt gggtacttct attacagtgg gagcacctac    180

tacaacccgt ccctcaagag tcgagttacc atatcagtag acacgtccaa gaaccagttc    240

tccctgaagc tgagctctgt gactgccgca gacacggccg tgtattactg               290


<210> SEQ ID NO 460
<211> LENGTH: 228
<212> TYPE: DNA
<213> ORGANISM: Homo sapiens
<220> FEATURE:
<221> NAME/KEY: modified_base
<222> LOCATION: (54)..(54)
<223> OTHER INFORMATION: a, c, t or g

<400> SEQUENCE: 460

ctctggtggc tccatcagca gtggtgatta ctactggagt tggatccgcc agcncccagg     60

gaagggcctg gagtggattg ggtacatcta ttacagtggg agcacctact acaacccgtc    120

cctcaagagt cgagtcacca tatcagtaga cacgtccaag aaccagttct ccctgaagct    180

gagctctgtg actgccgcag acacggccgt gtattactgt gccagaga                 228


<210> SEQ ID NO 461
<211> LENGTH: 227
<212> TYPE: DNA
<213> ORGANISM: Homo sapiens

<400> SEQUENCE: 461

tctggtggct ccatcagcag tggtgattac tactggagtt ggatccgcca gcacccaggg     60

aagggcctgg agtggattgg gtacatctat tacagtggga gcacctacta caacccgtcc    120

ctcaagagtc gagttaccat atcagtagac acgtccaaga accagttctc cctgaagctg    180

agctctgtga ctgccgcaga cacggccgtg tattactgtg ccagaga                  227


<210> SEQ ID NO 462
<211> LENGTH: 299
<212> TYPE: DNA
<213> ORGANISM: Homo sapiens

<400> SEQUENCE: 462

caggtgcagc tgcaggagtc gggcccagga ctggtgaagc cttcacagac cctgtccctc     60

acctgcactg tctctggtgg ctccatcagc agtggtggtt actactggag ctggatccgc    120

cagcacccag ggaagggcct ggagtggatt gggtacatct attacagtgg gagcacctac    180

tacaacccgt ccctcaagag tctagttacc atatcagtag acacgtctaa gaaccagttc    240

tccctgaagc tgagctctgt gactgccgcg gacacggccg tgtattactg tgcgagaga     299
```

<210> SEQ ID NO 463
<211> LENGTH: 299
<212> TYPE: DNA
<213> ORGANISM: Homo sapiens

<400> SEQUENCE: 463
caggtgcagc tgcaggagtc gggcccagga ctggtgaagc cttcacagac cctgtccctc 60
acctgtactg tctctggtgg ctccatcagc agtggtggtt actactggag ctggatccgc 120
cagcacccag ggaagggcct ggagtggatt gggtacatct attacagtgg gagcacctac 180
tacaacccgt ccctcaagag tcgagttacc atatcagtag acacgtctaa gaaccagttc 240
tccctgaagc tgagctctgt gactgccgcg gacacggccg tgtattactg tgcgagaga 299

<210> SEQ ID NO 464
<211> LENGTH: 299
<212> TYPE: DNA
<213> ORGANISM: Homo sapiens

<400> SEQUENCE: 464
caggtgcagc tgcaggagtc gggcccagga ctggtgaagc cttcacagac cctgtccctc 60
acctgcactg tctctggtgg ctccatcagc agtggtggtt actactggag ctggatccgc 120
cagcacccag ggaagggcct ggagtggatt gggtacatct attacagtgg gagcacctac 180
tacaacccgt ccctcaagag tcgagttacc atatcagtag acacgtctaa gaaccagttc 240
tccctgaagc tgagctctgt gactgccgcg gacacggccg tgtattactg tgcgagaga 299

<210> SEQ ID NO 465
<211> LENGTH: 294
<212> TYPE: DNA
<213> ORGANISM: Homo sapiens

<400> SEQUENCE: 465
caggtgcggc tgcaggagtc gggcccagga ctggtgaagc cttcacagac cctgtccctc 60
acctgcactg tctctggtgg ctccatcagc agtggtggtt actactggag ctggatccgc 120
cagcacccag ggaagggcct ggagtggatt gggtacatct attacagtgg gagcacctac 180
tacaacccgt ccctcaagag tcgagttacc atatcagtag acacgtctaa gaaccagttc 240
tccctgaagc tgagctctgt gactgccgcg gacacggccg tgtattactg tgcg 294

<210> SEQ ID NO 466
<211> LENGTH: 291
<212> TYPE: DNA
<213> ORGANISM: Homo sapiens

<400> SEQUENCE: 466
caggtgcagc tgcaggagtc gggcccagga ctggtgaagc cttcacagac cctgtccctc 60
acctgcactg tctctggtgg ctccatcagc agtggtggtt actactggag ctggatccgc 120
cagcacccag ggaagggcct ggagtggatt gggtacatct attacagtgg gagcacctac 180
tacaacccgt ccctcaagag tcgagttacc atatcagtag acacgtctaa gaaccagttc 240
tccctgaagc tgagctctgt gaccgcggac gcggccgtgt attactgtgc g 291

<210> SEQ ID NO 467
<211> LENGTH: 290
<212> TYPE: DNA
<213> ORGANISM: Homo sapiens

<400> SEQUENCE: 467
caggtgcagc tgcaggagtc gggcccagga ctggtgaagc cttcacagac cctgtccctc 60
acctgcactg tctctggtgg ctccatcagc agtggtagtt actactggag ctggatccgc 120
cagcacccag ggaagggcct ggagtggatt gggtacatct attacagtgg gagcacctac 180
tacaacccgt ccctcaagag tcgagttacc atatcagtag acacgtctaa gaaccagttc 240
tccctgaagc tgagctctgt gactgccgcg gacacggccg tgtattactg 290

<210> SEQ ID NO 468
<211> LENGTH: 290
<212> TYPE: DNA
<213> ORGANISM: Homo sapiens

<400> SEQUENCE: 468
caggtgcagc tgcaggagtc gggcccagga ctggtgaagc cttcacagac cctgtccctc 60
acctgcactg tctctggtgg atccatcagc agtggtggtt actactggag ctggatccgc 120
cagcacccag ggaagggcct ggagtggatt gggtacatct attacagtgg gagcacctac 180
tacaacccgt ccctcaagag tcgagttacc atatcagtag acacgtctaa gaaccagttc 240
tccctgaagc tgagctctgt gactgccgcg gacacggccg tgtattactg 290

<210> SEQ ID NO 469
<211> LENGTH: 290
<212> TYPE: DNA
<213> ORGANISM: Homo sapiens

<400> SEQUENCE: 469
caggtgcagc tgcaggagtc gggcccagga ctggtgaagc cttcacagac cctgtccctc 60
acctgcactg tctctggtgg ctccatcagc agtggtggtt actactggag ctggatccgc 120
cagcacccag ggaagggcct ggagtggatt gggtacatct attacagtgg gagcacctac 180
tacaacccgt ccctcaagag tcgagttacc atatccgtag acacgtccaa gaaccagttc 240
tccctgaagc tgagctctgt gactgccgcg gacacggccg tgtattactg 290

<210> SEQ ID NO 470
<211> LENGTH: 290
<212> TYPE: DNA
<213> ORGANISM: Homo sapiens

<400> SEQUENCE: 470
caggtgcagc tgcaggagtc gggcccagga ctggtgaagc cttcacagac cctgtccctc 60
acctgcactg tctctggtgg ctccatcagc agtggtggtt actactggag ctggatccgc 120
cagcacccag ggaagggcct ggagtggatt gggtacatct attacagtgg gagcacctac 180
tacaacccgt ccctcaagag tcgagttacc atatcagtag acaagtccaa gaaccagttc 240
tccctgaagc tgagctctgt gaccgccgcg gacacggccg tgtattactg 290

<210> SEQ ID NO 471
<211> LENGTH: 299
<212> TYPE: DNA
<213> ORGANISM: Homo sapiens

<400> SEQUENCE: 471
caggtgcagc tgcaggagtc gggcccagga ctgttgaagc cttcacagac cctgtccctc 60
acctgcactg tctctggtgg ctccatcagc agtggtggtt actactggag ctggatccgc 120
cagcacccag ggaagggcct ggagtggatt gggtgcatct attacagtgg gagcacctac 180

```
tacaacccgt ccctcaagag tcgagttacc atatcagtag acccgtccaa gaaccagttc    240

tccctgaagc cgagctctgt gactgccgcg gacacggccg tggattactg tgcgagaga    299

<210> SEQ ID NO 472
<211> LENGTH: 293
<212> TYPE: DNA
<213> ORGANISM: Homo sapiens

<400> SEQUENCE: 472

caggtgcagc tacagcagtg gggcgcagga ctgttgaagc cttcggagac cctgtccctc     60

acctgcgctg tctatggtgg gtccttcagt ggttactact ggagctggat ccgccagccc    120

ccagggaagg ggctggagtg gattggggaa atcaatcata gtggaagcac caactacaac    180

ccgtccctca agagtcgagt caccatatca gtagacacgt ccaagaacca gttctccctg    240

aagctgagct ctgtgaccgc cgcggacacg gctgtgtatt actgtgcgag agg           293

<210> SEQ ID NO 473
<211> LENGTH: 293
<212> TYPE: DNA
<213> ORGANISM: Homo sapiens

<400> SEQUENCE: 473

caggtgcagc tacaacagtg gggcgcagga ctgttgaagc cttcggagac cctgtccctc     60

acctgcgctg tctatggtgg gtccttcagt ggttactact ggagctggat ccgccagccc    120

ccagggaagg ggctggagtg gattggggaa atcaatcata gtggaagcac caactacaac    180

ccgtccctca agagtcgagt caccatatca gtagacacgt ccaagaacca gttctccctg    240

aagctgagct ctgtgaccgc cgcggacacg gctgtgtatt actgtgcgag agg           293

<210> SEQ ID NO 474
<211> LENGTH: 284
<212> TYPE: DNA
<213> ORGANISM: Homo sapiens

<400> SEQUENCE: 474

caggtgcagc tacagcagtg gggcgcagga ctgttgaagc cttcggagac cctgtccctc     60

acctgcgctg tctatggtgg gtccttcagt ggttactact ggagctggat ccgccagccc    120

ccagggaagg ggctggagtg gattggggaa atcaatcata gtggaagcac caactacaac    180

ccgtccctca agagtcgagt caccatatca gtagacacgt ccaagaacca gttctccctg    240

aagctgagct ctgtgaccgc cgcggacacg gccgtgtatt actg                     284

<210> SEQ ID NO 475
<211> LENGTH: 293
<212> TYPE: DNA
<213> ORGANISM: Homo sapiens

<400> SEQUENCE: 475

caggtgcagc tacagcagtg gggcgcagga ctgttgaagc cttcggagac cctgtccctc     60

acctgcgctg tctatggtgg gtccttcagt ggttactact ggagctggat ccgccagccc    120

ccagggaagg ggctggagtg gattggggaa atcaatcata gtggaagcac caacaacaac    180

ccgtccctca agagtcgagc caccatatca gtagacacgt ccaagaacca gttctccctg    240

aagctgagct ctgtgaccgc cgcggacacg gctgtgtatt actgtgcgag agg           293

<210> SEQ ID NO 476
<211> LENGTH: 293
```

<212> TYPE: DNA
<213> ORGANISM: Homo sapiens

<400> SEQUENCE: 476
caggtgcagc tacagcagtg gggcgcagga ctgttgaagc cttcggagac cctgtccctc 60
acctgcgctg tctatggtgg gtccttcagt ggttactact ggtgctggat ccgccagccc 120
ctagggaagg ggctggagtg gattggggaa atcaatcata gtggaagcac caacaacaac 180
ccgtccctca agagtcgagc caccatatca gtagacacgt ccaagaacca gttctccctg 240
aagctgagct ctgtgaccgc cgcggacacg gctgtgtatt actgtgcgag agg 293

<210> SEQ ID NO 477
<211> LENGTH: 284
<212> TYPE: DNA
<213> ORGANISM: Homo sapiens

<400> SEQUENCE: 477
caggtgcagc tacagcagtg gggcgcagga ctgttgaagc cttcggagac cctgtccctc 60
acctgcgctg tctatggtgg gtccttcagt ggttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
aagctgggct ctgtgaccgc cgcggacacg gccgtgtatt actg 284

<210> SEQ ID NO 478
<211> LENGTH: 284
<212> TYPE: DNA
<213> ORGANISM: Homo sapiens

<400> SEQUENCE: 478
caggtgcagc tacagcagtg gggcgcagga ctgttgaagc cttcggagac cctgtccctc 60
acctgcgctg tctatggtgg gtccttcagt ggttactact ggagctggat ccgccagccc 120
ccagggaagg ggctggagtg gattggggaa atcaaccata gtggaagcac caactacaac 180
ccgtccctca agagtcgagt caccatatca gtagacacgt ccaagaacca gttctccctg 240
aagctgagct ctgtgaccgc cgcggacacg gccgtgtatt actg 284

<210> SEQ ID NO 479
<211> LENGTH: 288
<212> TYPE: DNA
<213> ORGANISM: Homo sapiens

<400> SEQUENCE: 479
caggtgcagc tacagcagtg gggcgcagga ctgttgaagc cttcggagac cctgtccctc 60
acctgcgctg tctatggtgg gaccttcagt ggttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
aagctgagct ctgtgaccgc cgcggacacg gctgtgtatt actgtgcg 288

<210> SEQ ID NO 480
<211> LENGTH: 293
<212> TYPE: DNA
<213> ORGANISM: Homo sapiens

<400> SEQUENCE: 480
caggtgcagc tgcaggagtc gggcccagga ctggtgaagc cttcacagac cctgtccctc 60

-continued

```
acctgcgctg tctatggtgg gtccttcagt ggttactact ggagctggat ccgccagccc    120

ccagggaagg gactggagtg gattggggaa atcaatcata gtggaagcac caactacaac    180

ccgtccctca agagtcgagt taccatatca gtagacacgt ctaagaacca gttctccctg    240

aagctgagct ctgtgactgc cgcggacacg gccgtgtatt actgtgcgag aga          293
```

```
<210> SEQ ID NO 481
<211> LENGTH: 293
<212> TYPE: DNA
<213> ORGANISM: Homo sapiens

<400> SEQUENCE: 481

caggtgcagc tgcaggagtc gggcccagga ctggtgaagc cttcggagac cctgtccctc     60

acctgcgctg tctatggtgg gtccttcagt ggttactact ggagctggat ccgccagccc    120

ccagggaagg gactggagtg gattggggaa atcaatcata gtggaagcac caactacaac    180

ccgtccctca agagtcgaat caccatgtca gtagacacgt ccaagaacca gttctacctg    240

aagctgagct ctgtgaccgc cgcggacacg gccgtgtatt actgtgcgag ata          293
```

```
<210> SEQ ID NO 482
<211> LENGTH: 293
<212> TYPE: DNA
<213> ORGANISM: Homo sapiens

<400> SEQUENCE: 482

caggtgcagc tacagcagtg gggcgcagga ctgttgaagc cttcggagac cctgtccctc     60

acctgcgctg tctatggtgg gtccgtcagt ggttactact ggagctggat ccggcagccc    120

ccagggaagg ggctggagtg gattgggtat atctattata gtgggagcac caacaacaac    180

ccctccctca agagtcgagc caccatatca gtagacacgt ccaagaacca gttctccctg    240

aacctgagct ctgtgaccgc cgcggacacg gccgtgtatt gctgtgcgag aga          293
```

```
<210> SEQ ID NO 483
<211> LENGTH: 291
<212> TYPE: DNA
<213> ORGANISM: Homo sapiens

<400> SEQUENCE: 483

caggtgcagc tacagcagtg gggcgcagga ctgttgaagc cttcggagac cctgtccctc     60

acctgcgctg tctatggtgg gtccttcagt ggttactact ggagctggat ccgccagccc    120

ccagggaagg ggctggagtg gattggggaa atcattcata gtggaagcac caactacaac    180

ccgtccctca agagtcgagt caccatatca gtagacacgt ccaagaacca gttctccctg    240

aagctgagct ctgtgaccgc cgcggacacg gctgtgtatt actgtgcgag a            291
```

```
<210> SEQ ID NO 484
<211> LENGTH: 221
<212> TYPE: DNA
<213> ORGANISM: Homo sapiens

<400> SEQUENCE: 484

tatggtgggt ccttcagtgg ttactactgg agctggatcc gccagccccc agggaagggg     60

ctggagtgga ttggggaaat caatcatagt ggaagcacca actacaaccc ctccctcaag    120

agtcgagtca ccatatcagt agacacgtcc aagaaccagt tctccctgaa gctgagctct    180

gtgaccgccg cggacacggc tgtgtattac tgtgcgagag g                        221
```

<210> SEQ ID NO 485
<211> LENGTH: 299
<212> TYPE: DNA
<213> ORGANISM: Homo sapiens

<400> SEQUENCE: 485
cagctgcagc tgcaggagtc gggcccagga ctggtgaagc cttcggagac cctgtccctc 60
acctgcactg tctctggtgg ctccatcagc agtagtagtt actactgggg ctggatccgc 120
cagcccccag ggaaggggct ggagtggatt gggagtatct attatagtgg gagcacctac 180
tacaacccgt ccctcaagag tcgagtcacc atatccgtag acacgtccaa gaaccagttc 240
tccctgaagc tgagctctgt gaccgccgca gacacggctg tgtattactg tgcgagaca 299

<210> SEQ ID NO 486
<211> LENGTH: 299
<212> TYPE: DNA
<213> ORGANISM: Homo sapiens

<400> SEQUENCE: 486
cagctgcagc tgcaggagtc gggcccagga ctggtgaagc cttcggagac cctgtccctc 60
acctgcactg tctctggtgg ctccatcagc agtagtagtt actactgggg ctggatccgc 120
cagcccccag ggaaggggct ggagtggatt gggagtatct attatagtgg gagcacctac 180
tacaacccgt ccctcaagag tcgagtcacc atatccgtag acacgtccaa gaaccacttc 240
tccctgaagc tgagctctgt gaccgccgca gacacggctg tgtattactg tgcgagaga 299

<210> SEQ ID NO 487
<211> LENGTH: 290
<212> TYPE: DNA
<213> ORGANISM: Homo sapiens

<400> SEQUENCE: 487
cagctgcagc tgcaggagtc gggcccagga ctggtgaagc cttcggagac cctgtccctc 60
acctgcactg tctctggtgg ctccatcagc agtagtagtt actactgggg ctggatccgc 120
cagcccccag ggaaggggct ggagtggatt gggagtatct attatagtgg gagcacctac 180
tacaacccgt ccctcaagag tcgagtcacc atatccgtag acacgtccaa gaaccagttc 240
tccctgaagc tgagctctgt gaccgccgca gacacggccg tgtattactg 290

<210> SEQ ID NO 488
<211> LENGTH: 196
<212> TYPE: DNA
<213> ORGANISM: Homo sapiens

<400> SEQUENCE: 488
gctccatcag cagtagtagt tactactggg gctggatccg ccagccccca gggaaggggc 60
tggagtggat tgggagtatc tattatagtg ggagcaccta ctacaacccg tccctcaaga 120
gtcgagtcac catatccgta gacacgtcca agaaccagtt ctccctgaag ctgagctctg 180
tgaccgccgc ggacac 196

<210> SEQ ID NO 489
<211> LENGTH: 294
<212> TYPE: DNA
<213> ORGANISM: Homo sapiens

<400> SEQUENCE: 489
cagctgcagc tgcaggagtc gggcccagga ctggtgaagc cttcggagac cccgtccctc 60
acctgcactg tctctggtgg ctccatcagc agtagtagtt actactgggg ctggatccgc 120
cagcccccag ggaaggggct ggagtggatt gggagtatct attatagtgg gagcacctac 180
tacaacccgt ccctcaagag tcgagtcacc atatccgtag acacgtccaa gaaccagttc 240
tccctgaagc tgagctctgt gaccgccgca gacacggctg tgtattactg tgcg 294

<210> SEQ ID NO 490
<211> LENGTH: 299
<212> TYPE: DNA
<213> ORGANISM: Homo sapiens

<400> SEQUENCE: 490
cggctgcagc tgcaggagtc gggcccagga ctggtgaagc cttcggagac cctgtccctc 60
acctgcactg tctctggtgg ctccatcagc agtagtagtt actactgggg ctggatccgc 120
cagcccccag ggaaggggct ggagtggatt gggagtatct attatagtgg gagcacctac 180
tacaacccgt ccctcaagag tcgagtcacc atatcagtag acacgtccaa gaaccagttc 240
cccctgaagc tgagctctgt gaccgccgcg gacacggccg tgtattactg tgcgagaga 299

<210> SEQ ID NO 491
<211> LENGTH: 299
<212> TYPE: DNA
<213> ORGANISM: Homo sapiens

<400> SEQUENCE: 491
cagctgcagc tgcaggagtc gggcccagga ctggtgaagc cttcggagac cctgtccctc 60
acctgcactg tctctggtgg ctccatcagc agtagtagtt actactgggg ctggatccgc 120
cagcccccag ggaaggggct ggagtggatt gggagtatct attatagtgg gagcacctac 180
tacaacccgt ccctcaagag tcgagtcacc atatcagtag acacgtccaa gaaccagttc 240
tccctgaagc tgagctctgt gaccgccgcg gacacggccg tgtattactg tgcgagaga 299

<210> SEQ ID NO 492
<211> LENGTH: 296
<212> TYPE: DNA
<213> ORGANISM: Homo sapiens

<400> SEQUENCE: 492
caggtgcagc tgcaggagtc gggcccagga ctggtgaagc ctccggggac cctgtccctc 60
acctgcgctg tctctggtgg ctccatcagc agtagtaact ggtggagttg ggtccgccag 120
cccccaggga aggggctgga gtggattggg gaaatctatc atagtgggag caccaactac 180
aacccgtccc tcaagagtcg agtcaccata tcagtagaca agtccaagaa ccagttctcc 240
ctgaagctga gctctgtgac cgccgcggac acggccgtgt attgctgtgc gagaga 296

<210> SEQ ID NO 493
<211> LENGTH: 296
<212> TYPE: DNA
<213> ORGANISM: Homo sapiens

<400> SEQUENCE: 493
caggtgcagc tgcaggagtc gggcccagga ctggtgaagc cttcggggac cctgtccctc 60
acctgcgctg tctctggtgg ctccatcagc agtagtaact ggtggagttg ggtccgccag 120
cccccaggga aggggctgga gtggattggg gaaatctatc atagtgggag caccaactac 180
aacccgtccc tcaagagtcg agtcaccata tcagtagaca agtccaagaa ccagttctcc 240
ctgaagctga gctctgtgac cgccgcggac acggccgtgt attactgtgc gagaga 296

<210> SEQ ID NO 494
<211> LENGTH: 287
<212> TYPE: DNA
<213> ORGANISM: Homo sapiens

<400> SEQUENCE: 494
caggtgcagc tgcaggagtc gggcccagga ctggtgaagc ctccggggac cctgtccctc 60
acctgcgctg tctctggtgg ctccatcagc agtagtaact ggtggagttg ggtccgccag 120
cccccaggga aggggctgga gtggattggg gaaatctatc atagtgggag caccaactac 180
aacccgtccc tcaagagtcg agtcaccata tcagtagaca agtccaagaa ccagttctcc 240
ctgaagctga gctctgtgac cgccgcggac acggccgtgt attactg 287

<210> SEQ ID NO 495
<211> LENGTH: 287
<212> TYPE: DNA
<213> ORGANISM: Homo sapiens

<400> SEQUENCE: 495
caggtgcagc tgcaggagtc gggcccagga ctggtgaagc ctccggggac cctgtccctc 60
acctgcgcta tctctggtgg ctccatcagc agtagtaact ggtggagttg ggtccgccag 120
cccccaggga aggggctgga gtggattggg gaaatctatc atagtgggag caccaactac 180
aacccgtccc tcaagagtcg agtcaccata tcagtagaca agtccaagaa ccagttctcc 240
ctgaagctga gctctgtgac cgccgcggac acggccgtgt attactg 287

<210> SEQ ID NO 496
<211> LENGTH: 287
<212> TYPE: DNA
<213> ORGANISM: Homo sapiens

<400> SEQUENCE: 496
caggtgcagc tgcaggagtt gggcccagga ctggtgaagc ctccggggac cctgtccctc 60
acctgcgctg tctctggtgg ctccatcagc agtagtaact ggtggagttg ggtccgccag 120
cccccaggga aggggctgga gtggattggg gaaatctatc atagtgggag caccaactac 180
aacccgtccc tcaagagtcg agtcaccata tcagtagaca agtccaagaa ccagttctcc 240
ctgaagctga gctctgtgac cgccgcggac acggccgtgt attactg 287

<210> SEQ ID NO 497
<211> LENGTH: 224
<212> TYPE: DNA
<213> ORGANISM: Homo sapiens
<220> FEATURE:
<221> NAME/KEY: modified_base
<222> LOCATION: (59)..(61)
<223> OTHER INFORMATION: a, c, t or g

<400> SEQUENCE: 497
tctggtggct ccatcagcag tagtaactgg tggagttggg tccgccagcc cccagggann 60
nggctggagt ggattgggga aatctatcat agtgggagca ccaactacaa cccgtccctc 120
aagagtcgag tcaccatgtc agtagacacg tccaagaacc agttctccct gaagctgagc 180
tctgtgaccg ccgcggacac ggccgtgtat tactgtgcga gaga 224

<210> SEQ ID NO 498
<211> LENGTH: 293
<212> TYPE: DNA

<213> ORGANISM: Homo sapiens

<400> SEQUENCE: 498
caggtgcagc tgcaggagtc gggcccagga ctggtgaagc cttcggagac cctgtccctc 60
acctgcactg tctctggtgg ctccatcagt agttactact ggagctggat ccggcagccc 120
gccgggaagg gactggagtg gattgggcgt atctatacca gtgggagcac caactacaac 180
ccctccctca agagtcgagt caccatgtca gtagacacgt ccaagaacca gttctccctg 240
aagctgagct ctgtgaccgc cgcggacacg gccgtgtatt actgtgcgag aga 293

<210> SEQ ID NO 499
<211> LENGTH: 296
<212> TYPE: DNA
<213> ORGANISM: Homo sapiens

<400> SEQUENCE: 499
caggtgcagc tgcaggagtc gggcccagga ctggtgaagc cttcggagac cctgtccctc 60
atctgcgctg tctctggtga ctccatcagc agtggtaact ggtgaatctg ggtccgccag 120
cccccaggga aggggctgga gtggattggg gaaatccatc atagtgggag cacctactac 180
aacccgtccc tcaagagtcg aatcaccatg tccgtagaca cgtccaagaa ccagttctac 240
ctgaagctga gctctgtgac cgccgcggac acggccgtgt attactgtgc gagata 296

<210> SEQ ID NO 500
<211> LENGTH: 296
<212> TYPE: DNA
<213> ORGANISM: Homo sapiens

<400> SEQUENCE: 500
caggtgcagc tgcaggagtc gggcccagga ctggtgaagc cttcggagac cctgtccctc 60
atctgcgctg tctctggtga ctccatcagc agtggtaact ggtgaatctg ggtccgccag 120
cccccaggga aggggctgga gtggattggg gaaatccatc atagtgggag cacctactac 180
aacccgtccc tcaagagtcg aatcaccatg tcagtagaca cgtccaagaa ccagttctac 240
ctgaagctga gctctgtgac cgccgcggac acggccgtgt attactgtgc gagata 296

<210> SEQ ID NO 501
<211> LENGTH: 287
<212> TYPE: DNA
<213> ORGANISM: Homo sapiens

<400> SEQUENCE: 501
caggtgcagc tgcaggagtc gggcccagga ctggtgaagc cttcggagac cctgtccctc 60
atctgcgctg tctctggtga ctccatcagc agtggtaact ggtgaatctg ggtccgccag 120
cccccaggga aggggctgga gtggattggg gaaatccatc atagtgggag cacctactac 180
aacccgtccc tcaagagtcg aatcaccatg tcagtagaca cgtccaagaa ccagttctcc 240
ctgaagctga gctctgtgac cgccgcggac acggccgtgt attactg 287

<210> SEQ ID NO 502
<211> LENGTH: 287
<212> TYPE: DNA
<213> ORGANISM: Homo sapiens

<400> SEQUENCE: 502
caggtgcagc tgcaggagtc gggcccagga ctggtgaagc tttcggagac cctgtccctc 60
atctgcgctg tctctggtga ctccatcagc agtggtaact ggtgaatctg ggtccgccag 120
cccccaggga aggggctgga gtggattggg gaaatccatc atagtgggag cacctactac 180
aacccgtccc tcaagagtcg aatcaccatg tcagtagaca cgtccaagaa ccagttctac 240
ctgaagctga gctctgtgac cgccgcggac acggccgtgt attactg 287

<210> SEQ ID NO 503
<211> LENGTH: 287
<212> TYPE: DNA
<213> ORGANISM: Homo sapiens

<400> SEQUENCE: 503
caggtgcagc tgcaggagtc gggcccagga ctggtgaagc tttcggagac cctgtccctc 60
atctgcgctg tctctggtga ctccatcagc agtggtaact ggtgaatctg ggtccgccag 120
cccccaggga aggggctgga gtggattggg gaaatccatc atagtgggag cacctactac 180
aacccgtccc tcaagagtcg aatcaccatg tccgtagaca cgtccaagaa ccagttctac 240
ctgaagctga gctctgtgac cgccgcggac acggccgtgt attactg 287

<210> SEQ ID NO 504
<211> LENGTH: 287
<212> TYPE: DNA
<213> ORGANISM: Homo sapiens

<400> SEQUENCE: 504
caggtgcagc tgcaggagtc gggcccagga ctggtgaagc cttcggagac cctgtccctc 60
atctgcgctg tctctggtga ctccatcagc agtggtaact ggtgaatctg ggtccgccag 120
cccccaggga aggggctgga gtggattggg gaaatccatc atagtgggag cacctactac 180
aacccgtccc tcaagagtcg aatcaccatg tccgtagaca cgtccaagaa gcagttctac 240
ctgaagctga gctctgtgac cgctgcggac acggccgtgt attactg 287

<210> SEQ ID NO 505
<211> LENGTH: 286
<212> TYPE: DNA
<213> ORGANISM: Homo sapiens

<400> SEQUENCE: 505
caggtgcagc tgcaggagtc gggcccagga ctggtgaagc cttcggagac cctgtccctc 60
atctgcgctg tctctggtga ctccatcagc agtggtaact ggtgaatctg ggtccgccag 120
cccccaggga aggggctgga gtggattggg gaaatccatc atagtgggag cacctactac 180
aacccgtccc tcaagagtcg aatcaccatg tccgtagaca cgtccaggaa ccagttctcc 240
ctgaagctga gctctgtgac cgccgcagac acggccgtgt attact 286

<210> SEQ ID NO 506
<211> LENGTH: 296
<212> TYPE: DNA
<213> ORGANISM: Homo sapiens

<400> SEQUENCE: 506
caggtgcagc tgcaggagtc gggcccagga ctggtgaagc cttcggagac cctgtccctc 60
atctgcgctg tctctggtga ctccatcagc agtggtaact ggtgaatctg ggtccgccag 120
cccccaggga aggggctgga gtggattggg gaaatccatc atagtgggag cacctactac 180
aacccgtccc tcaagagtcg aatcaccatg tcagtagaca cgtccaagaa ccagttctac 240
ctgaagctga gctctgtgac cgccgcggac acggccgtgt attactgtgc gagaga 296

<210> SEQ ID NO 507
<211> LENGTH: 296
<212> TYPE: DNA
<213> ORGANISM: Homo sapiens

<400> SEQUENCE: 507
caggtgcagc tgcaggagtc gggcccagga ctggtgaagc cttcggagac cctgtccctc 60
atctgcgctg tctctggtga ctccatcagc agtggtaact ggtgaatctg ggtccgccag 120
cccccaggga aggggctgga gtggattggg gaaatccatc atagtgggag cacctactac 180
aacccgtccc tcaagagtcg aatcaccatg tccgtagaca cgtccaagaa ccagttctcc 240
ctgaagctga gctctgtgac cgccgtggac acggccgtgt attactgtgc gagaaa 296

<210> SEQ ID NO 508
<211> LENGTH: 293
<212> TYPE: DNA
<213> ORGANISM: Homo sapiens

<400> SEQUENCE: 508
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gattgggtat atctattaca gtgggagcac caactacaac 180
ccctccctca agagtcgagt caccatatca gtagacacgt ccaagaacca gttctccctg 240
aagctgagct ctgtgaccgc tgcggacacg gccgtgtatt actgtgcgag aga 293

<210> SEQ ID NO 509
<211> LENGTH: 293
<212> TYPE: DNA
<213> ORGANISM: Homo sapiens

<400> SEQUENCE: 509
caggtgcagc tgcaggagtc gggcccagga ctggtgaagc cttcggagac cctgtccctc 60
acctgcactg tctctggtgg ctccgtcagt agttactact ggagctggat ccggcagccc 120
ccagggaagg gactggagtg gattgggtat atctattaca gtgggagcac caactacaac 180
ccctccctca agagtcgagt caccatatca gtagacacgt ccaagaacca gttctccctg 240
aagctgagct ctgtgaccgc tgcggacacg gccgtgtatt actgtgcgag aga 293

<210> SEQ ID NO 510
<211> LENGTH: 288
<212> TYPE: DNA
<213> ORGANISM: Homo sapiens

<400> SEQUENCE: 510
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gattgggtat atctattaca gtgggagcac caactacaac 180
ccctccctca agagtcgagt caccatatca gtagacacgt ccaagaacca attctccctg 240
aagctgagct ctgtgaccgc tgcggacacg gccgtgtatt actgtgcg 288

<210> SEQ ID NO 511
<211> LENGTH: 288
<212> TYPE: DNA
<213> ORGANISM: Homo sapiens

<400> SEQUENCE: 511

```
caggtgcagc tgcaggagtc gggcccagga ctggtgaagc cttcggagac cctgtccctc     60

acctgcactg tctctggtgg ctccatcagt agttactact ggagctggat ccggcagccc    120

ccagggaagg gactggagtg gattgggtat atctattata gtgggagcac ctactacaac    180

ccgtccctca agagtcgagt caccatgtca gtagacacgt ccaagaacca gttctccctg    240

aagctgagct ctgtgaccgc cgcagacacg gctgtgtatt actgtgcg                 288


<210> SEQ ID NO 512
<211> LENGTH: 288
<212> TYPE: DNA
<213> ORGANISM: Homo sapiens

<400> SEQUENCE: 512

caggtgcagc tgcaggagtc gggcccagga ctggtgaagc cttcggagac cctgtccctc     60

acctgcactg tctctggtgg ctccatcagt agttactact ggagctggat ccggcagccg    120

ccggggaagg gactggagtg gattgggcgt atctattata gtgggagcac ctactacaac    180

ccgtccctca agagtcgagt caccatatcc gtagacacgt ccaagaacca gttctccctg    240

aagctgagct ctgtgaccgc cgcagacacg gctgtgtatt actgtgcg                 288


<210> SEQ ID NO 513
<211> LENGTH: 288
<212> TYPE: DNA
<213> ORGANISM: Homo sapiens

<400> SEQUENCE: 513

caggtgcagc tgcaggagtc gggcccagga ctggtgaagc cttcggagac cctgtccctc     60

acctgcactg tcactggtgg ctccatcagt agttactact ggagctggat ccggcagccc    120

gctgggaagg gcctggagtg gattgggtac atctattaca gtgggagcac ctactacaac    180

ccgtccctca agagtcgagt taccatatca gtagacacgt ctaagaacca gttctccctg    240

aagctgagct ctgtgactgc cgcggacacg gccgtgtatt actgtgcg                 288


<210> SEQ ID NO 514
<211> LENGTH: 291
<212> TYPE: DNA
<213> ORGANISM: Homo sapiens

<400> SEQUENCE: 514

caggtgcagc tgcaggagtc gggcccagga ctggtgaagc cttcggacac cctgtccctc     60

acctgcactg tctctggtgg ctccatcagt agttactact ggagctggat ccggcagccc    120

ccagggaagg gactggagtg gattgggtat atctattaca gtgggagcac caactacaac    180

ccctccctca agagtcgagt caccatatca gtagacacgt ccaagaacca gttctccctg    240

aagctgagct ctgtgaccgc tgcggacacg gccgtgtatt actgtgcgag a             291


<210> SEQ ID NO 515
<211> LENGTH: 237
<212> TYPE: DNA
<213> ORGANISM: Homo sapiens
<220> FEATURE:
<221> NAME/KEY: modified_base
<222> LOCATION: (36)..(36)
<223> OTHER INFORMATION: a, c, t or g
<220> FEATURE:
<221> NAME/KEY: modified_base
<222> LOCATION: (214)..(214)
<223> OTHER INFORMATION: a, c, t or g
```

<400> SEQUENCE: 515
tccctcacct gcactgtctc tggtggctcc atcagnagtt actactggag ctggatccgg 60
cagcccccag ggaagggact ggagtggatt gggtatatct attacagtgg gagcaccaac 120
tacaacccct ccctcaagag tcgagtcacc atatcagtag acacgtccaa gaaccagttc 180
tccctgaagc tgagctctgt gaccgccgca gacncggccg tgtattactg tgcgaga 237

<210> SEQ ID NO 516
<211> LENGTH: 221
<212> TYPE: DNA
<213> ORGANISM: Homo sapiens
<220> FEATURE:
<221> NAME/KEY: modified_base
<222> LOCATION: (54)..(54)
<223> OTHER INFORMATION: a, c, t or g
<220> FEATURE:
<221> NAME/KEY: modified_base
<222> LOCATION: (56)..(58)
<223> OTHER INFORMATION: a, c, t or g

<400> SEQUENCE: 516
tctggtggct ccatcagtag ttactactgg agctggatcc ggcagccccc aggnannnga 60
ctggagtgga ttgggtatat ctattacagt gggagcacca actacaaccc ctccctcaag 120
agtcgagtca ccatatcagt agacacgtcc aagaaccagt tctccctgaa gctgagctct 180
gtgaccgctg cggacacggc cgtgtattac tgtgcgagag g 221

<210> SEQ ID NO 517
<211> LENGTH: 293
<212> TYPE: DNA
<213> ORGANISM: Homo sapiens

<400> SEQUENCE: 517
caggtgcagc tacagcagtg gggcgcagga ctgttgaagc cttcggagac cctgtccctc 60
acctgcgctg tctatggtgg ctccatcagt agttactact ggagctggat ccggcagccc 120
gccgggaagg ggctggagtg gattgggcgt atctatacca gtgggagcac caactacaac 180
ccctccctca agagtcgagt caccatgtca gtagacacgt ccaagaacca gttctccctg 240
aagctgagct ctgtgaccgc cgcggacacg gccgtgtatt actgtgcgag ata 293

<210> SEQ ID NO 518
<211> LENGTH: 299
<212> TYPE: DNA
<213> ORGANISM: Homo sapiens

<400> SEQUENCE: 518
caggtgcagc tgcaggagtc gggcccagga ctggtgaagc cttcggagac cctgtccctc 60
acctgcactg tctctggtgg ctccgtcagc agtggtagtt actactggag ctggatccgg 120
cagcccccag ggaagggact ggagtggatt gggtatatct attacagtgg gagcaccaac 180
tacaacccct ccctcaagag tcgagtcacc atatcagtag acacgtccaa gaaccagttc 240
tccctgaagc tgagctctgt gaccgctgcg gacacggccg tgtattactg tgcgagaga 299

<210> SEQ ID NO 519
<211> LENGTH: 299
<212> TYPE: DNA
<213> ORGANISM: Homo sapiens

<400> SEQUENCE: 519
caggtgcagc tgcaggagtc gggcccagga ctggtgaagc cttcacagac cctgtccctc 60
acctgcactg tctctggtgg ctccatcagc agtggtagtt actactggag ctggatccgg 120
cagcccgccg ggaagggact ggagtggatt gggcgtatct ataccagtgg gagcaccaac 180
tacaacccct ccctcaagag tcgagtcacc atatcagtag acacgtccaa gaaccagttc 240
tccctgaagc tgagctctgt gaccgccgca gacacggccg tgtattactg tgcgagaga 299

<210> SEQ ID NO 520
<211> LENGTH: 299
<212> TYPE: DNA
<213> ORGANISM: Homo sapiens

<400> SEQUENCE: 520
caggtgcagc tgcaggagtc gggcccagga ctggtgaagc cttcggagac cctgtccctc 60
acctgcactg tctctggtgg ctccgtcagc agtggtagtt actactggag ctggatccgg 120
cagcccccag ggaagggact ggagtggatt gggtatatct attacagtgg gagcaccaac 180
tacaacccct ccctcaagag tcgagtcacc atatcagtag acacgtccaa gaaccacttc 240
tccctgaagc tgagctctgt gaccgctgcg gacacggccg tgtattactg tgcgagaga 299

<210> SEQ ID NO 521
<211> LENGTH: 287
<212> TYPE: DNA
<213> ORGANISM: Homo sapiens

<400> SEQUENCE: 521
caggtgcagc tgcaggagtc gggcccagga ctggtgaagc cttcggagac cctgtccctc 60
acctgcactg tctctggtgg ctccgtcagc agtggtagtt actactggag ctggatccgg 120
cagcccccag ggaagggact ggagtggatt ggatatatct attacagtgg gagcaccaac 180
tacaacccct ccctcaagag tcgagtcacc atatcagtag acacgtccaa gaaccagttc 240
tccctgaagc tgagctctgt gaccgctgac acggccgtgt attactg 287

<210> SEQ ID NO 522
<211> LENGTH: 297
<212> TYPE: DNA
<213> ORGANISM: Homo sapiens

<400> SEQUENCE: 522
cagctgcagc tgcaggagtc gggcccagga ctggtgaagc cttcggagac cctgtccctc 60
acctgcactg tctctggtgg ctccatcagc agtagtagtt actactgggg ctggatccgg 120
cagcccccag ggaagggact ggagtggatt gggtatatct attacagtgg gagcaccaac 180
tacaacccct ccctcaagag tcgagtcacc atatcagtag acaagtccaa gaaccagttc 240
tccctgaagc tgagctctgt gaccgccgcg gacacggccg tgtattactg tgcgaga 297

<210> SEQ ID NO 523
<211> LENGTH: 227
<212> TYPE: DNA
<213> ORGANISM: Homo sapiens

<400> SEQUENCE: 523
tctggtggct ccgtcagcag tggtagttac tactggagct ggatccggca gcccccaggg 60
aagggactgg agtggattgg gtatatctat tacagtggga gcaccaacta caacccctcc 120
ctcaagagtc gagtcaccat atcagtagac acgtccaaga accagttctc cctgaagctg 180
agctctgtga ccgccgcgga cacggccgtg tattactgtg ccagaga 227

<210> SEQ ID NO 524
<211> LENGTH: 227
<212> TYPE: DNA
<213> ORGANISM: Homo sapiens

<400> SEQUENCE: 524
tctggtggct ccgtcagcag tggtagttac tactggagct ggatccggca gcccccaggg 60
aagggactgg agtggattgg gtatatctat tacagtggga gcaccaacta caacccctcc 120
ctcaagagtc gagtcaccat atcagtagac acgtccaaga accagttctc cctgaagctg 180
agctctgtga ccgctgcgga cacggccgtg tattactgtg cgagaca 227

<210> SEQ ID NO 525
<211> LENGTH: 299
<212> TYPE: DNA
<213> ORGANISM: Homo sapiens

<400> SEQUENCE: 525
caggtgcagc tgcaggagtc gggcccagga ctggtgaagc cttcggagac cctgtccctc 60
acctgcactg tctctggtgg ctccgtcagc agtggtggtt actactggag ctggatccgg 120
cagcccccag ggaagggact ggagtggatt gggtatatct attacagtgg gagcaccaac 180
tacaacccct ccctcaagag tcgagtcacc atatcagtag acacgtccaa gaaccagttc 240
tccctgaagc tgagctctgt gaccgctgcg gacacggccg tgtattactg tgcgagaga 299

<210> SEQ ID NO 526
<211> LENGTH: 294
<212> TYPE: DNA
<213> ORGANISM: Homo sapiens

<400> SEQUENCE: 526
caggtgcagc tgcaggagtc gggcccagga ctggtgaagc cttcggagac cctgtccctc 60
acctgcgctg tctctggtta ctccatcagc agtggttact actggggctg gatccggcag 120
cccccaggga aggggctgga gtggattggg agtatctatc atagtgggag cacctactac 180
aacccgtccc tcaagagtcg agtcaccata tcagtagaca cgtccaagaa ccagttctcc 240
ctgaagctga gctctgtgac cgccgcagac acggccgtgt attactgtgc gaga 294

<210> SEQ ID NO 527
<211> LENGTH: 294
<212> TYPE: DNA
<213> ORGANISM: Homo sapiens

<400> SEQUENCE: 527
caggtgcagc tgcaggagtc gggcccagga ctggtgaagc cttcggagac cctgtccctc 60
acctgcactg tctctggtta ctccatcagc agtggttact actggggctg gatccggcag 120
cccccaggga aggggctgga gtggattggg agtatctatc atagtgggag cacctactac 180
aacccgtccc tcaagagtcg agtcaccata tcagtagaca cgtccaagaa ccagttctcc 240
ctgaagctga gctctgtgac cgccgcagac acggccgtgt attactgtgc gaga 294

<210> SEQ ID NO 528
<211> LENGTH: 296
<212> TYPE: DNA
<213> ORGANISM: Homo sapiens

<400> SEQUENCE: 528
caggtgcagc tgcaggagtc gggcccagga ctggtgaagc cttcggagac cctgtccctc 60
acctgcgttg tctctggtgg ctccatcagc agtagtaact ggtggagctg ggtccgccag 120
cccccaggga aggggctgga gtggattggg gaaatctatc atagtgggaa ccccaactac 180
aacccgtccc tcaagagtcg agtcaccata tcaatagaca agtccaagaa ccaattctcc 240
ctgaagctga gctctgtgac cgccgcggac acggccgtgt attactgtgc gagaga 296

<210> SEQ ID NO 529
<211> LENGTH: 296
<212> TYPE: DNA
<213> ORGANISM: Homo sapiens

<400> SEQUENCE: 529
gaggtgcagc tggtgcagtc tggagcagag gtgaaaaagc ccggggagtc tctgaagatc 60
tcctgtaagg gttctggata cagctttacc agctactgga tcggctgggt gcgccagatg 120
cccgggaaag gcctggagtg gatggggatc atctatcctg gtgactctga taccagatac 180
agcccgtcct tccaaggcca ggtcaccatc tcagccgaca agtccatcag caccgcctac 240
ctgcagtgga gcagcctgaa ggcctcggac accgccatgt attactgtgc gagaca 296

<210> SEQ ID NO 530
<211> LENGTH: 296
<212> TYPE: DNA
<213> ORGANISM: Homo sapiens

<400> SEQUENCE: 530
gaggtgcagc tggtgcagtc tggagcagag gtgaaaaagc ccggggagtc tctgaagatc 60
tcctgtaagg gttctggata cagctttacc agctactgga ccggctgggt gcgccagatg 120
cccgggaaag gcttggagtg gatggggatc atctatcctg gtgactctga taccagatac 180
agcccgtcct tccaaggcca ggtcaccatc tcagccgaca agtccatcag caccgcctac 240
ctgcagtgga gcagcctgaa ggcctcggac accgccatgt attactgtgc gagaca 296

<210> SEQ ID NO 531
<211> LENGTH: 294
<212> TYPE: DNA
<213> ORGANISM: Homo sapiens

<400> SEQUENCE: 531
gaggtgcagc tggtgcagtc tggagcagag gtgaaaaagc cgggggagtc tctgaagatc 60
tcctgtaagg gttctggata cagctttacc agctactgga tcggctgggt gcgccagatg 120
cccgggaaag gcctggagtg gatggggatc atctatcctg gtgactctga taccagatac 180
agcccgtcct tccaaggcca ggtcaccatc tcagccgaca agtccatcag caccgcctac 240
ctgcagtgga gcagcctgaa ggcctcggac accgccatgt attactgtgc gaga 294

<210> SEQ ID NO 532
<211> LENGTH: 294
<212> TYPE: DNA
<213> ORGANISM: Homo sapiens

<400> SEQUENCE: 532
gaggtgcagc tggtgcagtc tggagcagag gtgaaaaagc cgggggagtc tctgaagatc 60
tcctgtaagg gttctggata cagctttacc agctactgga tcggctgggt gcgccagatg 120
cccgggaaag gcctggagtg gatggggatc atctatcctg gtgactctga taccagatac 180
agcccgtcct tccaaggcca ggtcaccatc tcagccgaca agcccatcag caccgcctac 240
ctgcagtgga gcagcctgaa ggcctcggac accgccatgt attactgtgc gaga 294

<210> SEQ ID NO 533
<211> LENGTH: 245
<212> TYPE: DNA
<213> ORGANISM: Homo sapiens

<400> SEQUENCE: 533
aaaagcccgg ggagtctctg aagatctcct gtaagggttc tggatacagc tttaccagct 60
actggatcgg ctgggtgcgc cagatgccca ggaaaggcct ggagtggatg gggatcatct 120
atcctggtga ctctgatacc agatacagcc cgtccttcca aggccaggtc accatctcag 180
ccgacaagtc catcagcacc gcctacctgc agtggagcag cctgaaggcc tcggacaccg 240
ccatg 245

<210> SEQ ID NO 534
<211> LENGTH: 294
<212> TYPE: DNA
<213> ORGANISM: Homo sapiens

<400> SEQUENCE: 534
gaggtgcagc tgttgcagtc tgcagcagag gtgaaaagac ccggggagtc tctgaggatc 60
tcctgtaaga cttctggata cagctttacc agctactgga tccactgggt gcgccagatg 120
cccgggaaag aactggagtg gatggggagc atctatcctg ggaactctga taccagatac 180
agcccatcct tccaaggcca cgtcaccatc tcagccgaca gctccagcag caccgcctac 240
ctgcagtgga gcagcctgaa ggcctcggac gccgccatgt attattgtgt gaga 294

<210> SEQ ID NO 535
<211> LENGTH: 294
<212> TYPE: DNA
<213> ORGANISM: Homo sapiens

<400> SEQUENCE: 535
gaagtgcagc tggtgcagtc tggagcagag gtgaaaaagc ccggggagtc tctgaggatc 60
tcctgtaagg gttctggata cagctttacc agctactgga tcagctgggt gcgccagatg 120
cccgggaaag gcctggagtg gatggggagg attgatccta gtgactctta taccaactac 180
agcccgtcct tccaaggcca cgtcaccatc tcagctgaca agtccatcag cactgcctac 240
ctgcagtgga gcagcctgaa ggcctcggac accgccatgt attactgtgc gaga 294

<210> SEQ ID NO 536
<211> LENGTH: 295
<212> TYPE: DNA
<213> ORGANISM: Homo sapiens

<400> SEQUENCE: 536
gaagtgcagc tggtgcagtc tggagcagag gtgaaaaagc ccggggagtc tctgaggatc 60
tcctgtaagg gttctggata cagctttacc agctactgga tcagctgggt gcgccagatg 120
cccgggaaag gcttggagtg gatggggagg attgatccta gtgactctta taccaactac 180
agcccgtcct tccaaggcca cgtcaccatc tcagctgaca agtccatcag cactgcctac 240
ctgcagtgga gcagcctgaa ggctcggaca ccgccatgta ttactgtgcg agaca 295

<210> SEQ ID NO 537
<211> LENGTH: 294
<212> TYPE: DNA
<213> ORGANISM: Homo sapiens

<400> SEQUENCE: 537
gaagtgcagc tggtgcagtc cggagcagag gtgaaaaagc ccggggagtc tctgaggatc 60
tcctgtaagg gttctggata cagctttacc agctactgga tcagctgggt gcgccagatg 120
cccgggaaag gcctggagtg gatggggagg attgatccta gtgactctta taccaactac 180
agcccgtcct tccaaggcca cgtcaccatc tcagctgaca agtccatcag cactgcctac 240
ctgcagtgga gcagcctgaa ggcctcggac accgccatgt attactgtgc gaga 294

<210> SEQ ID NO 538
<211> LENGTH: 294
<212> TYPE: DNA
<213> ORGANISM: Homo sapiens

<400> SEQUENCE: 538
gaagtgcagc tggtgcagtc tggagcagag gtgaaaaagc ccggggagtc tctgaggatc 60
tcctgtaagg gttctggata cagctttacc agctactgga tcagctgggt gcgccagatg 120
cccgggaaag gcctggagtg gatggggagg attgatccta gtgactctta taccaactac 180
agcccgtcct tccaaggcca ggtcaccatc tcagctgaca agtccatcag cactgcctac 240
ctgcagtgga gcagcctgaa ggcctcggac accgccatgt attactgtgc gaga 294

<210> SEQ ID NO 539
<211> LENGTH: 305
<212> TYPE: DNA
<213> ORGANISM: Homo sapiens

<400> SEQUENCE: 539
caggtacagc tgcagcagtc aggtccagga ctggtgaagc cctcgcagac cctctcactc 60
acctgtgcca tctccgggga cagtgtctct agcaacagtg ctgcttggaa ctggatcagg 120
cagtccccat cgagaggcct tgagtggctg ggaaggacat actacaggtc caagtggtat 180
aatgattatg cagtatctgt gaaaagtcga ataaccatca acccagacac atccaagaac 240
cagttctccc tgcagctgaa ctctgtgact cccgaggaca cggctgtgta ttactgtgca 300
agaga 305

<210> SEQ ID NO 540
<211> LENGTH: 305
<212> TYPE: DNA
<213> ORGANISM: Homo sapiens

<400> SEQUENCE: 540
caggtacagc tgcagcagtc aggtccggga ctggtgaagc cctcgcagac cctctcactc 60
acctgtgcca tctccgggga cagtgtctct agcaacagtg ctgcttggaa ctggatcagg 120
cagtccccat cgagaggcct tgagtggctg ggaaggacat actacaggtc caagtggtat 180
aatgattatg cagtatctgt gaaaagtcga ataaccatca acccagacac atccaagaac 240
cagttctccc tgcagctgaa ctctgtgact cccgaggaca cggctgtgta ttactgtgca 300
agaga 305

<210> SEQ ID NO 541
<211> LENGTH: 294
<212> TYPE: DNA
<213> ORGANISM: Homo sapiens

<400> SEQUENCE: 541
caggtgcagc tggtgcaatc tgggtctgag ttgaagaagc ctggggcctc agtgaaggtt 60
tcctgcaagg cttctggata caccttcact agctatgcta tgaattgggt gcgacaggcc 120
cctggacaag ggcttgagtg gatgggatgg atcaacacca acactgggaa cccaacgtat 180
gcccagggct tcacaggacg gtttgtcttc tccttggaca cctctgtcag cacggcatat 240
ctgcagatct gcagcctaaa ggctgaggac actgccgtgt attactgtgc gaga 294

<210> SEQ ID NO 542
<211> LENGTH: 296
<212> TYPE: DNA
<213> ORGANISM: Homo sapiens

<400> SEQUENCE: 542
caggtgcagc tggtgcaatc tgggtctgag ttgaagaagc ctggggcctc agtgaaggtt 60
tcctgcaagg cttctggata caccttcact agctatgcta tgaattgggt gcgacaggcc 120
cctggacaag ggcttgagtg gatgggatgg atcaacacca acactgggaa cccaacgtat 180
gcccagggct tcacaggacg gtttgtcttc tccttggaca cctctgtcag cacggcatat 240
ctgcagatca gcagcctaaa ggctgaggac actgccgtgt attactgtgc gagaga 296

<210> SEQ ID NO 543
<211> LENGTH: 274
<212> TYPE: DNA
<213> ORGANISM: Homo sapiens

<400> SEQUENCE: 543
caggtgcagc tggtgcaatc tgggtctgag ttgaagaagc ctggggcctc agtgaaggtt 60
tcctgcaagg cttctggata caccttcact agctatgcta tgaattgggt gcgacaggcc 120
cctggacaag ggcttgagtg gatgggatgg atcaacacca acactgggaa cccaacgtat 180
gcccagggct tcacaggacg gtttgtcttc tccttggaca cctctgtcag cacggcatat 240
ctgcagatca gcacgctaaa ggctgaggac actg 274

<210> SEQ ID NO 544
<211> LENGTH: 289
<212> TYPE: DNA
<213> ORGANISM: Homo sapiens

<400> SEQUENCE: 544
ctgcagctgg tgcagtctgg gcctgaggtg aagaagcctg ggcctcagt gaaggtctcc 60 tataagtctt ctggttacac cttcaccatc tatggtatga attgggtatg atagacccct 120
ggacagggct ttgagtggat gtgatggatc atcacctaca ctgggaaccc aacgtatacc 180
cacggcttca caggatggtt tgtcttctcc atggacacgt ctgtcagcac ggcgtgtctt 240
cagatcagca gcctaaaggc tgaggacacg gccgagtatt actgtgcga 289

<210> SEQ ID NO 545
<211> LENGTH: 296
<212> TYPE: DNA
<213> ORGANISM: Homo sapiens

<400> SEQUENCE: 545
caggtgcagc tggtgcagtc tggccatgag gtgaagcagc ctggggcctc agtgaaggtc 60
tcctgcaagg cttctggtta cagtttcacc acctatggta tgaattgggt gccacaggcc 120
cctggacaag ggcttgagtg gatgggatgg ttcaacacct acactgggaa cccaacatat 180
gcccagggct tcacaggacg gtttgtcttc tccatggaca cctctgccag cacagcatac 240
ctgcagatca gcagcctaaa ggctgaggac atggccatgt attactgtgc gagata 296

<210> SEQ ID NO 546
<211> LENGTH: 26
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TCR gamma primer

<400> SEQUENCE: 546
ggaggggaag gccccacagt gtcttc 26

<210> SEQ ID NO 547
<211> LENGTH: 28
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TCR gamma primer

<400> SEQUENCE: 547
ccaaatcagg ctttggagca cctgatct 28

<210> SEQ ID NO 548
<211> LENGTH: 27
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TCR gamma primer

<400> SEQUENCE: 548
caaaggctta gaatatttat tacatgt 27

<210> SEQ ID NO 549
<211> LENGTH: 27
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TCR gamma primer

<400> SEQUENCE: 549
tgaagtcata cagttcctgg tgtccat 27

<210> SEQ ID NO 550
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer
<220> FEATURE:
<221> NAME/KEY: modified_base
<222> LOCATION: (8)..(8)
<223> OTHER INFORMATION: a, c, t or g

<400> SEQUENCE: 550

-continued tgggtgcnac aggcccctgg acaagggctt gagtgg 36

<210> SEQ ID NO 551
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 551
tgggtgcgac aggctcctgg aaaagggctt gagtgg 36

<210> SEQ ID NO 552
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 552
tgggtgcgcc aggcccccgg acaaaggctt gagtgg 36

<210> SEQ ID NO 553
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 553
tgggtgcgac aggcccccgg acaagcgctt gagtgg 36

<210> SEQ ID NO 554
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 554
tgggtgcgac aggcccccag acaagcgctt gagtgg 36

<210> SEQ ID NO 555
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 555
tgggtgcgac aggctcgtgg acaacgcctt gagtgg 36

<210> SEQ ID NO 556
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 556
tggttgcaac aggcccctgg acaagggctt gaaagg 36

<210> SEQ ID NO 557
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 557
tgggtgcgac aggccactgg acaagggctt gagtgg 36

<210> SEQ ID NO 558
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 558
tgggtgcaac agtcccctgg acaagggctt gagtgg 36

<210> SEQ ID NO 559
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 559
tgggtgcaac aggcccctgg aaaagggctt gagtgg 36

<210> SEQ ID NO 560
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer
<220> FEATURE:
<221> NAME/KEY: modified_base
<222> LOCATION: (31)..(31)
<223> OTHER INFORMATION: a, c, t or g

<400> SEQUENCE: 560
tgggtgtgac aaagccctgg acaagggcat nagtgg 36

<210> SEQ ID NO 561
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 561
tgggtgcgac aggcccctgg acaagagctt gggtgg 36

<210> SEQ ID NO 562
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 562
tgggtgtgac aggcccctga acaagggctt gagtgg 36

<210> SEQ ID NO 563
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 563
tggatgcgcc aggcccctgg acaaaggctt gagtgg 36

<210> SEQ ID NO 564
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 564
tggatgcgcc aggcccctgg acaaggcttc gagtgg 36

<210> SEQ ID NO 565
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 565
tgggtgtgac aggcccctgg acaaggactt gagtgg 36

<210> SEQ ID NO 566
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 566
tgggtgcacc aggtccatgc acaagggctt gagtgg 36

<210> SEQ ID NO 567
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 567
tgggtgcgcc aggtccatgc acaagggctt gagtgg 36

<210> SEQ ID NO 568
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 568
tgggtgtgcc aggcccatgc acaagggctt gagtgg 36

<210> SEQ ID NO 569
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 569
tagatctgtc agccctcagc aaaggccctg gagtgg 36

<210> SEQ ID NO 570
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 570
tggatccgtc agcccccagg gaaggccctg gagtgg 36

<210> SEQ ID NO 571
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:

<223> OTHER INFORMATION: IGHV primer

<400> SEQUENCE: 571
tggatccgtc agcccccagg aaaggccctg gagtgg 36

<210> SEQ ID NO 572
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 572
tggatccgtc agcccccggg gaaggccctg gagtgg 36

<210> SEQ ID NO 573
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 573
tgggtccgcc aggctccagg gaaagggctg gagtgg 36

<210> SEQ ID NO 574
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 574
tgggtccggc aagctccagg gaagggcctg gagtgg 36

<210> SEQ ID NO 575
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 575
tggatccgcc aggctccagg gaaggggctg gagtgg 36

<210> SEQ ID NO 576
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 576

-continued tgggtccgcc aagctacagg aaaaggtctg gagtgg 36

<210> SEQ ID NO 577
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 577
tgggtccgcc aggctccagg gaaggggctg gagtgg 36

<210> SEQ ID NO 578
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 578
tgggcccgca aggctccagg aaaggggctg gagtgg 36

<210> SEQ ID NO 579
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 579
tgggtccgcc aggctccagg aaaggggctg gagtgg 36

<210> SEQ ID NO 580
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 580
tgggtccgcc aagctccagg gaaggggctg gagtgg 36

<210> SEQ ID NO 581
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 581
ggggtccgcc aggctcccgg gaaggggctg gaatgg 36

<210> SEQ ID NO 582

<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 582
tgtgtccgcc aggctccagg gaatgggctg gagttg 36

<210> SEQ ID NO 583
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 583
tgggtccgcc aggctccagg caaggggcta gagtgg 36

<210> SEQ ID NO 584
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 584
tgggtccgcc aggctccagg caaggggctg gagtgg 36

<210> SEQ ID NO 585
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 585
tgggtccgcc aggccccagg caaggggcta gagtgg 36

<210> SEQ ID NO 586
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 586
tgggtccgcc aggctccggg caaggggcta gagtgg 36

<210> SEQ ID NO 587
<211> LENGTH: 36
<212> TYPE: DNA
<213> ORGANISM: Artificial Sequence
<220> FEATURE:

<223> OTHER INFORMATION: Description of Artificial Sequence: Synthetic
      primer
<220> FEATURE:
<223> OTHER INFORMATION: IGHV primer

<400> SEQUENCE: 587
cgagttcacc agtctccagg caaggggctg gagtga 36

<210> SEQ ID NO 588
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: IGHV primer

<400> SEQUENCE: 588
tgggtccatc aggctccagg aaaggggctg gagtgg 36

<210> SEQ ID NO 589
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: IGHV primer

<400> SEQUENCE: 589
tgggtccgtc aagctccggg gaagggtctg gagtgg 36

<210> SEQ ID NO 590
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: IGHV primer

<400> SEQUENCE: 590
tgggtccgtc aagctccagg gaagggtctg gagtgg 36

<210> SEQ ID NO 591
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: IGHV primer

<400> SEQUENCE: 591
tgggttcgcc gggctccagg gaagggtctg gagtgg 36

<210> SEQ ID NO 592
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: IGHV primer

<400> SEQUENCE: 592
tgggttcgcc gggctccagg gaagggtccg gagtgg 36

<210> SEQ ID NO 593
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 593
tggttccgcc aggctccagg gaaggggctg gagtgg 36

<210> SEQ ID NO 594
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 594
tgggtctgcc aggctccgga gaaggggctg gagtgg 36

<210> SEQ ID NO 595
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 595
tgggtctgcc aggctccgga gaaggggcag gagtgg 36

<210> SEQ ID NO 596
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 596
tgggtccgcc agcctccagg gaaggggctg gagtgg 36

<210> SEQ ID NO 597
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 597
tcagattccc aagctccagg gaaggggctg gagtga 36

<210> SEQ ID NO 598
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 598
tcagattccc aggctccagg gaaggggctg gagtga 36

<210> SEQ ID NO 599
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 599
tgggtccgcc aggctccaag aaagggtttg tagtgg 36

<210> SEQ ID NO 600
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 600
tgggtcaatg agactctagg gaaggggctg gaggga 36

<210> SEQ ID NO 601
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 601
tgggtccgcc aggctccagg gaagggactg gaatat 36

<210> SEQ ID NO 602
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 602
tgggtccgcc aggctcccgg gaaggggctg gagtgg 36

<210> SEQ ID NO 603
<211> LENGTH: 36

<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 603
tgggtccgcc aggcttccgg gaaagggctg gagtgg 36

<210> SEQ ID NO 604
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 604
tgggtccgcc aagctccagg gaaggggctg gtgtgg 36

<210> SEQ ID NO 605
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 605
tgggtccgcc aggctccagg gaagggtctg gagtgg 36

<210> SEQ ID NO 606
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 606
tgggtccgcc aggctcaagg gaaagggcta gagttg 36

<210> SEQ ID NO 607
<211> LENGTH: 36
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: IGHV primer

<400> SEQUENCE: 607
tgggtccgcc aggctccagg gaagggactg gagtgg 36

<210> SEQ ID NO 608
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 608
tgggttcgcc aggctccagg aaaaggtctg gagtgg 36

<210> SEQ ID NO 609
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 609
tggatccacc aggctccagg gaagggtctg gagtgg 36

<210> SEQ ID NO 610
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 610
tgggtccgcc aatctccagg gaaggggctg gtgtga 36

<210> SEQ ID NO 611
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 611
tgggtcctct aggctccagg aaaggggctg gagtgg 36

<210> SEQ ID NO 612
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 612
tggatccggc agcccccagg gaagggactg gagtgg 36

<210> SEQ ID NO 613
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 613
tggatccggc agccaccagg gaagggcctg gagtgg 36

<210> SEQ ID NO 614
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 614
tggatccgcc agcccccagg gaagggcctg gagtgg 36

<210> SEQ ID NO 615
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer
<220> FEATURE:
<221> NAME/KEY: modified_base
<222> LOCATION: (14)..(14)
<223> OTHER INFORMATION: a, c, t or g

<400> SEQUENCE: 615
tggatccgcc agcncccagg gaagggcctg gagtgg 36

<210> SEQ ID NO 616
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 616
tggatccgcc agcacccagg gaagggcctg gagtgg 36

<210> SEQ ID NO 617
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 617
tggatccgcc agcccccagg gaaggggctg gagtgg 36

<210> SEQ ID NO 618
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 618
tggatccgcc agcccctagg gaaggggctg gagtgg 36

<210> SEQ ID NO 619
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 619
tggatccgcc agcccccagg gaagggactg gagtgg 36

<210> SEQ ID NO 620
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 620
tggatccggc agcccccagg gaaggggctg gagtgg 36

<210> SEQ ID NO 621
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 621
tgggtccgcc agcccccagg gaaggggctg gagtgg 36

<210> SEQ ID NO 622
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 622
tggatccggc agcccgccgg gaagggactg gagtgg 36

<210> SEQ ID NO 623
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 623
tggatccggc agccgccggg gaagggactg gagtgg 36

<210> SEQ ID NO 624
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 624
tggatccggc agcccgctgg gaagggcctg gagtgg 36

<210> SEQ ID NO 625
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 625
tggatccggc agcccgccgg gaaggggctg gagtgg 36

<210> SEQ ID NO 626
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 626
tgggtgcgcc agatgcccgg gaaaggcctg gagtgg 36

<210> SEQ ID NO 627
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 627
tgggtgcgcc agatgcccgg gaaaggcttg gagtgg 36

<210> SEQ ID NO 628
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 628
tgggtgcgcc agatgcccag gaaaggcctg gagtgg 36

<210> SEQ ID NO 629
<211> LENGTH: 36
<212> TYPE: DNA

<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 629
tgggtgcgcc agatgcccgg gaaagaactg gagtgg 36

<210> SEQ ID NO 630
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 630
tggatcaggc agtccccatc gagaggcctt gagtgg 36

<210> SEQ ID NO 631
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 631
tgcgacaggc ccctggacaa gggcttgagt ggatgg 36

<210> SEQ ID NO 632
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 632
tgggtatgat agacccctgg acagggcttt gagtgg 36

<210> SEQ ID NO 633
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHV primer

<400> SEQUENCE: 633
tgggtgccac aggcccctgg acaagggctt gagtgg 36

<210> SEQ ID NO 634
<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TCR gamma primer

<400> SEQUENCE: 634
atcacgagtg ttgttccact gccaaagagt ttc 33

<210> SEQ ID NO 635
<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TCR gamma primer

<400> SEQUENCE: 635
atcacgagct ttgttccggg accaaatacc ttg 33

<210> SEQ ID NO 636
<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TCR gamma primer

<400> SEQUENCE: 636
atcacgctta gtcccttcag caaatatctt gaa 33

<210> SEQ ID NO 637
<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TCR gamma primer

<400> SEQUENCE: 637
atcacgccta gtcccttttg caaacgtctt gat 33

<210> SEQ ID NO 638
<211> LENGTH: 27
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHJ primer

<400> SEQUENCE: 638
gctccccgct atccccagac agcagac 27

<210> SEQ ID NO 639
<211> LENGTH: 27
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHJ primer

<400> SEQUENCE: 639
agactgggag ggggctgcag tgggact 27

<210> SEQ ID NO 640
<211> LENGTH: 28
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHJ primer

<400> SEQUENCE: 640
agagaaagga ggcagaagga aagccatc 28

<210> SEQ ID NO 641
<211> LENGTH: 28
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHJ primer

<400> SEQUENCE: 641
cttcagagtt aaagcaggag agaggttg 28

<210> SEQ ID NO 642
<211> LENGTH: 28
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHJ primer

<400> SEQUENCE: 642
tccctaagtg gactcagaga gggggtgg 28

<210> SEQ ID NO 643
<211> LENGTH: 28
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: IGHJ primer

<400> SEQUENCE: 643
gaaaacaaag gccctagagt ggccattc 28

<210> SEQ ID NO 644
<211> LENGTH: 36
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV25-1 primer

<400> SEQUENCE: 644
ggagatcttt cctctgagtc aacagtctcc agaata 36

<210> SEQ ID NO 645
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV12-1 primer

<400> SEQUENCE: 645
ggattgattc tcagcacaga tgcctgatgt 30

<210> SEQ ID NO 646
<211> LENGTH: 32
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV12-5 primer

<400> SEQUENCE: 646
gattctcagc agagatgcct gatgcaactt ta 32

<210> SEQ ID NO 647
<211> LENGTH: 41
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV2 primer

<400> SEQUENCE: 647
aagtctgaaa tattcgatga tcaattctca gttgaaaggc c 41

<210> SEQ ID NO 648
<211> LENGTH: 26
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV16 primer

<400> SEQUENCE: 648
agctaagtgc ctcccaaatt caccct 26

<210> SEQ ID NO 649
<211> LENGTH: 25
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV5-1 primer

<400> SEQUENCE: 649
cgattctcag ggcgccagtt ctcta 25

<210> SEQ ID NO 650
<211> LENGTH: 29
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV14 primer

<400> SEQUENCE: 650
tcttagctga aaggactgga gggacgtat 29

<210> SEQ ID NO 651
<211> LENGTH: 32
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV12-4 primer

<400> SEQUENCE: 651
gaggatcgat tctcagctaa gatgcctaat gc 32

<210> SEQ ID NO 652
<211> LENGTH: 29
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV28 primer

<400> SEQUENCE: 652
tcctgagggg tacagtgtct ctagagaga 29

<210> SEQ ID NO 653
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV27 primer

<400> SEQUENCE: 653
gatgttcctg aagggtacaa agtctctcga aaag 34

<210> SEQ ID NO 654
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV5-4 primer

<400> SEQUENCE: 654
ctcctagatt ctcaggtctc cagttcccta 30

<210> SEQ ID NO 655
<211> LENGTH: 25
<212> TYPE: DNA
<213> ORGANISM: Artificial Sequence
<220> FEATURE:
<223> OTHER INFORMATION: Description of Artificial Sequence: Synthetic primer
<220> FEATURE:

<223> OTHER INFORMATION: TRBV7-1 primer

<400> SEQUENCE: 655
cgtgatcggt tctctgcaca gaggt 25

<210> SEQ ID NO 656
<211> LENGTH: 25
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV19 primer

<400> SEQUENCE: 656
gctgaagggt acagcgtctc tcggg 25

<210> SEQ ID NO 657
<211> LENGTH: 25
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV5-3 primer

<400> SEQUENCE: 657
cgattctcag ggcgccagtt ccatg 25

<210> SEQ ID NO 658
<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV9 primer

<400> SEQUENCE: 658
caacagttcc ctgacttgca ctctgaacta aac 33

<210> SEQ ID NO 659
<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV6-7 primer

<400> SEQUENCE: 659
agaagttccc aatggctaca atgtctccag atc 33

<210> SEQ ID NO 660
<211> LENGTH: 31
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV6-4 primer

<400> SEQUENCE: 660
aagtccctga tggttatagt gtctccagag c 31

<210> SEQ ID NO 661
<211> LENGTH: 29
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV6-1 primer

<400> SEQUENCE: 661
gtccccaatg gctacaatgt ctccagatt 29

<210> SEQ ID NO 662
<211> LENGTH: 27
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV7-9 primer

<400> SEQUENCE: 662
ttctctgcag agaggcctaa gggatct 27

<210> SEQ ID NO 663
<211> LENGTH: 24
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV7-3 primer

<400> SEQUENCE: 663
gcccaacgat cggttctttg cagt 24

<210> SEQ ID NO 664
<211> LENGTH: 23
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV7-4 primer

<400> SEQUENCE: 664
ccagtggtcg gttctctgca gag 23

<210> SEQ ID NO 665
<211> LENGTH: 28
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV5-6 primer

<400> SEQUENCE: 665
gcaacttccc tgatcgattc tcaggtca 28

<210> SEQ ID NO 666

<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV5-8 primer

<400> SEQUENCE: 666
cagaggaaac ttccctccta gattttcagg tcg 33

<210> SEQ ID NO 667
<211> LENGTH: 26
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV7-8 primer

<400> SEQUENCE: 667
gcccagtgat cgcttctttg cagaaa 26

<210> SEQ ID NO 668
<211> LENGTH: 26
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV12-2 primer

<400> SEQUENCE: 668
cgattctcag ctgagaggcc tgatgg 26

<210> SEQ ID NO 669
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV15 primer

<400> SEQUENCE: 669
aggccgaaca cttctttctg ctttcttgac 30

<210> SEQ ID NO 670
<211> LENGTH: 27
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV6-2 primer

<400> SEQUENCE: 670
caaaggagag gtccctgatg gctacaa 27

<210> SEQ ID NO 671
<211> LENGTH: 28
<212> TYPE: DNA
<213> ORGANISM: Artificial Sequence
<220> FEATURE:

<223> OTHER INFORMATION: Description of Artificial Sequence: Synthetic
      primer
<220> FEATURE:
<223> OTHER INFORMATION: TRBV23-1 primer

<400> SEQUENCE: 671
gattctcatc tcaatgcccc aagaacgc 28

<210> SEQ ID NO 672
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: TRBV10-2 primer

<400> SEQUENCE: 672
cagataaagg agaagtcccc gatggctatg t 31

<210> SEQ ID NO 673
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: TRBV30 primer

<400> SEQUENCE: 673
caggaccggc agttcatcct gagt 24

<210> SEQ ID NO 674
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: TRBV10-3 primer

<400> SEQUENCE: 674
agatactgac aaaggagaag tctcagatgg ctatag 36

<210> SEQ ID NO 675
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: TRBV6-6 primer

<400> SEQUENCE: 675
gacaaaggag aagtcccgaa tggctacaac 30

<210> SEQ ID NO 676
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: TRBV13 primer

<400> SEQUENCE: 676
ccctgatcga ttctcagctc aacagttcag t 31

<210> SEQ ID NO 677
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV4-1 primer

<400> SEQUENCE: 677
cctgaatgcc ccaacagctc tctcttaaac 30

<210> SEQ ID NO 678
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV4-3 primer

<400> SEQUENCE: 678
cctgaatgcc ccaacagctc tcacttattc 30

<210> SEQ ID NO 679
<211> LENGTH: 37
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV26 primer

<400> SEQUENCE: 679
ggagatgtct ctgagaggta tcatgtttct tgaaata 37

<210> SEQ ID NO 680
<211> LENGTH: 37
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV6-8 primer

<400> SEQUENCE: 680
tacaatgtct ctagattaaa cacagaggat ttcccac 37

<210> SEQ ID NO 681
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV3-2 primer

<400> SEQUENCE: 681
ttctcacctg actctccaga caaagctcat 30

<210> SEQ ID NO 682
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV11-2 primer

<400> SEQUENCE: 682
cctaaggatc gattttctgc agagaggctc 30

<210> SEQ ID NO 683
<211> LENGTH: 29
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV2 primer

<400> SEQUENCE: 683
cctgaatgcc ctgacagctc tcgcttata 29

<210> SEQ ID NO 684
<211> LENGTH: 37
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV3-1 primer

<400> SEQUENCE: 684
gcttctcacc taaatctcca gacaaagctc acttaaa 37

<210> SEQ ID NO 685
<211> LENGTH: 29
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV29-1 primer

<400> SEQUENCE: 685
catcagccgc ccaaacctaa cattctcaa 29

<210> SEQ ID NO 686
<211> LENGTH: 29
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV18 primer

<400> SEQUENCE: 686
attttctgct gaatttccca aagagggcc 29

<210> SEQ ID NO 687
<211> LENGTH: 29

<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: TRBV17 primer

<400> SEQUENCE: 687
attcacagct gaaagaccta acggaacgt 29

<210> SEQ ID NO 688
<211> LENGTH: 26
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: TRBV20-1 primer

<400> SEQUENCE: 688
caagcctgac cttgtccact ctgaca 26

<210> SEQ ID NO 689
<211> LENGTH: 24
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: TRBV7-6 primer

<400> SEQUENCE: 689
ggttctctgc agagaggcct gagg 24

<210> SEQ ID NO 690
<211> LENGTH: 34
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: TRBV24-1 primer

<400> SEQUENCE: 690
gagagatctc tgatggatac agtgtctctc gaca 34

<210> SEQ ID NO 691
<211> LENGTH: 26
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: TRBV7-2 primer

<400> SEQUENCE: 691
gatcgcttct ctgcagagag gactgg 26

<210> SEQ ID NO 692
<211> LENGTH: 29
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV6-9 primer

<400> SEQUENCE: 692
aaggagaagt ccccgatggc tacaatgta 29

<210> SEQ ID NO 693
<211> LENGTH: 29
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV6-5 primer

<400> SEQUENCE: 693
aaggagaagt ccccaatggc tacaatgtc 29

<210> SEQ ID NO 694
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV5-5 primer

<400> SEQUENCE: 694
aagaggaaac ttccctgatc gattctcagc 30

<210> SEQ ID NO 695
<211> LENGTH: 35
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBV10-1 primer

<400> SEQUENCE: 695
gacactaaca aaggagaagt ctcagatggc tacag 35

<210> SEQ ID NO 696
<211> LENGTH: 35
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBJ1-1 primer

<400> SEQUENCE: 696
ttacctacaa ctgtgagtct ggtgccttgt ccaaa 35

<210> SEQ ID NO 697
<211> LENGTH: 30
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBJ1-2 primer

<400> SEQUENCE: 697
tacaacggtt aacctggtcc ccgaaccgaa 30

<210> SEQ ID NO 698
<211> LENGTH: 34
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBJ1-3 primer

<400> SEQUENCE: 698
acctacaaca gtgagccaac ttccctctcc aaaa 34

<210> SEQ ID NO 699
<211> LENGTH: 31
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBJ1-4 primer

<400> SEQUENCE: 699
caagacagag agctgggttc cactgccaaa a 31

<210> SEQ ID NO 700
<211> LENGTH: 33
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBJ1-5 primer

<400> SEQUENCE: 700
acctaggatg gagagtcgag tcccatcacc aaa 33

<210> SEQ ID NO 701
<211> LENGTH: 28
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBJ1-6 primer

<400> SEQUENCE: 701
tcacagtgag cctggtcccg ttcccaaa 28

<210> SEQ ID NO 702
<211> LENGTH: 25
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBJ2-1 primer

<400> SEQUENCE: 702
cggtgagccg tgtccctggc ccgaa 25

<210> SEQ ID NO 703
<211> LENGTH: 31
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBJ2-2 primer

<400> SEQUENCE: 703
ccagtacggt cagcctagag ccttctccaa a 31

<210> SEQ ID NO 704
<211> LENGTH: 26
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBJ2-3 primer

<400> SEQUENCE: 704
actgtcagcc gggtgcctgg gccaaa 26

<210> SEQ ID NO 705
<211> LENGTH: 22
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBJ2-4 primer

<400> SEQUENCE: 705
agagccgggt cccggcgccg aa 22

<210> SEQ ID NO 706
<211> LENGTH: 22
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBJ2-5 primer

<400> SEQUENCE: 706
ggagccgcgt gcctggcccg aa 22

<210> SEQ ID NO 707
<211> LENGTH: 23
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: TRBJ2-6 primer

<400> SEQUENCE: 707
gtcagcctgc tgccggcccc gaa 23

<210> SEQ ID NO 708
<211> LENGTH: 23
<212> TYPE: DNA

<213> ORGANISM: Artificial Sequence
<220> FEATURE:
<223> OTHER INFORMATION: Description of Artificial Sequence: Synthetic
primer
<220> FEATURE:
<223> OTHER INFORMATION: TRBJ2-7 primer

<400> SEQUENCE: 708
gtgagcctgg tgcccggccc gaa 23

<210> SEQ ID NO 709
<211> LENGTH: 22
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV01p probe
<220> FEATURE:
<223> OTHER INFORMATION: 5'FAM
<220> FEATURE:
<223> OTHER INFORMATION: 3' MGB-NFQ

<400> SEQUENCE: 709
actgcagcaa gaagactcag ct 22

<210> SEQ ID NO 710
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV02 probe
<220> FEATURE:
<223> OTHER INFORMATION: 5'FAM
<220> FEATURE:
<223> OTHER INFORMATION: 3' MGB-NFQ

<400> SEQUENCE: 710
aagatccggt ccacaaagct 20

<210> SEQ ID NO 711
<211> LENGTH: 22
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV03-1 probe
<220> FEATURE:
<223> OTHER INFORMATION: 5'FAM
<220> FEATURE:
<223> OTHER INFORMATION: 3' MGB-NFQ

<400> SEQUENCE: 711
aattccctgg agcttggtga ct 22

<210> SEQ ID NO 712
<211> LENGTH: 22
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV03-2p probe
<220> FEATURE:

<223> OTHER INFORMATION: 5'FAM
<220> FEATURE:
<223> OTHER INFORMATION: 3' MGB-NFQ

<400> SEQUENCE: 712
aattccctgg agcttggtga ct 22

<210> SEQ ID NO 713
<211> LENGTH: 22
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV04-1 probe
<220> FEATURE:
<223> OTHER INFORMATION: 5'FAM
<220> FEATURE:
<223> OTHER INFORMATION: 3' MGB-NFQ

<400> SEQUENCE: 713
cagaagactc agccctgtat ct 22

<210> SEQ ID NO 714
<211> LENGTH: 21
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV04-2 probe
<220> FEATURE:
<223> OTHER INFORMATION: 5'FAM
<220> FEATURE:
<223> OTHER INFORMATION: 3' MGB-NFQ

<400> SEQUENCE: 714
agaagactcg gccctgtatc t 21

<210> SEQ ID NO 715
<211> LENGTH: 21
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV04-3 probe
<220> FEATURE:
<223> OTHER INFORMATION: 5'FAM
<220> FEATURE:
<223> OTHER INFORMATION: 3' MGB-NFQ

<400> SEQUENCE: 715
agaagactcg gccctgtatc t 21

<210> SEQ ID NO 716
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV05-1 probe
<220> FEATURE:
<223> OTHER INFORMATION: 5'FAM
<220> FEATURE:
<223> OTHER INFORMATION: 3' MGB-NFQ

<400> SEQUENCE: 716
aatgtgagca ccttggagct 20

<210> SEQ ID NO 717
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV05-2p probe
<220> FEATURE:
<223> OTHER INFORMATION: 5'FAM
<220> FEATURE:
<223> OTHER INFORMATION: 3' MGB-NFQ

<400> SEQUENCE: 717
actgagtcaa acacggagct 20

<210> SEQ ID NO 718
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV05-3 probe
<220> FEATURE:
<223> OTHER INFORMATION: 5'FAM
<220> FEATURE:
<223> OTHER INFORMATION: 3' MGB-NFQ

<400> SEQUENCE: 718
aatgtgagtg ccttggagct 20

<210> SEQ ID NO 719
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV05-4 probe
<220> FEATURE:
<223> OTHER INFORMATION: 5'FAM
<220> FEATURE:
<223> OTHER INFORMATION: 3' MGB-NFQ

<400> SEQUENCE: 719
aatgtgaacg ccttggagct 20

<210> SEQ ID NO 720
<211> LENGTH: 18
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV05-5 probe
<220> FEATURE:
<223> OTHER INFORMATION: 5'FAM
<220> FEATURE:
<223> OTHER INFORMATION: 3' MGB-NFQ

<400> SEQUENCE: 720
tgtgaacgcc ttgttgct 18

<210> SEQ ID NO 721
<211> LENGTH: 18
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV05-6 probe
<220> FEATURE:
<223> OTHER INFORMATION: 5'FAM
<220> FEATURE:
<223> OTHER INFORMATION: 3' MGB-NFQ

<400> SEQUENCE: 721
tgtgaacgcc ttgttgct 18

<210> SEQ ID NO 722
<211> LENGTH: 18
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV05-7 probe
<220> FEATURE:
<223> OTHER INFORMATION: 5'FAM
<220> FEATURE:
<223> OTHER INFORMATION: 3' MGB-NFQ

<400> SEQUENCE: 722
tgtgaacgcc ttgttgct 18

<210> SEQ ID NO 723
<211> LENGTH: 18
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV05-8 probe
<220> FEATURE:
<223> OTHER INFORMATION: 5'FAM
<220> FEATURE:
<223> OTHER INFORMATION: 3' MGB-NFQ

<400> SEQUENCE: 723
tgtgaacgcc ttgttgct 18

<210> SEQ ID NO 724
<211> LENGTH: 22
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV06-1 probe
<220> FEATURE:
<223> OTHER INFORMATION: 5'FAM
<220> FEATURE:
<223> OTHER INFORMATION: 3' MGB-NFQ

<400> SEQUENCE: 724
cctcccagac atctgtgtac tt 22

<210> SEQ ID NO 725
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV06-2 probe
<220> FEATURE:
<223> OTHER INFORMATION: 5'FAM
<220> FEATURE:
<223> OTHER INFORMATION: 3' MGB-NFQ

<400> SEQUENCE: 725
tccctcccaa acatctgtgt 20

<210> SEQ ID NO 726
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV06-3 probe
<220> FEATURE:
<223> OTHER INFORMATION: 5'FAM
<220> FEATURE:
<223> OTHER INFORMATION: 3' MGB-NFQ

<400> SEQUENCE: 726
tccctcccaa acatctgtgt 20

<210> SEQ ID NO 727
<211> LENGTH: 22
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV06-4 probe
<220> FEATURE:
<223> OTHER INFORMATION: 5'FAM
<220> FEATURE:
<223> OTHER INFORMATION: 3' MGB-NFQ

<400> SEQUENCE: 727
tgctgtaccc tctcagacat ct 22

<210> SEQ ID NO 728
<211> LENGTH: 22
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV06-5 probe
<220> FEATURE:
<223> OTHER INFORMATION: 5'FAM
<220> FEATURE:
<223> OTHER INFORMATION: 3' MGB-NFQ

<400> SEQUENCE: 728
cctcccagac atctgtgtac tt 22

<210> SEQ ID NO 729
<211> LENGTH: 22
<212> TYPE: DNA

<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV06-6 probe
<220> FEATURE:
<223> OTHER INFORMATION: 5'FAM
<220> FEATURE:
<223> OTHER INFORMATION: 3' MGB-NFQ

<400> SEQUENCE: 729
cctcccagac atctgtgtac tt 22

<210> SEQ ID NO 730
<211> LENGTH: 22
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV06-7 probe
<220> FEATURE:
<223> OTHER INFORMATION: 5'FAM
<220> FEATURE:
<223> OTHER INFORMATION: 3' MGB-NFQ

<400> SEQUENCE: 730
tgctccctct cagacttctg tt 22

<210> SEQ ID NO 731
<211> LENGTH: 22
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV06-8 probe
<220> FEATURE:
<223> OTHER INFORMATION: 5'FAM
<220> FEATURE:
<223> OTHER INFORMATION: 3' MGB-NFQ

<400> SEQUENCE: 731
cctcccagac atctgtgtac tt 22

<210> SEQ ID NO 732
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV06-9 probe
<220> FEATURE:
<223> OTHER INFORMATION: 5'FAM
<220> FEATURE:
<223> OTHER INFORMATION: 3' MGB-NFQ

<400> SEQUENCE: 732
tccctcccag acatctgtat 20

<210> SEQ ID NO 733
<211> LENGTH: 17
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV07-1 probe
<220> FEATURE:
<223> OTHER INFORMATION: 5'FAM
<220> FEATURE:
<223> OTHER INFORMATION: 3' MGB-NFQ

<400> SEQUENCE: 733
aagttccagc gcacaca 17

<210> SEQ ID NO 734
<211> LENGTH: 17
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV07-2 probe
<220> FEATURE:
<223> OTHER INFORMATION: 5'FAM
<220> FEATURE:
<223> OTHER INFORMATION: 3' MGB-NFQ

<400> SEQUENCE: 734
atccagcgca cacagca 17

<210> SEQ ID NO 735
<211> LENGTH: 17
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV07-3 probe
<220> FEATURE:
<223> OTHER INFORMATION: 5'FAM
<220> FEATURE:
<223> OTHER INFORMATION: 3' MGB-NFQ

<400> SEQUENCE: 735
aagatccagc gcacaga 17

<210> SEQ ID NO 736
<211> LENGTH: 17
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV07-4 probe
<220> FEATURE:
<223> OTHER INFORMATION: 5'FAM
<220> FEATURE:
<223> OTHER INFORMATION: 3' MGB-NFQ

<400> SEQUENCE: 736
aagatccagc gcacaga 17

<210> SEQ ID NO 737
<211> LENGTH: 18
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV07-5p probe
<220> FEATURE:
<223> OTHER INFORMATION: 5'FAM
<220> FEATURE:
<223> OTHER INFORMATION: 3' MGB-NFQ

<400> SEQUENCE: 737
atccagcgca cagagcaa 18

<210> SEQ ID NO 738
<211> LENGTH: 17
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV07-6 probe
<220> FEATURE:
<223> OTHER INFORMATION: 5'FAM
<220> FEATURE:
<223> OTHER INFORMATION: 3' MGB-NFQ

<400> SEQUENCE: 738
atccagcgca cagagca 17

<210> SEQ ID NO 739
<211> LENGTH: 17
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV07-7 probe
<220> FEATURE:
<223> OTHER INFORMATION: 5'FAM
<220> FEATURE:
<223> OTHER INFORMATION: 3' MGB-NFQ

<400> SEQUENCE: 739
attcagcgca cagagca 17

<210> SEQ ID NO 740
<211> LENGTH: 17
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV07-8 probe
<220> FEATURE:
<223> OTHER INFORMATION: 5'FAM
<220> FEATURE:
<223> OTHER INFORMATION: 3' MGB-NFQ

<400> SEQUENCE: 740
aagatccagc gcacaca 17

<210> SEQ ID NO 741
<211> LENGTH: 17
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV07-9 probe
<220> FEATURE:
<223> OTHER INFORMATION: 5'FAM
<220> FEATURE:

<223> OTHER INFORMATION: 3' MGB-NFQ

<400> SEQUENCE: 741
atccagcgca cagagca 17

<210> SEQ ID NO 742
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV08-1p probe
<220> FEATURE:
<223> OTHER INFORMATION: 5'FAM
<220> FEATURE:
<223> OTHER INFORMATION: 3' MGB-NFQ

<400> SEQUENCE: 742
aaccctggag tctactagca 20

<210> SEQ ID NO 743
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV08-2p probe
<220> FEATURE:
<223> OTHER INFORMATION: 5'FAM
<220> FEATURE:
<223> OTHER INFORMATION: 3' MGB-NFQ

<400> SEQUENCE: 743
agccagacct atctgtacca 20

<210> SEQ ID NO 744
<211> LENGTH: 16
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV09 probe
<220> FEATURE:
<223> OTHER INFORMATION: 5'FAM
<220> FEATURE:
<223> OTHER INFORMATION: 3' MGB-NFQ

<400> SEQUENCE: 744
agctctctgg agctgg 16

<210> SEQ ID NO 745
<211> LENGTH: 22
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV10-1 probe
<220> FEATURE:
<223> OTHER INFORMATION: 5'FAM
<220> FEATURE:
<223> OTHER INFORMATION: 3' MGB-NFQ

<400> SEQUENCE: 745
cctcctccca gacatctgta ta 22

<210> SEQ ID NO 746
<211> LENGTH: 22
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV10-2 probe
<220> FEATURE:
<223> OTHER INFORMATION: 5'FAM
<220> FEATURE:
<223> OTHER INFORMATION: 3' MGB-NFQ

<400> SEQUENCE: 746
cgctcccaga catctgtgta tt 22

<210> SEQ ID NO 747
<211> LENGTH: 22
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV10-3 probe
<220> FEATURE:
<223> OTHER INFORMATION: 5'FAM
<220> FEATURE:
<223> OTHER INFORMATION: 3' MGB-NFQ

<400> SEQUENCE: 747
agctcccaga catctgtgta ct 22

<210> SEQ ID NO 748
<211> LENGTH: 21
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV11-1 probe
<220> FEATURE:
<223> OTHER INFORMATION: 5'FAM
<220> FEATURE:
<223> OTHER INFORMATION: 3' MGB-NFQ

<400> SEQUENCE: 748
aagatccagc ctgcagagct t 21

<210> SEQ ID NO 749
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV11-2 probe
<220> FEATURE:
<223> OTHER INFORMATION: 5'FAM
<220> FEATURE:
<223> OTHER INFORMATION: 3' MGB-NFQ

<400> SEQUENCE: 749
atccagcctg caaagcttga 20

<210> SEQ ID NO 750
<211> LENGTH: 21
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV11-3 probe
<220> FEATURE:
<223> OTHER INFORMATION: 5'FAM
<220> FEATURE:
<223> OTHER INFORMATION: 3' MGB-NFQ

<400> SEQUENCE: 750
aagatccagc ctgcagagct t 21

<210> SEQ ID NO 751
<211> LENGTH: 22
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV12-1p probe
<220> FEATURE:
<223> OTHER INFORMATION: 5'FAM
<220> FEATURE:
<223> OTHER INFORMATION: 3' MGB-NFQ

<400> SEQUENCE: 751
ccagggactt gggcctatat tt 22

<210> SEQ ID NO 752
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV12-2p probe
<220> FEATURE:
<223> OTHER INFORMATION: 5'FAM
<220> FEATURE:
<223> OTHER INFORMATION: 3' MGB-NFQ

<400> SEQUENCE: 752
aagatccagc ctgcagagca 20

<210> SEQ ID NO 753
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV12-3 probe
<220> FEATURE:
<223> OTHER INFORMATION: 5'FAM
<220> FEATURE:
<223> OTHER INFORMATION: 3' MGB-NFQ

<400> SEQUENCE: 753
agggactcag ctgtgtactt 20

<210> SEQ ID NO 754
<211> LENGTH: 20

<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV12-4 probe
<220> FEATURE:
<223> OTHER INFORMATION: 5'FAM
<220> FEATURE:
<223> OTHER INFORMATION: 3' MGB-NFQ

<400> SEQUENCE: 754
agggactcag ctgtgtactt 20

<210> SEQ ID NO 755
<211> LENGTH: 22
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV12-5 probe
<220> FEATURE:
<223> OTHER INFORMATION: 5'FAM
<220> FEATURE:
<223> OTHER INFORMATION: 3' MGB-NFQ

<400> SEQUENCE: 755
ccagggactc agctgtgtat tt 22

<210> SEQ ID NO 756
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV13 probe
<220> FEATURE:
<223> OTHER INFORMATION: 5'FAM
<220> FEATURE:
<223> OTHER INFORMATION: 3' MGB-NFQ

<400> SEQUENCE: 756
aacatgagct ccttggagct 20

<210> SEQ ID NO 757
<211> LENGTH: 22
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: TCRBV14 probe
<220> FEATURE:
<223> OTHER INFORMATION: 5'FAM
<220> FEATURE:
<223> OTHER INFORMATION: 3' MGB-NFQ

<400> SEQUENCE: 757
tgcagaactg gaggattctg ga 22

<210> SEQ ID NO 758
<211> LENGTH: 16
<212> TYPE: DNA
<213> ORGANISM: Artificial Sequence
<220> FEATURE:

<223> OTHER INFORMATION: Description of Artificial Sequence: Synthetic probe
<220> FEATURE:
<223> OTHER INFORMATION: TCRBV15 probe
<220> FEATURE:
<223> OTHER INFORMATION: 5'FAM
<220> FEATURE:
<223> OTHER INFORMATION: 3' MGB-NFQ

<400> SEQUENCE: 758
acgcagccat gtacct 16

<210> SEQ ID NO 759
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV16 probe
<220> FEATURE:
<223> OTHER INFORMATION: 5'FAM
<220> FEATURE:
<223> OTHER INFORMATION: 3' MGB-NFQ

<400> SEQUENCE: 759
atccaggcta cgaagcttga 20

<210> SEQ ID NO 760
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV17p probe
<220> FEATURE:
<223> OTHER INFORMATION: 5'FAM
<220> FEATURE:
<223> OTHER INFORMATION: 3' MGB-NFQ

<400> SEQUENCE: 760
agggactcag ccgtgtatct 20

<210> SEQ ID NO 761
<211> LENGTH: 22
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV18 probe
<220> FEATURE:
<223> OTHER INFORMATION: 5'FAM
<220> FEATURE:
<223> OTHER INFORMATION: 3' MGB-NFQ

<400> SEQUENCE: 761
cgaggagatt cggcagctta tt 22

<210> SEQ ID NO 762
<211> LENGTH: 18
<212> TYPE: DNA
<213> ORGANISM: Artificial Sequence
<220> FEATURE:
<223> OTHER INFORMATION: Description of Artificial Sequence: Synthetic probe
<220> FEATURE:

<223> OTHER INFORMATION: TCRBV19 probe
<220> FEATURE:
<223> OTHER INFORMATION: 5'FAM
<220> FEATURE:
<223> OTHER INFORMATION: 3' MGB-NFQ

<400> SEQUENCE: 762
agaacccgac agctttct 18

<210> SEQ ID NO 763
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV20-1 probe
<220> FEATURE:
<223> OTHER INFORMATION: 5'FAM
<220> FEATURE:
<223> OTHER INFORMATION: 3' MGB-NFQ

<400> SEQUENCE: 763
tcctgaagac agcagcttct 20

<210> SEQ ID NO 764
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV21-1p probe
<220> FEATURE:
<223> OTHER INFORMATION: 5'FAM
<220> FEATURE:
<223> OTHER INFORMATION: 3' MGB-NFQ

<400> SEQUENCE: 764
agatccagtc cacggagtca 20

<210> SEQ ID NO 765
<211> LENGTH: 18
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV22p probe
<220> FEATURE:
<223> OTHER INFORMATION: 5'FAM
<220> FEATURE:
<223> OTHER INFORMATION: 3' MGB-NFQ

<400> SEQUENCE: 765
acaccagcca aacagctt 18

<210> SEQ ID NO 766
<211> LENGTH: 19
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV23-1p probe
<220> FEATURE:
<223> OTHER INFORMATION: 5'FAM

<220> FEATURE:
<223> OTHER INFORMATION: 3' MGB-NFQ

<400> SEQUENCE: 766
ggcaatcctg tcctcagaa 19

<210> SEQ ID NO 767
<211> LENGTH: 22
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV24-1 probe
<220> FEATURE:
<223> OTHER INFORMATION: 5'FAM
<220> FEATURE:
<223> OTHER INFORMATION: 3' MGB-NFQ

<400> SEQUENCE: 767
cccaaccaga cagctcttta ct 22

<210> SEQ ID NO 768
<211> LENGTH: 22
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV25-1 probe
<220> FEATURE:
<223> OTHER INFORMATION: 5'FAM
<220> FEATURE:
<223> OTHER INFORMATION: 3' MGB-NFQ

<400> SEQUENCE: 768
cctcacatac ctctcagtac ct 22

<210> SEQ ID NO 769
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV26p probe
<220> FEATURE:
<223> OTHER INFORMATION: 5'FAM
<220> FEATURE:
<223> OTHER INFORMATION: 3' MGB-NFQ

<400> SEQUENCE: 769
agcaccaacc agacatctgt 20

<210> SEQ ID NO 770
<211> LENGTH: 22
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV27-1 probe
<220> FEATURE:
<223> OTHER INFORMATION: 5'FAM
<220> FEATURE:
<223> OTHER INFORMATION: 3' MGB-NFQ

<400> SEQUENCE: 770
ccaaccagac ctctctgtac tt 22

<210> SEQ ID NO 771
<211> LENGTH: 18
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV28 probe
<220> FEATURE:
<223> OTHER INFORMATION: 5'FAM
<220> FEATURE:
<223> OTHER INFORMATION: 3' MGB-NFQ

<400> SEQUENCE: 771
agcaccaacc agacatct 18

<210> SEQ ID NO 772
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV29-1 probe
<220> FEATURE:
<223> OTHER INFORMATION: 5'FAM
<220> FEATURE:
<223> OTHER INFORMATION: 3' MGB-NFQ

<400> SEQUENCE: 772
tgagcaacat gagccctgaa 20

<210> SEQ ID NO 773
<211> LENGTH: 22
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: TCRBV30 probe
<220> FEATURE:
<223> OTHER INFORMATION: 5'FAM
<220> FEATURE:
<223> OTHER INFORMATION: 3' MGB-NFQ

<400> SEQUENCE: 773
tccttctcag tgactctggc tt 22

<210> SEQ ID NO 774
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 774
tccggtccac aaagctggag 20

<210> SEQ ID NO 775
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 775
ctggagcttg gtgactctgc 20

<210> SEQ ID NO 776
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 776
ccctgtatct ctgcgccagc 20

<210> SEQ ID NO 777
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 777
ttggagctgg gggactcg 18

<210> SEQ ID NO 778
<211> LENGTH: 21
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 778
tgagctgaat gtgaacgcct t 21

<210> SEQ ID NO 779
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 779
tctgtgtact tctgtgccag ca 22

<210> SEQ ID NO 780
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 780
agctgctccc tctcagactt 20

<210> SEQ ID NO 781

<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 781
tgctccctcc cagacatctg 20

<210> SEQ ID NO 782
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 782
tctgaagttc cagcgcacac 20

<210> SEQ ID NO 783
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 783
ctgtgccagc agcttagc 18

<210> SEQ ID NO 784
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 784
aagatccagc gcacagagc 19

<210> SEQ ID NO 785
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 785
tttgtatttc tgtgccagca gc 22

<210> SEQ ID NO 786
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 786
tctgcgccag cagtgagt 18

<210> SEQ ID NO 787
<211> LENGTH: 20

<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 787
tcactctgga gtccgctacc 20

<210> SEQ ID NO 788
<211> LENGTH: 24
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 788
agtagactcc actctcaaga tcca 24

<210> SEQ ID NO 789
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 789
tttctgtgcc agcagctttg 20

<210> SEQ ID NO 790
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 790
tcggccgtgt atgtctgtg 19

<210> SEQ ID NO 791
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 791
atccagccct cagaacccag 20

<210> SEQ ID NO 792
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 792
acatgagctc cttggagctg 20

<210> SEQ ID NO 793
<211> LENGTH: 21
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 793
tgcagaactg gaggattctg g 21

<210> SEQ ID NO 794
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 794
tgtacctgtg tgccaccagc 20

<210> SEQ ID NO 795
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 795
tttgtgccag cagccaatc 19

<210> SEQ ID NO 796
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 796
atccagcagg tagtgcgagg 20

<210> SEQ ID NO 797
<211> LENGTH: 19

<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 797
cactgtgaca tcggcccaa 19

<210> SEQ ID NO 798
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 798
cagtgcccat cctgaagaca 20

<210> SEQ ID NO 799
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 799
agcctggcaa tcctgtcctc 20

<210> SEQ ID NO 800
<211> LENGTH: 21
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 800
tgtccctaga gtctgccatc c 21

<210> SEQ ID NO 801
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 801
caggccctca catacctctc 20

-continued

<210> SEQ ID NO 802
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 802
tctctgtact tctgtgccag c 21

<210> SEQ ID NO 803
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 803
ccagcaccaa ccagacatct 20

<210> SEQ ID NO 804
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 804
tgtgagcaac atgagccctg 20

<210> SEQ ID NO 805
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 805
tggcttctat ctctgtgcct g 21

<210> SEQ ID NO 806
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 806
ccctgcagcc agaagact 18

<210> SEQ ID NO 807
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 807
tgcgccagca gcttg 15

<210> SEQ ID NO 808
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 808
agtgccttgg agctggg 17

<210> SEQ ID NO 809
<211> LENGTH: 16
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 809
tggagtcggc tgctcc 16

<210> SEQ ID NO 810
<211> LENGTH: 16
<212> TYPE: DNA
<213> ORGANISM: Artificial Sequence
<220> FEATURE:
<223> OTHER INFORMATION: Description of Artificial Sequence: Synthetic
primer

<400> SEQUENCE: 810
tcacgttggc gtctgc 16

<210> SEQ ID NO 811
<211> LENGTH: 18
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 811
tgctccctcc cagacatc 18

<210> SEQ ID NO 812
<211> LENGTH: 16
<212> TYPE: DNA
<213> ORGANISM: Artificial Sequence
<220> FEATURE:
<223> OTHER INFORMATION: Description of Artificial Sequence: Synthetic
primer

<400> SEQUENCE: 812
ccagcgcaca cagcag 16

<210> SEQ ID NO 813
<211> LENGTH: 18
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 813
agatccagcg cacagagc 18

<210> SEQ ID NO 814
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 814
cagcgcacag agcagc 16

<210> SEQ ID NO 815
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'FAM
<220> FEATURE:
<223> OTHER INFORMATION: 3' MGB

<400> SEQUENCE: 815
tgagctctct ggagctgg 18

<210> SEQ ID NO 816
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'FAM
<220> FEATURE:
<223> OTHER INFORMATION: 3' MGB

<400> SEQUENCE: 816
ccttgagatc caggctacg 19

<210> SEQ ID NO 817
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 817
ttcccctgac cctggag 17

<210> SEQ ID NO 818
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'FAM

<220> FEATURE:
<223> OTHER INFORMATION: 3' MGB

<400> SEQUENCE: 818
tggagtcgcc cagcc 15

<210> SEQ ID NO 819
<211> LENGTH: 17
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 819
aggagcgctt ctccctg 17

<210> SEQ ID NO 820
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 820
tccttctcag tgactctggc 20

<210> SEQ ID NO 821
<211> LENGTH: 17
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 821
agcaccttgg agctggg 17

<210> SEQ ID NO 822
<211> LENGTH: 18
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 822
tgagtgcctt ggagctgg 18

<210> SEQ ID NO 823
<211> LENGTH: 18
<212> TYPE: DNA

<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 823
ctggagtcag ctgctccc 18

<210> SEQ ID NO 824
<211> LENGTH: 19
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 824
actctgaaga tccagcgca 19

<210> SEQ ID NO 825
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 825
tccatctcca ctctgacga 19

<210> SEQ ID NO 826
<211> LENGTH: 16
<212> TYPE: DNA
<213> ORGANISM: Artificial Sequence
<220> FEATURE:
<223> OTHER INFORMATION: Description of Artificial Sequence: Synthetic
primer

<400> SEQUENCE: 826
tctgctgcct cctccc 16

<210> SEQ ID NO 827
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 827
atttccccct cactctgg 18

<210> SEQ ID NO 828
<211> LENGTH: 16
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM

<220> FEATURE:
<223> OTHER INFORMATION: 3' MGB

<400> SEQUENCE: 828
tccagcgcac agagca 16

<210> SEQ ID NO 829
<211> LENGTH: 16
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 829
cagcgggact cagcca 16

<210> SEQ ID NO 830
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 830
tcaaacacag aggacctccc 20

<210> SEQ ID NO 831
<211> LENGTH: 20
<212> TYPE: DNA
<213> ORGANISM: Artificial Sequence
<220> FEATURE:
<223> OTHER INFORMATION: Description of Artificial Sequence: Synthetic
probe
<220> FEATURE:
<223> OTHER INFORMATION: 5'FAM
<220> FEATURE:
<223> OTHER INFORMATION: 3' MGB

<400> SEQUENCE: 831
cactctggag tcagctaccc 20

<210> SEQ ID NO 832
<211> LENGTH: 15
<212> TYPE: DNA
<213> ORGANISM: Artificial Sequence
<220> FEATURE:
<223> OTHER INFORMATION: Description of Artificial Sequence: Synthetic
primer

<400> SEQUENCE: 832
ctgcagccag aagac 15

<210> SEQ ID NO 833
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 833
tcacgttggc gtctgctgta ccctc 25

<210> SEQ ID NO 834
<211> LENGTH: 13
<212> TYPE: DNA
<213> ORGANISM: Artificial Sequence
<220> FEATURE:
<223> OTHER INFORMATION: Description of Artificial Sequence: Synthetic primer

<400> SEQUENCE: 834
cagcgcacac agc 13

<210> SEQ ID NO 835
<211> LENGTH: 17
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 835
tcacctacac gccctgc 17

<210> SEQ ID NO 836
<211> LENGTH: 17
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 836
acacaccctg cagccag 17

<210> SEQ ID NO 837
<211> LENGTH: 19
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 837
cacagatgat ttccccctc 19

<210> SEQ ID NO 838
<211> LENGTH: 18
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM

<220> FEATURE:
<223> OTHER INFORMATION: 3' MGB

<400> SEQUENCE: 838
ctgaagttcc agcgcaca 18

<210> SEQ ID NO 839
<211> LENGTH: 19
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5'FAM
<220> FEATURE:
<223> OTHER INFORMATION: 3' MGB

<400> SEQUENCE: 839
tccgtctcca ctctgacga 19

<210> SEQ ID NO 840
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 840
agatttggac ctgcgagc 18

<210> SEQ ID NO 841
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 841
gagcggctgt ctccacaagt 20

<210> SEQ ID NO 842
<211> LENGTH: 15
<212> TYPE: DNA
<213> ORGANISM: Artificial Sequence
<220> FEATURE:
<223> OTHER INFORMATION: Description of Artificial Sequence: Synthetic probe

<400> SEQUENCE: 842
ccgcgcagag ccttc 15

<210> SEQ ID NO 843
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 843
tatagctgaa gggtacagcg tctctcggg 29

<210> SEQ ID NO 844
<211> LENGTH: 29

<212> TYPE: DNA
<213> ORGANISM: Artificial Sequence
<220> FEATURE:
<223> OTHER INFORMATION: Description of Artificial Sequence: Synthetic primer

<400> SEQUENCE: 844
ttcgatgatc aattctcagt tgaaaggcc 29

<210> SEQ ID NO 845
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 845
cctaaatctc cagacaaagc tcacttaaa 29

<210> SEQ ID NO 846
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 846
ctgaatgccc caacagctct ctcttaaac 29

<210> SEQ ID NO 847
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 847
ctgaatgccc caacagctct cacttattc 29

<210> SEQ ID NO 848
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 848
tggtcgattc tcagggcgcc agttctcta 29

<210> SEQ ID NO 849
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 849
taatcgattc tcagggcgcc agttccatg 29

<210> SEQ ID NO 850
<211> LENGTH: 29
<212> TYPE: DNA

<213> ORGANISM: Artificial Sequence
<220> FEATURE:
<223> OTHER INFORMATION: Description of Artificial Sequence: Synthetic
primer

<400> SEQUENCE: 850
tcctagattc tcaggtctcc agttcccta 29

<210> SEQ ID NO 851
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 851
ggcaacttcc ctgatcgatt ctcaggtca 29

<210> SEQ ID NO 852
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 852
ggaaacttcc ctcctagatt ttcaggtcg 29

<210> SEQ ID NO 853
<211> LENGTH: 29
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Oligonucleotide Primer

<400> SEQUENCE: 853
gccaaaggag aggtccctga tggctacaa 29

<210> SEQ ID NO 854
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 854
gtccctgatg gttatagtgt ctccagagc 29

<210> SEQ ID NO 855
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 855
gttcccaatg gctacaatgt ctccagatc 29

<210> SEQ ID NO 856
<211> LENGTH: 29

<212> TYPE: DNA
<213> ORGANISM: Artificial Sequence
<220> FEATURE:
<223> OTHER INFORMATION: Description of Artificial Sequence: Synthetic primer

<400> SEQUENCE: 856
ctctagatta aacacagagg atttcccac 29

<210> SEQ ID NO 857
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 857
tccccgtgat cggttctctg cacagaggt 29

<210> SEQ ID NO 858
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 858
agtgatcgct tctctgcaga gaggactgg 29

<210> SEQ ID NO 859
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 859
ggctgcccaa cgatcggttc tttgcagt 28

<210> SEQ ID NO 860
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 860
ggcggcccag tggtcggttc tctgcagag 29

<210> SEQ ID NO 861
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 861
atgatcggtt ctctgcagag aggcctgagg 30

<210> SEQ ID NO 862
<211> LENGTH: 29
<212> TYPE: DNA

<213> ORGANISM: Artificial Sequence
<220> FEATURE:
<223> OTHER INFORMATION: Description of Artificial Sequence: Synthetic
primer

<400> SEQUENCE: 862
gctgcccagt gatcgcttct ttgcagaaa 29

<210> SEQ ID NO 863
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 863
ggttctctgc agagaggcct aagggatct 29

<210> SEQ ID NO 864
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 864
gttccctgac ttgcactctg aactaaac 28

<210> SEQ ID NO 865
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 865
aacaaaggag aagtctcaga tggctacag 29

<210> SEQ ID NO 866
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 866
gataaaggag aagtccccga tggctatgt 29

<210> SEQ ID NO 867
<211> LENGTH: 29
<212> TYPE: DNA
<213> ORGANISM: Artificial Sequence
<220> FEATURE:
<223> OTHER INFORMATION: Description of Artificial Sequence: Synthetic
primer
<220> FEATURE:
<223> OTHER INFORMATION: Oligonucleotide Primer

<400> SEQUENCE: 867
gacaaaggag aagtctcaga tggctatag 29

<210> SEQ ID NO 868
<211> LENGTH: 29

<212> TYPE: DNA
<213> ORGANISM: Artificial Sequence
<220> FEATURE:
<223> OTHER INFORMATION: Description of Artificial Sequence: Synthetic
primer

<400> SEQUENCE: 868
ctaaggatcg attttctgca gagaggctc 29

<210> SEQ ID NO 869
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 869
tcgattctca gctaagatgc ctaatgc 27

<210> SEQ ID NO 870
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 870
ttctcagcag agatgcctga tgcaacttta 30

<210> SEQ ID NO 871
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 871
ctgatcgatt ctcagctcaa cagttcagt 29

<210> SEQ ID NO 872
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 872
gccgaacact tctttctgct ttcttgac 28

<210> SEQ ID NO 873
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 873
ttcagctaag tgcctcccaa attcaccct 29

<210> SEQ ID NO 874
<211> LENGTH: 29
<212> TYPE: DNA

<213> ORGANISM: Artificial Sequence
<220> FEATURE:
<223> OTHER INFORMATION: Description of Artificial Sequence: Synthetic
primer

<400> SEQUENCE: 874
tatagctgaa gggtacagcg tctctcggg 29

<210> SEQ ID NO 875
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 875
atgcaagcct gaccttgtcc actctgaca 29

<210> SEQ ID NO 876
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 876
atctctgatg gatacagtgt ctctcgaca 29

<210> SEQ ID NO 877
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 877
tttcctctga gtcaacagtc tccagaata 29

<210> SEQ ID NO 878
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 878
tcctgaaggg tacaaagtct ctcgaaaag 29

<210> SEQ ID NO 879
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 879
gaccccagga ccggcagttc atcctgagt 29

<210> SEQ ID NO 880
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 880
acctacaacg gttaacctgg tccccgaacc gaa 33

<210> SEQ ID NO 881
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 881
acctacaaca gtgagccaac ttccctctcc aaa 33

<210> SEQ ID NO 882
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 882
ccaagacaga gagctgggtt ccactgccaa a 31

<210> SEQ ID NO 883
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 883
ctgtcacagt gagcctggtc ccgttcccaa a 31

<210> SEQ ID NO 884
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 884
acaactgtga gtctggtgcc ttgtccaaag aaa 33

<210> SEQ ID NO 885
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 885
acaacggtta acctggtccc cgaaccgaag gtg 33

<210> SEQ ID NO 886
<211> LENGTH: 33
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 886
acaacagtga gccaacttcc ctctccaaaa tat 33

<210> SEQ ID NO 887
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 887
aagacagaga gctgggttcc actgccaaaa aac 33

<210> SEQ ID NO 888
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 888
aggatggaga gtcgagtccc atcaccaaaa tgc 33

<210> SEQ ID NO 889
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 889
gtcacagtga gcctggtccc gttcccaaag tgg 33

<210> SEQ ID NO 890
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 890
agcacggtga gccgtgtccc tggcccgaag aac 33

<210> SEQ ID NO 891
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 891
agtacggtca gcctagagcc ttctccaaaa aac 33

<210> SEQ ID NO 892
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 892
agcactgtca gccgggtgcc tgggccaaaa tac 33

<210> SEQ ID NO 893
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 893
agcactgaga gccgggtccc ggcgccgaag tac 33

<210> SEQ ID NO 894
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 894
agcaccagga gccgcgtgcc tggcccgaag tac 33

<210> SEQ ID NO 895
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 895
agcacggtca gcctgctgcc ggccccgaaa gtc 33

<210> SEQ ID NO 896
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 896
gtgaccgtga gcctggtgcc cggcccgaag tac 33

<210> SEQ ID NO 897
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 897
tgaggagacg gtgaccaggg ttccttggcc ccag 34

<210> SEQ ID NO 898
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 898
tgaggagacg gtgaccaggg tcccttggcc ccag 34

<210> SEQ ID NO 899
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 899
tgaggagacg gtgaccaggg ttccctggcc ccag 34

<210> SEQ ID NO 900
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 900
ctgaagagac ggtgaccatt gtcccttggc cccag 35

<210> SEQ ID NO 901
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 901
ctgaggagac ggtgaccgtg gtcccttgcc cccag 35

<210> SEQ ID NO 902
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 902
tgaggagacg gtgaccgtgg tcccttggcc ccag 34

<210> SEQ ID NO 903
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 903
ctgaggagac ggtgaccgtg gtccctttgc cccag 35

<210> SEQ ID NO 904
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 904
ctgaggagac agtgaccagg gtgccacggc cccag 35

<210> SEQ ID NO 905
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 905
ctgaggagac ggtgaccagg gttccttggc cccag 35

<210> SEQ ID NO 906
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 906
ctgaggagac ggtgaccagg gttccctggc cccag 35

<210> SEQ ID NO 907
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 907
ctgaggagac ggtgaccagg gtgccctggc cccag 35

<210> SEQ ID NO 908
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' FAM
<220> FEATURE:
<223> OTHER INFORMATION: 3' MGB

<400> SEQUENCE: 908
tccggtccac aaagctggag 20

<210> SEQ ID NO 909
<211> LENGTH: 20
<212> TYPE: DNA
<213> ORGANISM: Artificial Sequence
<220> FEATURE:
<223> OTHER INFORMATION: Description of Artificial Sequence: Synthetic probe
<220> FEATURE:
<223> OTHER INFORMATION: 5' FAM
<220> FEATURE:
<223> OTHER INFORMATION: 3' MGB

<400> SEQUENCE: 909
ctggagcttg gtgactctgc 20